(12) United States Patent
Zhao et al.

(10) Patent No.: US 11,725,003 B2
(45) Date of Patent: Aug. 15, 2023

(54) AMINE DERIVATIVE AND AN ORGANIC ELECTROLUMINESCENT DEVICE THEREOF

(71) Applicant: Changchun Hyperions Technology Co., Ltd, Changchun (CN)

(72) Inventors: Qian Zhao, Changchun (CN); Hui Liu, Changchun (CN); Yingxue Wang, Changchun (CN)

(73) Assignee: Changchun Hyperions Technology Co., Ltd, Changchun (CN)

( * ) Notice: Subject to any disclaimer, the term of this patent is extended or adjusted under 35 U.S.C. 154(b) by 456 days.

(21) Appl. No.: 16/848,401

(22) Filed: Apr. 14, 2020

(65) Prior Publication Data

US 2021/0009574 A1    Jan. 14, 2021

(30) Foreign Application Priority Data

Jul. 12, 2019    (CN) .......................... 201910631205.2

(51) Int. Cl.
| | | |
|---|---|---|
| C07D 263/57 | (2006.01) | |
| C07D 277/66 | (2006.01) | |
| C07D 235/18 | (2006.01) | |
| C07D 413/12 | (2006.01) | |
| C07D 403/12 | (2006.01) | |
| C07D 417/12 | (2006.01) | |
| H01L 51/00 | (2006.01) | |

(52) U.S. Cl.
CPC ......... *C07D 413/12* (2013.01); *C07D 235/18* (2013.01); *C07D 263/57* (2013.01); *C07D 277/66* (2013.01); *C07D 403/12* (2013.01); *C07D 417/12* (2013.01); *H01L 51/006* (2013.01); *H01L 51/0073* (2013.01)

(58) Field of Classification Search
CPC ... C07D 263/57; C07D 277/66; C07D 235/18
See application file for complete search history.

(56) References Cited

U.S. PATENT DOCUMENTS

| 4,769,292 A | * | 9/1988 | Tang | ...................... H05B 33/28 |
|---|---|---|---|---|
| | | | | 428/917 |
| 2012/0001127 A1 | | 1/2012 | Brown et al. | |
| 2012/0330025 A1 | | 12/2012 | Osaka et al. | |

FOREIGN PATENT DOCUMENTS

| CN | 104509211 A | 4/2015 | | |
|---|---|---|---|---|
| CN | 107068914 A | 8/2017 | | |
| CN | 107936955 | 4/2018 | | |
| CN | 108047130 | 5/2018 | | |
| CN | 108191744 | 6/2018 | | |
| CN | 108203406 | 6/2018 | | |
| CN | 109535012 | 3/2019 | | |
| CN | 109574857 | 4/2019 | | |
| CN | 110669025 A | * | 1/2020 | ........... C07D 277/66 |
| EP | 0879868 | 11/1998 | | |
| EP | 2861044 | 4/2015 | | |
| JP | 2001106678 | 4/2001 | | |
| KR | 20130118811 A | 10/2013 | | |
| TW | 201506128 | 2/2015 | | |
| WO | WO2013094951 | 6/2013 | | |

OTHER PUBLICATIONS

European Search Report dated Oct. 5, 2020 in EP Patent Application No. 20166566.8, pp. 1-6.
Liao, Y.L., et al., "A Novel Ambipolar Spirobifluorene Derivative that Behaves as an Efficient Blue-Light Emitter in Organic Light-Emitting Diodes", In Organic Letters, vol. 9, No. 22, Aug. 15, 2007, pp. 4511-4514.
Office Action dated May 24, 2021 in JP Patent Application No. 2020-079126, pp. 1-6.
Ran, X.Q., et al., "Theoretical Study on Photophysical Properties of Ambipolar Spirobifluorene Derivatives as Efficient Blue-Light-Emitting Materials", In J. Phys. Chem. A, vol. 113, May 23, 2009, pp. 7933-7939.
Saragi, T.P.I., et al., "Spiro Compounds for Organic Optoelectronics", In Chem. Rev., vol. 107, Mar. 24, 2007, pp. 1011-1065.
Office Action dated Nov. 13, 2019 in CN Patent Application No. 201910631205.2.

* cited by examiner

*Primary Examiner* — Laura L Stockton
(74) *Attorney, Agent, or Firm* — Byrne Poh LLP; Nina R. Horan

(57) ABSTRACT

The present disclosure discloses an amine derivative and an organic electroluminescent device thereof, and relates to a technical field of organic photoelectric materials. The technical problem to be solved by the present disclosure is that the current light extraction material has poor thermal stability and the organic electroluminescent device has short service life. The amine derivative of the present disclosure is a diamine with a bridging group containing a fluorenyl group or a spirofluorenyl group, and the substituent group on N contains at least one benzoxazolyl group, benzothiazolyl group or benzimidazolyl group. The organic electroluminescent device of the present disclosure comprises an anode, an organic layer, a cathode and a light extraction layer, the organic layer is located between the anode and the cathode, and the light extraction layer comprises the amine derivative of Formula I according to the present disclosure.

7 Claims, 20 Drawing Sheets

AMINE DERIVATIVE AND AN ORGANIC ELECTROLUMINESCENT DEVICE THEREOF

CROSS-REFERENCE TO RELATED APPLICATIONS

The application claims the benefit of the earlier filing date of Chinese Patent Application No. 201910631205.2 filed on Jul. 12, 2019 to the China National Intellectual Property Administration, the contents of which are incorporated by reference herein in its entirety.

TECHNICAL FIELD

The present disclosure relates to the technical field of organic photoelectric materials, in particular to an amine derivative and an organic electroluminescent device thereof.

BACKGROUND

Organic electroluminescence represents a phenomenon that an organic material emits light under the excitation of a current or an electric field. Due to its importance in applications, the research and exploration of electroluminescence has always been a science of great interest. Electroluminescence has been hailed as a phenomenon that can produce "cold light". Depending on the use of varied organic electroluminescent materials, a device made of a small organic molecule as a light-emitting material is called an organic light-emitting device, which is abbreviated as an OLED; and a device made of a polymer as an electroluminescent material is called a polymer light-emitting device, which is abbreviated as a PLED. However, these two are generally referred to as organic electroluminescent devices, also abbreviated as OLED.

Compared with the earlier developed inorganic electroluminescence, organic electroluminescence has many advantages such as a wide selection range of materials, capability of achieving full color display from blue light to red light regions, low driving voltage, high luminance and luminous efficiency, wide viewing angle, fast response speed, relatively simple production process, low cost, and flexible display, and the like. The organic electroluminescent device is generally considered to be the mainstream of the next generation of display device.

An Organic electroluminescent device mostly uses a sandwich structure, that is, an organic functional layer is sandwiched between an anode and a cathode on both sides of the device, which usually use a metal or metal oxide having a higher work function as an anode, and a metal having a lower work function as a cathode. After a certain voltage is applied across the device, holes and electrons generated from the anode and the cathode move towards the other side along the HOMO level and the LUMO level of the material, respectively. When the two meet at the light emitting layer, tightly bound hole-electron pairs, i.e., excitons, are formed. Since the excitons are not stable, they will jump to a lower energy level and return to a stable state. During the transition, a part of the energy will be converted to heat energy and dissipated, while the other part of the energy will be emitted as light energy.

According to the number of organic functional layers in the organic electroluminescent device, the structure of the device can be roughly classified into four types: a single-layer, a double-layer, a three-layer, and a multi-layer. According to the different paths of light emission, the device is further divided into two types: a top emitting device and a bottom emitting device. Organic electroluminescence has evolved from the original single-layer device to various complex device structures, and the luminescent properties have also made a qualitative leap.

Light from the bottom emitting device propagates from the anode through the substrate to the outside of the device, and light from the top emitting device propagates through the cathode to the outside of the device. Regardless of whether it is a bottom emitting device or a top emitting device, it is required to have high transmittance and good carrier injection characteristics for the electrode on the light emitting side. The bottom emitting device emits light from the anode, and ITO with excellent transmittance is generally used as the anode material. Light from the top emitting device propagates through the cathode, and it is required for the cathode to have a high transmittance, and its work function is required to satisfy the electron injection characteristic. Currently, the cathode material commonly used is a metal composite film, which is generally consisting of a less absorbed metal such as Ag, etc., matching with a metal having a lower work function such as Mg, and Al, etc.

The concept of the top emitting device has been developed rapidly in terms of both theory and technology since it was put forward, and the top emitting device has rapidly entered the commercial market with its wide color gamut and high brightness. Due to the presence of the composite metal cathode, the top emitting device is affected by the plasma loss and the waveguide mode, and its external photocoupling efficiency is greatly lost. The usual improvement method is to deposit a light extraction layer on the surface of the cathode to further improve the luminous efficiency of the device, however, the thermal stability of the light extraction material currently used is mostly poor, resulting in a short service life of the device. Therefore, how to improve the thermal stability of the light extraction material to obtain an organic electroluminescent device with a longer lifetime has become one of the concerns that researchers focus on currently.

SUMMARY

In order to solve the problem that the current light extraction material has poor thermal stability and a short service life of the organic electroluminescent device, the present disclosure provides an amine derivative and an organic electroluminescent device thereof.

The present disclosure can achieve the above objects by using an amine derivative represented by Formula I below as the light extraction material of the organic electroluminescent device, thereby completing the present disclosure.

The present disclosure provides an amine derivative, which is represented by Formula I,

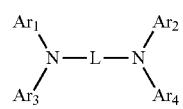

I wherein $Ar_1$ and $Ar_2$ are independently selected from the group consisting of a substituted or unsubstituted C6-C30 aryl group, a substituted or unsubstituted C3-C30 heteroaryl group, and at least one of $Ar_1$ and $Ar_2$ are selected from a group as shown in Formula II,

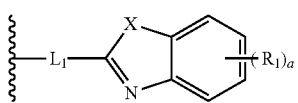

L₁ is selected from the group consisting of a single bond, a substituted or unsubstituted C6-C18 arylene group, a substituted or unsubstituted C3-C18 heteroarylene group; a is selected from an integer of 0 to 4, and $R_1$ is selected from the group consisting of a substituted or unsubstituted C1-C15 alkyl group, a substituted or unsubstituted C6-C18 aryl group, and when a is greater than 1, each $R_1$ is the same or different, X is selected from O, S or N ($R_x$), and $R_x$ is selected from the group consisting of a substituted or unsubstituted C1-C15 alkyl group, a substituted or unsubstituted C6-C18 aryl group;

$Ar_3$ and $Ar_4$ are independently selected from the group consisting of a substituted or unsubstituted C6-C30 aryl group, and a substituted or unsubstituted C3-C30 heteroaryl group;

L is selected from the group consisting of the groups as shown below,

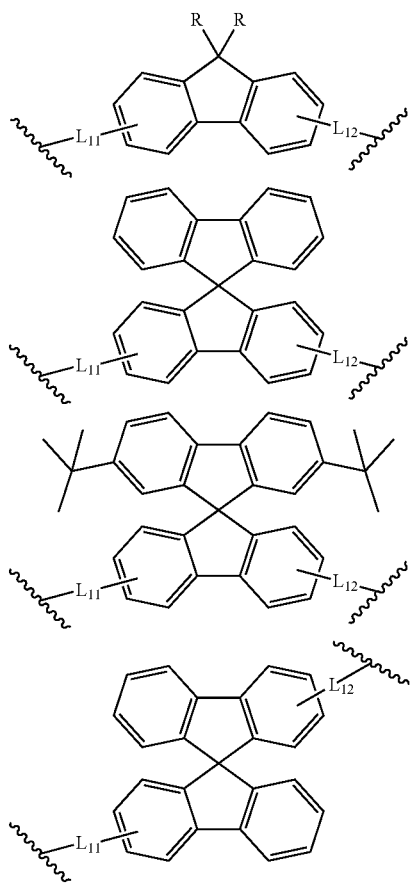

R is selected from the group consisting of hydrogen, a substituted or unsubstituted C1-C15 alkyl group, a substituted or unsubstituted C6-C18 aryl group, and a substituted or unsubstituted C3-C18 heteroaryl group;

$L_{11}$ and $L_{12}$ are independently selected from the group consisting of a single bond, a substituted or unsubstituted C6-C18 arylene group, and a substituted or unsubstituted C3-C18 heteroarylene group.

In addition, the present disclosure further provides an organic electroluminescent device comprising an anode, an organic layer, a cathode and a light extraction layer, the organic layer being located between the anode and the cathode, the organic layer comprising a hole transport layer, a light emitting layer, and an electron transport layer, with the hole transport layer being located between the anode and the light emitting layer, and the electron transport layer being located between the light emitting layer and the cathode, the light extraction layer being located on a side of the cathode away from the anode, and the light extraction layer contains the above-described amine derivative as shown in Formula I according to the present disclosure.

Beneficial effects: The amine derivative of the present disclosure has a high glass transition temperature and good thermal stability. Therefore, the amine derivative of the present disclosure is a more stable optical material, and when it is used as a light extraction material of an organic electroluminescent device, the organic electroluminescent device exhibits a longer service life.

In addition, the amine derivative of the present disclosure has a high refractive index to light, and when it is used as a light extraction layer of an organic electroluminescent device, it can reduce surface plasma loss and adverse effects caused by the waveguide mode, and increase the output efficiency of photocoupling, so that the luminous efficiency of the organic electroluminescent device is effectively improved.

DETAILED DESCRIPTION

Figure 1:
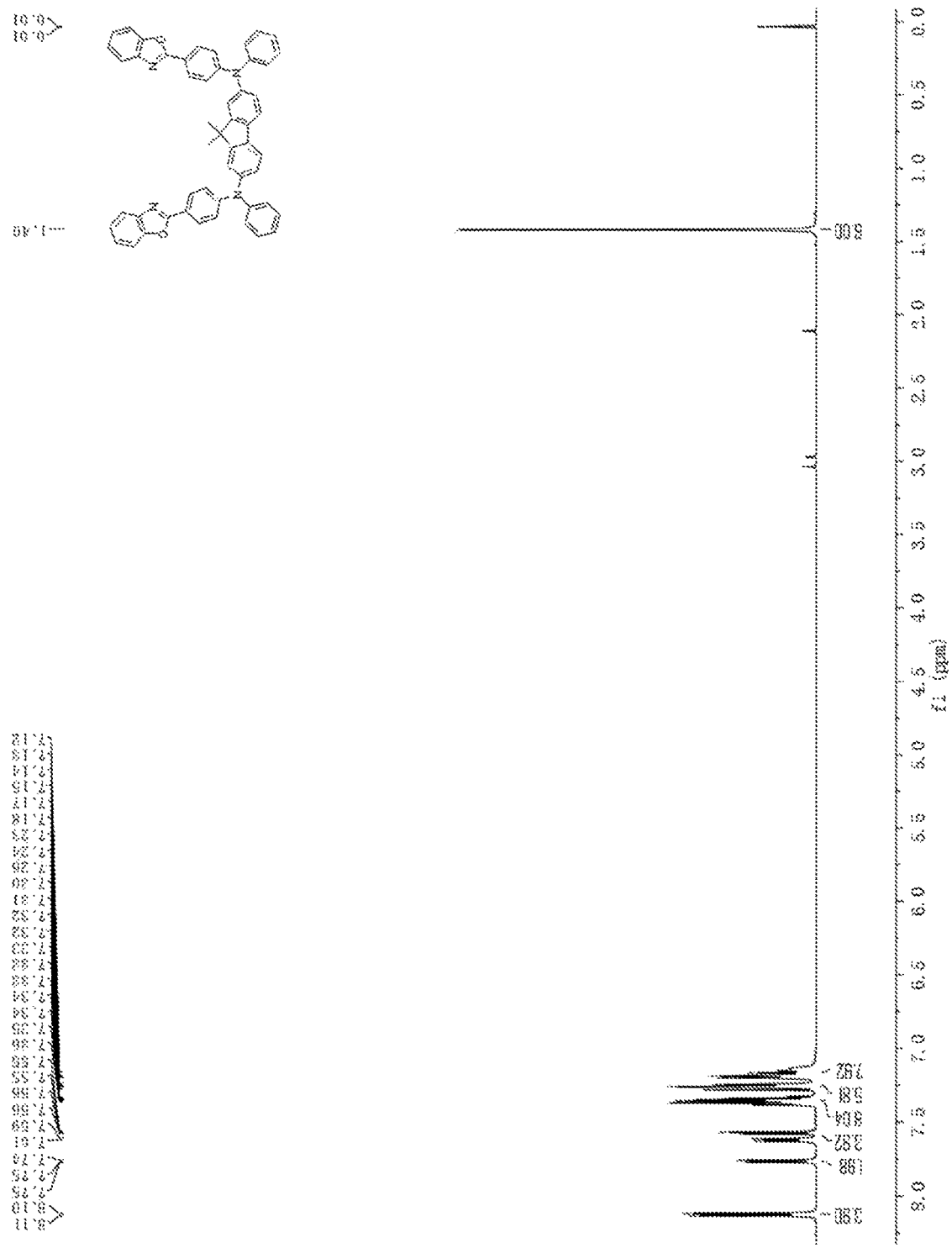
FIG. 1 is a ¹H NMR spectrum of the compound 1 of the present disclosure.
Figure 2:
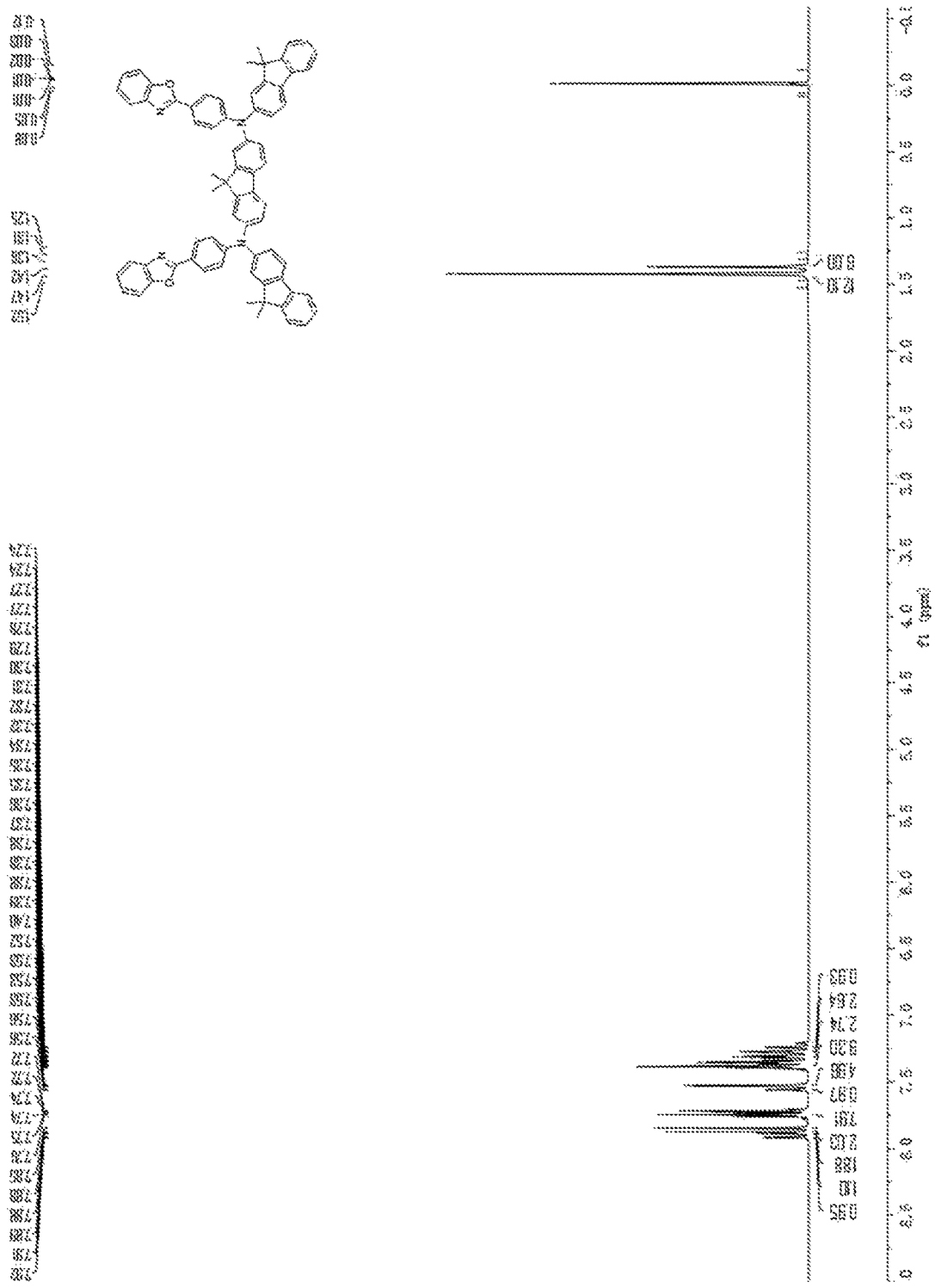
FIG. 2 is a ¹H NMR spectrum of the compound 22 of the present disclosure.
Figure 3:
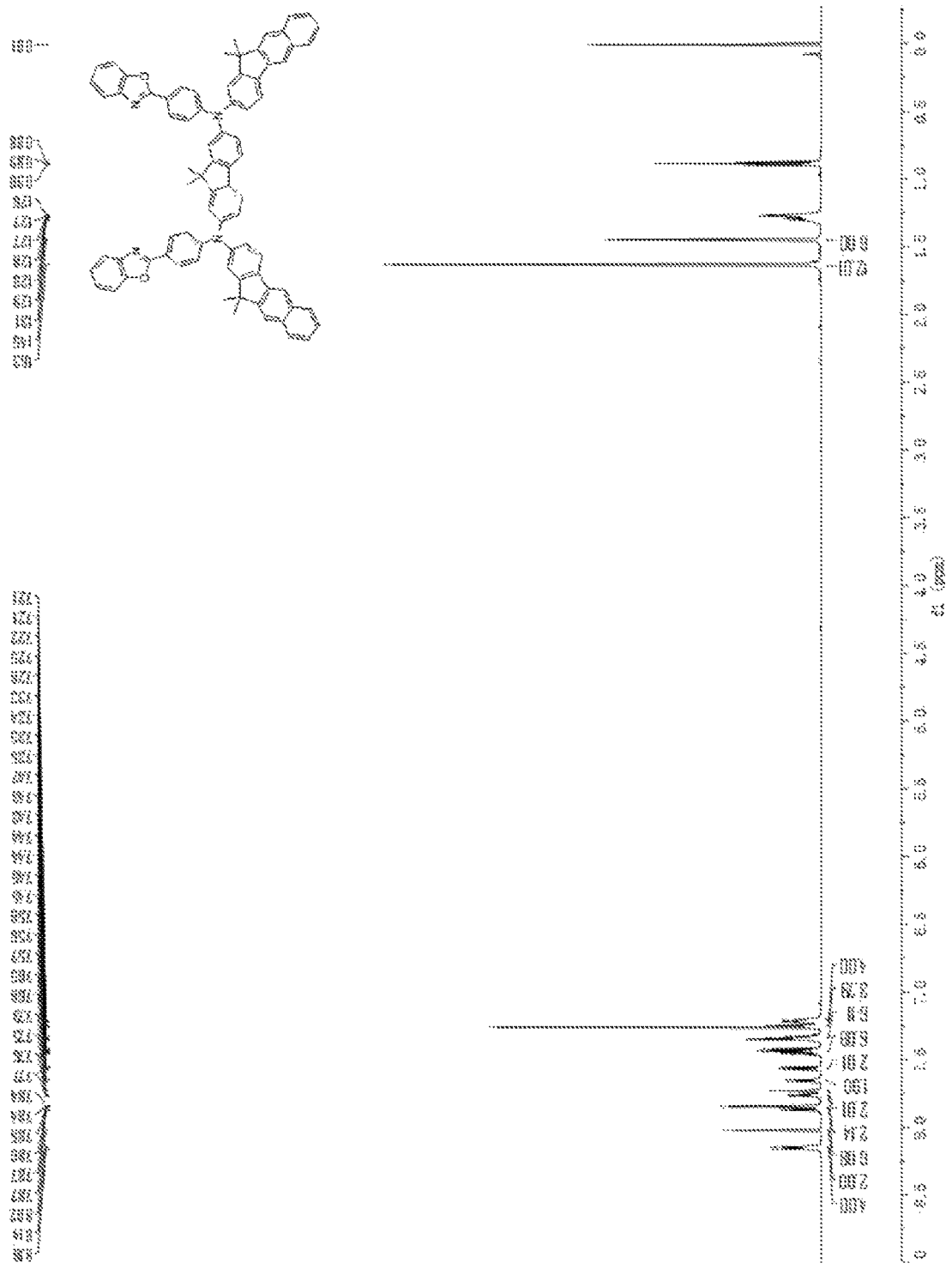
FIG. 3 is a ¹H NMR spectrum of the compound 26 of the present disclosure.
Figure 4:
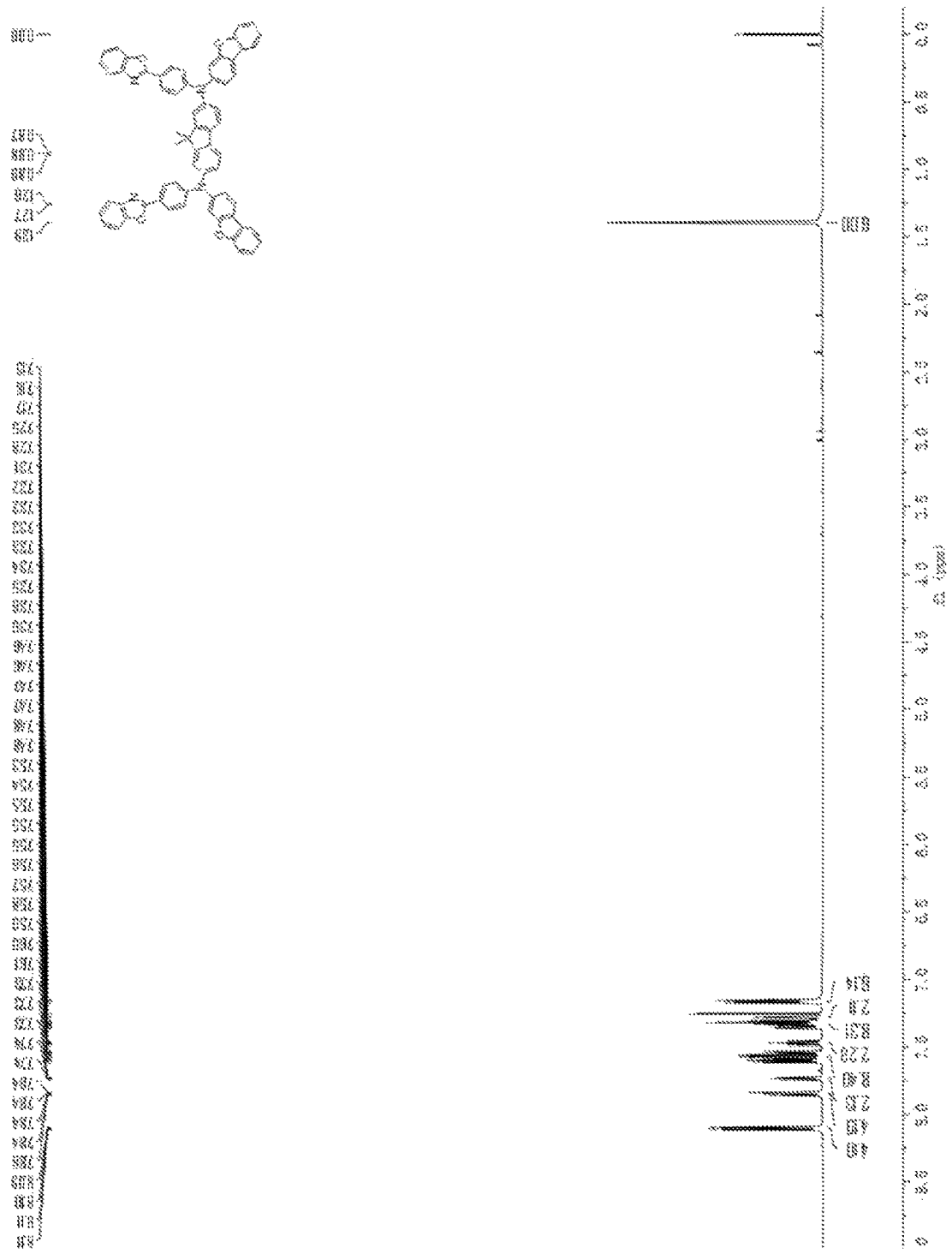
FIG. 4 is a ¹H NMR spectrum of the compound 35 of the present disclosure.
Figure 5:
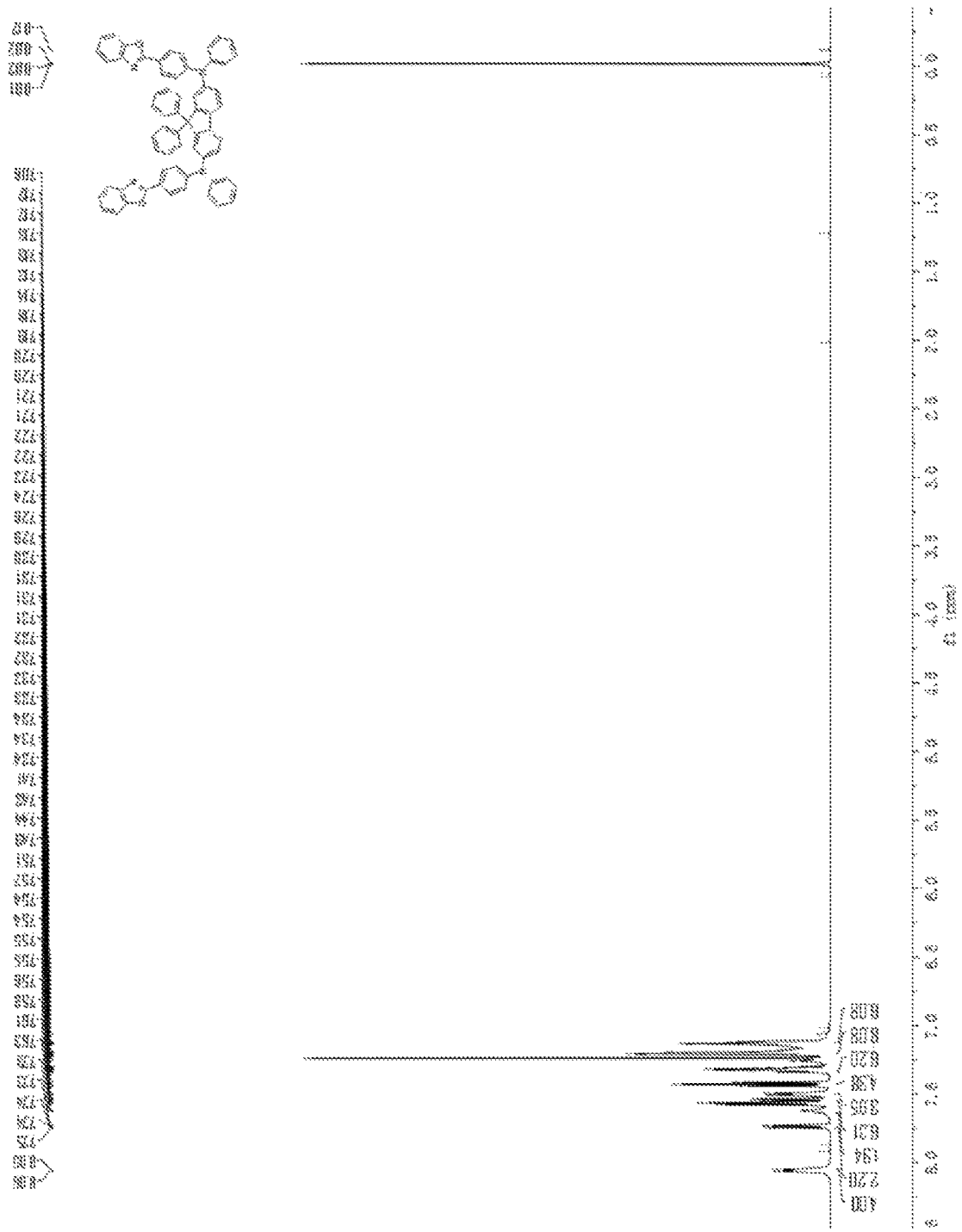
FIG. 5 is a ¹H NMR spectrum of the compound 41 of the present disclosure.
Figure 6:
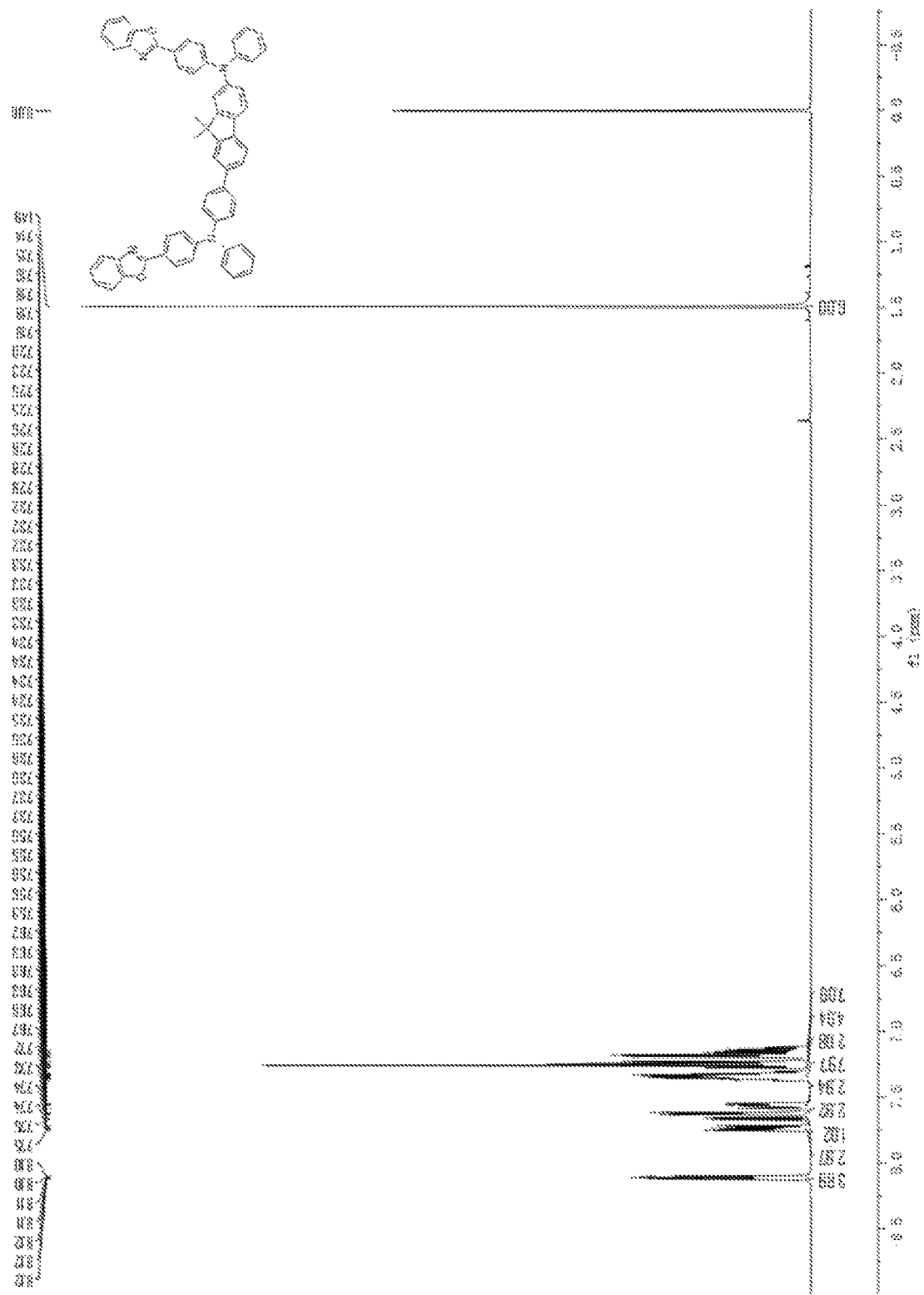
FIG. 6 is a ¹H NMR spectrum of the compound 73 of the present disclosure.
Figure 7:
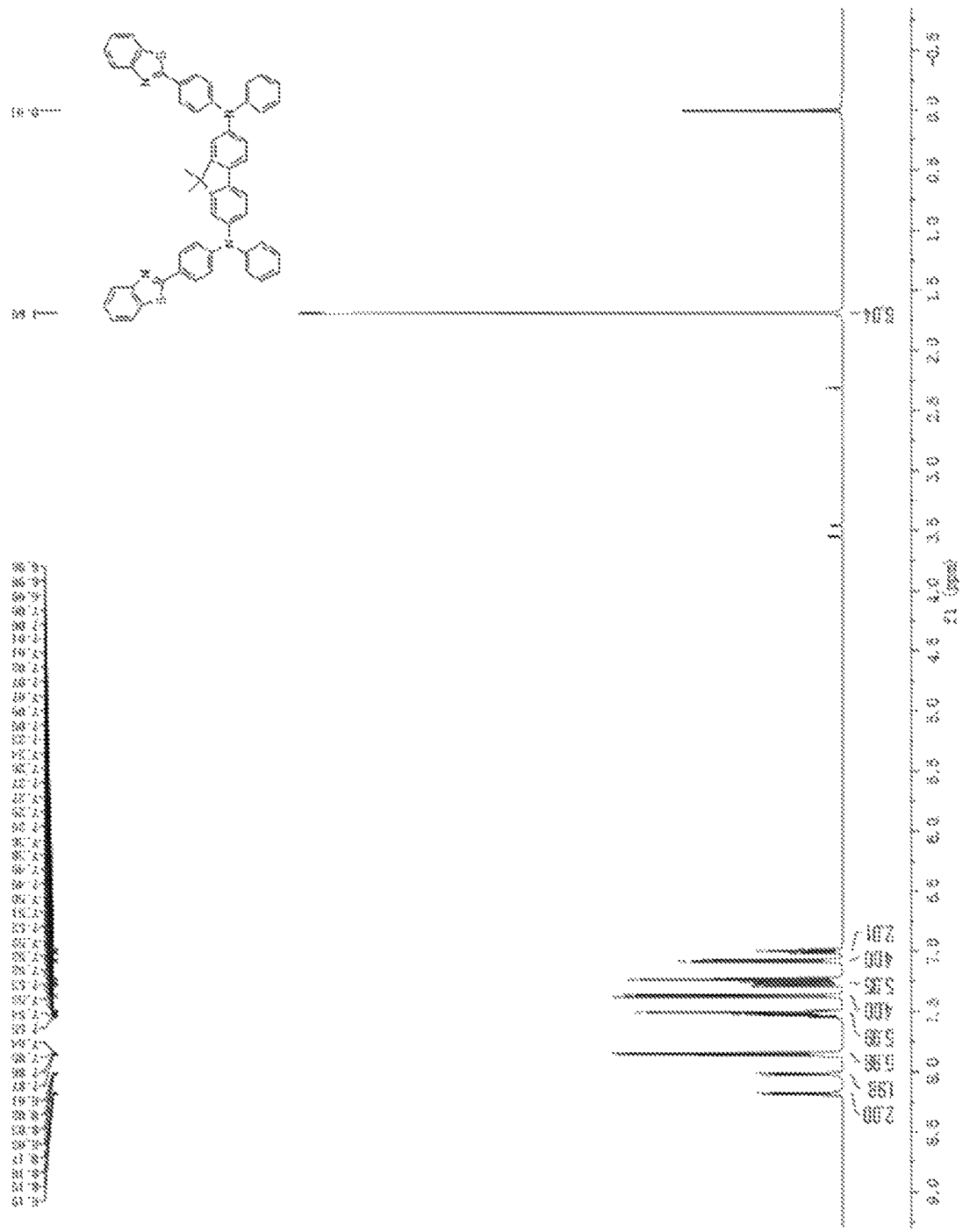
FIG. 7 is a ¹H NMR spectrum of the compound 101 of the present disclosure.
Figure 8:
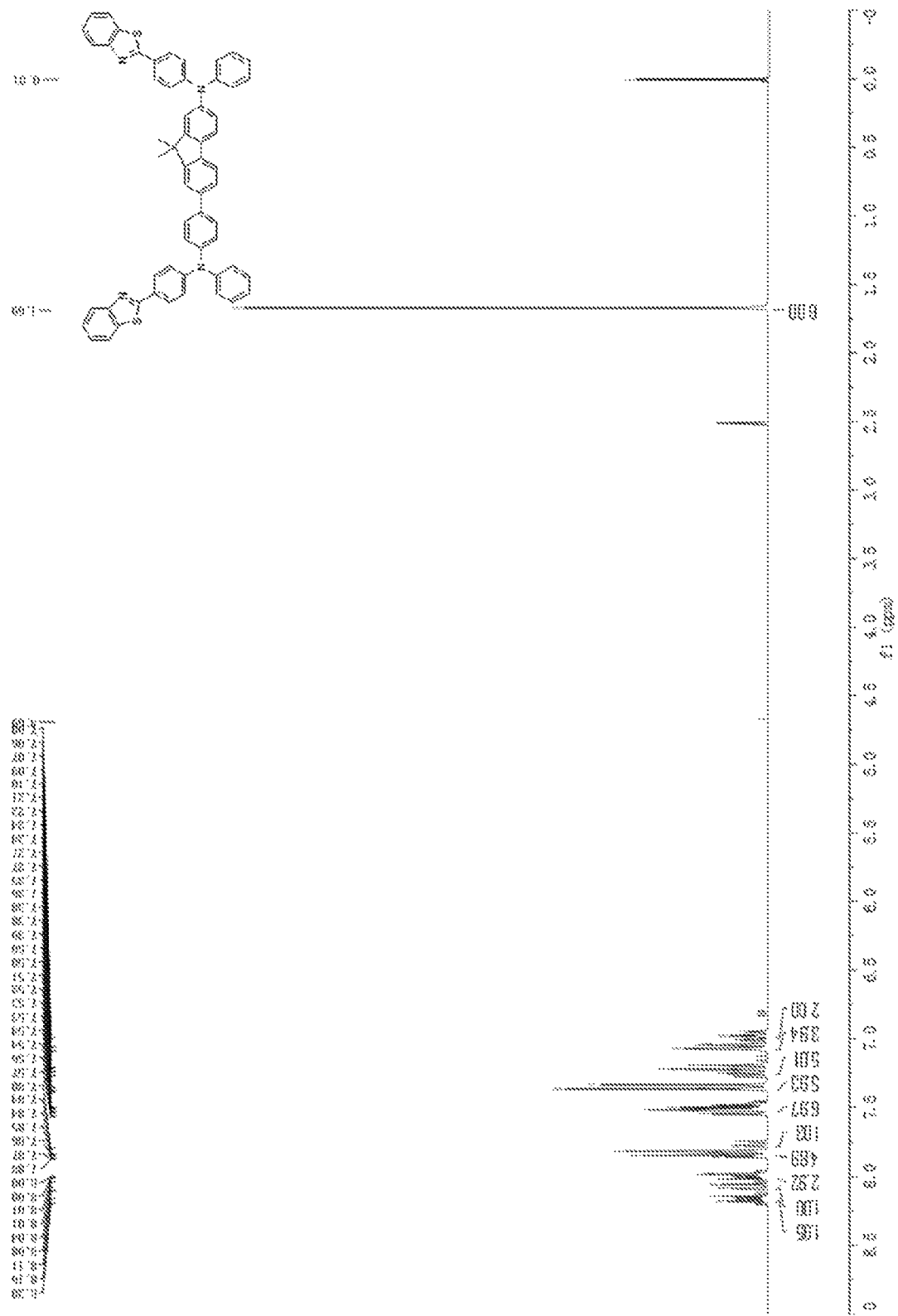
FIG. 8 is a ¹H NMR spectrum of the compound 121 of the present disclosure.
Figure 9:
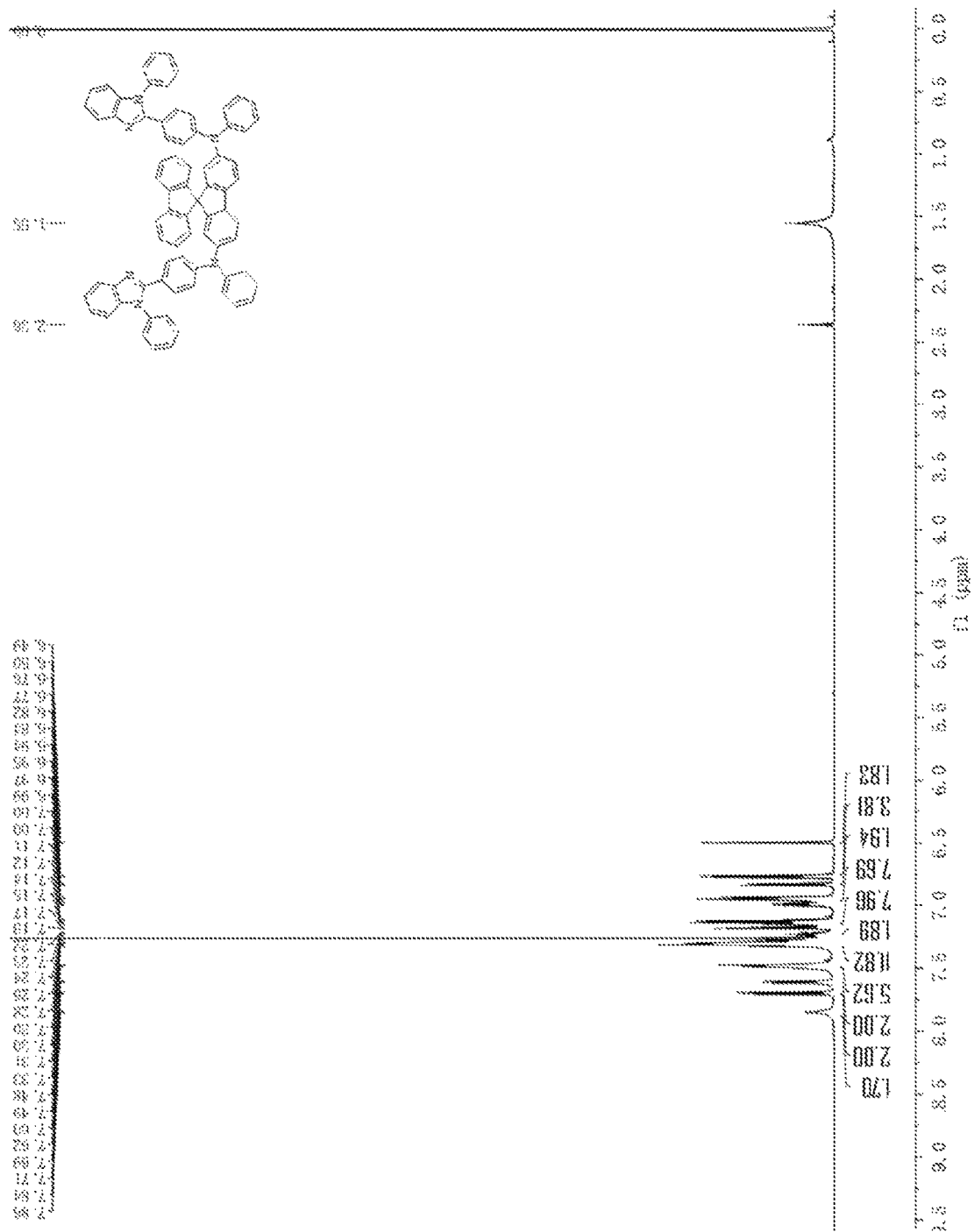
FIG. 9 is a ¹H NMR spectrum of the compound 143 of the present disclosure.
Figure 10:
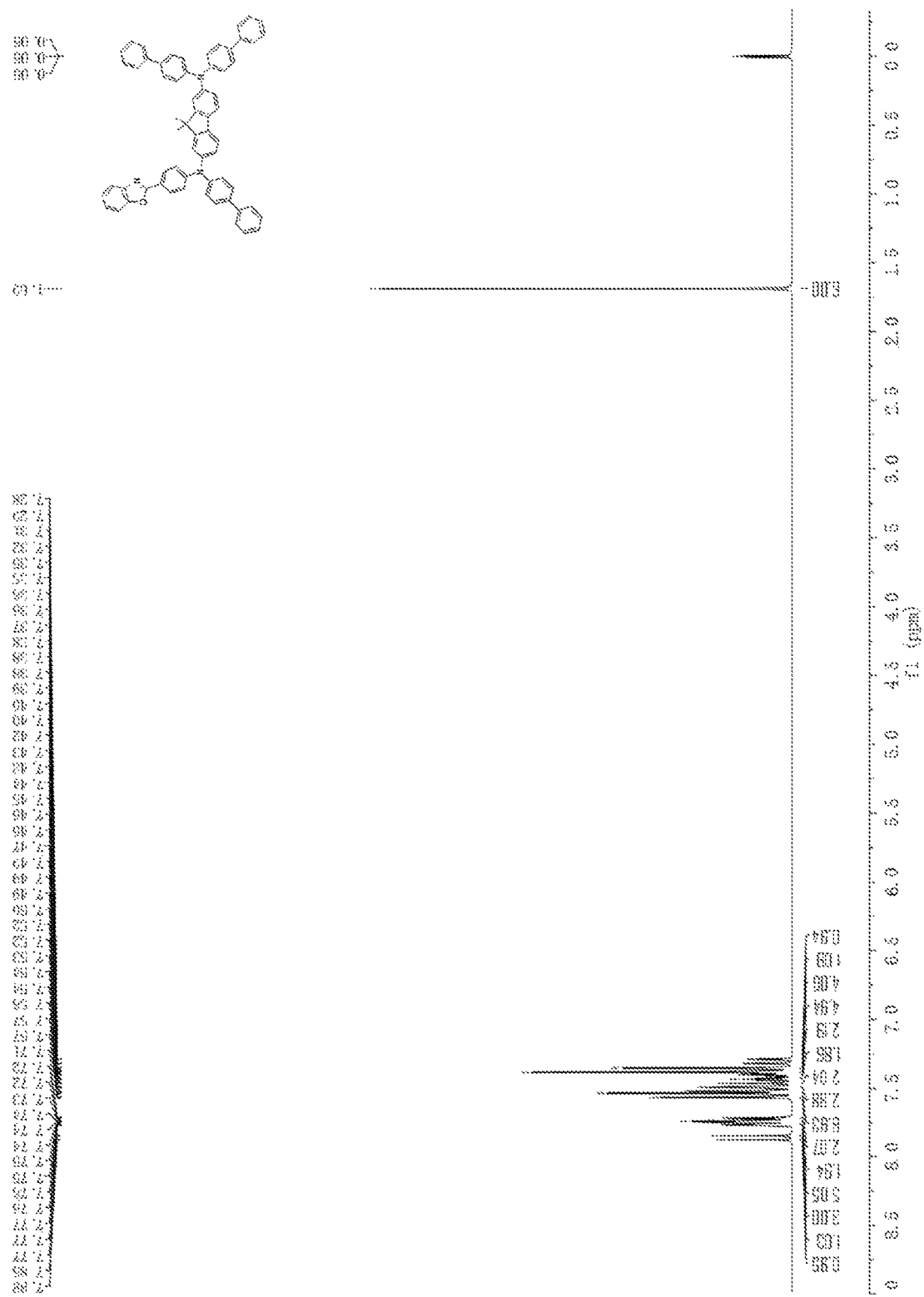
FIG. 10 is a ¹H NMR spectrum of the compound 146 of the present disclosure.
Figure 11:
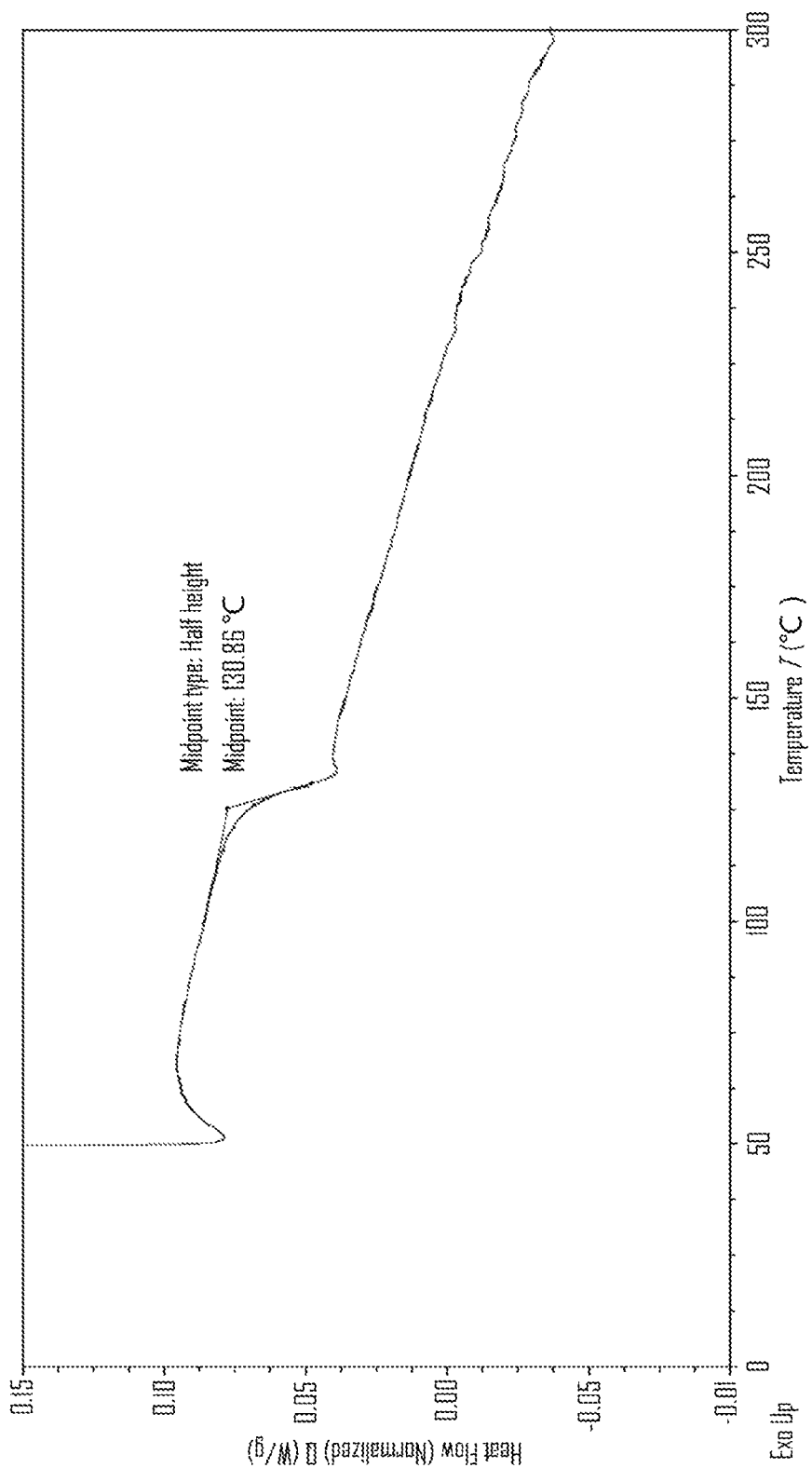
FIG. 11 is a DSC graph of the compound 1 of the present disclosure.
Figure 12:
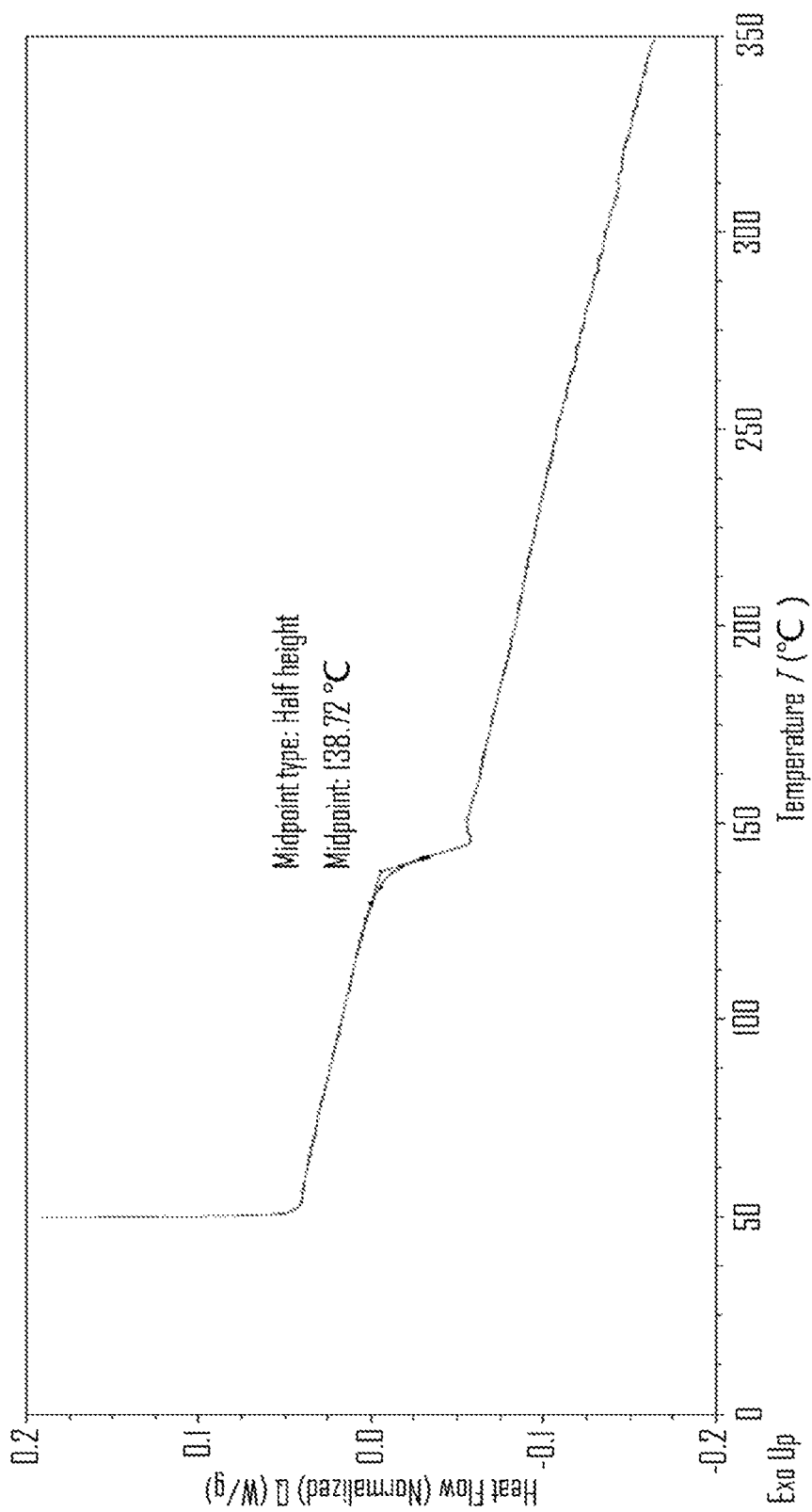
FIG. 12 is a DSC graph of the compound 22 of the present disclosure.
Figure 13:
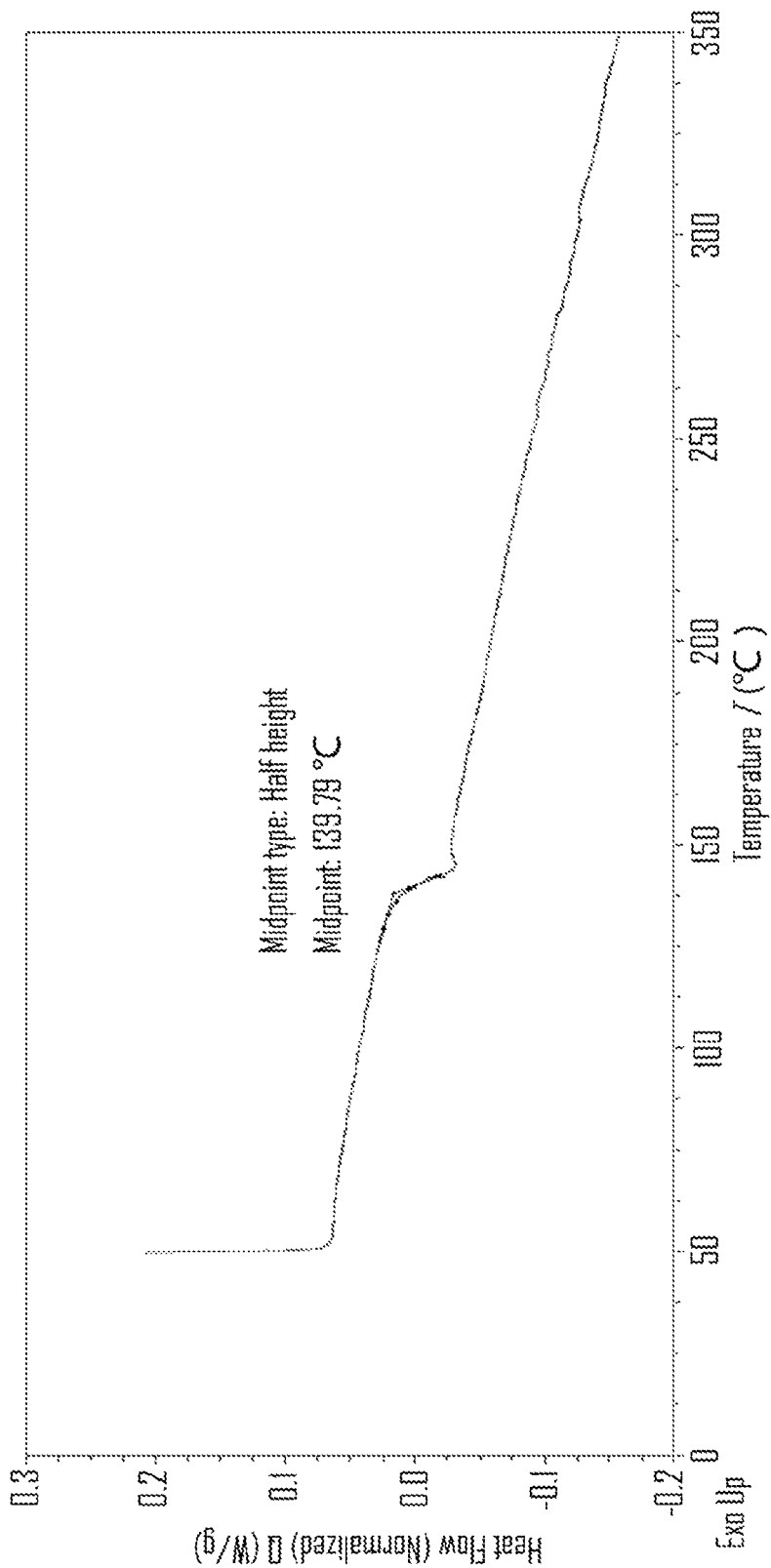
FIG. 13 is a DSC graph of the compound 26 of the present disclosure.
Figure 14:
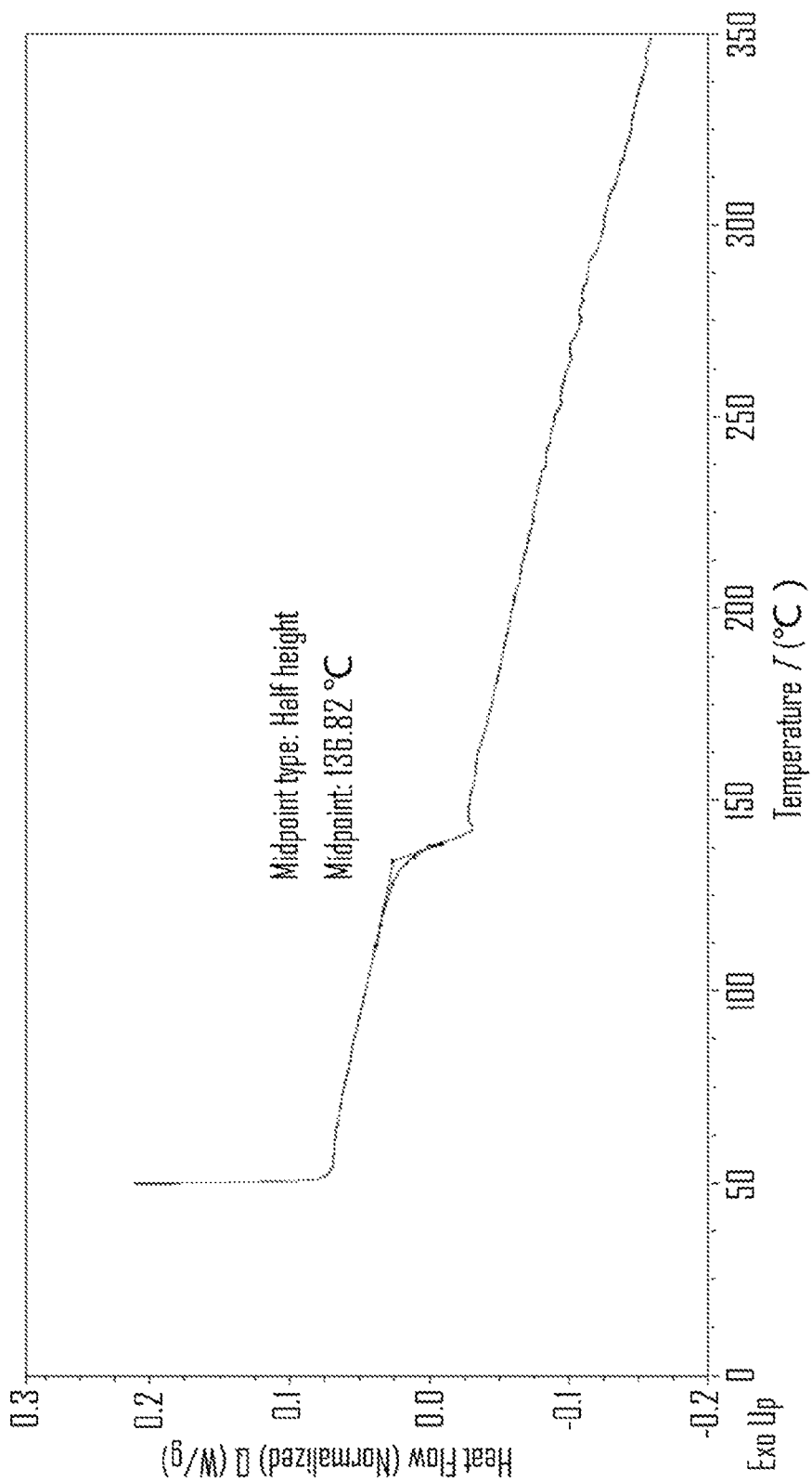
FIG. 14 is a DSC graph of the compound 35 of the present disclosure.
Figure 15:
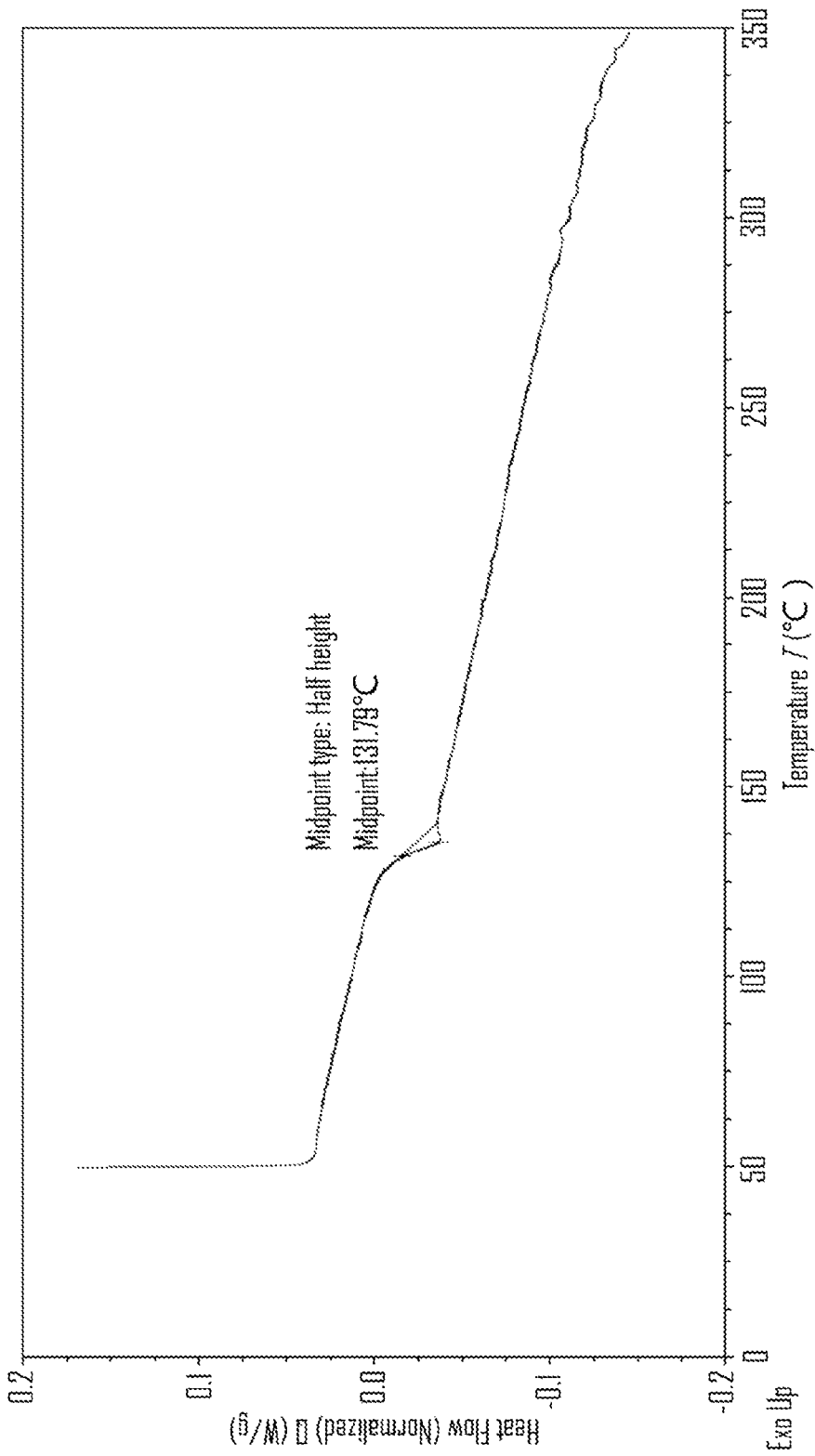
FIG. 15 is a DSC graph of the compound 41 of the present disclosure.
Figure 16:
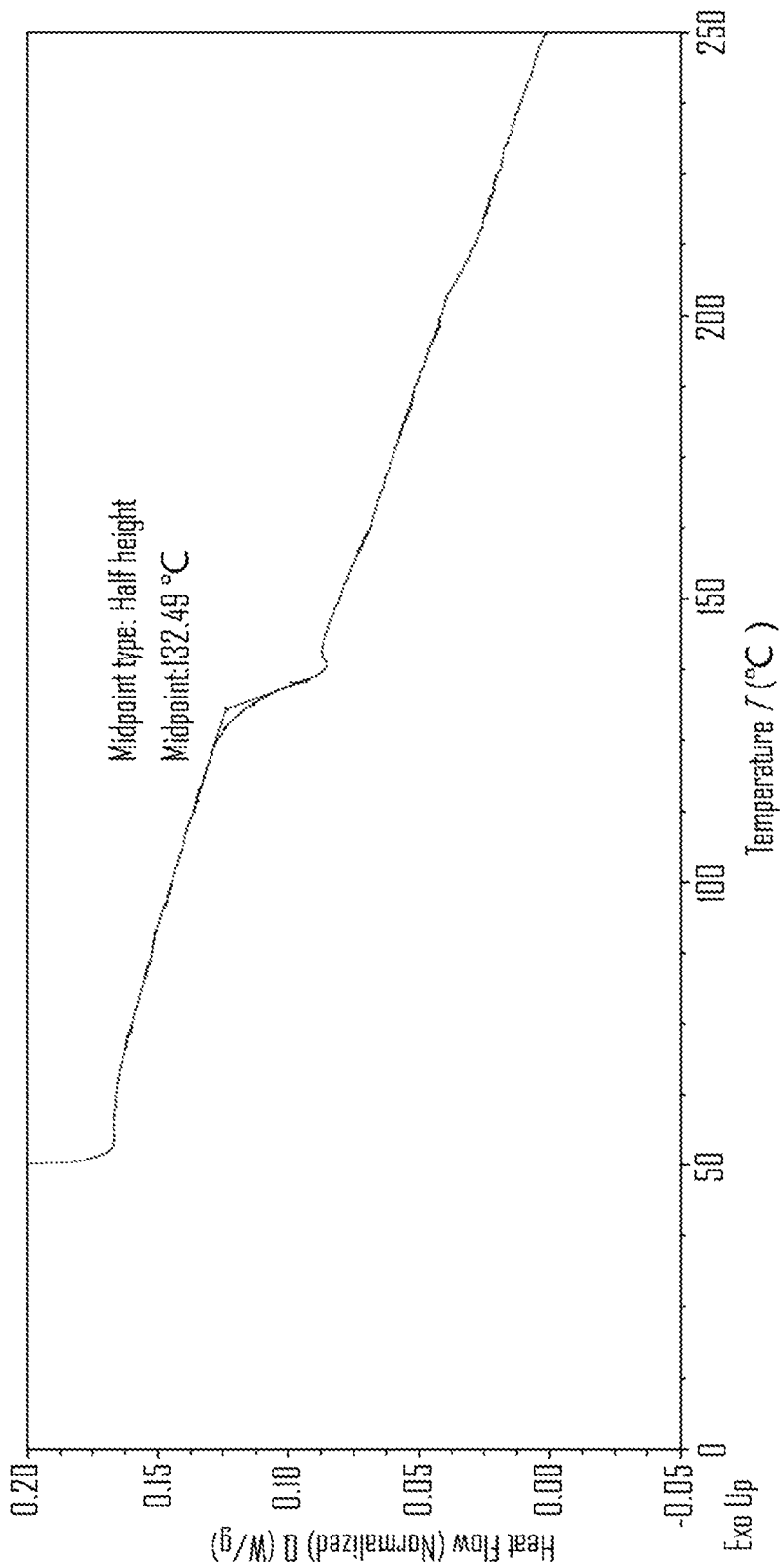
FIG. 16 is a DSC graph of the compound 73 of the present disclosure.
Figure 17:
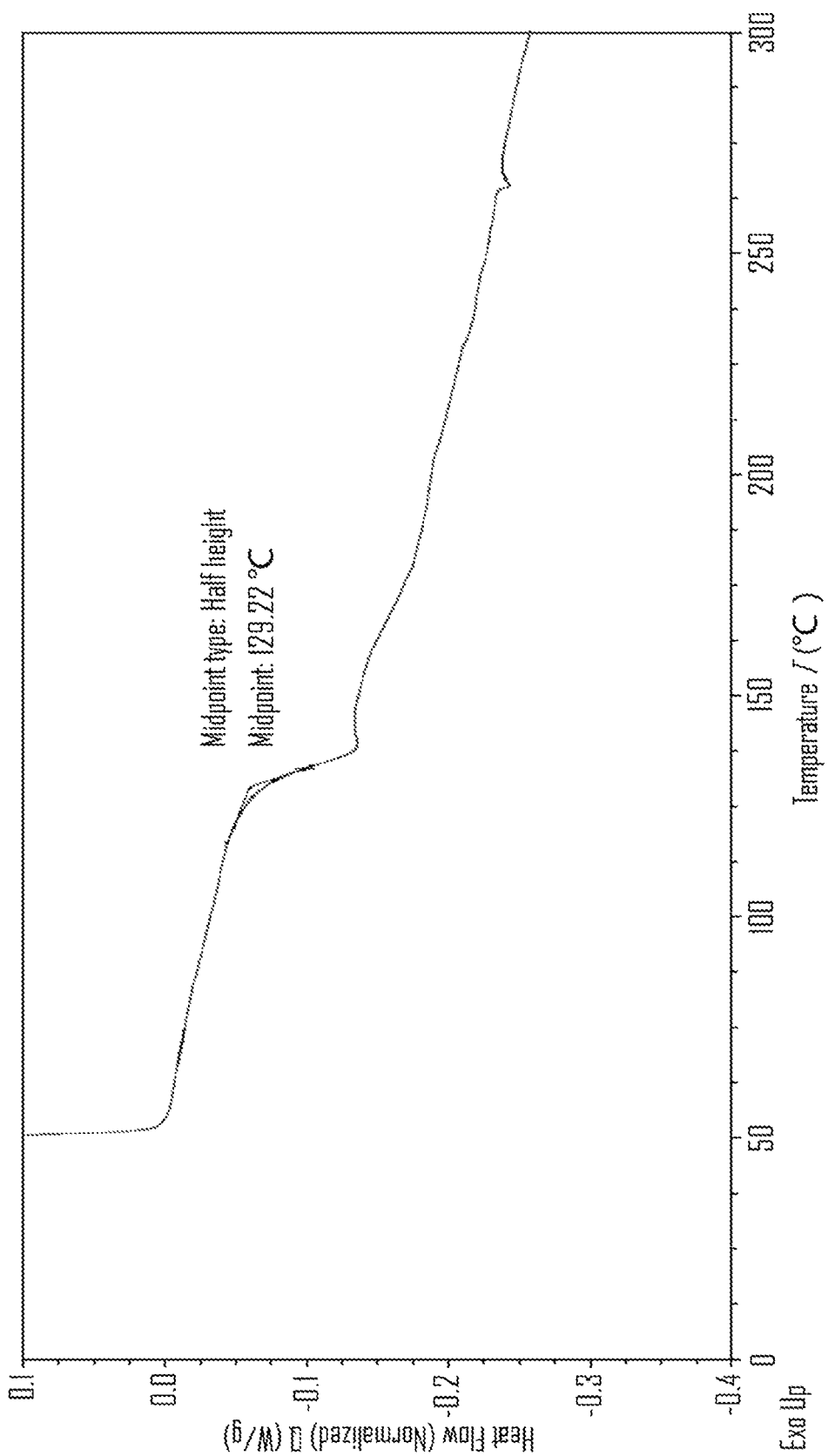
FIG. 17 is a DSC graph of the compound 101 of the present disclosure.
Figure 18:
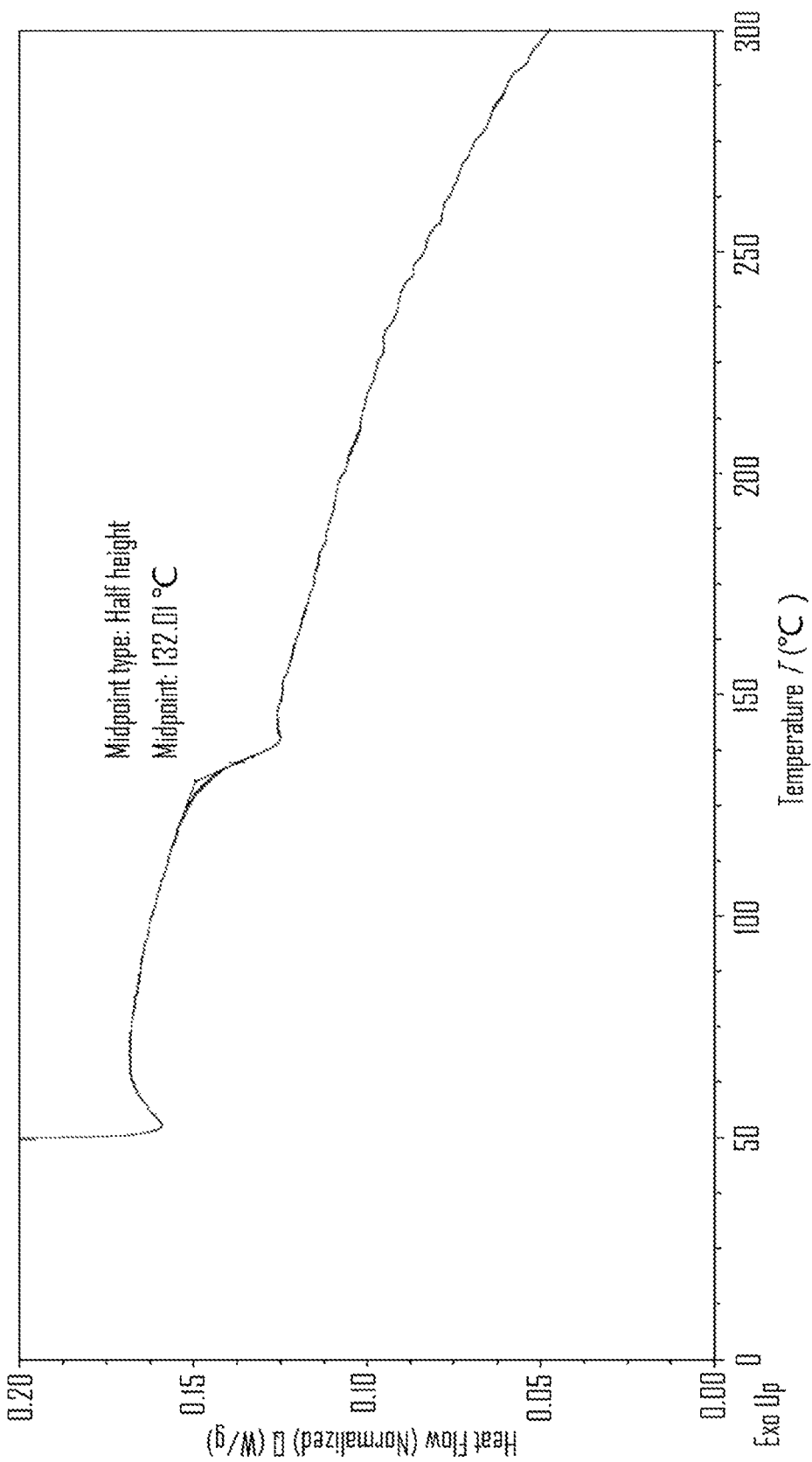
FIG. 18 is a DSC graph of the compound 121 of the present disclosure.
Figure 19:
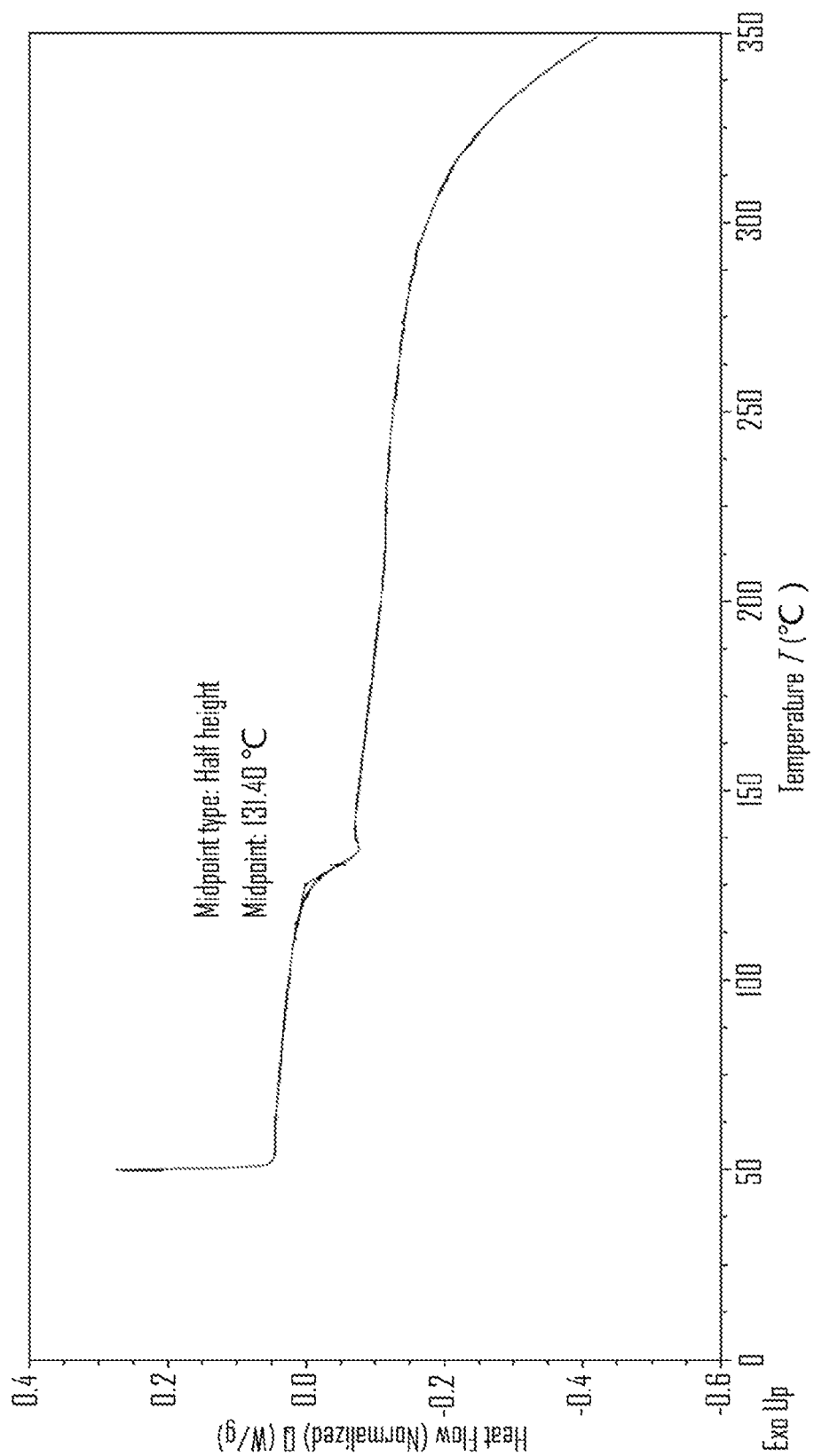
FIG. 19 is a DSC graph of the compound 143 of the present disclosure.
Figure 20:
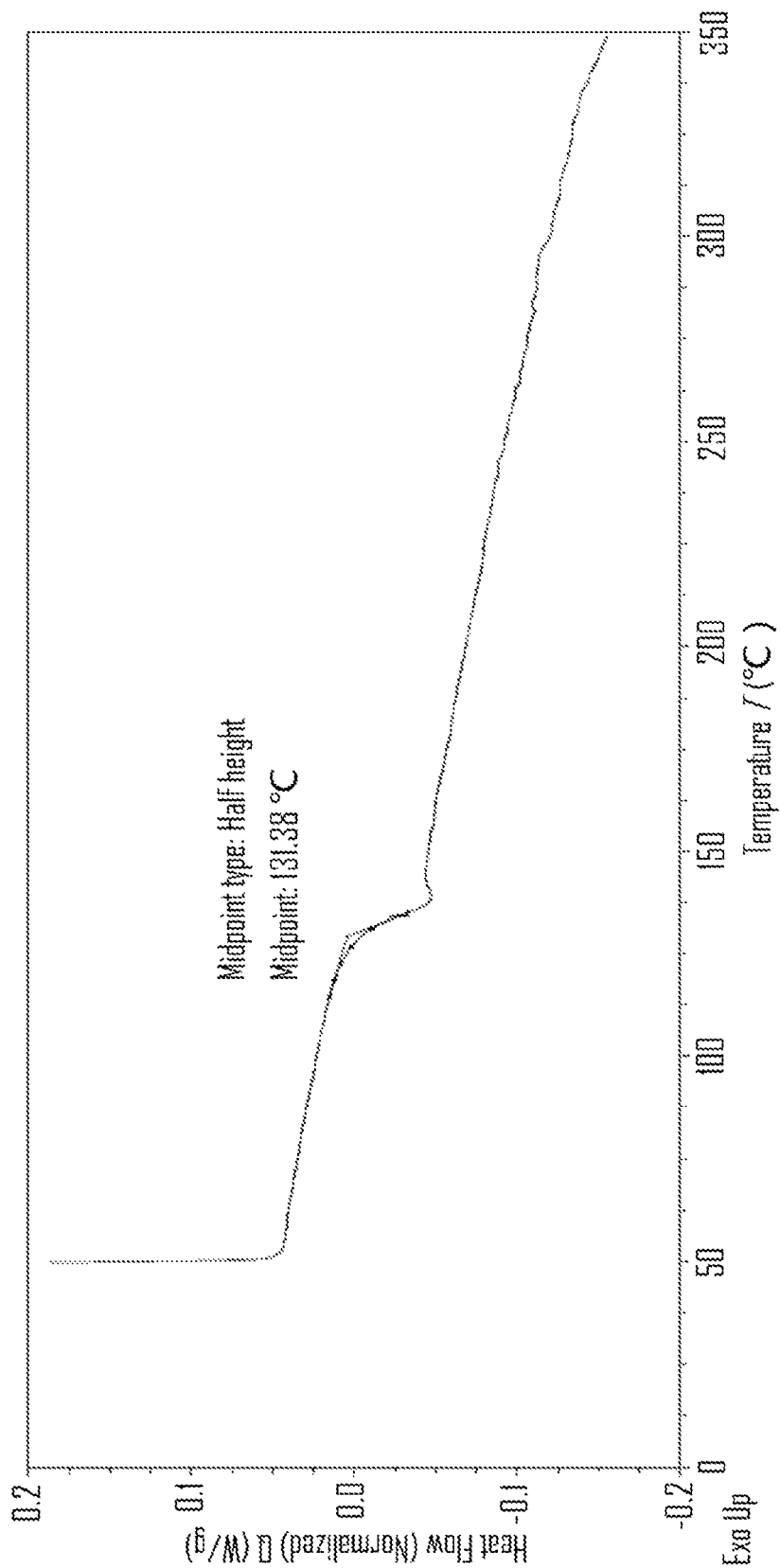
FIG. 20 is a DSC graph of the compound 146 of the present disclosure.

The present disclosure will be further set forth in combination with the following specific examples, which are construed as illustrative of the present disclosure only and not to limit the scope of the present disclosure. Upon reading the present disclosure, various equivalent modifications to the present disclosure by those skilled in the art fall within the claimed protection scope of the present application.

According to the present disclosure, "C6-C30" in the "substituted or unsubstituted C6-C30 aryl group" means the number of carbon atoms contained in the unsubstituted aryl group, and the number of carbon atoms of the substituent is excluded; "C3-C30" in the "substituted or unsubstituted C3-C30 heteroaryl group" means the number of carbon atoms contained in the unsubstituted heteroaryl group, and the number of carbon atoms of the substituent is excluded; "C6-C18" in the "substituted or unsubstituted C6-C18 arylene group" means the number of carbon atoms contained in the unsubstituted arylene group, and the number of carbon atoms of the substituent is excluded; "C3-C18" in the "substituted or unsubstituted C3-C18 heteroarylene group" means the number of carbon atoms contained in the unsubstituted heteroarylene group, and the number of carbon atoms of the substituent is excluded; and "C1-C15" in the "substituted or unsubstituted C1-C15 alkyl group" means the number of carbon atoms contained in the unsubstituted alkyl group, and the number of carbon atoms of the substituent is excluded. The rest can be done in the same manner.

According to the present disclosure, the chain alkyl group having a carbon number of more than two such as a propyl, a butyl or a pentyl includes isomers thereof, such as isopropyl, isobutyl, sec-butyl, tert-butyl, isopentyl, neopentyl, and tert-pentyl, etc., but are not limited thereto.

According to the present disclosure, an alkyl group means a hydrocarbyl group in which one hydrogen atom is missing from an alkane molecule, and it may be a linear alkyl, a branched alkyl or a cycloalkyl. The linear alkyl includes methyl, ethyl, n-propyl, n-butyl, n-pentyl, n-hexyl, n-heptyl, n-octyl, n-nonyl, n-decyl, undecyl, and dodecyl, etc., but is not limited thereto; the branched alkyl includes isopropyl, isobutyl, sec-butyl, tert-butyl, an isomeric group of n-pentyl, an isomeric group of n-hexyl, an isomeric group of n-heptyl, an isomeric group of n-octyl, an isomeric group of n-nonyl group, and an isomeric group of n-decyl, etc., but is not limited thereto; the cycloalkyl group includes cyclopropyl, cyclobutyl, a cyclopentyl, cyclohexyl, etc., but is not limited thereto. The above alkyl is preferably methyl, ethyl, n-propyl, isopropyl, n-butyl, isobutyl, sec-butyl and t-butyl.

According to the present disclosure, the aryl group means a general term for a monovalent group remaining after removing one hydrogen atom from an aromatic nucleus carbon of an aromatic compound molecule, which may be a monocyclic aryl, a polycyclic aryl or a fused ring aryl. The monocyclic aryl means an aryl having only one aromatic ring in the molecule, for example, a phenyl, etc., but is not limited thereto; the polycyclic aryl means an aryl having two or more independent aromatic rings in the molecule, for example, a biphenyl, a terphenyl, etc., but is not limited thereto; the fused ring aryl means an aryl having two or more aromatic rings and fused to each other by sharing two adjacent carbon atoms in the molecule, for example, a naphthyl, an anthracenyl, a phenanthryl, a fluorenyl, a benzofluorenyl, a pyrenyl, a triphenylene, a fluoranthenyl, a spirobifluorenyl, etc., but is not limited thereto. The above aryl is preferably a phenyl, a biphenyl, a terphenyl, a naphthyl, a phenanthryl, a fluorenyl, a benzofluorenyl, a triphenylene or a spirobifluorenyl.

According to the present disclosure, the heteroaryl means a general term for a group obtained by substituting one or more aromatic nucleus carbon atoms in an aryl group with a heteroatom, the heteroatom includes but is not limited to oxygen, sulfur, nitrogen or phosphorus atoms. The linkage site of the heteroaryl may be located on a ring-forming carbon atom or on a ring-forming nitrogen atom, and the heteroaryl group may be a monocyclic heteroaryl, a polycyclic heteroaryl or a fused ring heteroaryl. The monocyclic heteroaryl group includes a pyridyl, a pyrimidinyl, a triazinyl, a furyl, a thienyl, a pyrrolyl, and an imidazolyl, etc., but is not limited thereto; the polycyclic heteroaryl includes a bipyridyl, a bipyrimidinyl, and a phenylpyridinyl, etc., but is not limited thereto; the fused ring heteroaryl includes a quinolyl, an isoquinolyl, an indolyl, a phenanthrolinyl, a dibenzofuranyl, a benzodibenzofuranyl a dibenzothiophenyl, a benzodibenzothienyl, a carbazolyl, a benzocarbazolyl, an acridinyl, a 9,10-dihydroacridinyl, a phenoxazinyl, an oxanthracene group, a thianthracene group, etc., but is not limited thereto. The above heteroaryl is preferably a furyl, a thienyl, a dibenzofuranyl, a benzodibenzofuranyl a dibenzothiophenyl, a benzodibenzothienyl, a carbazolyl, a benzocarbazolyl, an acridinyl, a 9,10-dihydroacridinyl, a phenoxazinyl, an oxanthracene group, a thianthracene group, etc.

According to the present disclosure, the arylene group means a general term for a bivalent group remaining after removing two hydrogen atoms from an aromatic nucleus carbon of a substituted or unsubstituted aromatic compound molecule, which may be a monocyclic arylene group, a polycyclic arylene group or a fused ring arylene group. The monocyclic arylene group includes a phenylene group, etc., but is not limited thereto; the polycyclic arylene group includes a biphenylene group, a terphenylylene group, etc., but is not limited thereto; the fused ring arylene group includes a naphthylene group, an anthranylene group, a phenanthrylene group, a fluorenylidene group, a pyrenylene group, a terphenylenylidene group, a fluoranthenylidene group, and a phenylenefluorenyl group, etc., but is not limited thereto. The above arylene group is preferably a phenylene group, a biphenylylene group, a terphenylylene group, a naphthylene group, a fluorenylidene group or a phenylenefluorenyl group.

According to the present disclosure, the heteroarylene group means a general term for a group obtained by substituting one or more aromatic nucleus carbon atoms in an arylene group with a heteroatom, the heteroatom includes but is not limited to oxygen, sulfur, nitrogen or phosphorus atoms. The heteroarylene group may be a monocyclic heteroarylene group, a polycyclic heteroarylene group or a fused ring heteroarylene group. The monocyclic heteroarylene group includes a pyridylene group, a pyrimidinylene group, a furylene group, a thienylene group, etc., but is not limited thereto; the polycyclic heteroarylene group includes a bipyridylene group, a bipyrimidylene group, a phenylene pyridyl group, etc., but is not limited thereto; the fused ring heteroarylene includes a quinolinylene group, an isoquinolinylene group, a phenanthrolinylene group, a dibenzofuranylene group, a dibenzothiophenylene group, a carbazolylene group, etc., but is not limited thereto The above heteroarylene group is preferably a phenanthrolinylene group, a dibenzofuranylene group or a dibenzothiophenylene group.

According to the present disclosure, the substituted alkyl group means a general term for a group in which a hydrogen on an alkyl group is replaced by a substituent group, and the substituent group may be one or more, and when there are more than one substituent groups, they may be the same or different, and the substituent group includes deuterium, a halogen, a cyano, a nitro, a hydroxyl, a carbonyl, a substituted or unsubstituted C6-C30 aryl, a substituted or unsubstituted C3-C30 heteroaryl, with the aryl, and heteroaryl being as defined above.

According to the present disclosure, the substituted aryl group means a general term for a group in which a hydrogen on an aryl group is replaced by a substituent group, and the substituent group may be one or more, and when there are more than one substituent groups, they may be the same or different, and the substituent group includes deuterium, a halogen, a cyano, a nitro, a hydroxyl, a carbonyl, a substituted or unsubstituted C1-C15 alkyl, a substituted or unsubstituted C6-C30 aryl, a substituted or unsubstituted C3-C30 heteroaryl, with the alkyl, aryl, and heteroaryl being as defined above.

According to the present disclosure, the substituted heteroaryl group means a general term for a group in which a hydrogen on a heteroaryl group is replaced by a substituent group, and the substituent group may be one or more, and when there are more than one substituent groups, they may be the same or different, and the substituent group includes deuterium, a halogen, a cyano, a nitro, a hydroxyl, a carbonyl, a substituted or unsubstituted C1-C15 alkyl, a substituted or unsubstituted C6-C30 aryl, a substituted or unsubstituted C3-C30 heteroaryl, with the alkyl, aryl, and heteroaryl being as defined above.

According to the present disclosure, the substituted arylene group means a general term for a group in which a hydrogen on an arylene group is replaced by a substituent group, and the substituent group may be one or more, and when there are more than one substituent groups, they may be the same or different, and the substituent group includes deuterium, a halogen, a cyano, a nitro, a hydroxyl, a carbonyl, a substituted or unsubstituted C1-C15 alkyl, a substituted or unsubstituted C6-C30 aryl, a substituted or unsubstituted C3-C30 heteroaryl, with the alkyl, aryl, and heteroaryl being as defined above.

According to the present disclosure, the substituted heteroarylene group means a general term for a group in which a hydrogen on a heteroarylene group is replaced by a substituent group, and the substituent group may be one or more, and when there are more than one substituent groups, they may be the same or different, and the substituent group includes deuterium, a halogen, a cyano, a nitro, a hydroxyl, a carbonyl, a substituted or unsubstituted C1-C15 alkyl, a substituted or unsubstituted C6-C30 aryl, a substituted or unsubstituted C3-C30 heteroaryl, with the alkyl, aryl, and heteroaryl being as defined above.

The present disclosure provides an amine derivative, which is represented by Formula I,

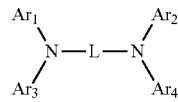

wherein the $Ar_1$ and $Ar_2$ are independently selected from the group consisting of a substituted or unsubstituted C6-C30 aryl group, a substituted or unsubstituted C3-C30 heteroaryl group, and at least one of $Ar_1$ and $Ar_2$ are selected from a group as shown in Formula II,

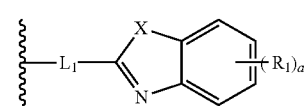

$L_1$ is selected from the group consisting of a single bond, a substituted or unsubstituted C6-C18 arylene group, a substituted or unsubstituted C3-C18 heteroarylene group; a is selected from an integer of 0 to 4, and $R_1$ is selected from the group consisting of a substituted or unsubstituted C1-C15 alkyl group, a substituted or unsubstituted C6-C18 aryl group, and when a is greater than 1, each $R_1$ is the same or different, X is selected from O, S or $N(R_x)$, and $R_x$ is selected from the group consisting of a substituted or unsubstituted C1-C15 alkyl group, a substituted or unsubstituted C6-C18 aryl group;

$Ar_3$ and $Ar_4$ are independently selected from the group consisting of a substituted or unsubstituted C6-C30 aryl group, and a substituted or unsubstituted C3-C30 heteroaryl group;

L is selected from the group consisting of the groups as shown below,

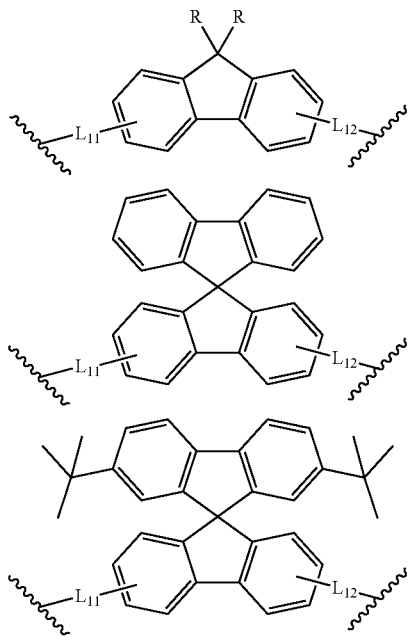

-continued

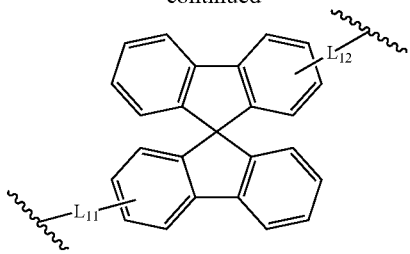

R is selected from the group consisting of hydrogen, a substituted or unsubstituted C1-C15 alkyl group, a substituted or unsubstituted C6-C18 aryl group, and a substituted or unsubstituted C3-C18 heteroaryl group;

$L_{11}$ and $L_{12}$ are independently selected from the group consisting of a single bond, a substituted or unsubstituted C6-C18 arylene group, and a substituted or unsubstituted C3-C18 heteroarylene group.

Preferably, Formula II is selected from the group consisting of the groups as shown below,

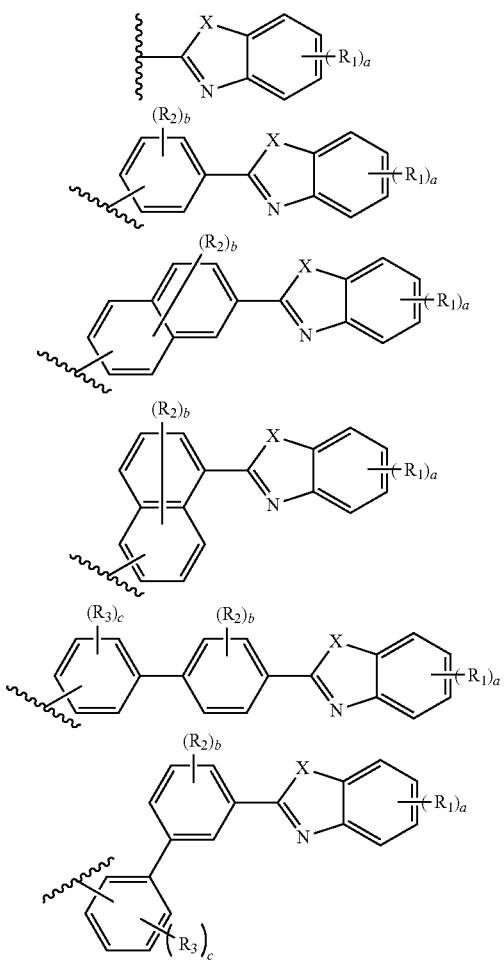

wherein, b is selected from an integer of 0 to 4, and $R_2$ is selected from the group consisting of a substituted or unsubstituted C1-C10 alkyl group, a substituted or unsubstituted C6-C18 aryl group, when b is greater than 1, each $R_2$ is the same or different;

c is selected from an integer of 0 to 4, and $R_3$ is selected from the group consisting of a substituted or unsubstituted C1-C10 alkyl group, a substituted or unsubstituted C6-C18 aryl group, when c is greater than 1, each $R_3$ is the same or different.

Preferably, the amine derivative is as shown in Formula I-1,

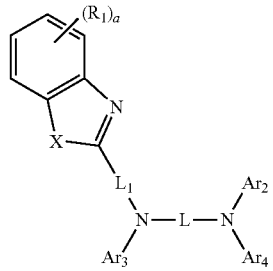

I-1

$Ar_2$ is selected from the group consisting of a substituted or unsubstituted C6-C30 aryl group, and a substituted or unsubstituted C3-C30 heteroaryl group, and $Ar_2$ is not Formula II;

$Ar_3$ and $Ar_4$ are independently selected from the group consisting of a substituted or unsubstituted C6-C30 aryl group, and a substituted or unsubstituted C3-C30 heteroaryl group.

Preferably, $Ar_2$ and $Ar_4$ are selected from the same substituents.

Preferably, the amine derivative is as shown in Formula I-2,

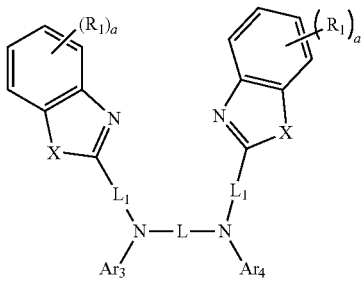

I-2

$Ar_3$ and $Ar_4$ are independently selected from the group consisting of a substituted or unsubstituted C6-C30 aryl group, and a substituted or unsubstituted C3-C30 heteroaryl group.

Preferably, $Ar_3$ and $Ar_4$ are independently selected from the group consisting of the groups as shown below,

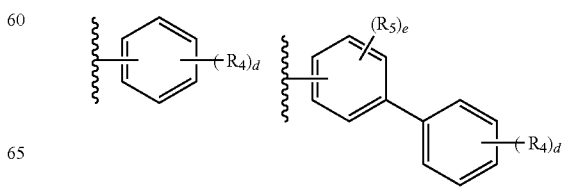

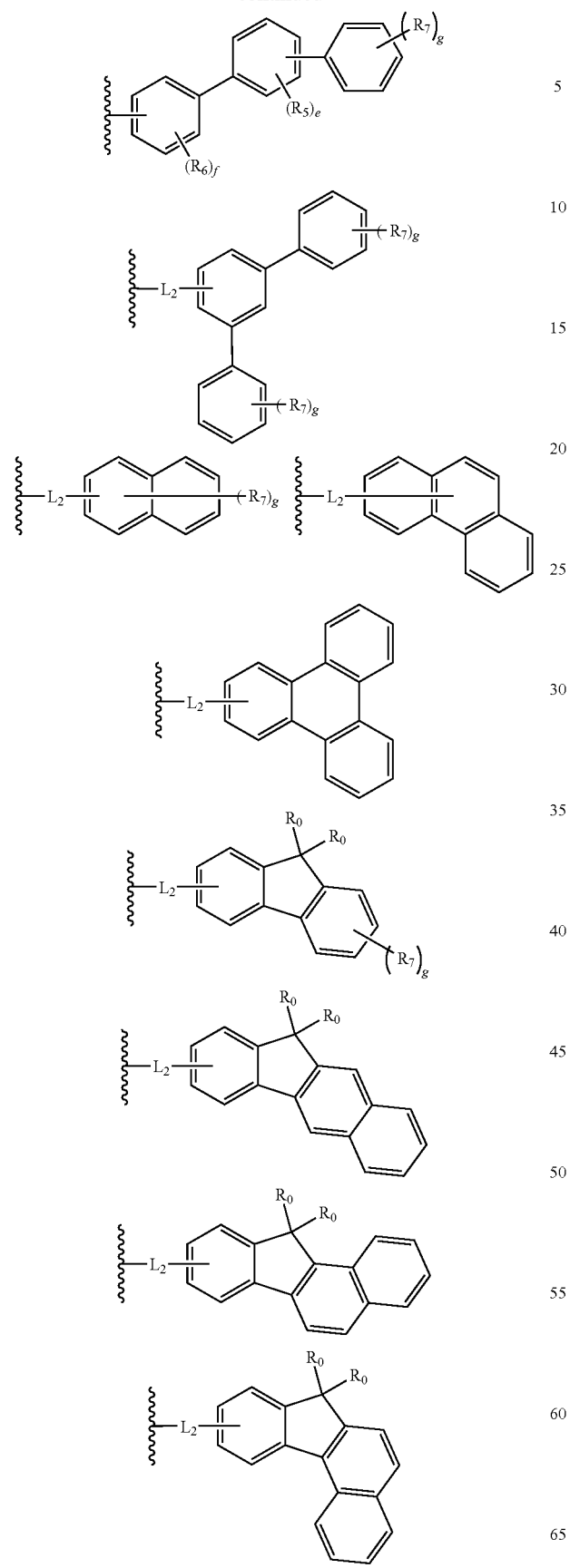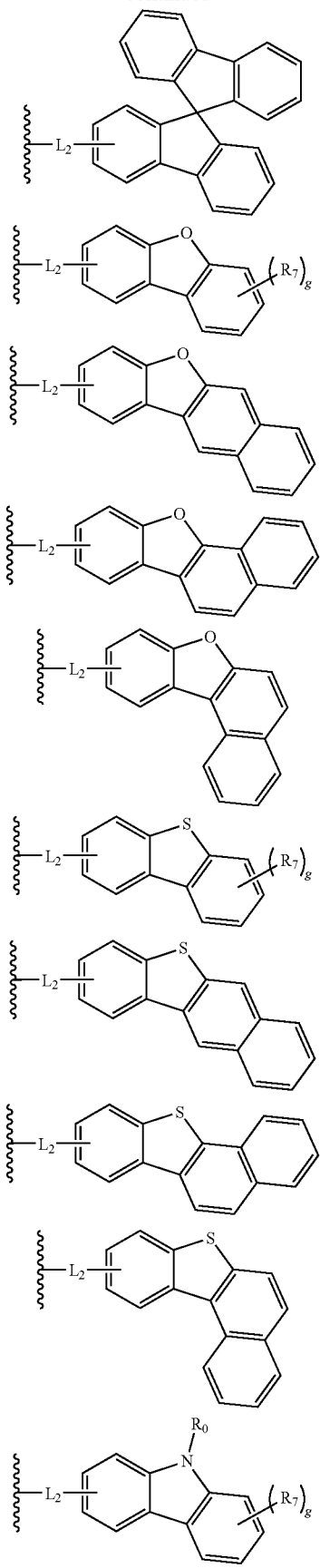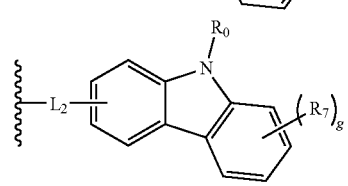

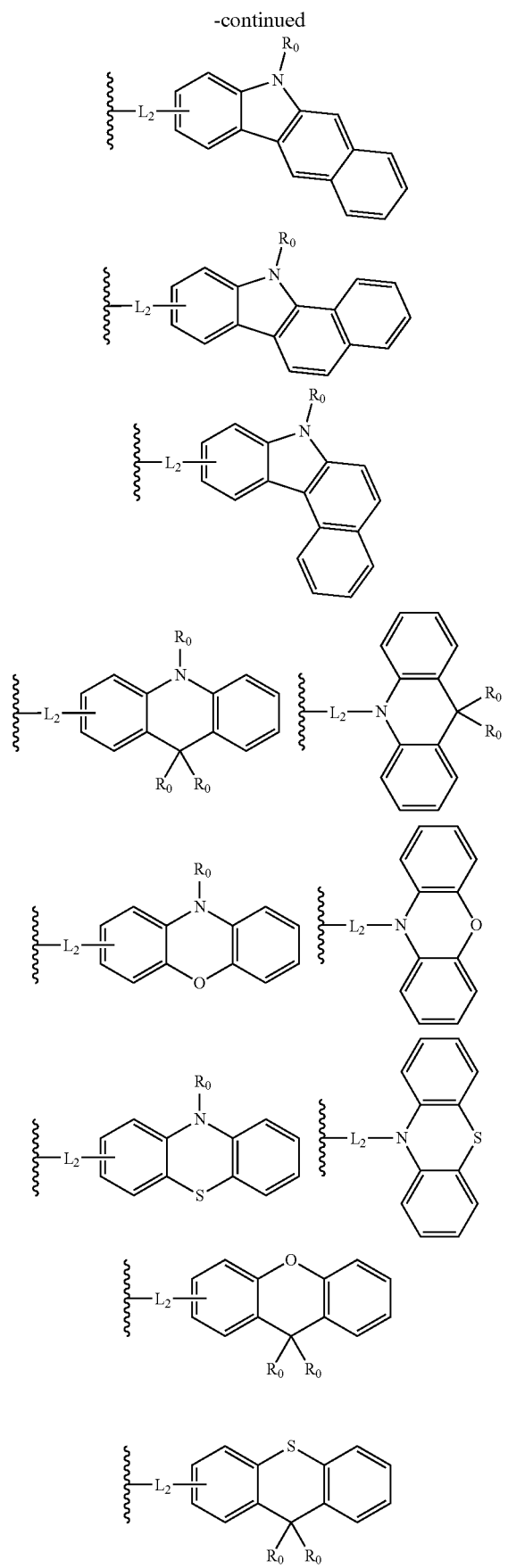

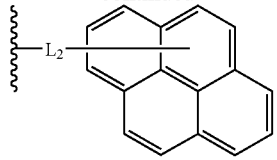

wherein, d is selected from an integer of 0 to 5, and $R_4$ is selected from a substituted or unsubstituted C1-C10 alkyl group, when d is greater than 1, each $R_4$ is the same or different;

e is selected from an integer of 0 to 4, and $R_5$ is selected from the group consisting of a substituted or unsubstituted C1-C10 alkyl group, a substituted or unsubstituted C6-C18 aryl group, when e is greater than 1, each $R_5$ is the same or different;

f is selected from an integer of 0 to 4, and $R_6$ is selected from the group consisting of a substituted or unsubstituted C1-C10 alkyl group, a substituted or unsubstituted C6-C18 aryl group, when f is greater than 1, each $R_6$ is the same or different;

g is selected from an integer of 0 to 5, and $R_7$ is selected from the group consisting of a substituted or unsubstituted C1-C10 alkyl group, a substituted or unsubstituted C6-C18 aryl group, when g is greater than 1, each $R_7$ is the same or different;

$R_0$ is selected from the group consisting of a substituted or unsubstituted C1-C10 alkyl group, a substituted or unsubstituted C6-C18 aryl group;

$L_2$ is selected from the group consisting of a single bond, a substituted or unsubstituted C6-C18 arylene group, and a substituted or unsubstituted C3-C18 heteroarylene group.

Preferably, $Ar_3$ and $Ar_4$ are independently selected from the group consisting of the groups as shown below,

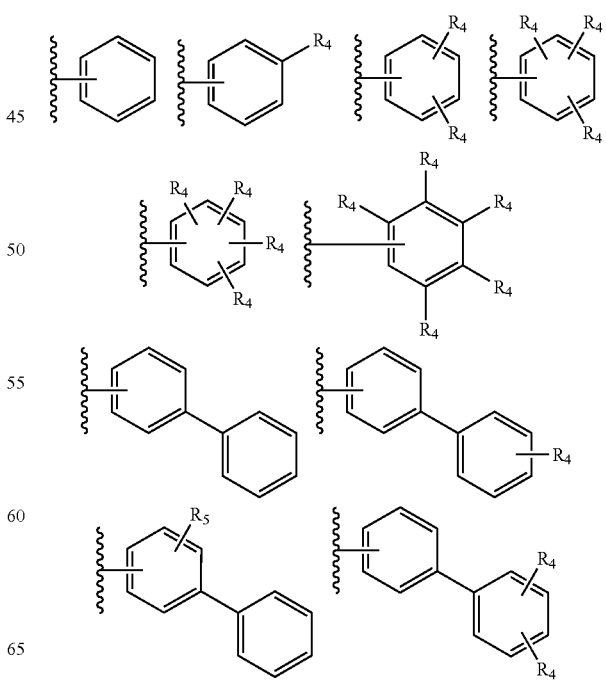

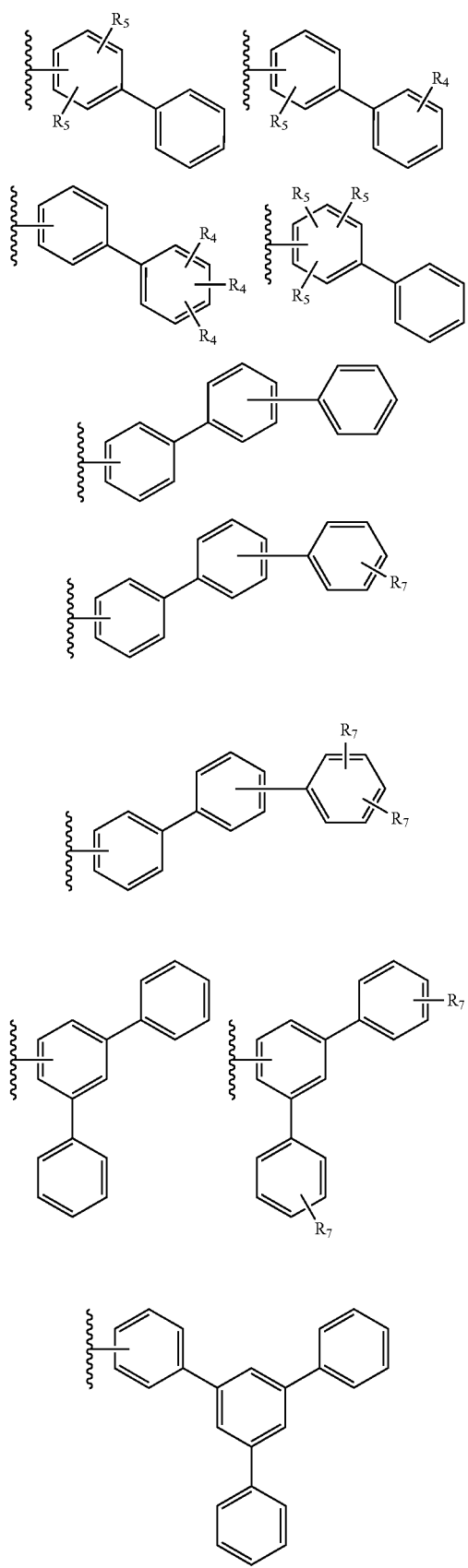
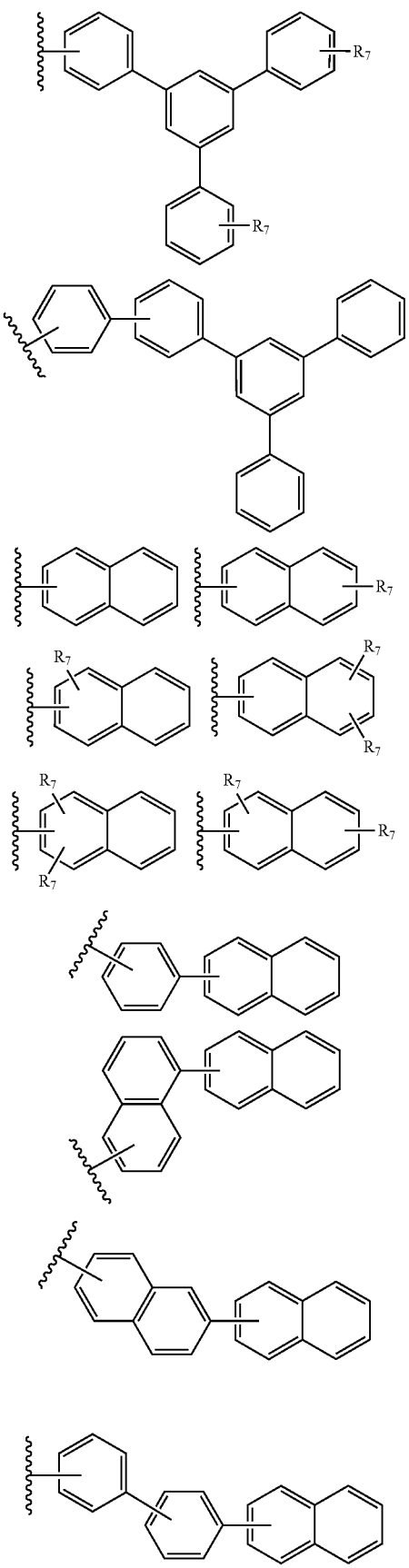

-continued
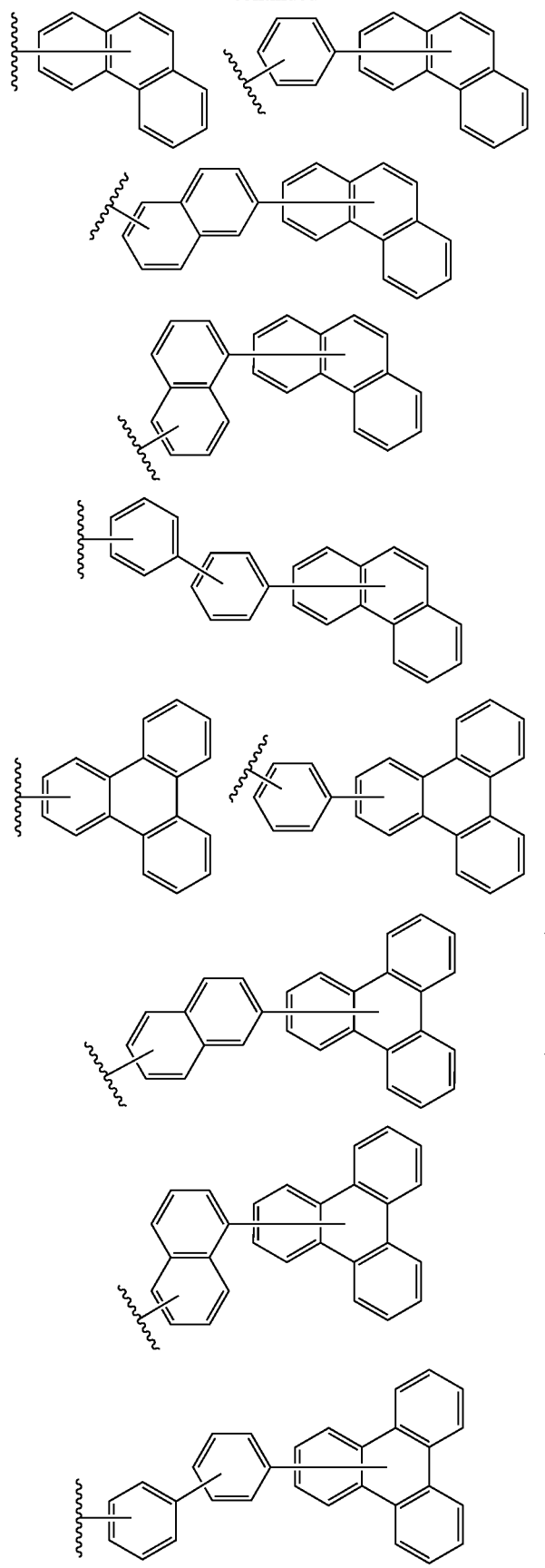
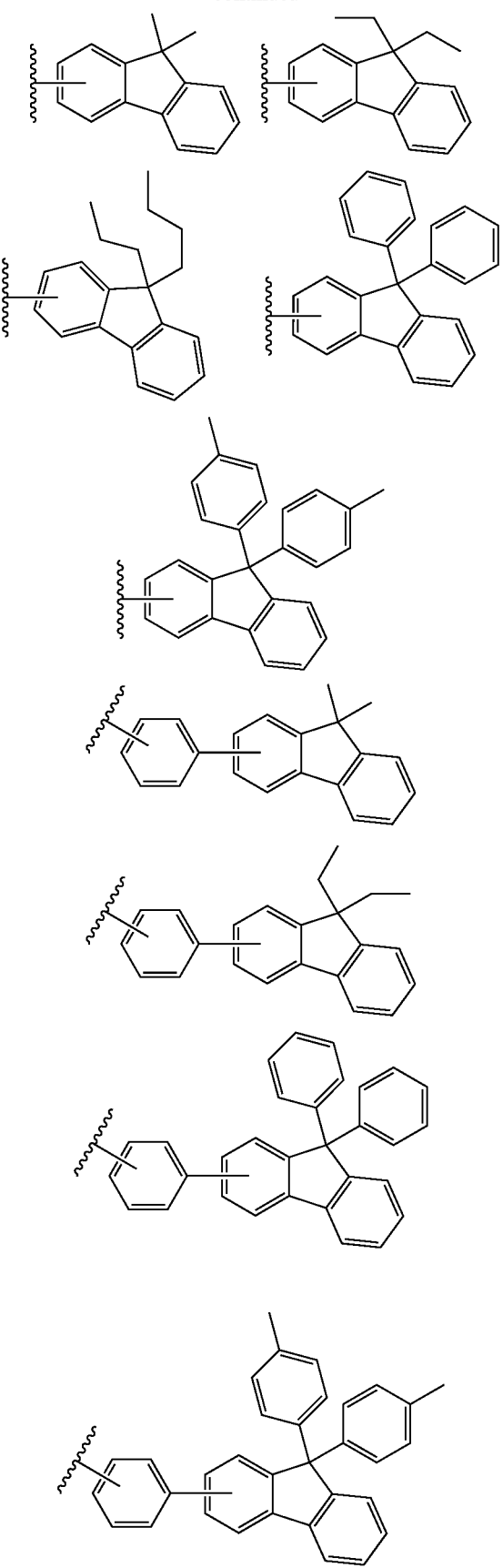

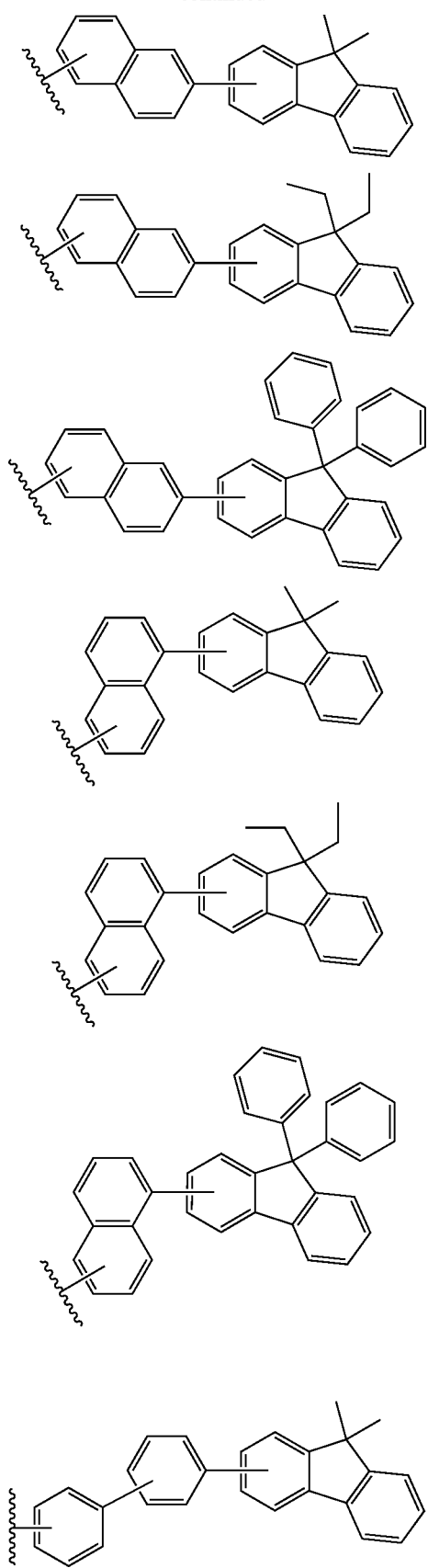
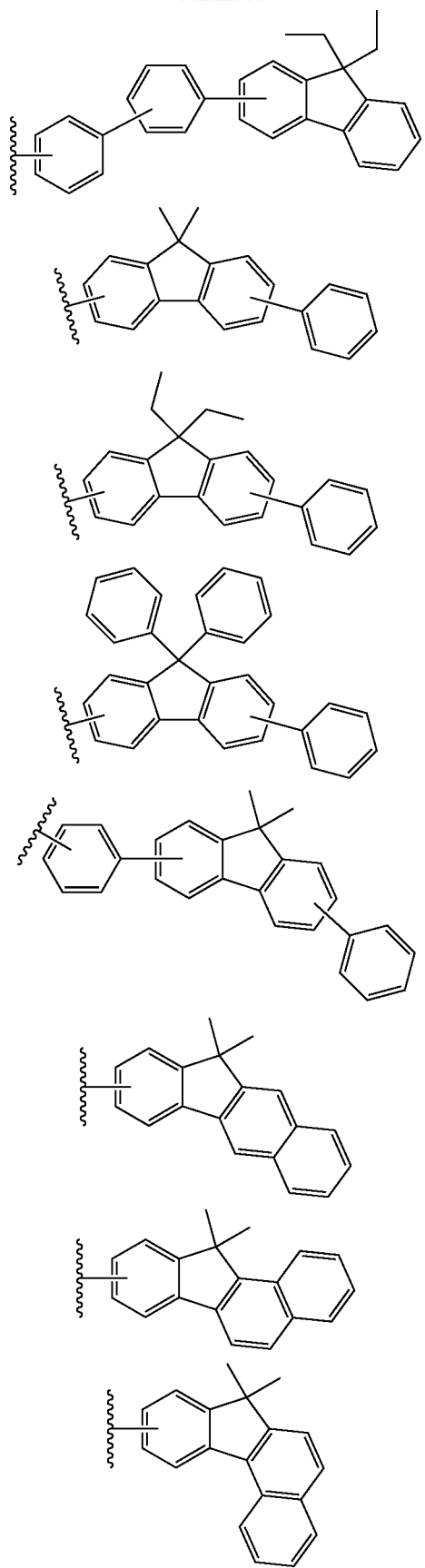

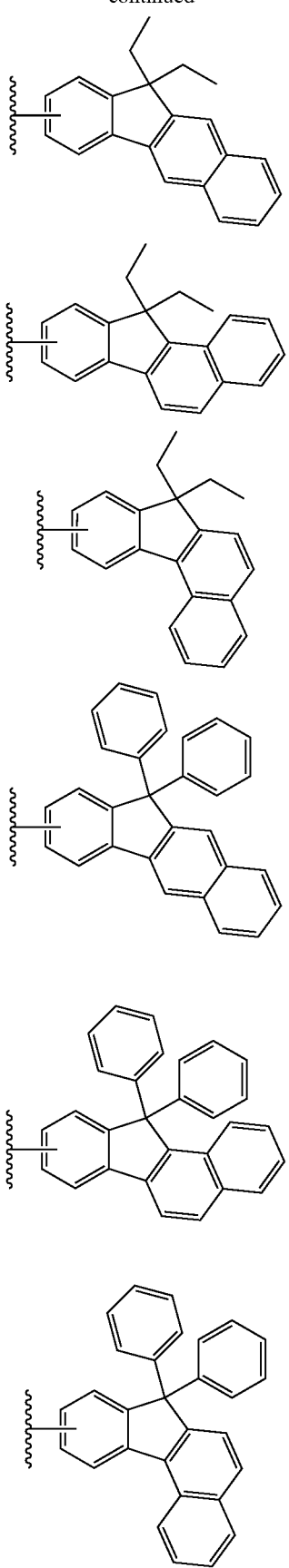
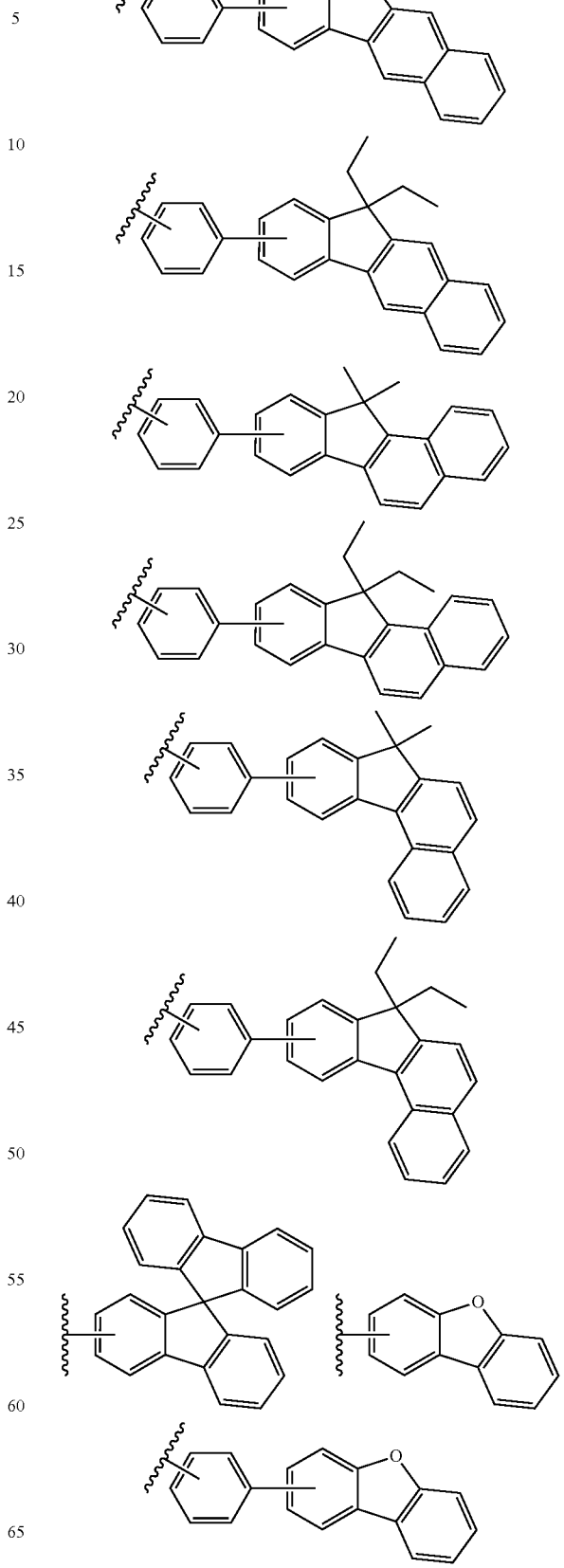

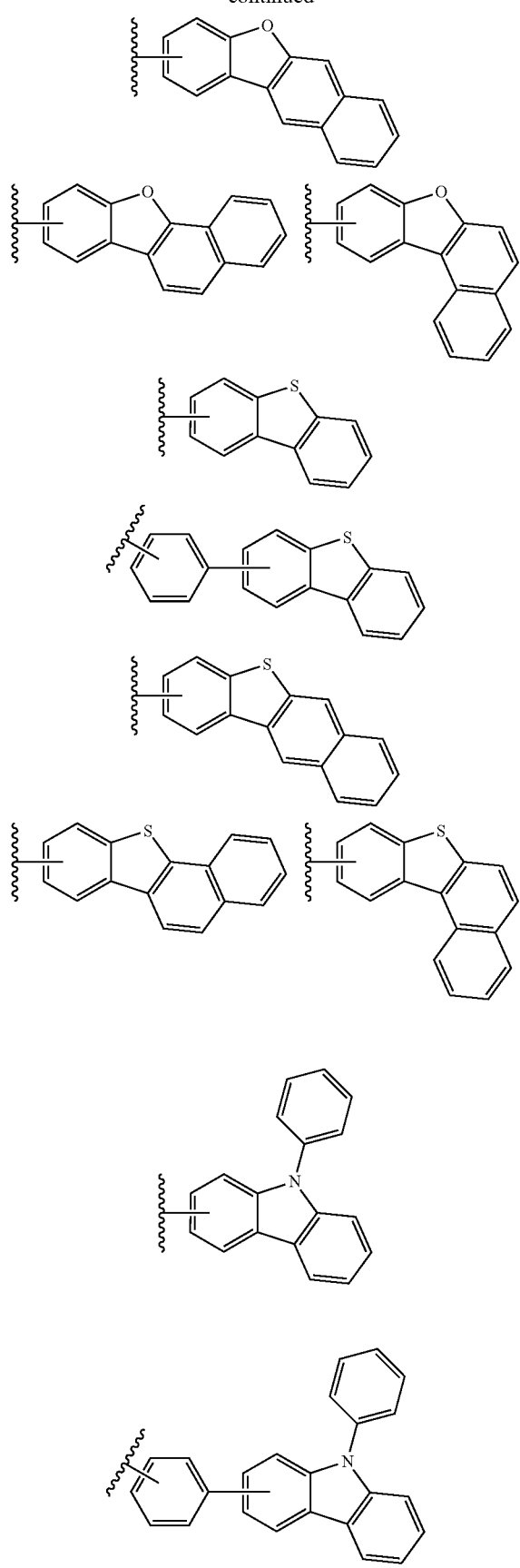
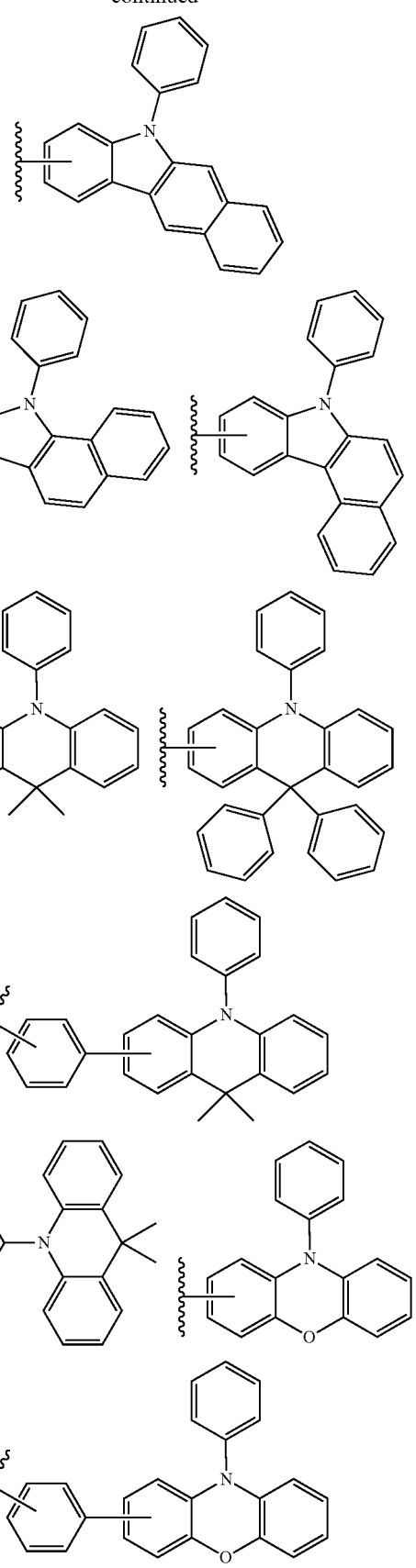

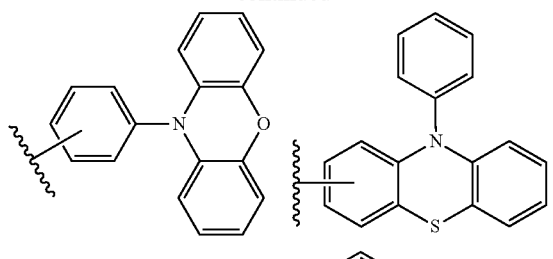
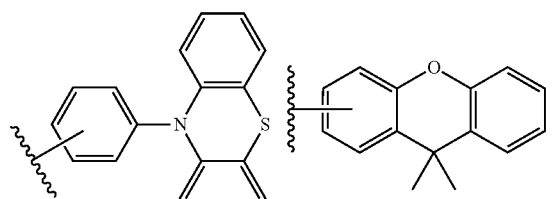
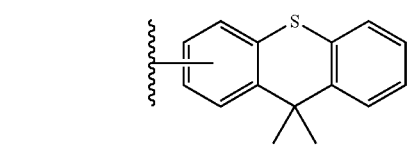
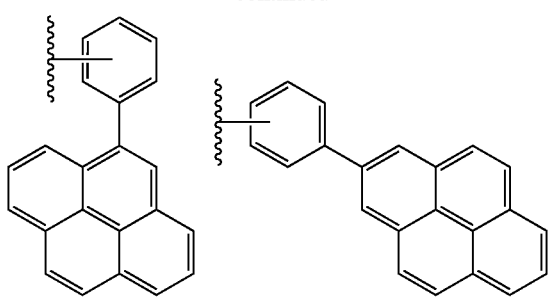

wherein, $R_4$ is selected from the group consisting of methyl, ethyl, propyl, butyl, pentyl, hexyl, heptyl, and octyl, and each $R_4$ is the same or different;

$R_5$ is selected from the group consisting of methyl, ethyl, propyl, and butyl, and each $R_5$ is the same or different;

$R_7$ is selected from the group consisting of methyl, ethyl, propyl, butyl, phenyl, tolyl, and ethylphenyl, and each $R_7$ is the same or different.

Preferably, Formula II is selected from the group consisting of the groups as shown below,

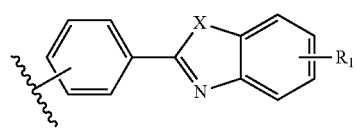
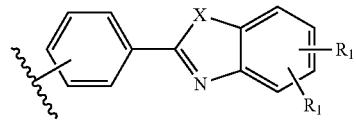
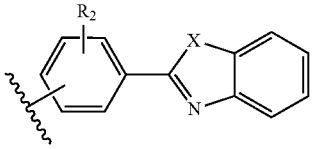
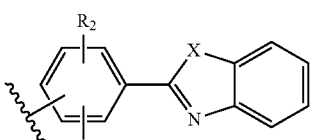
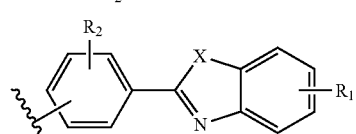
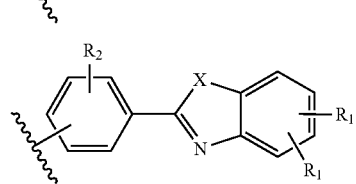

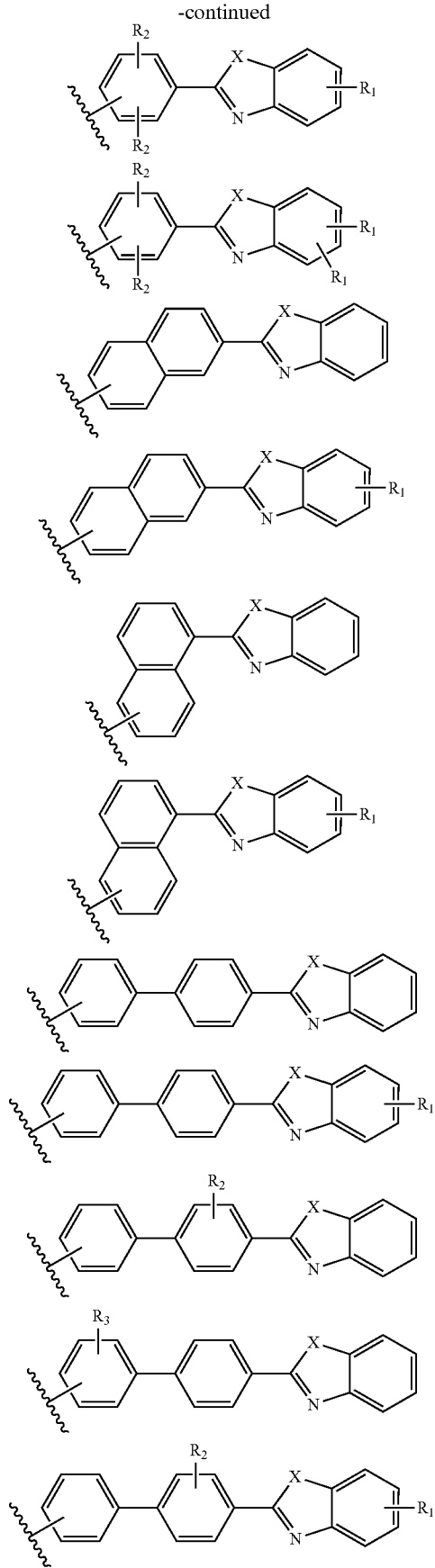
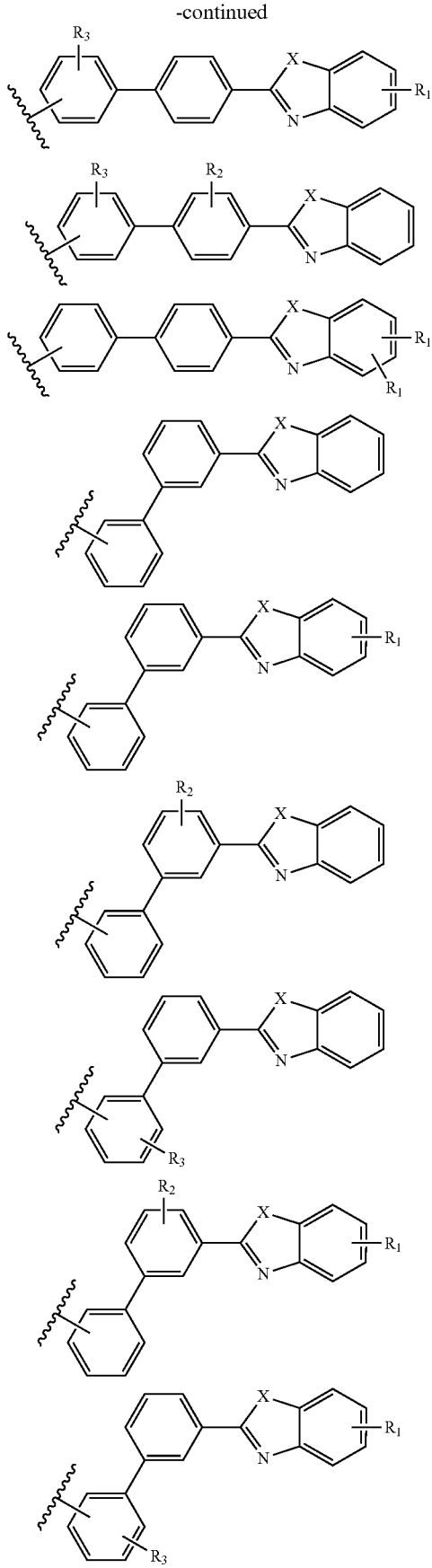

-continued

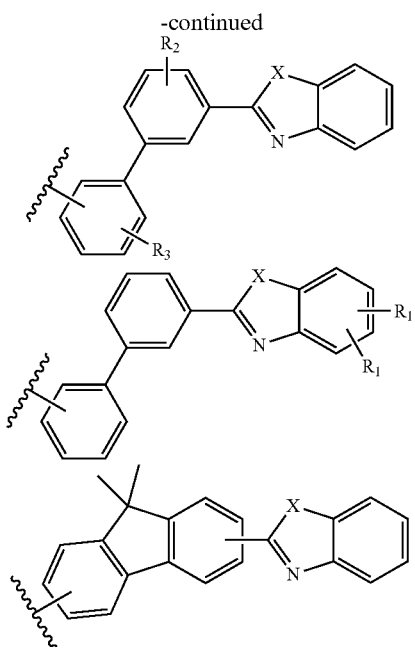

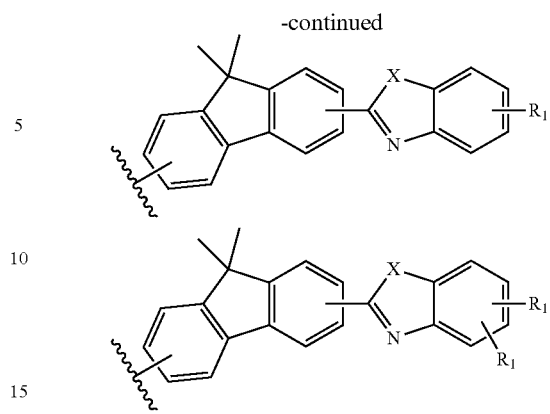

wherein, $R_1$ is selected from the group consisting of methyl, ethyl, propyl, butyl, pentyl, hexyl, heptyl, and octyl, and each $R_1$ is the same or different;

$R_2$ is selected from the group consisting of methyl, ethyl, propyl, and butyl, and each $R_2$ is the same or different;

$R_3$ is selected from the group consisting of methyl, ethyl, propyl, and butyl.

Further, the amine derivative is selected from one of the structures as shown below,

1

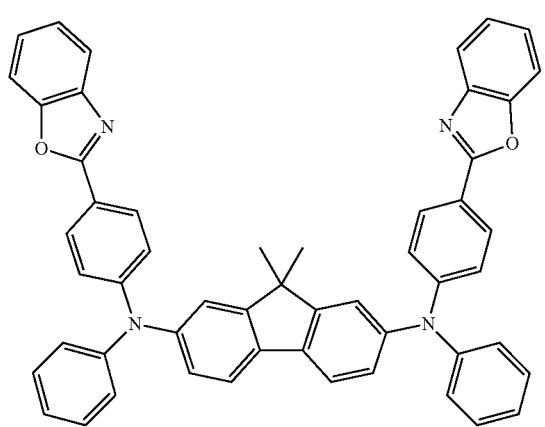

2

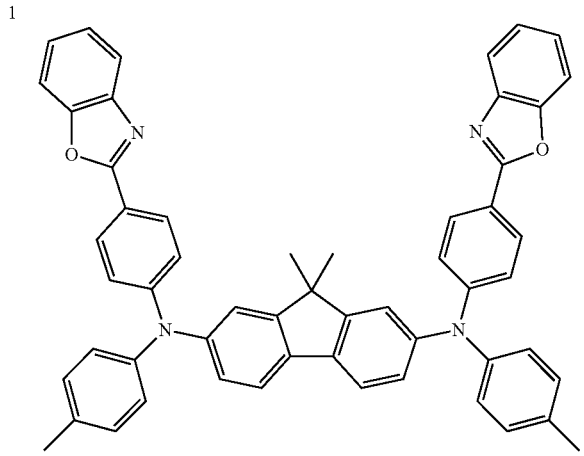

3

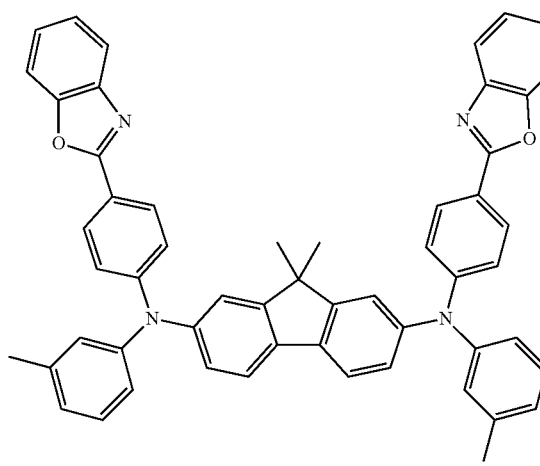

4

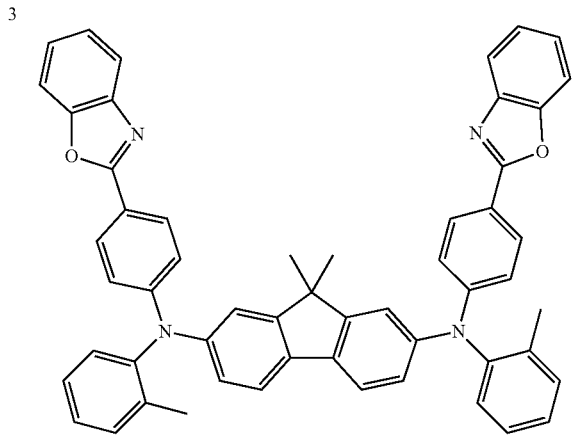

-continued
5
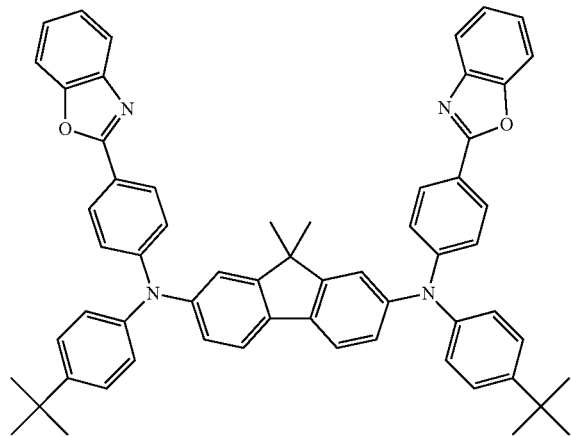
6
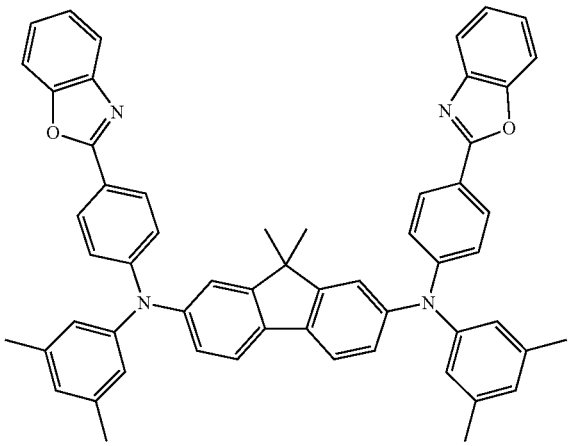
7
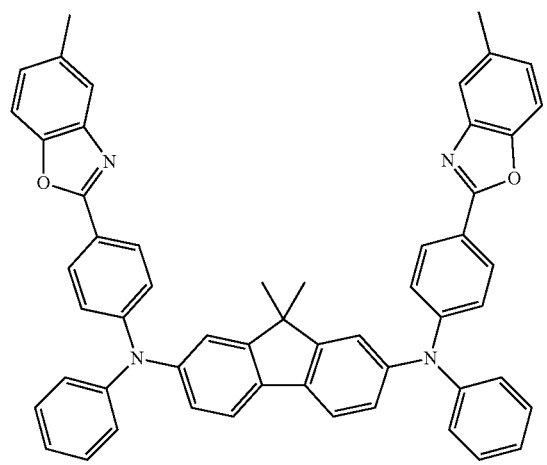
8
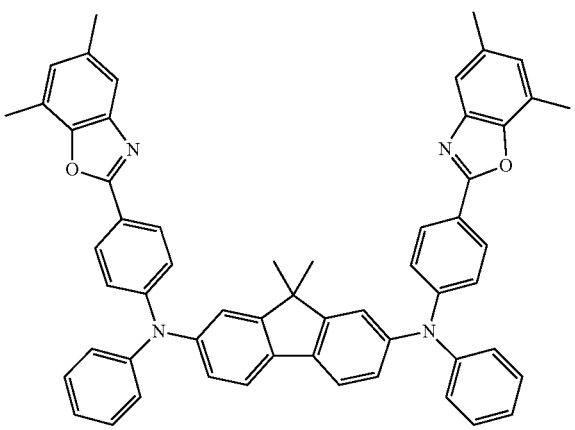
9
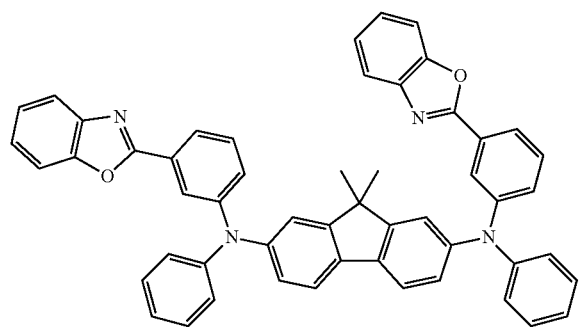
10
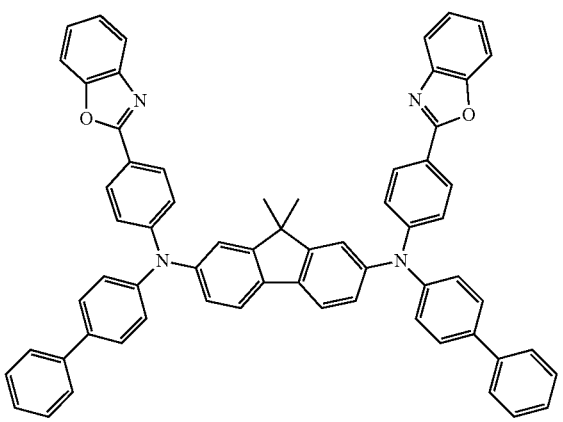

-continued
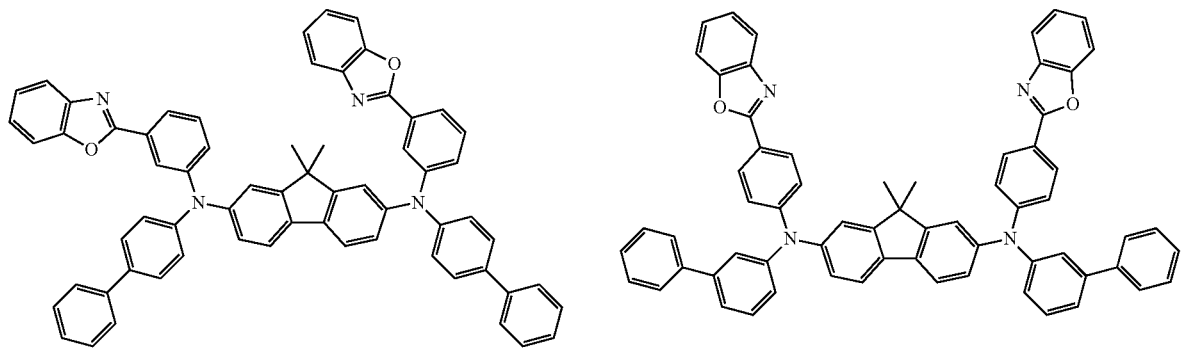
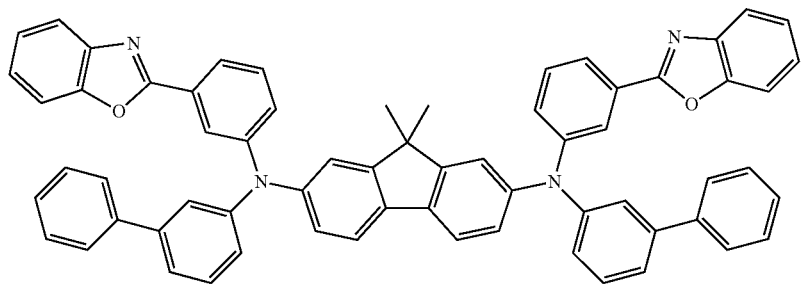
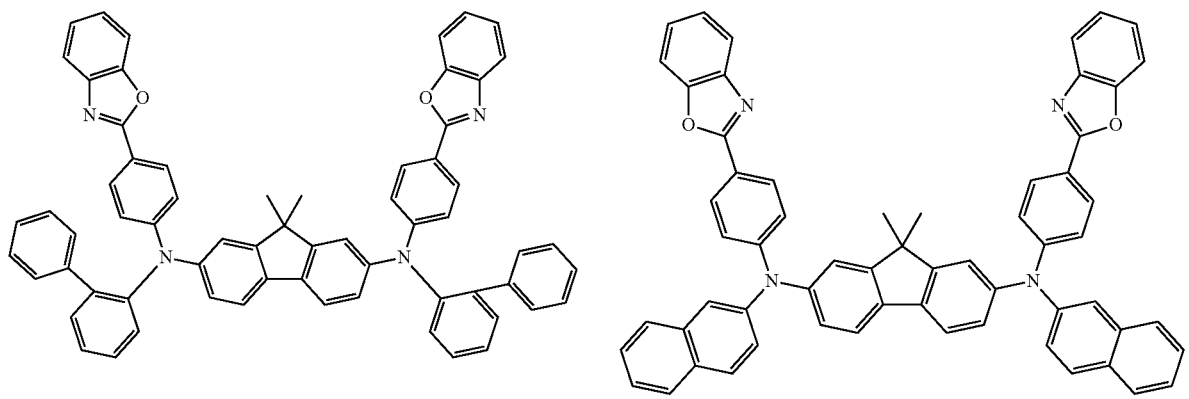
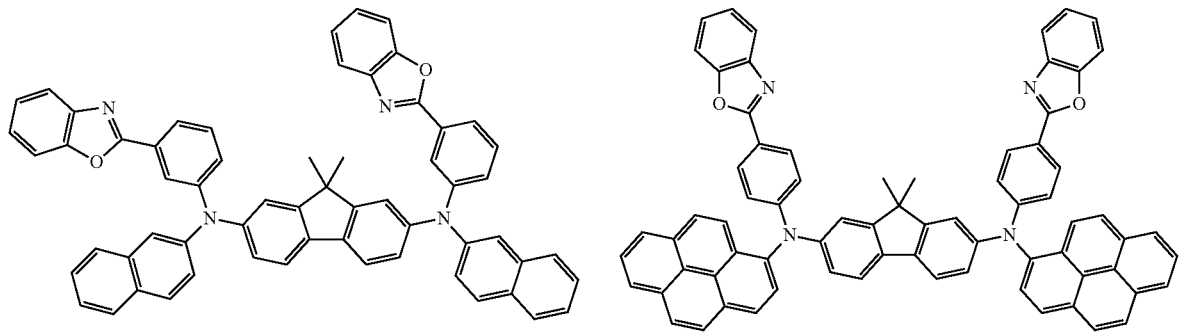

-continued
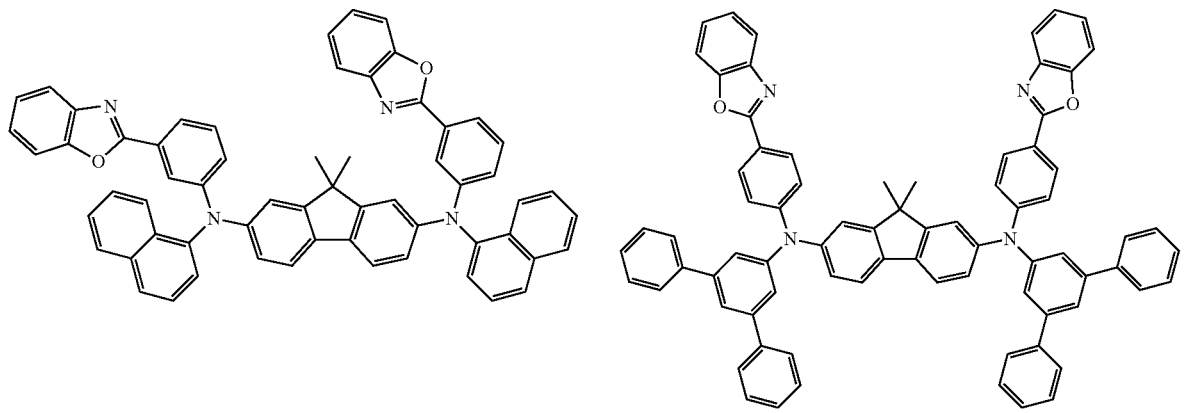
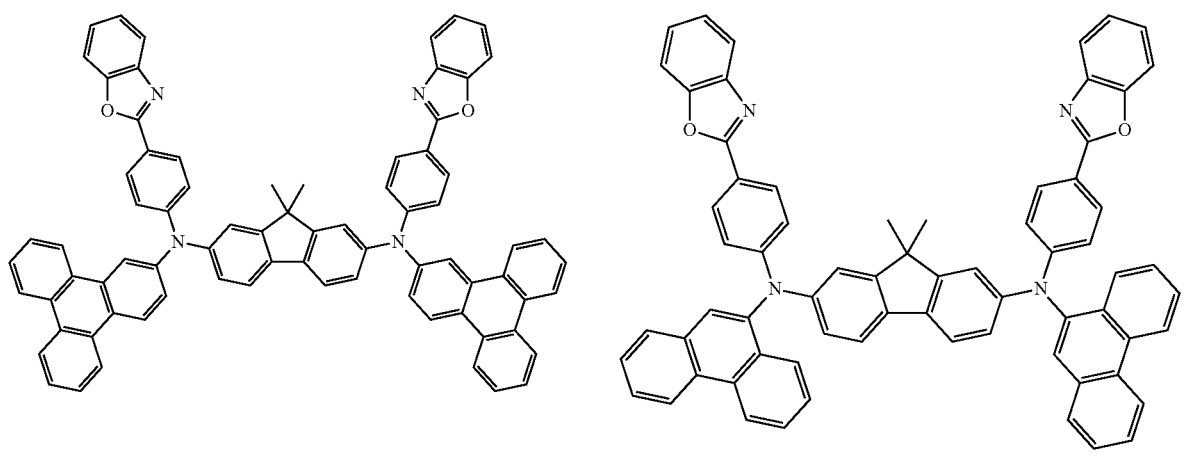
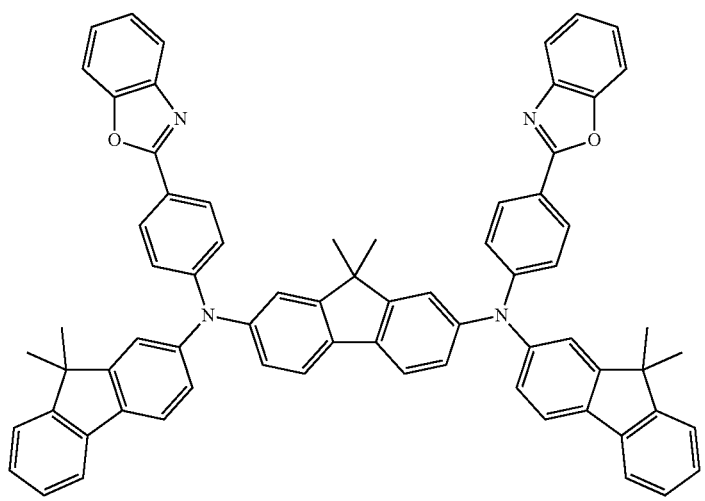

23
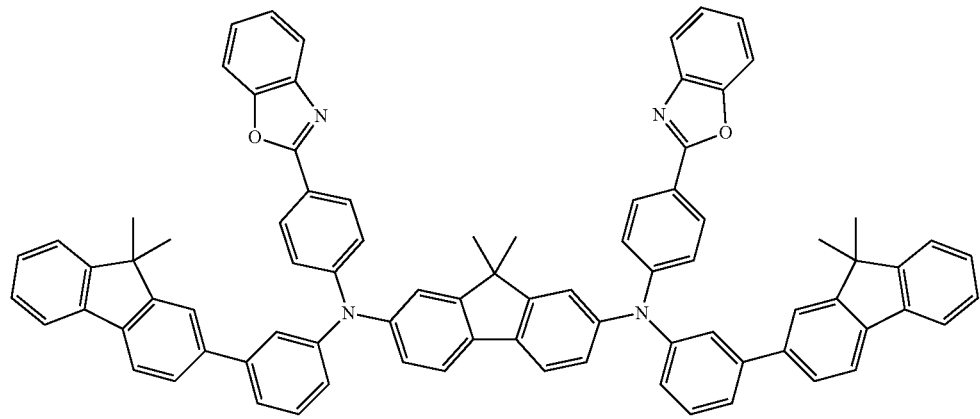
24
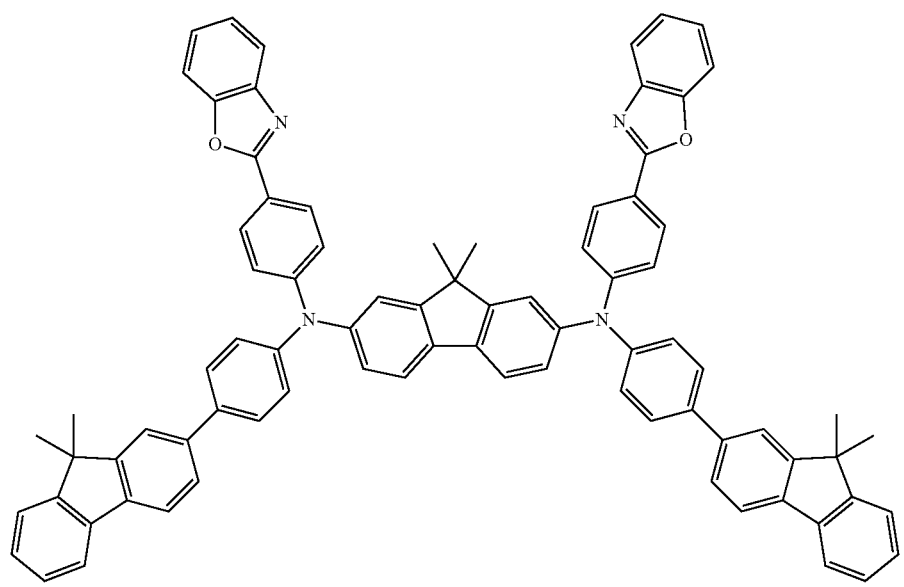
25
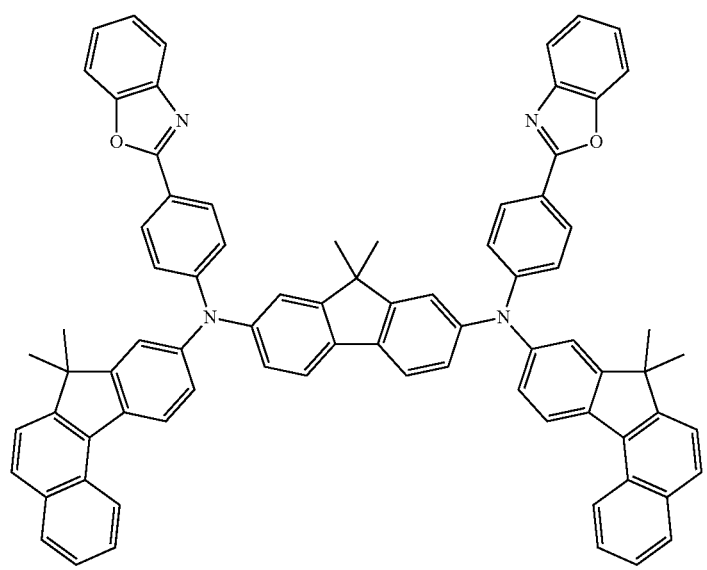

26
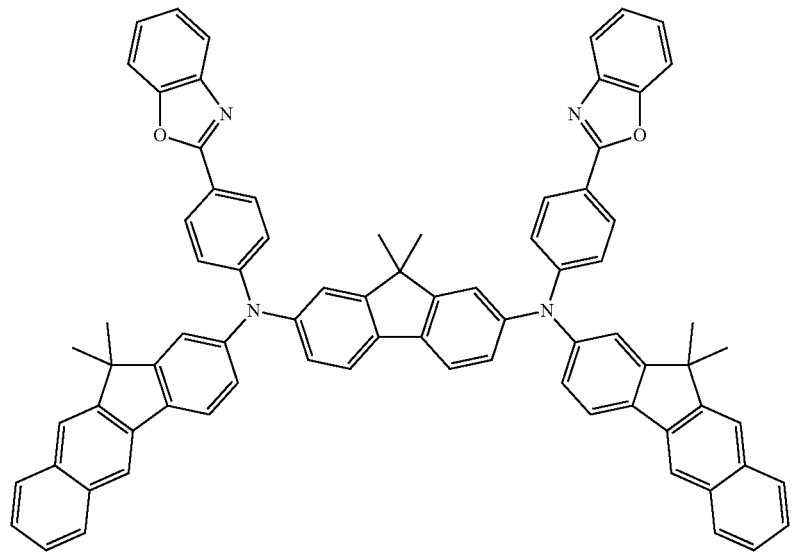
27
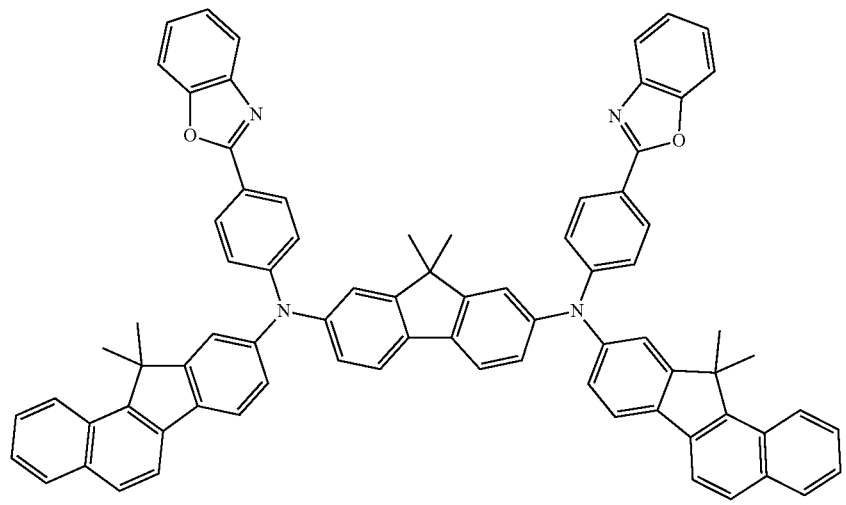
28  29
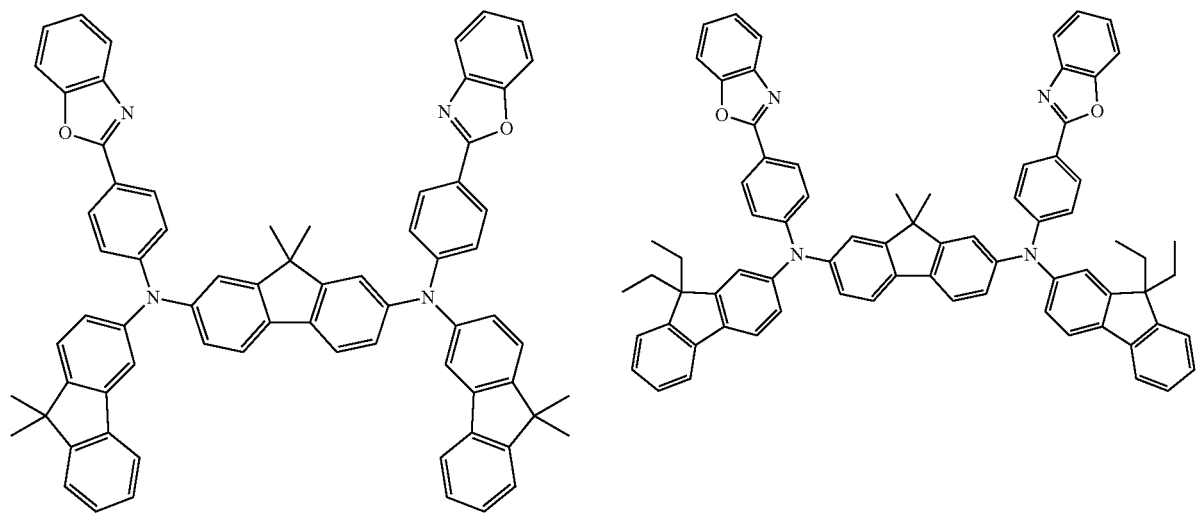

30
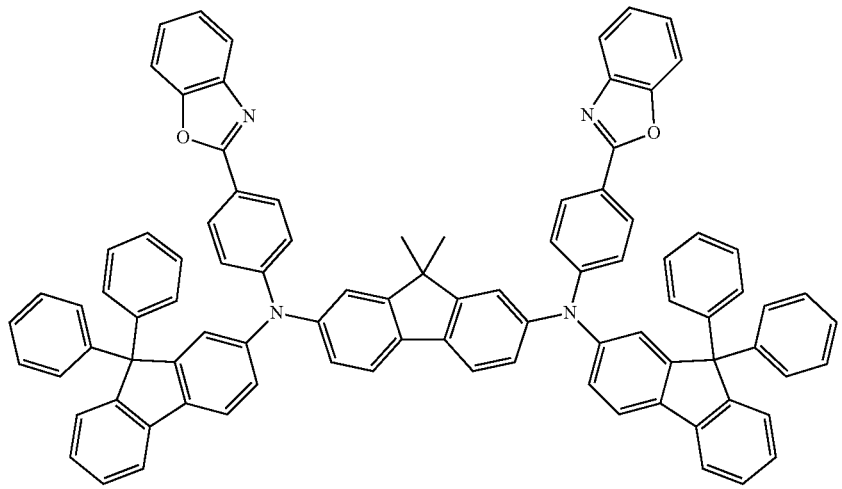
31
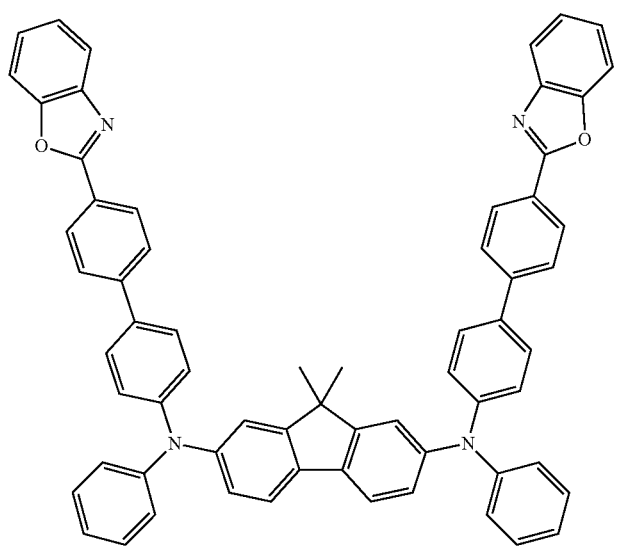
32
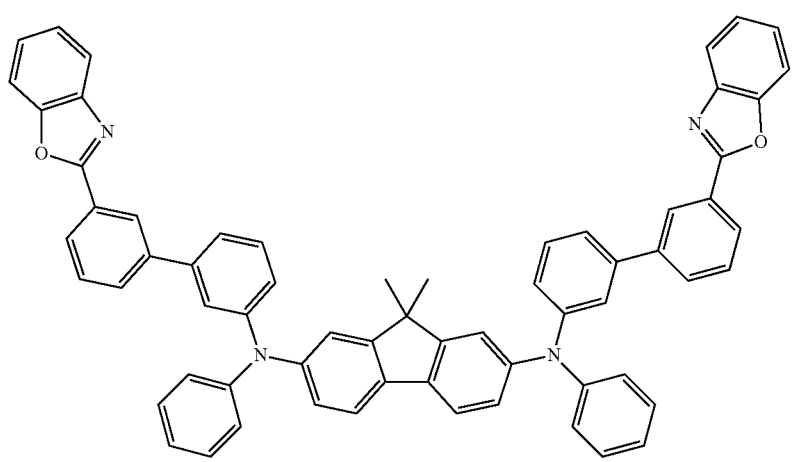

-continued
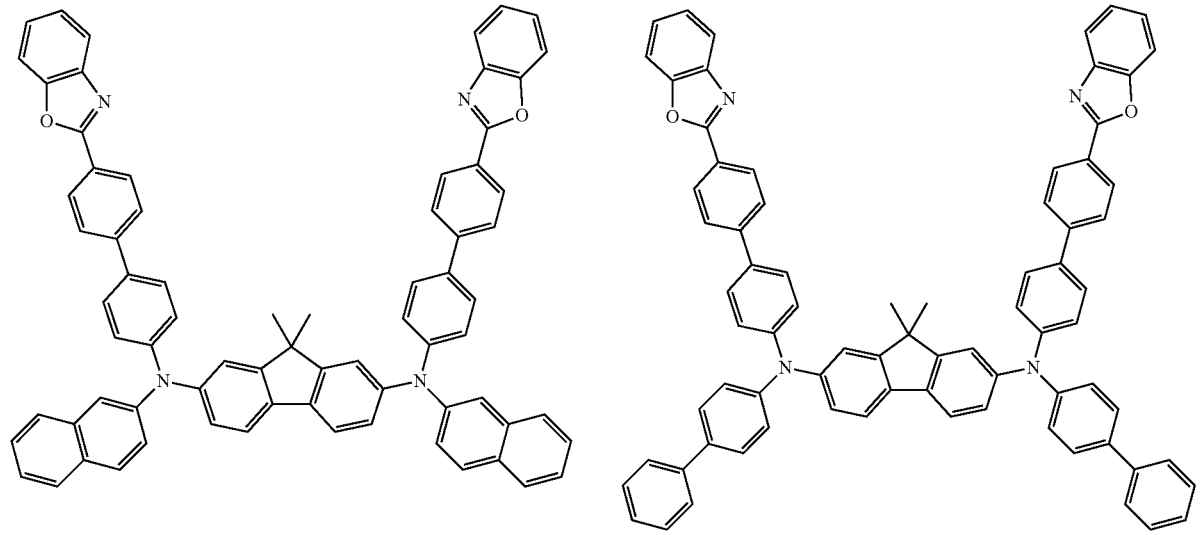
33
34
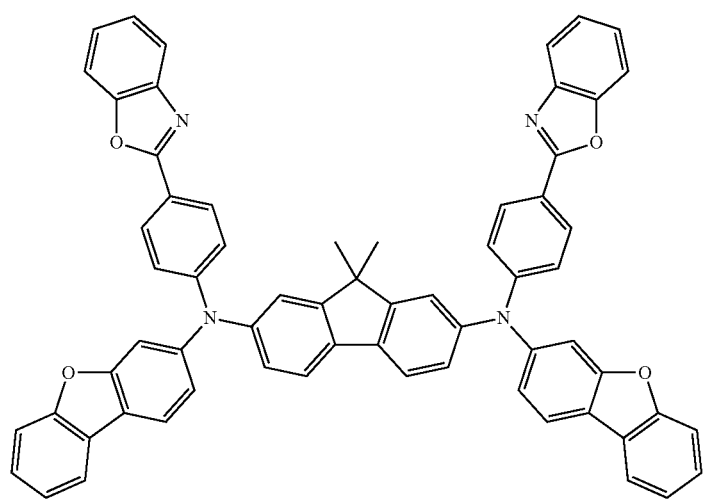
35
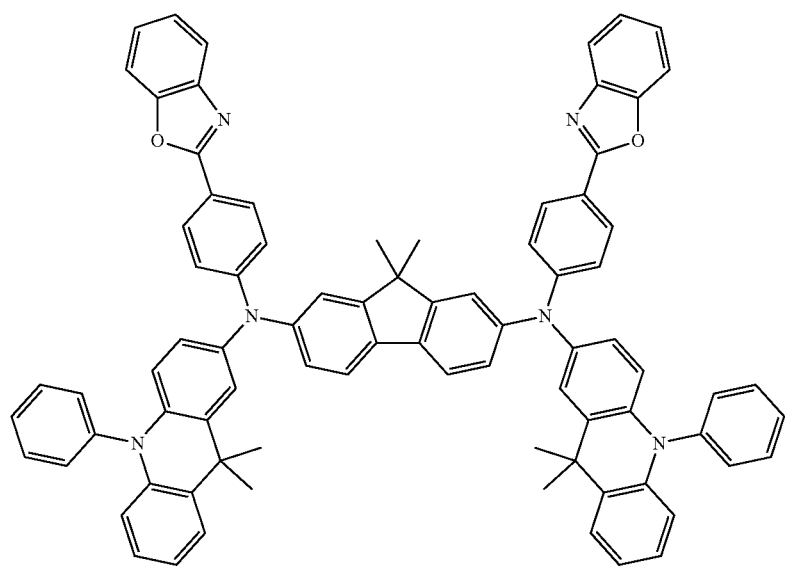
36

-continued
37
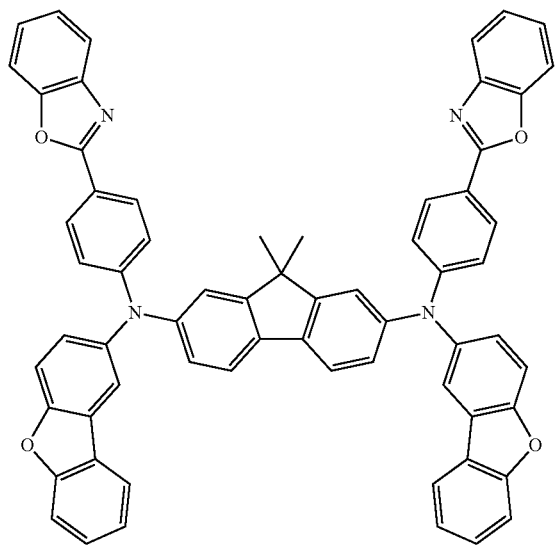
38
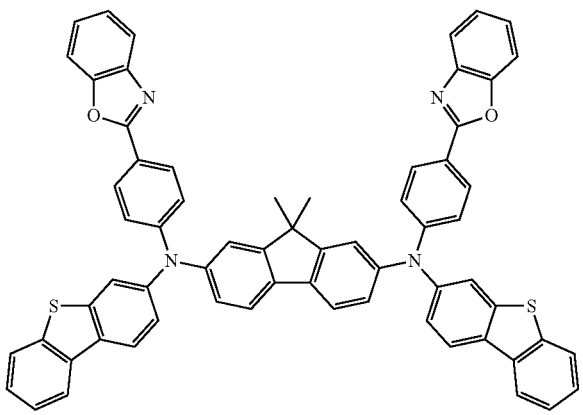
39
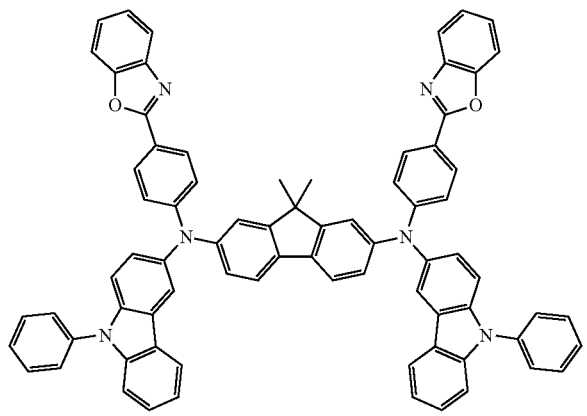
40
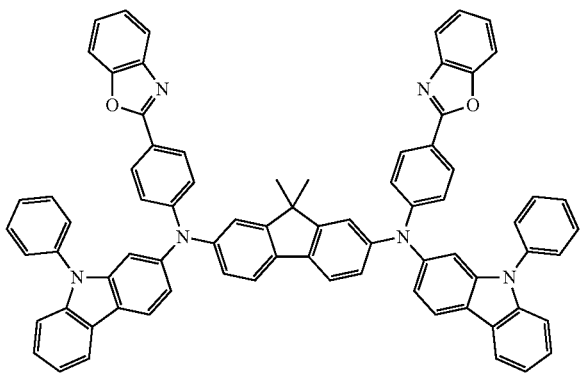
41
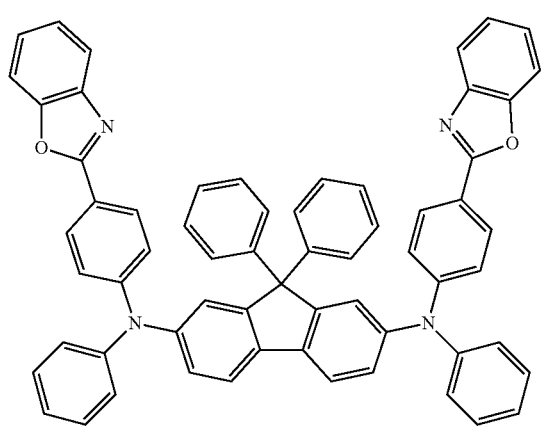

-continued
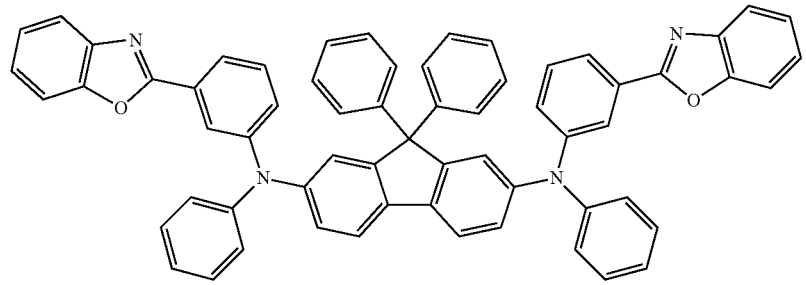
42
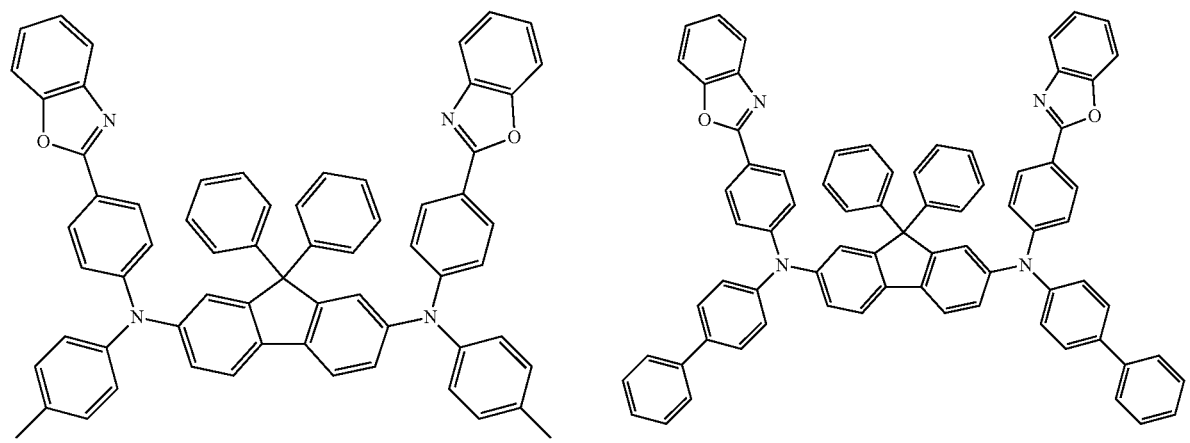
43
44
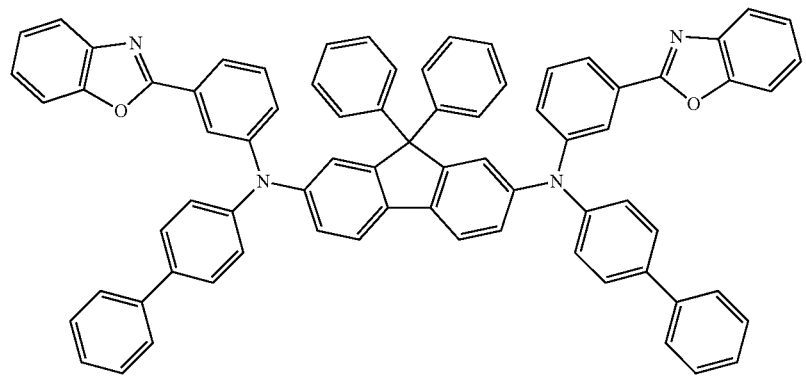
45
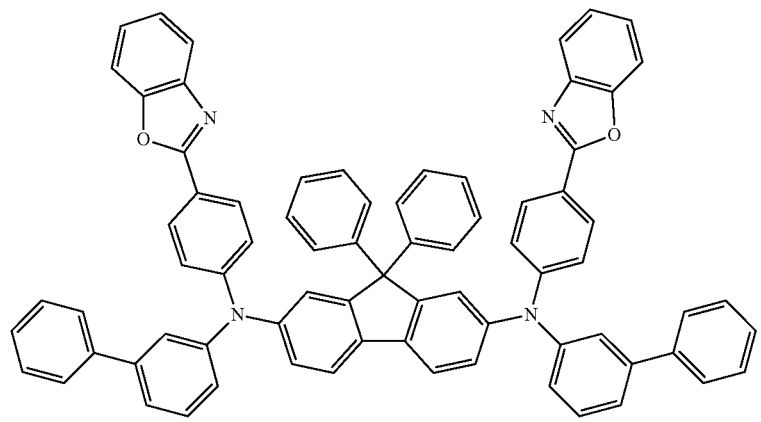
46

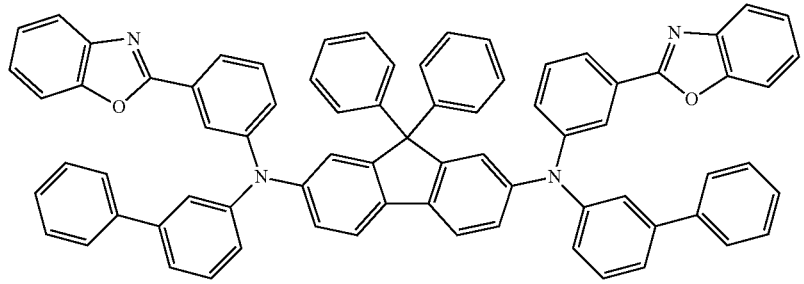
47
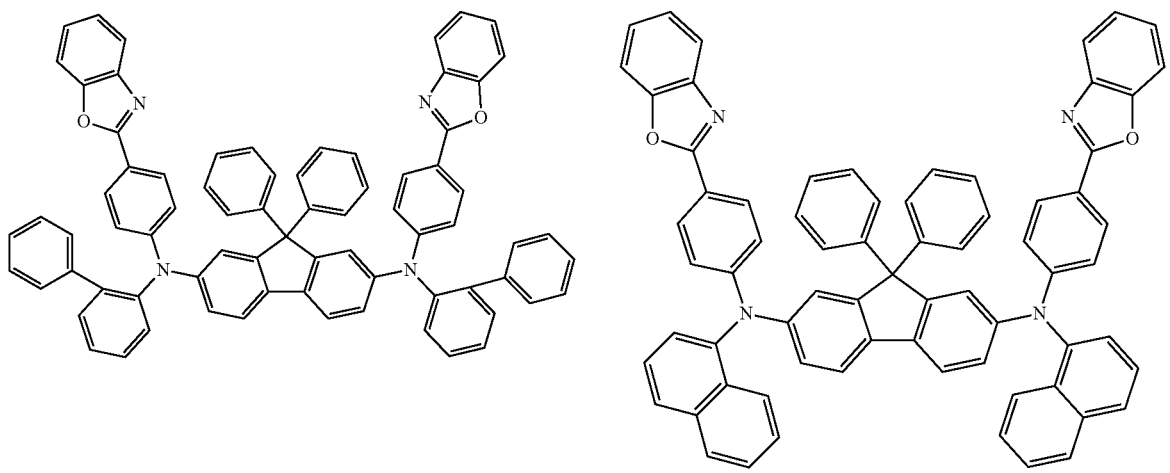
48
49
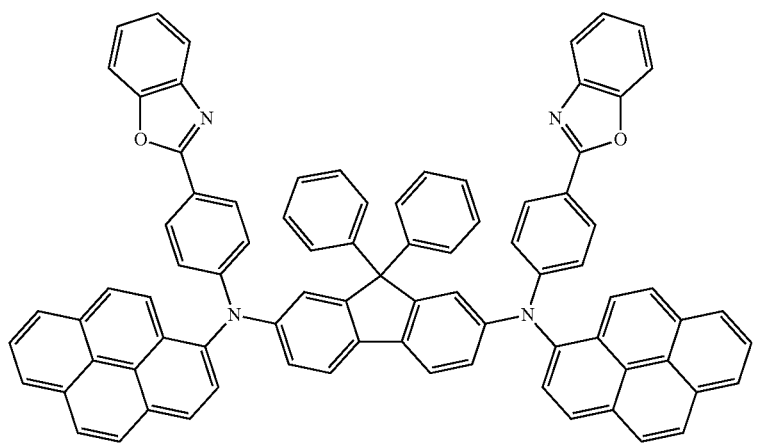
50
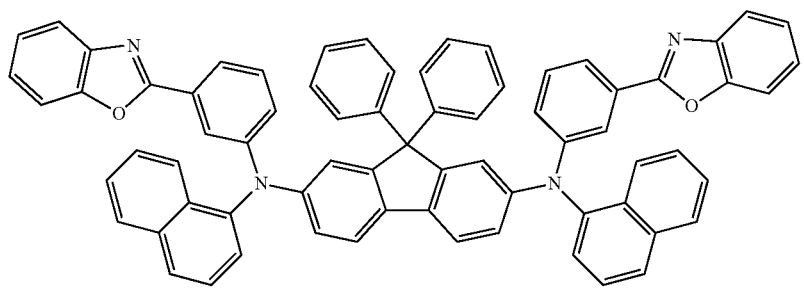
51

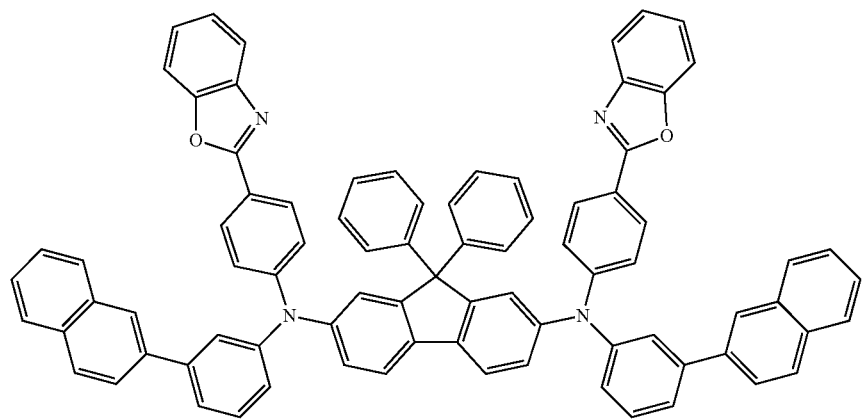
52
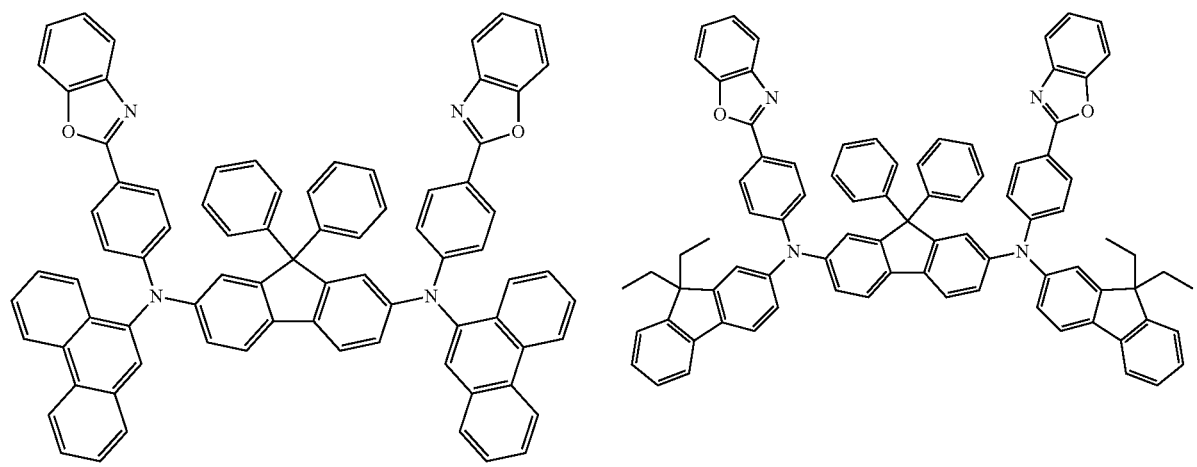
53
54
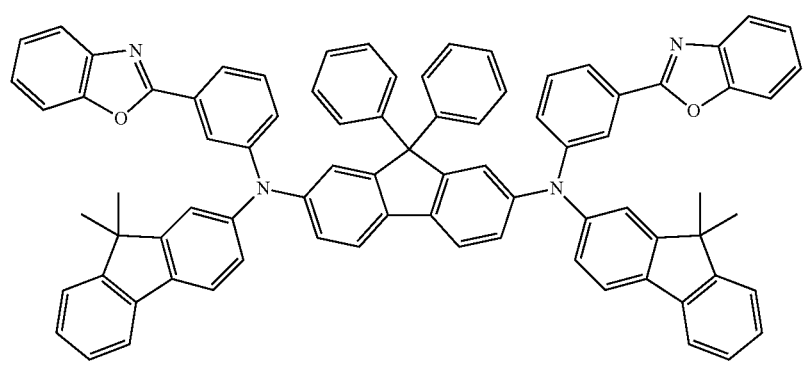
55

-continued
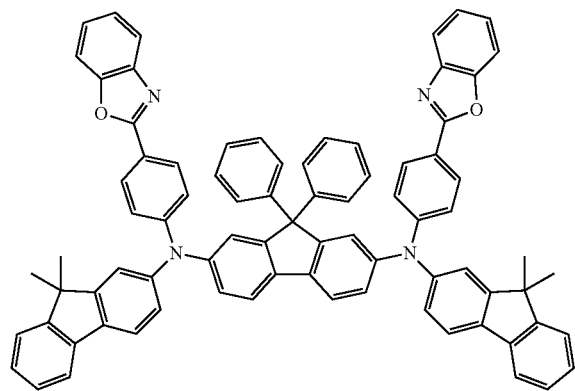
56
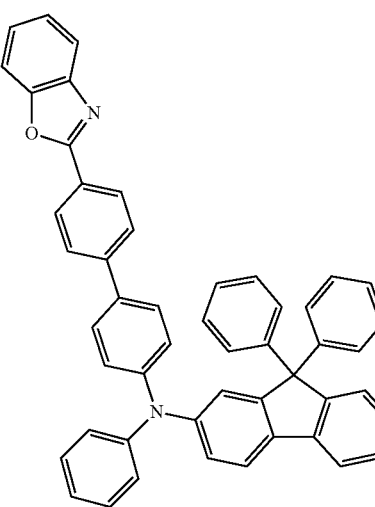
57
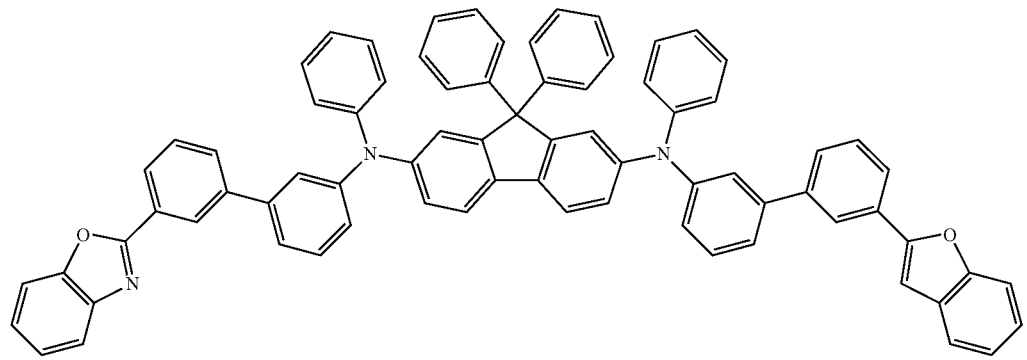
58
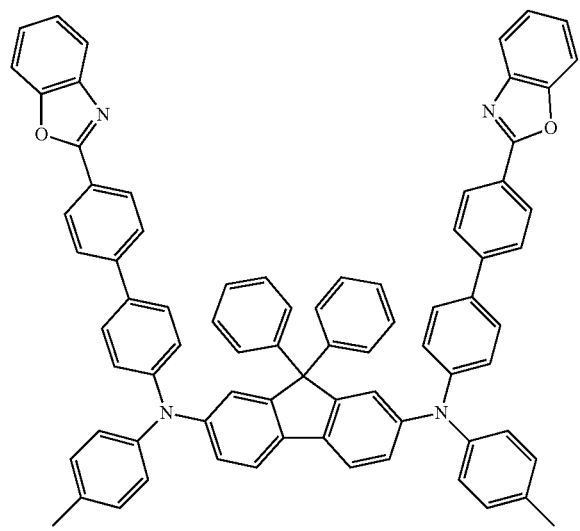
59
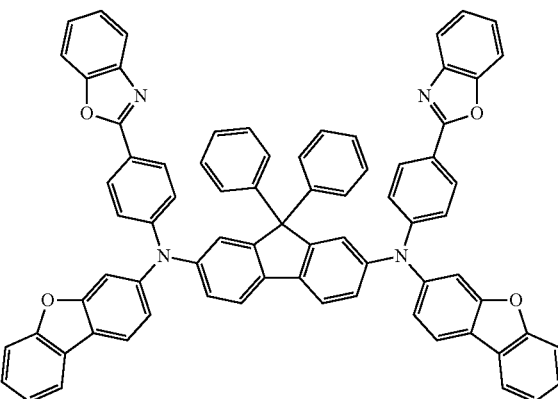
60

-continued
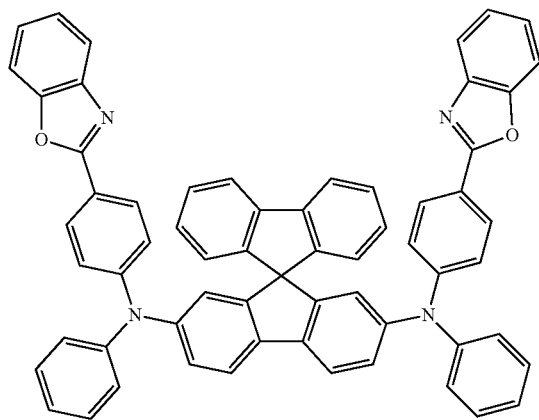
61
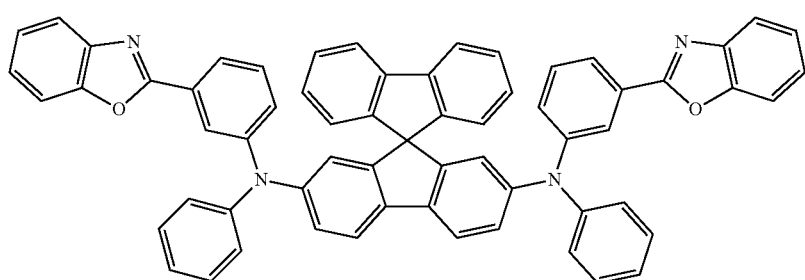
62
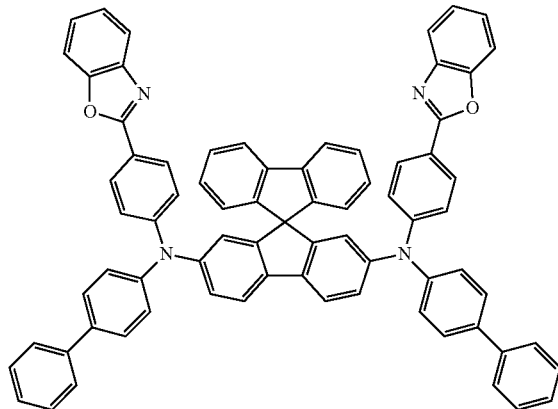
63
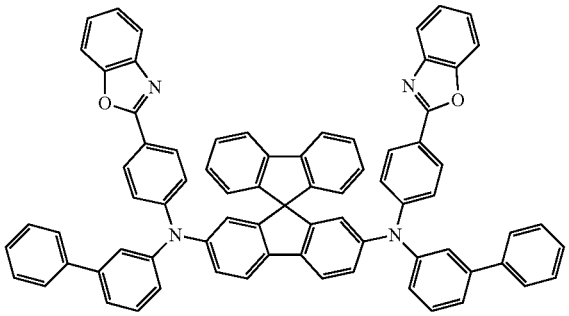
64
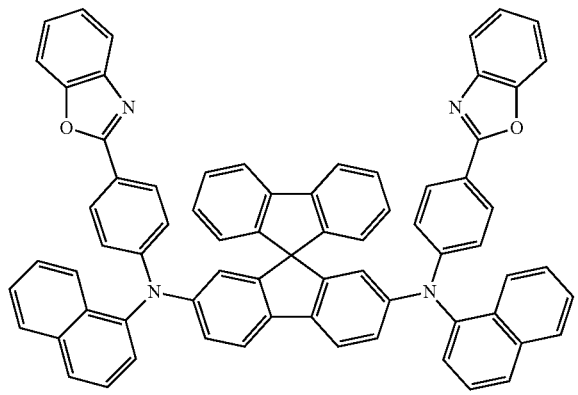
65
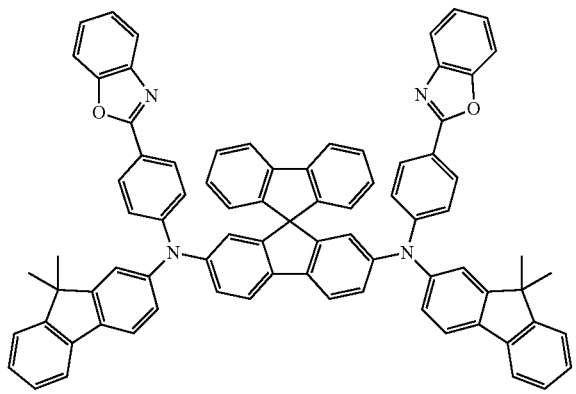
66

67 68
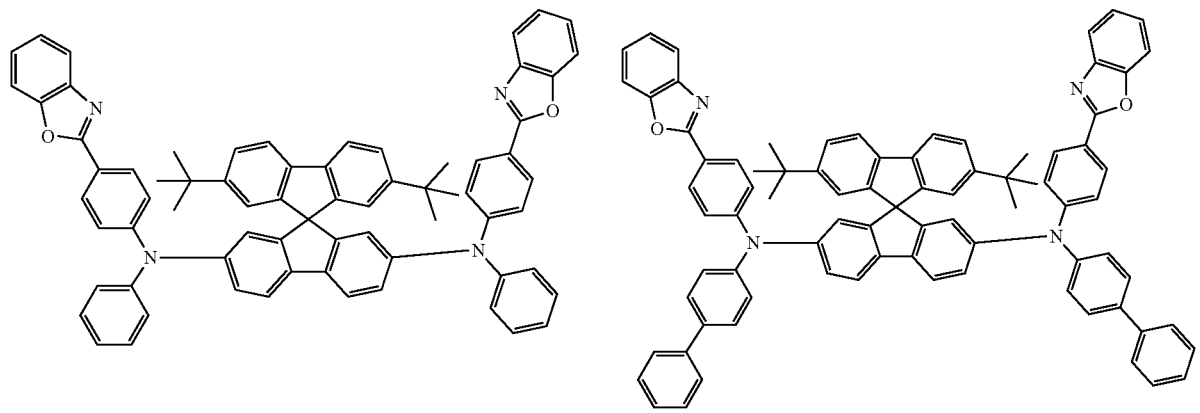
69 70
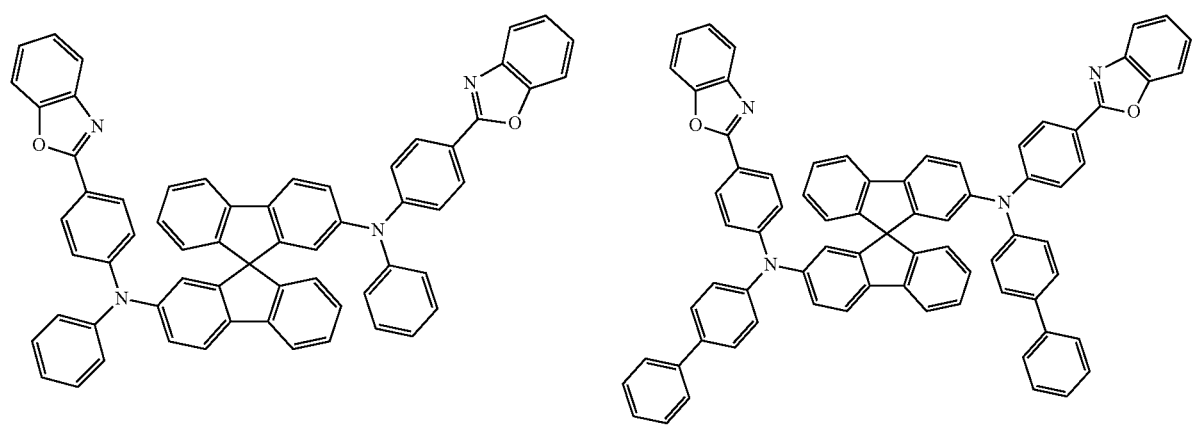
71
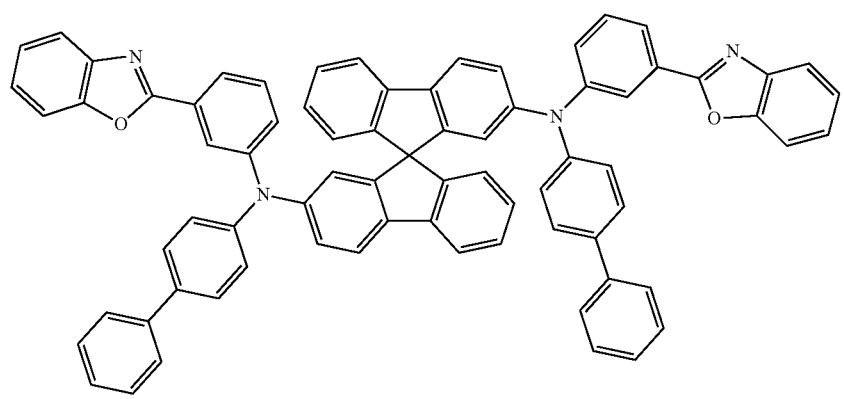

-continued
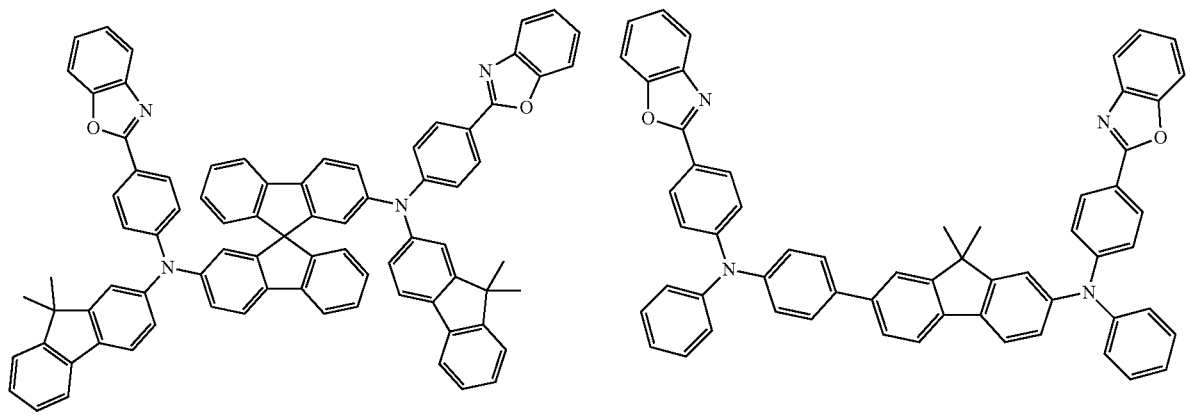
72
73
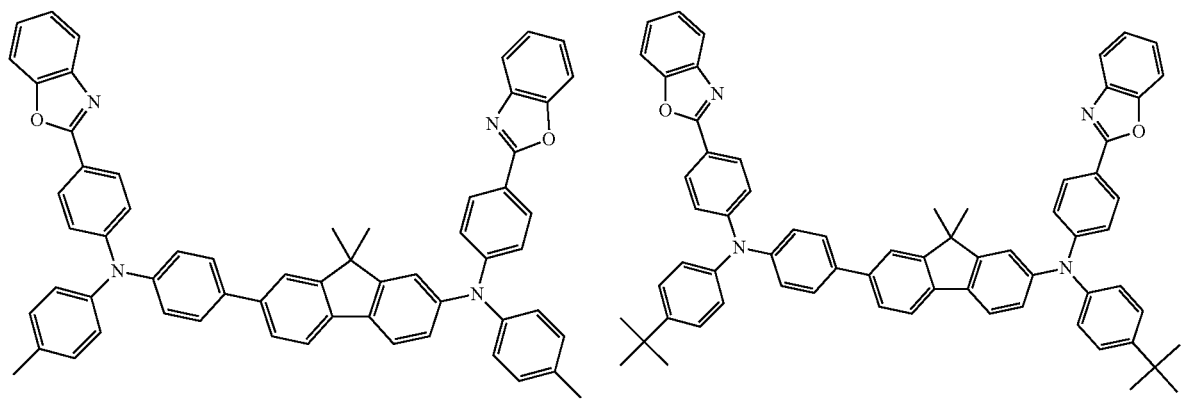
74
75
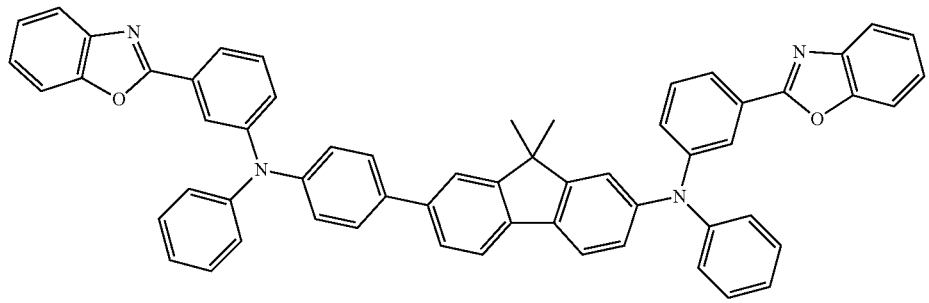
76
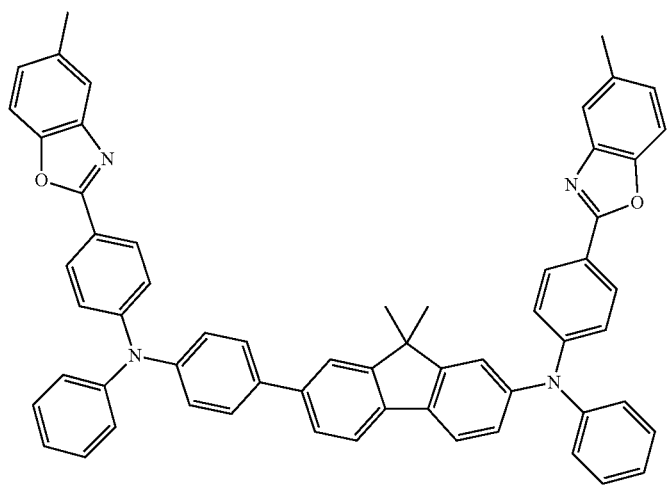
77

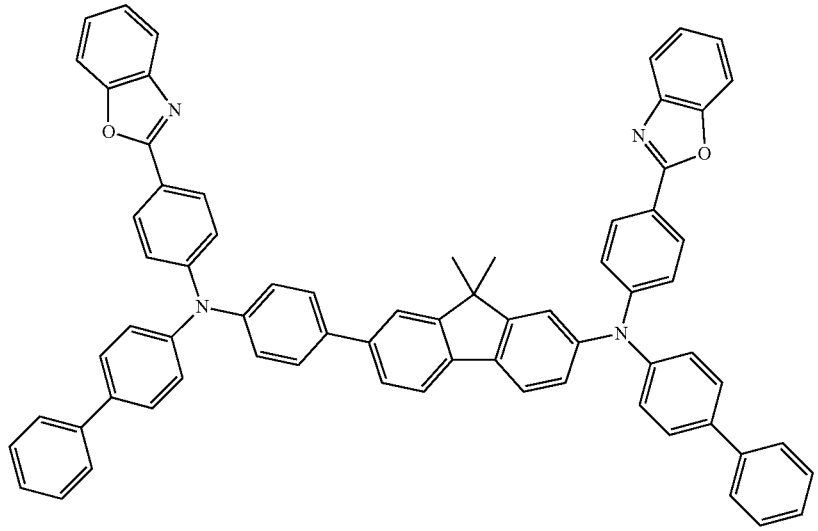
78
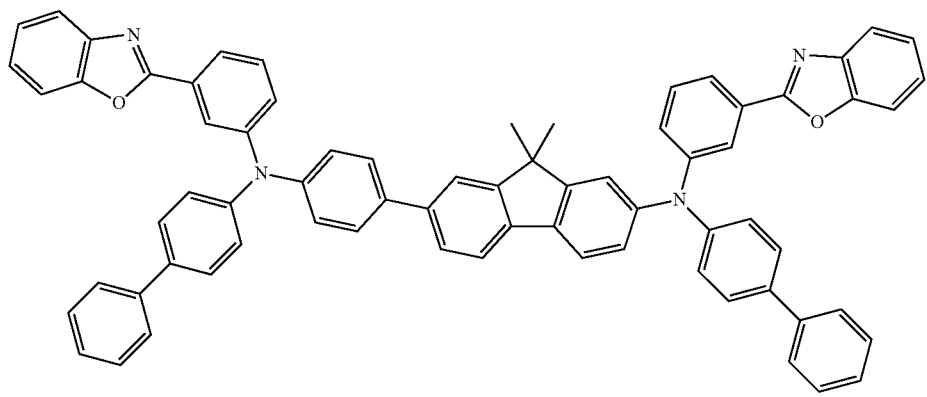
79
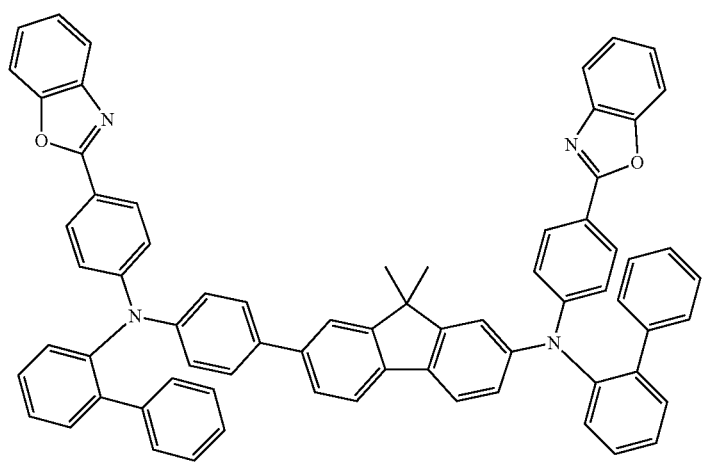
80

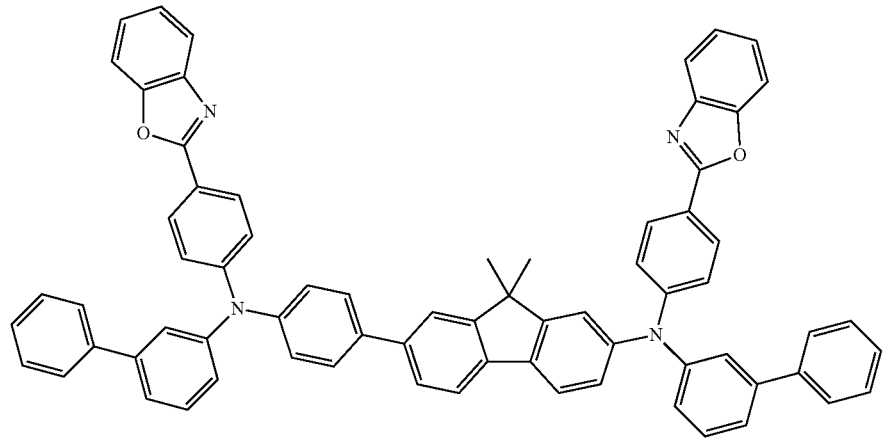
81
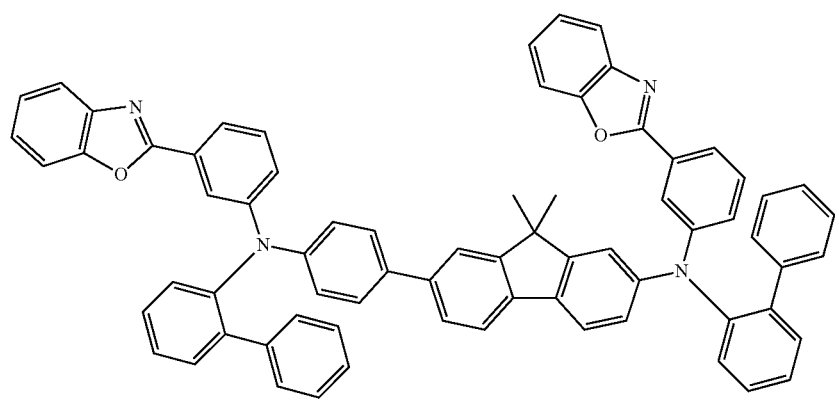
82
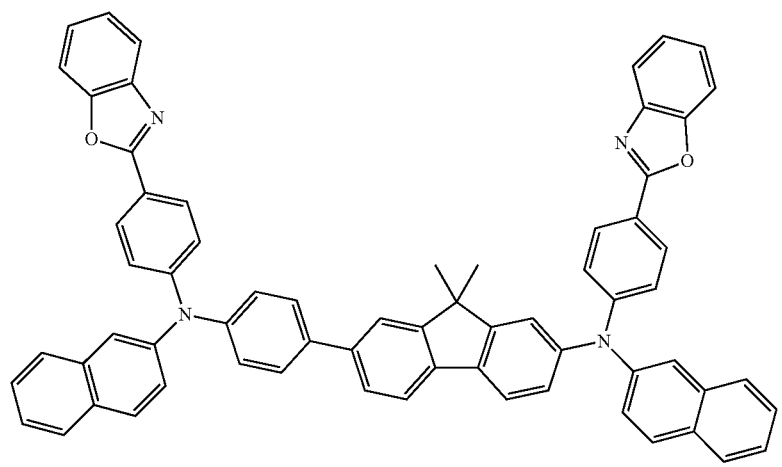
83

84
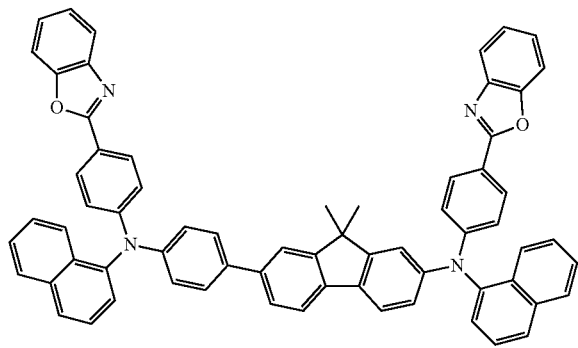
85
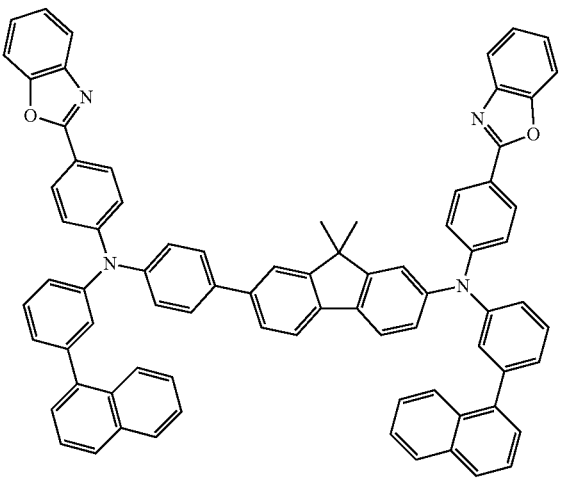
86
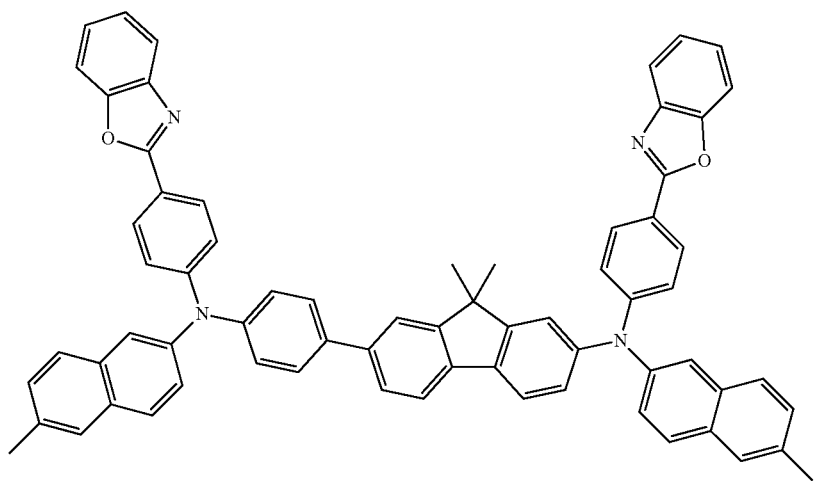
87
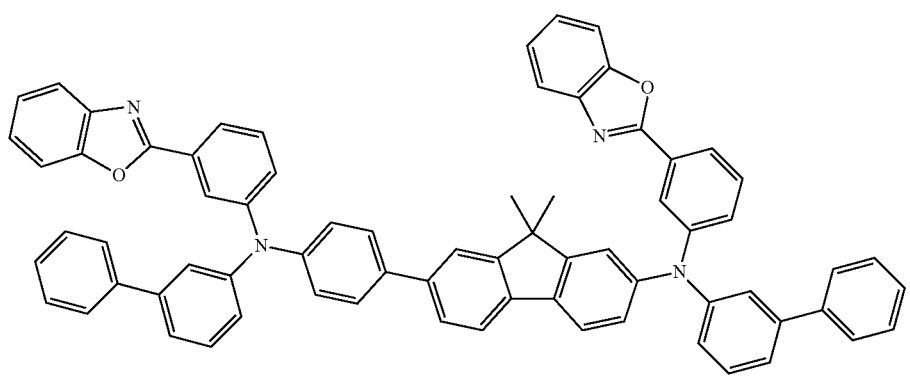

-continued
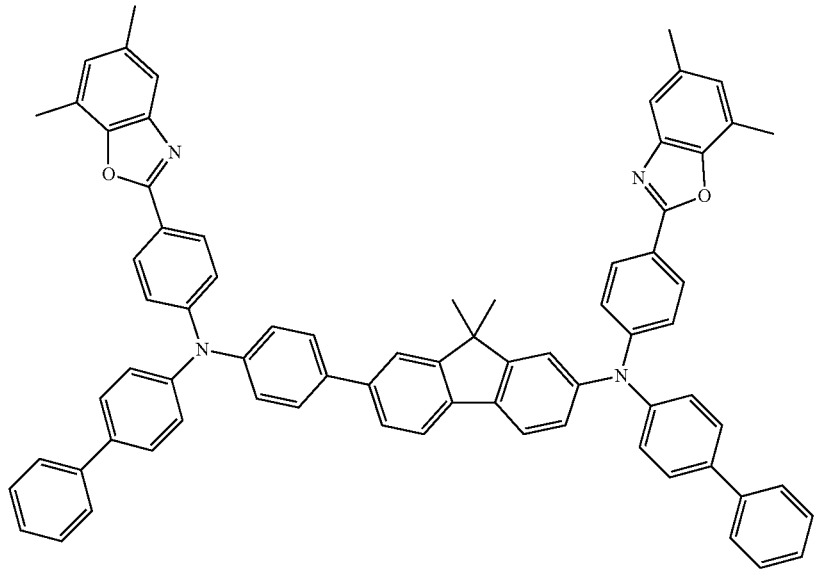
88
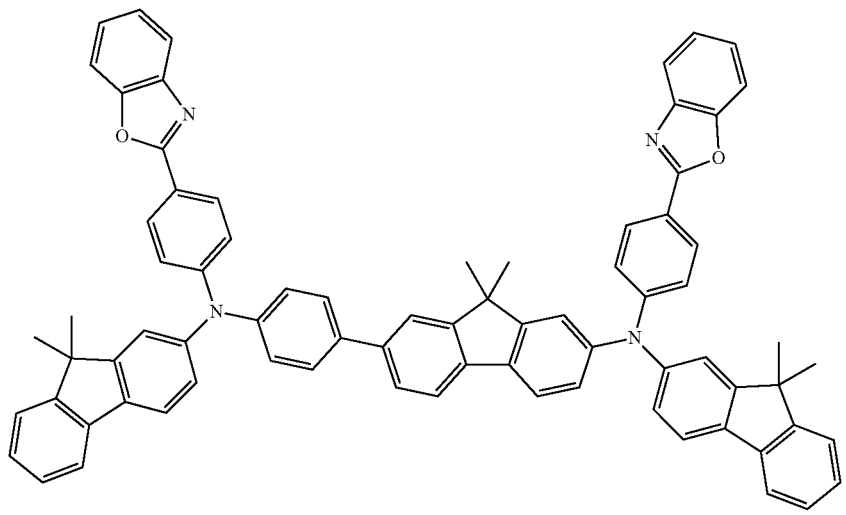
89
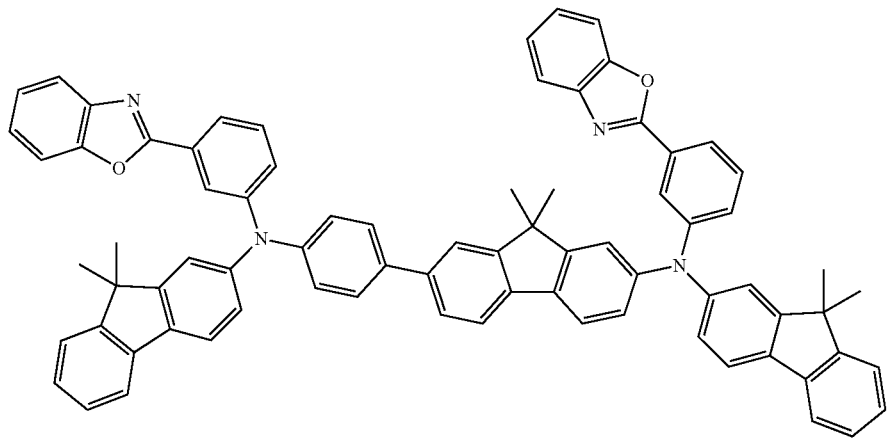
90

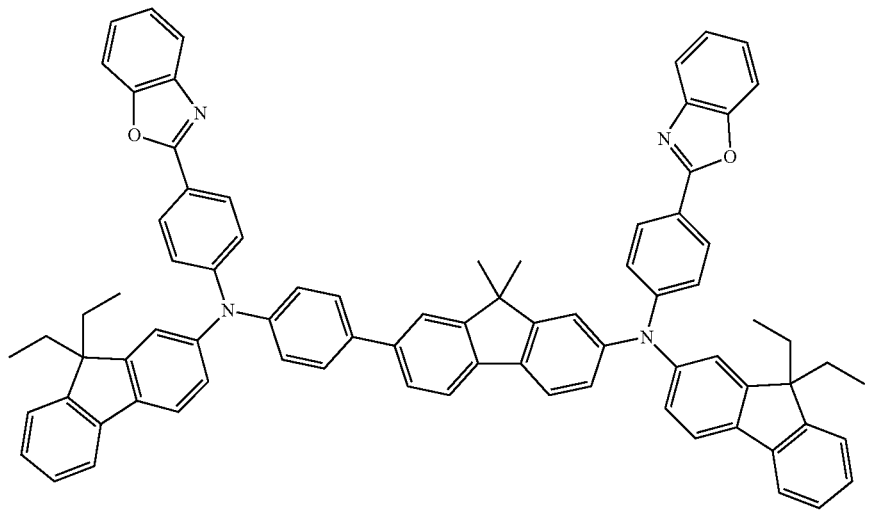
91
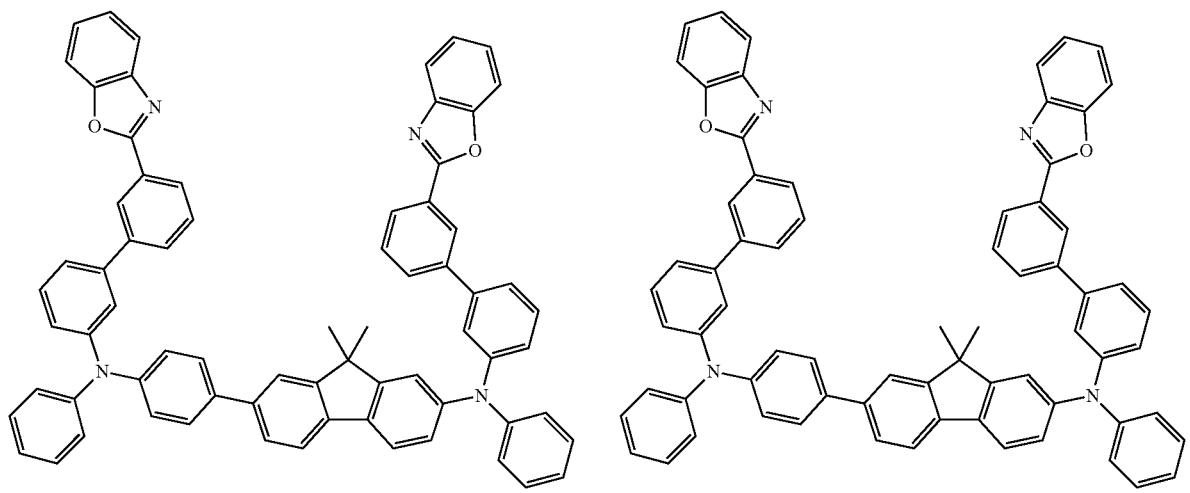
92
93
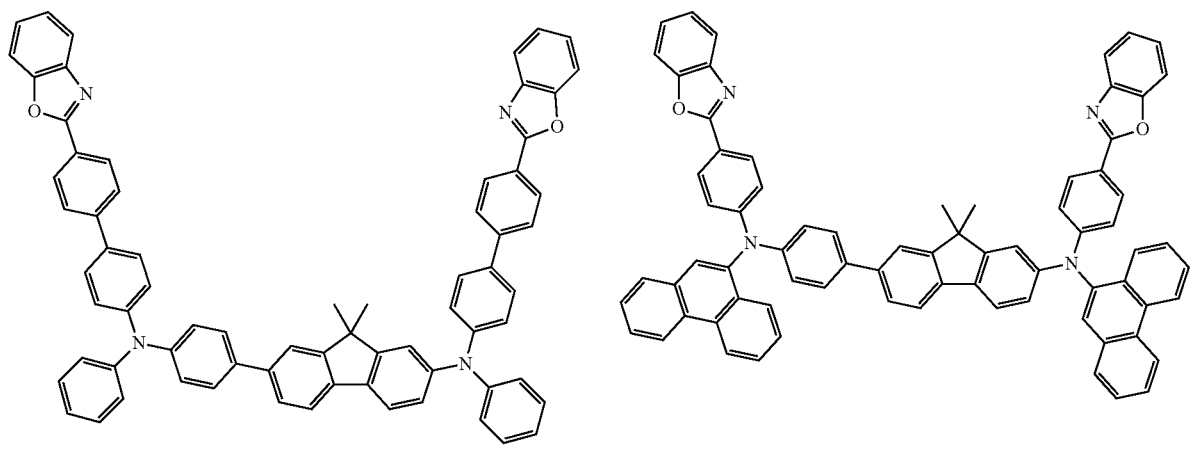
94
95

96
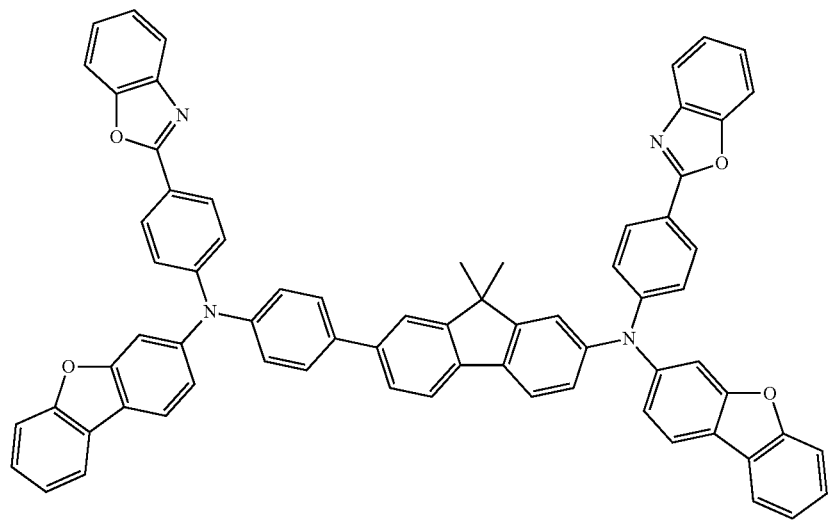
97
98
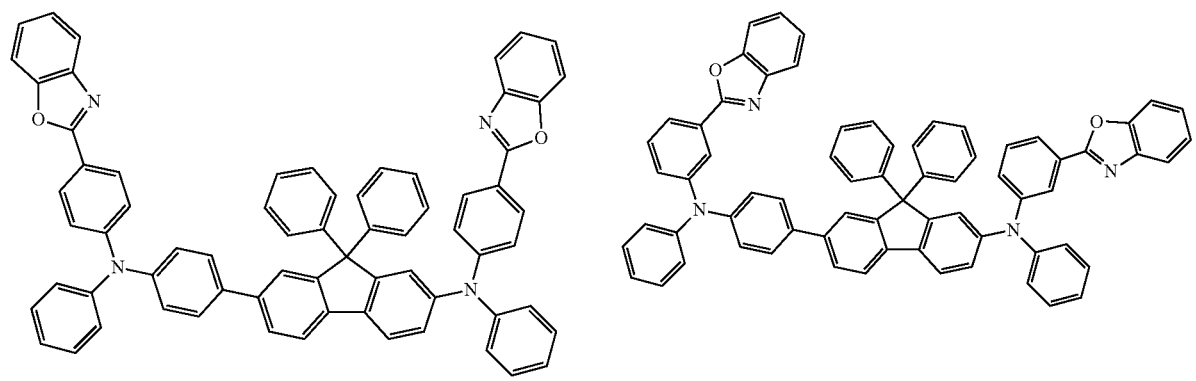
99
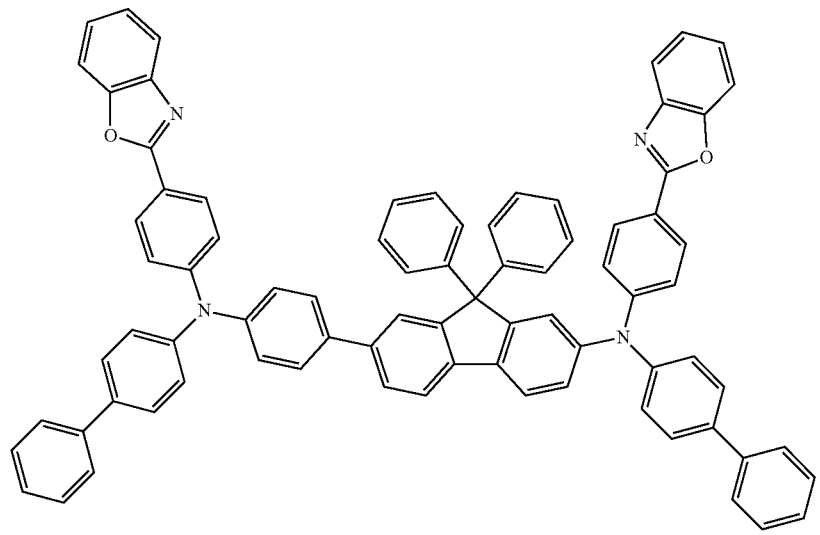

-continued
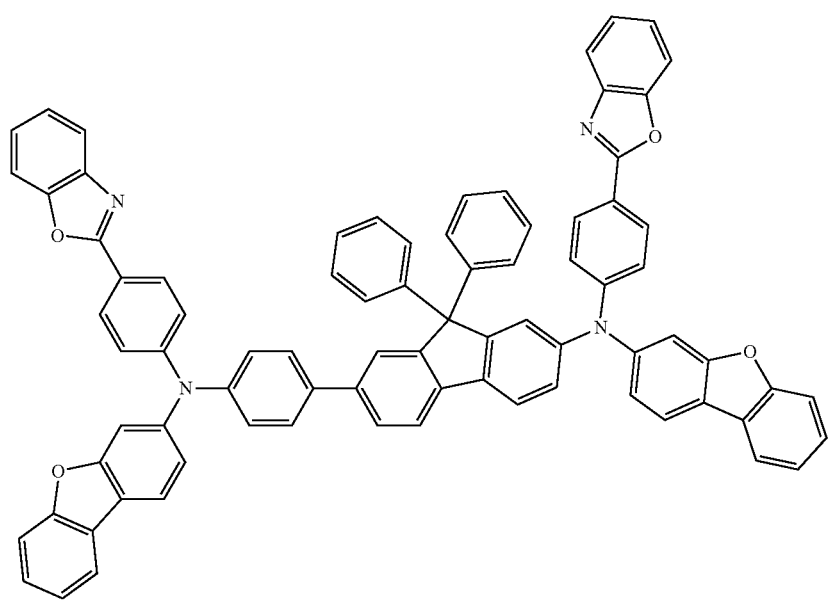
100
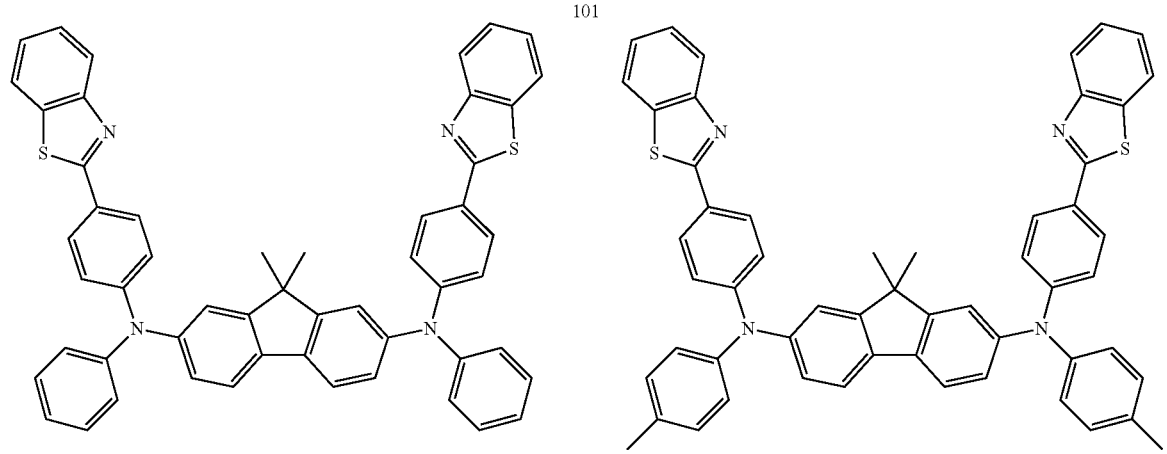
101
102
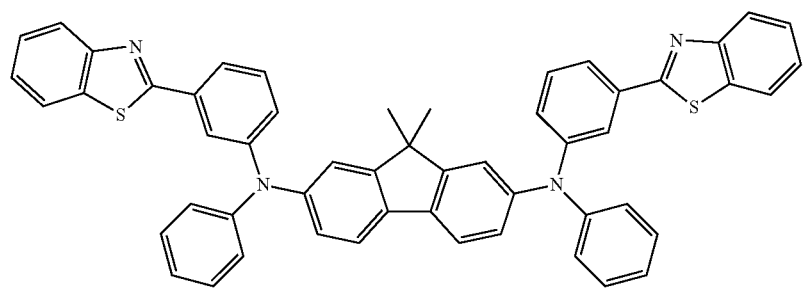
103

-continued
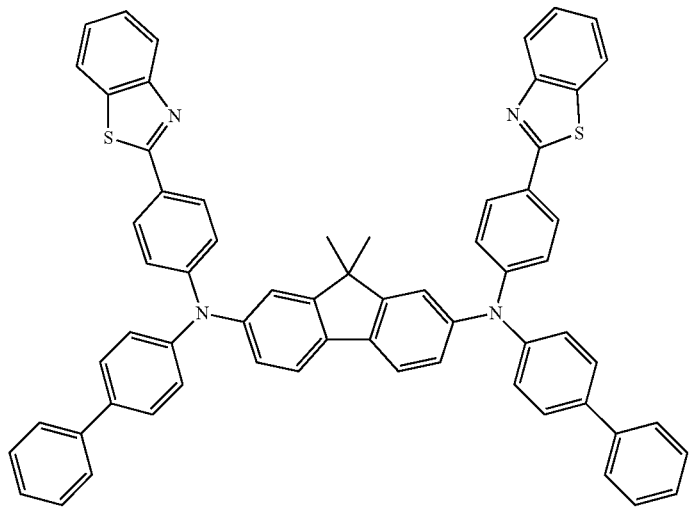
104
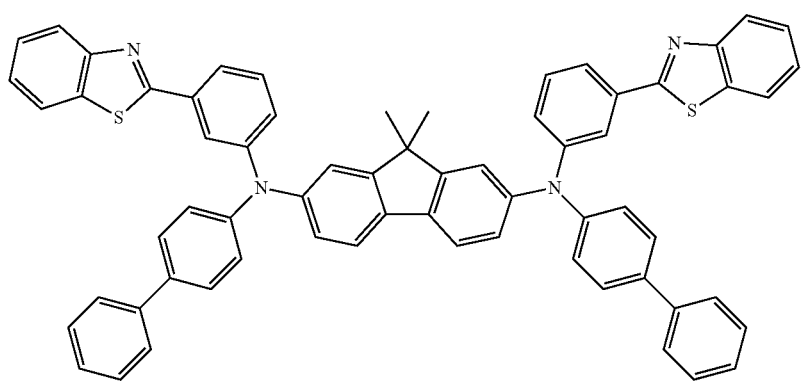
105
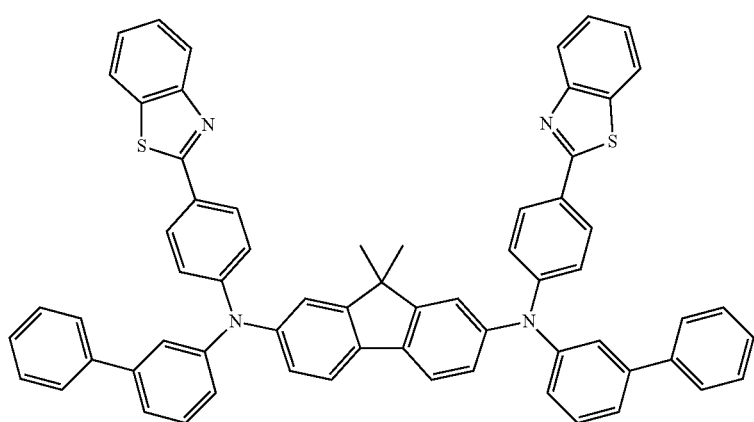
106

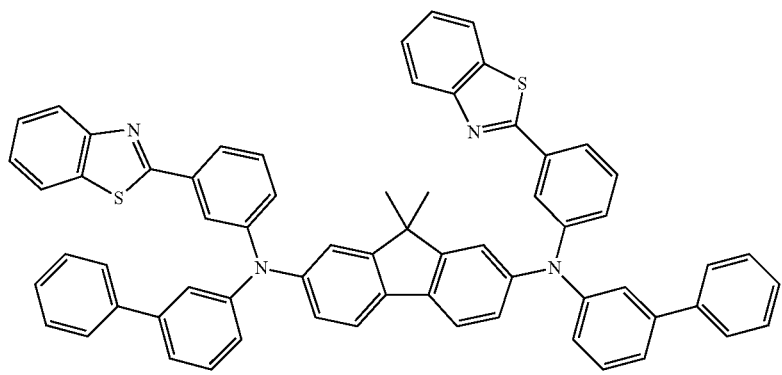
107
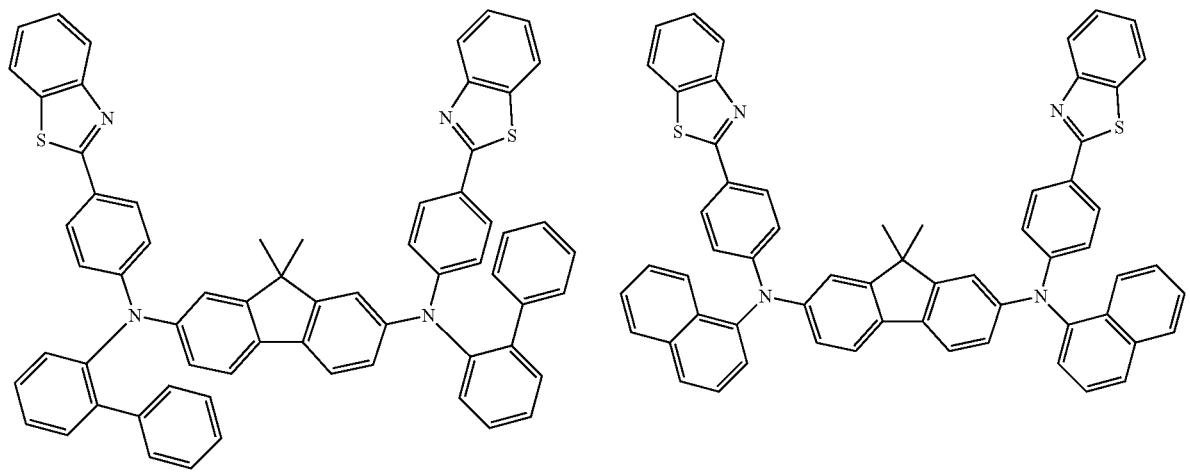
108 109
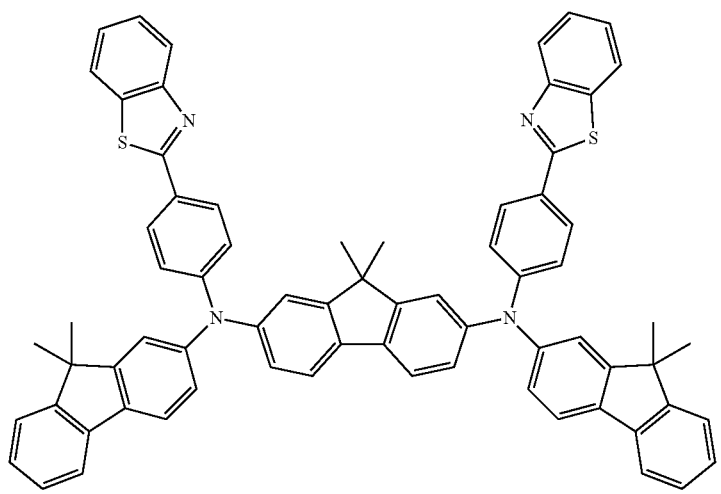
110

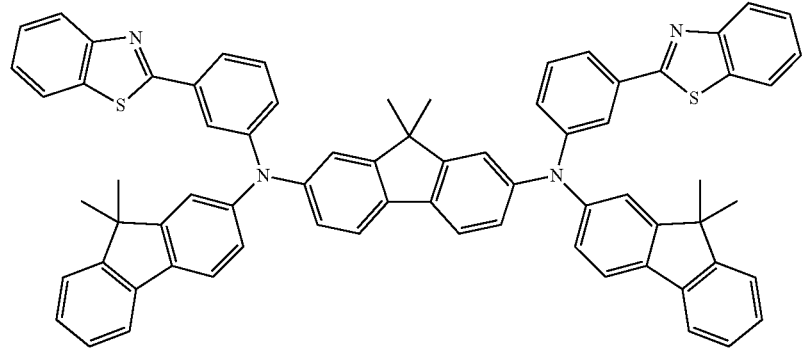
111
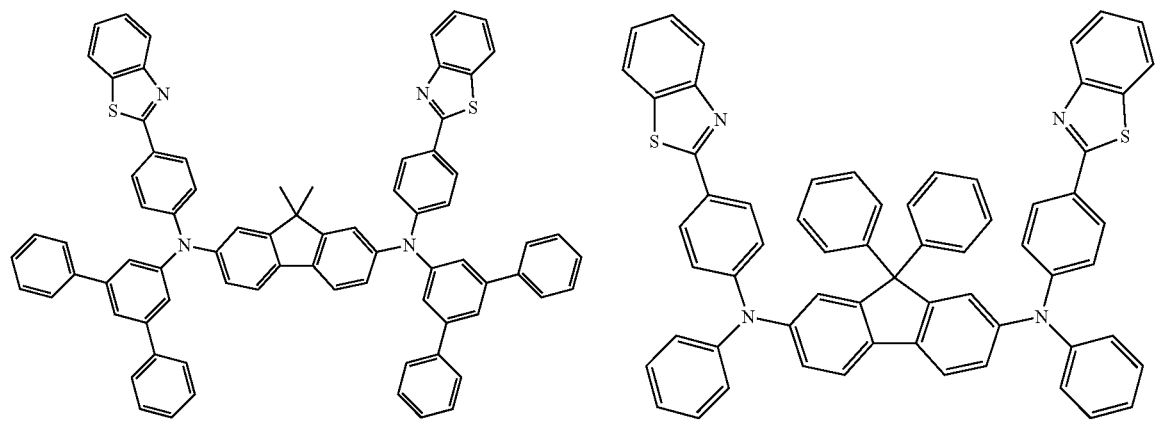
112
113
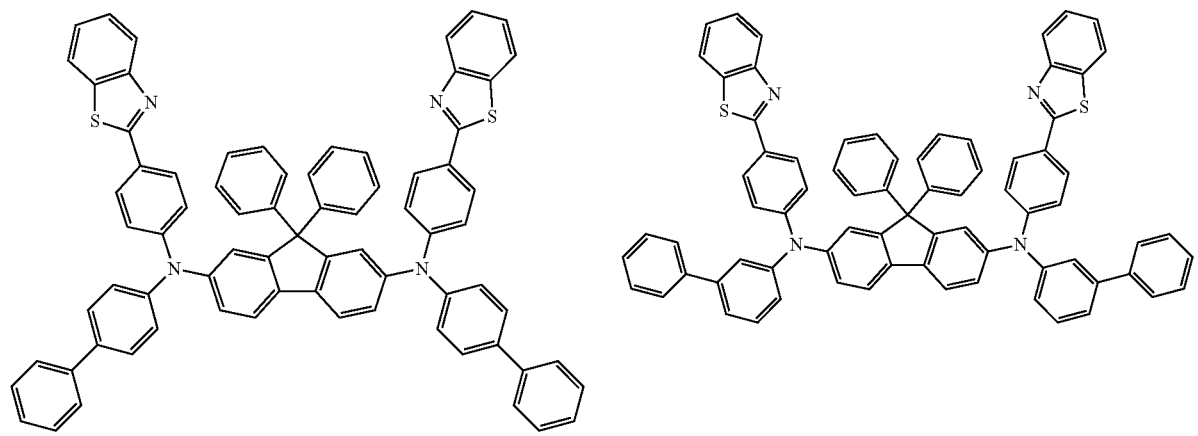
114
115

-continued
116
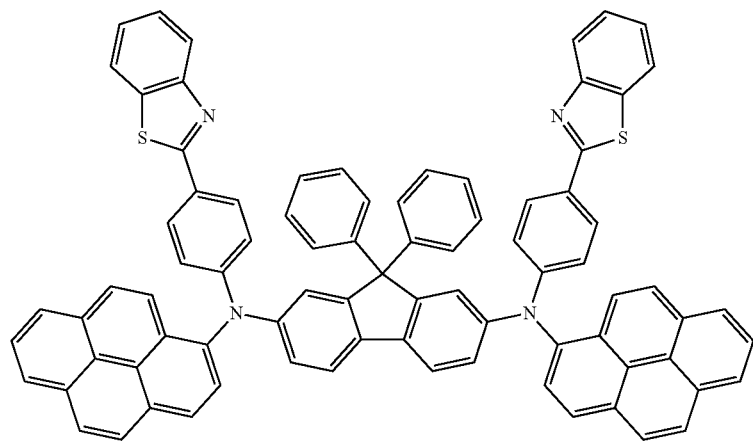
117
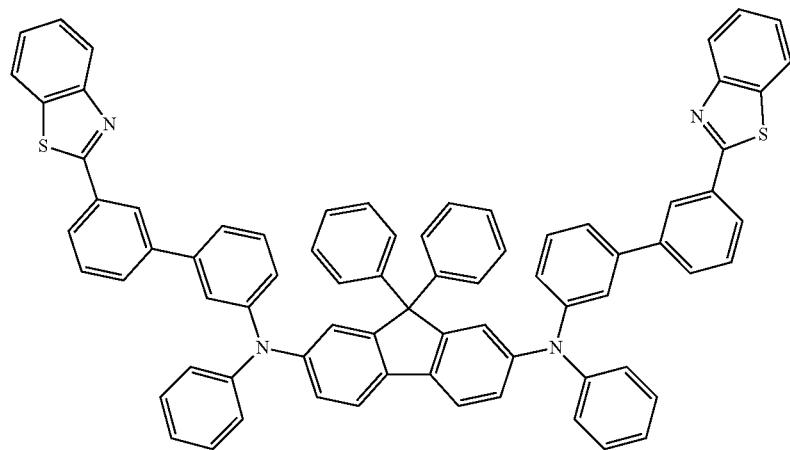
118 119
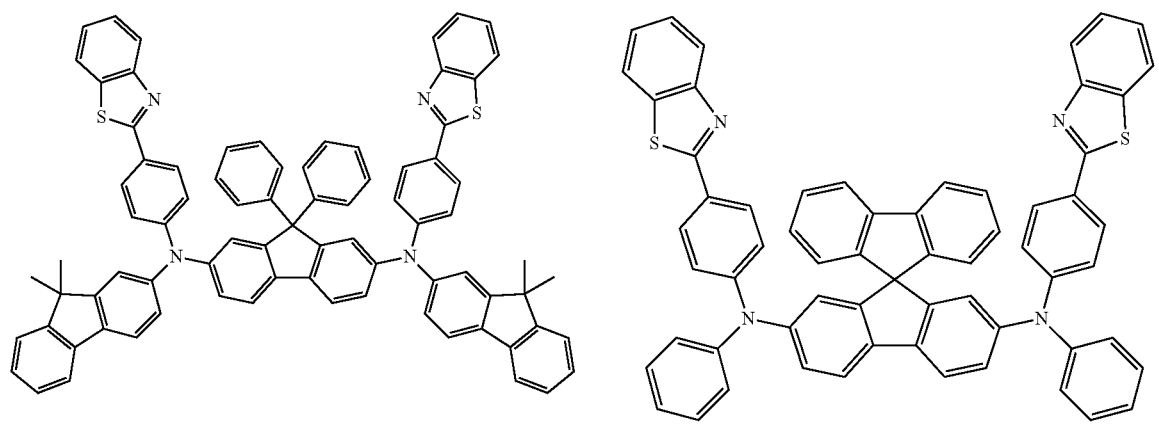

-continued
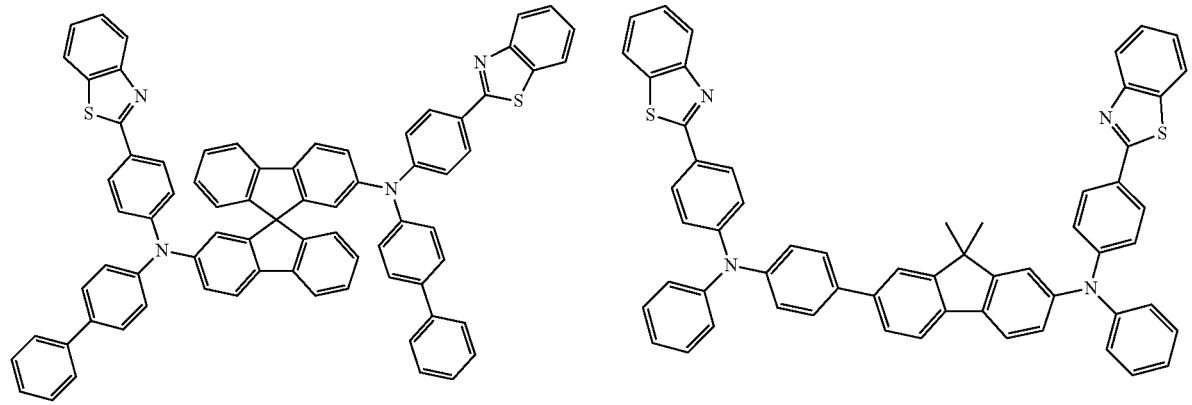
120
121
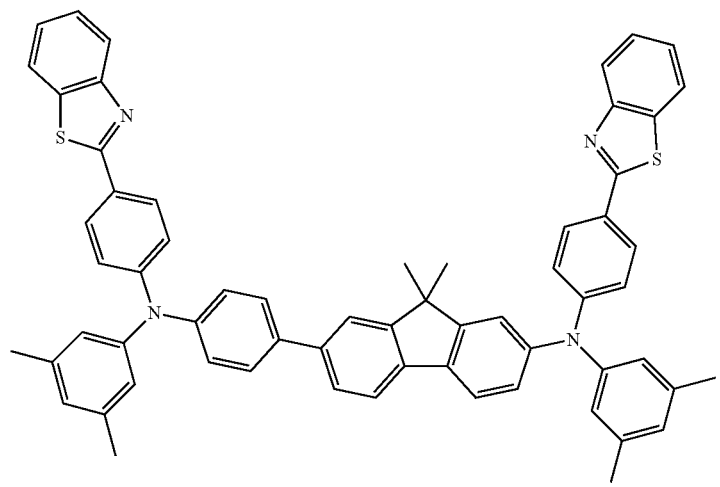
122
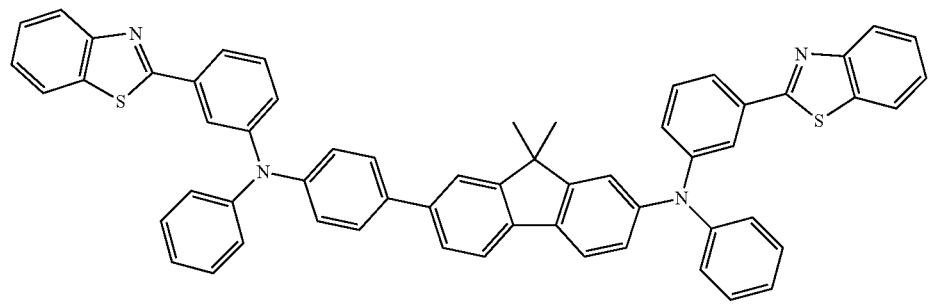
123

-continued
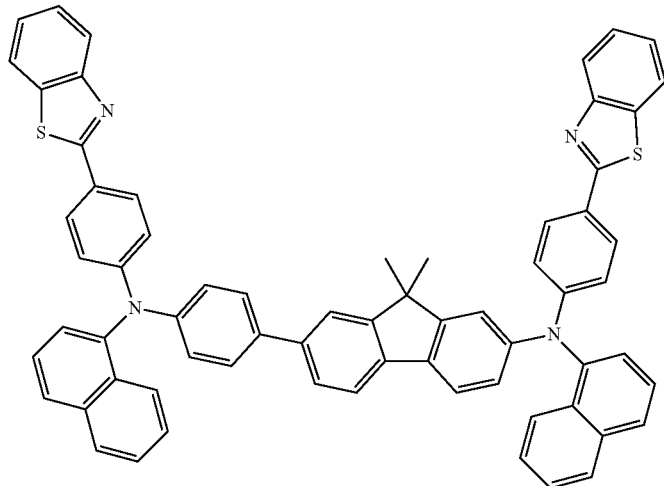
124
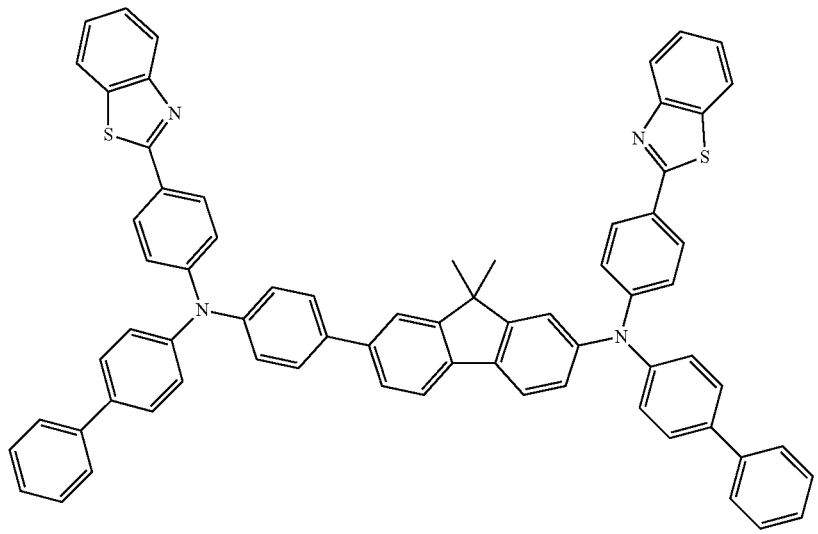
125
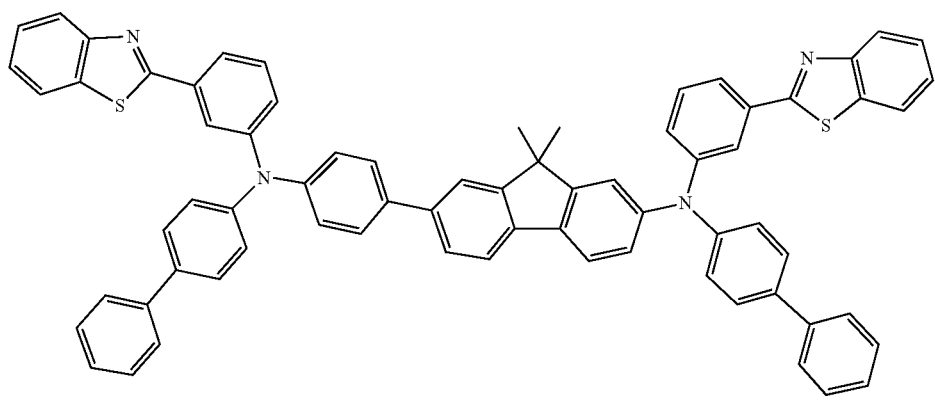
126

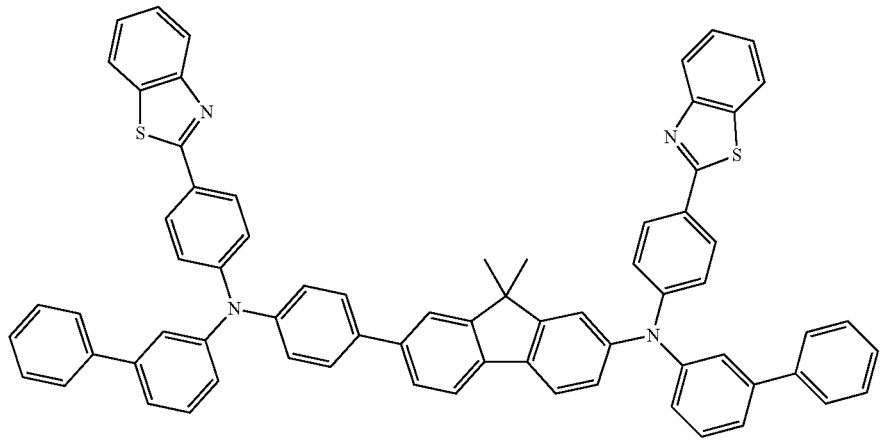
127
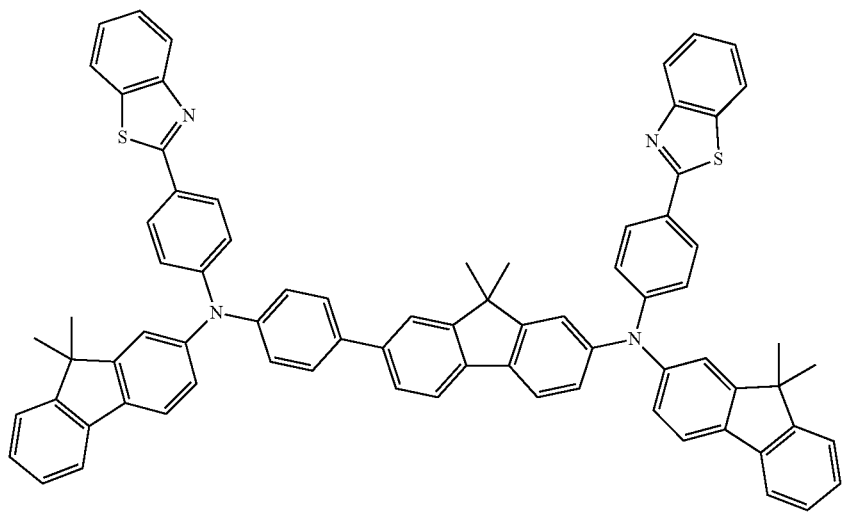
128
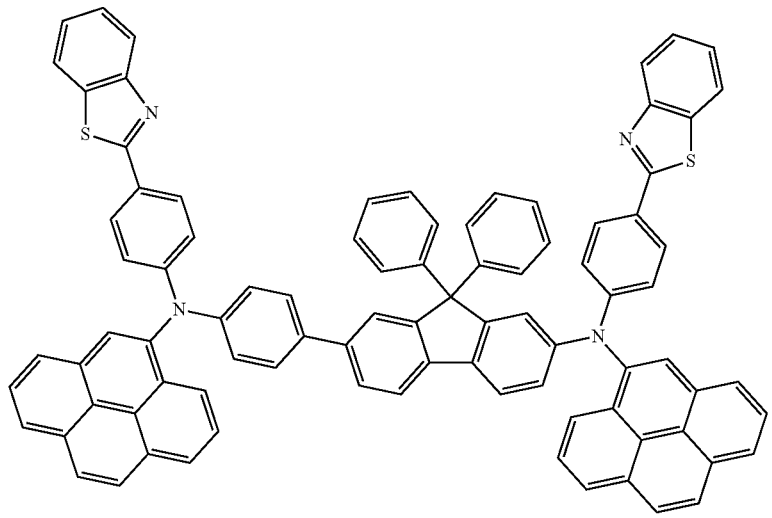
129

130
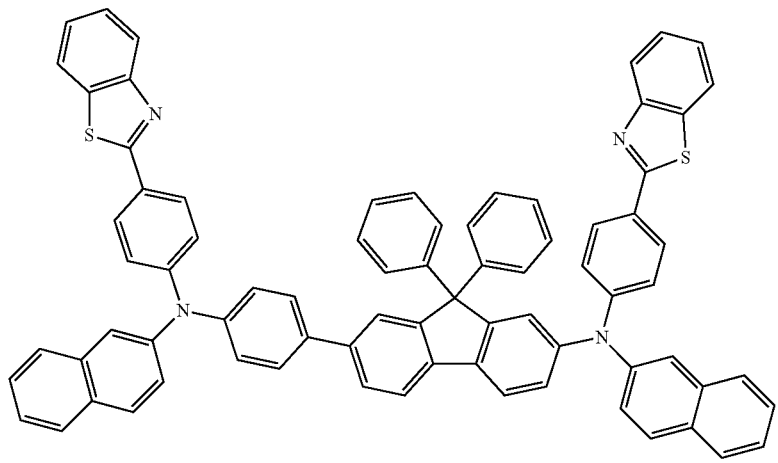
131
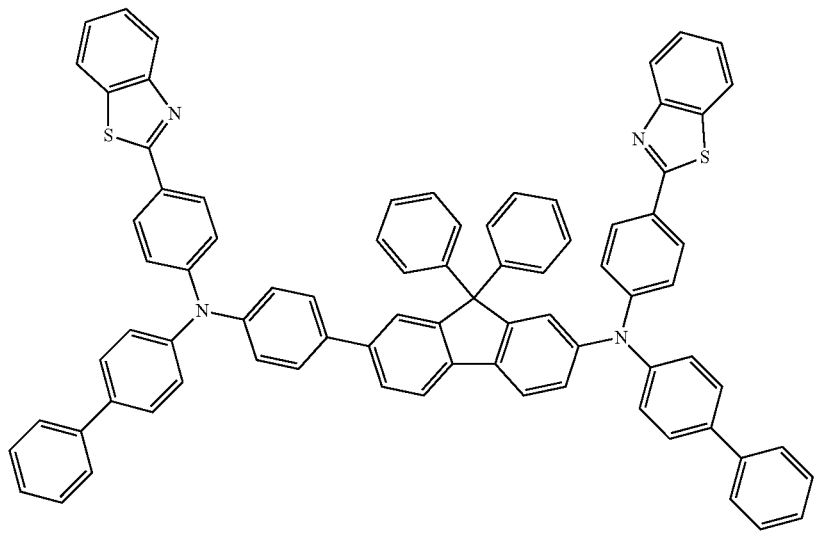
132
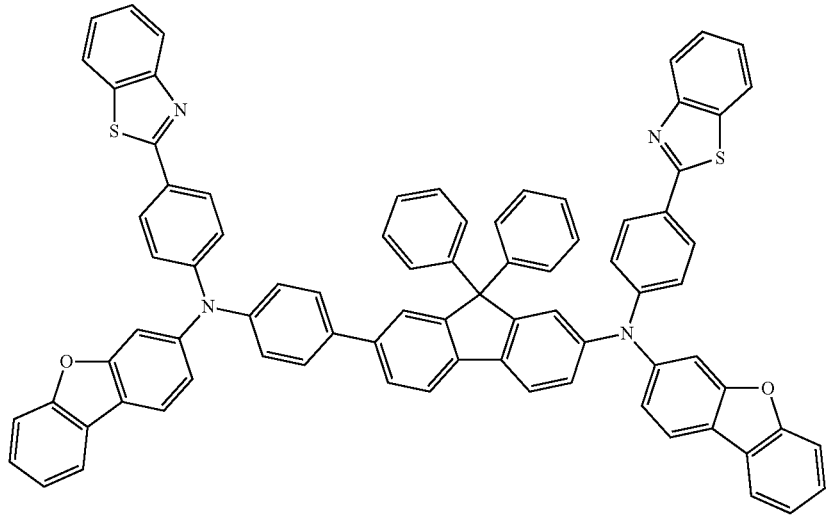

133 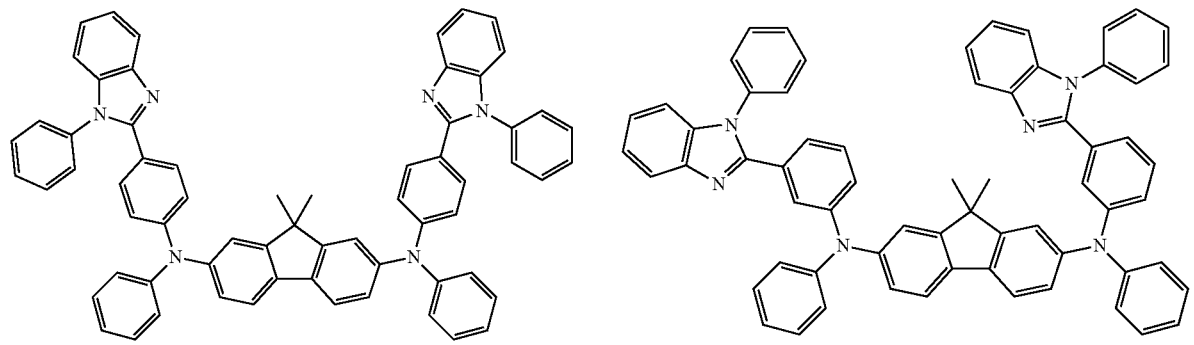 134
135 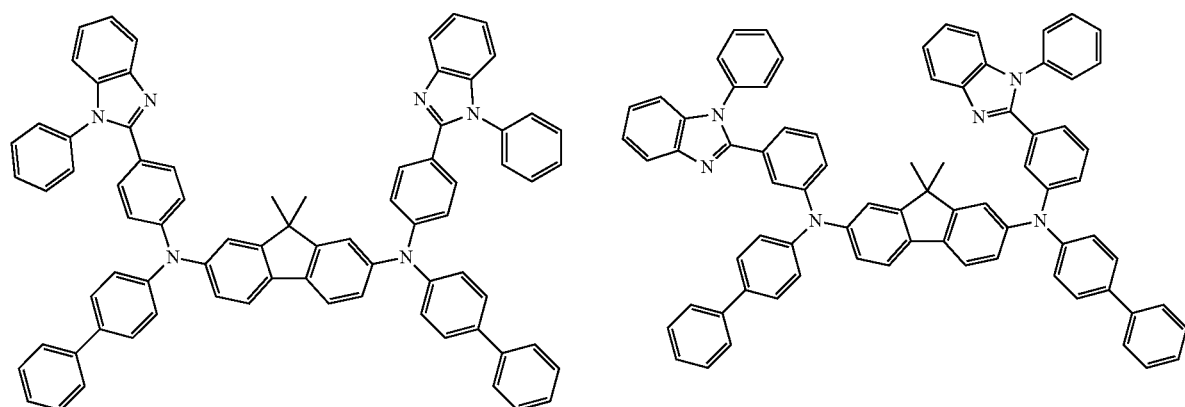 136
137 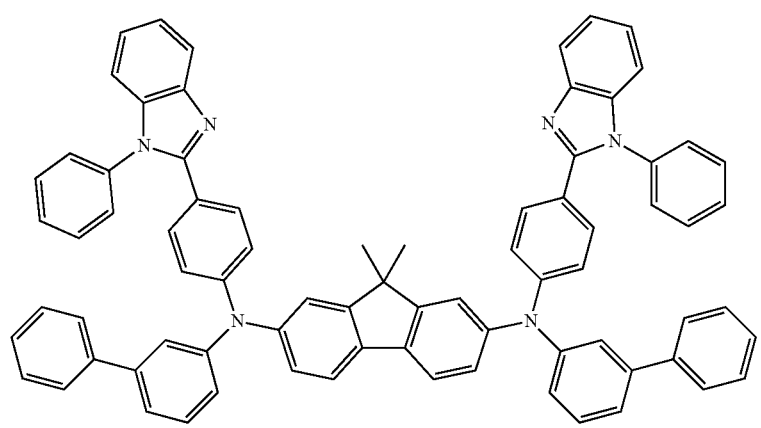

138
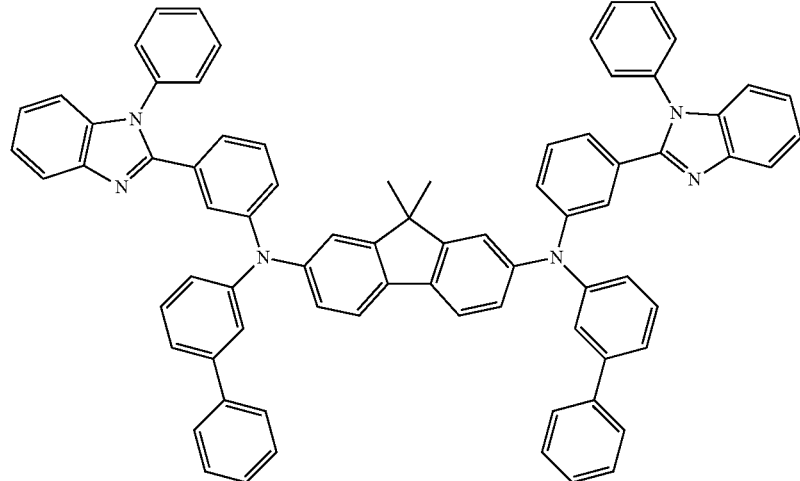
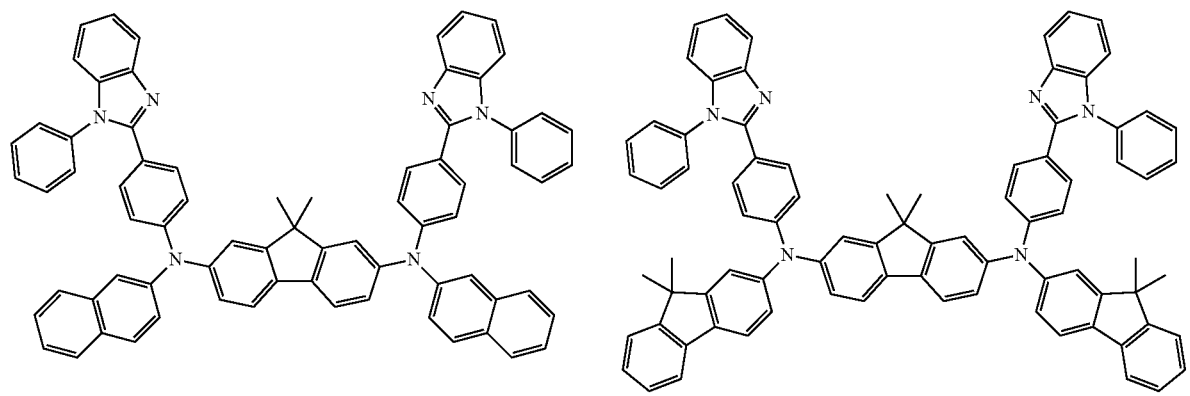
139
140
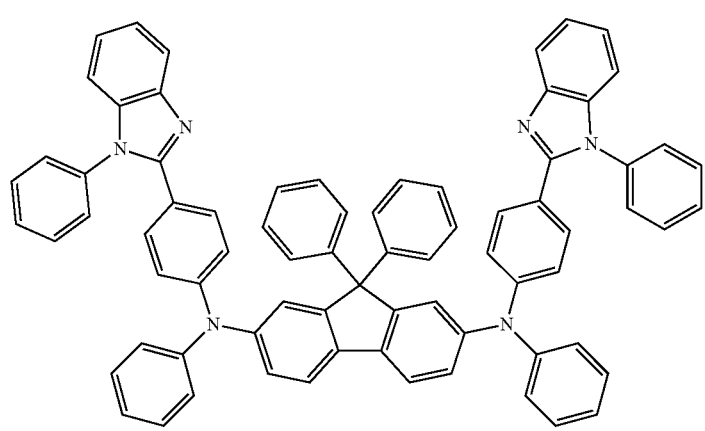
141

142
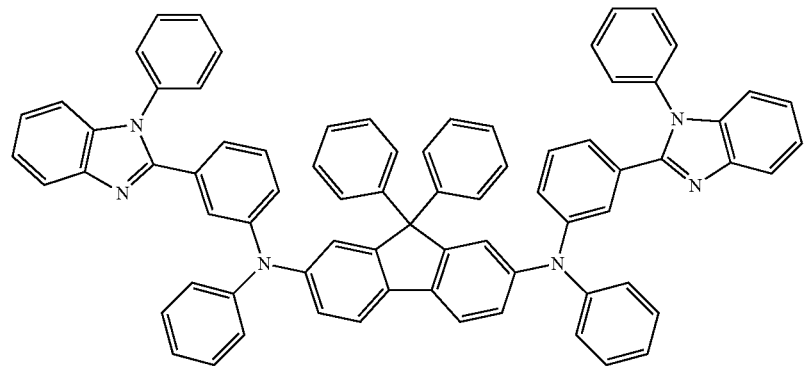
143
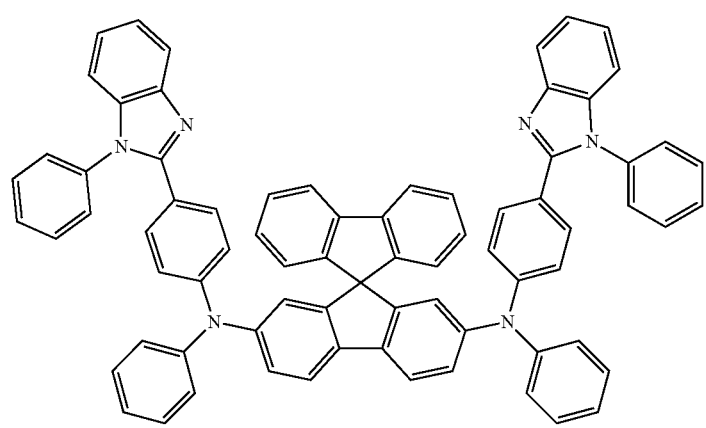
144
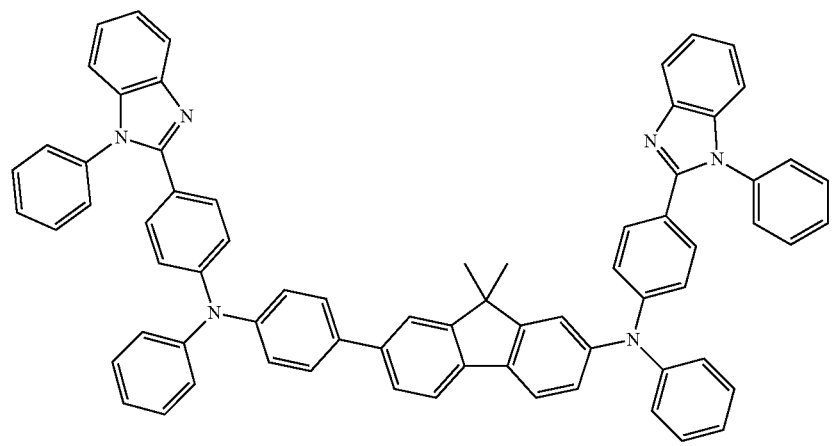

145
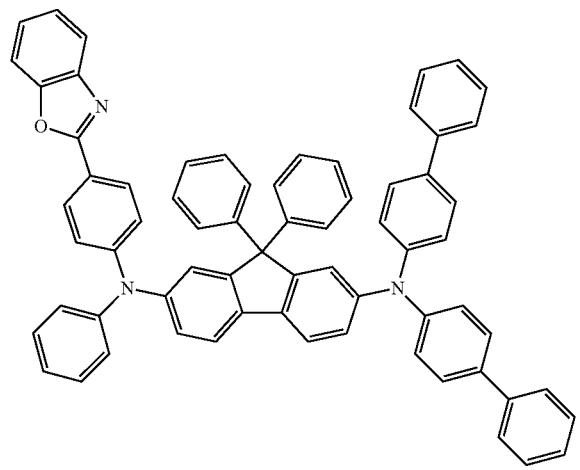
146
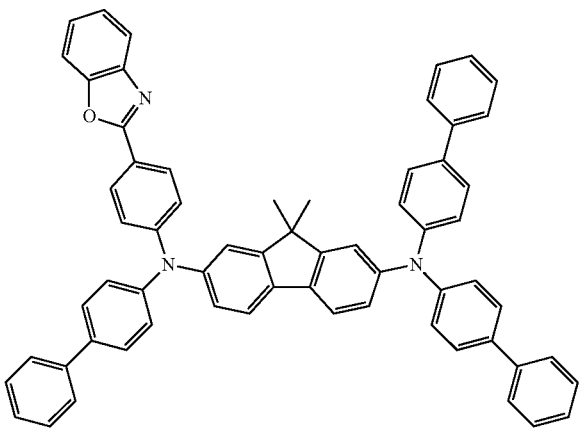
147
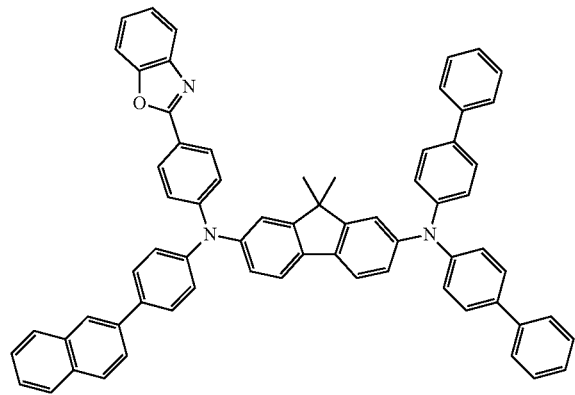
148
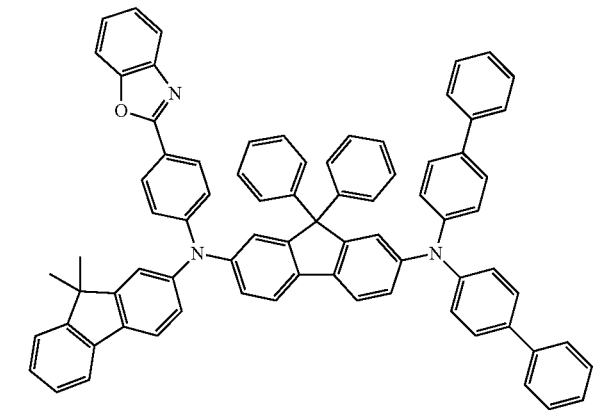
149
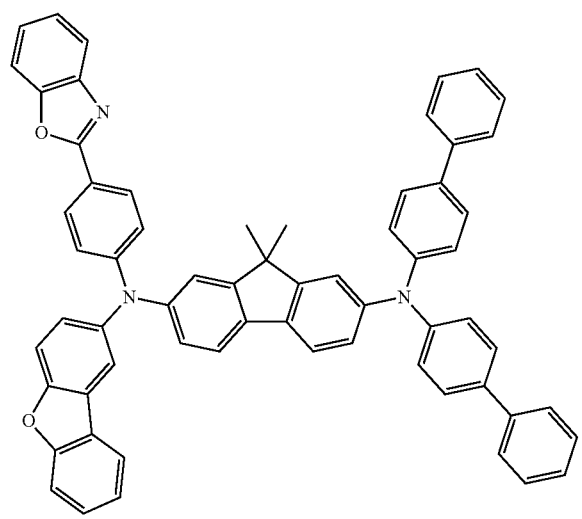
150
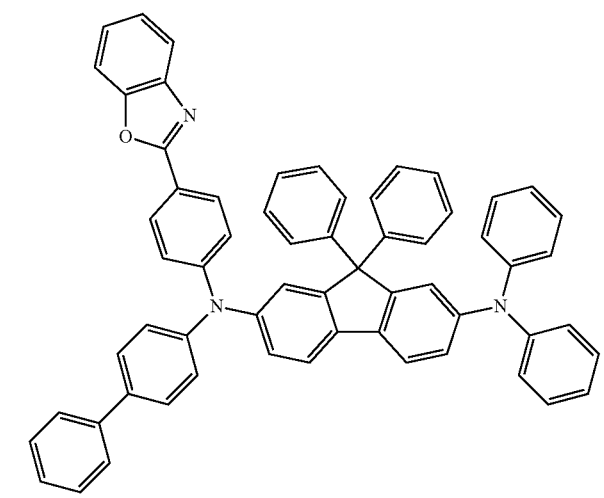

151

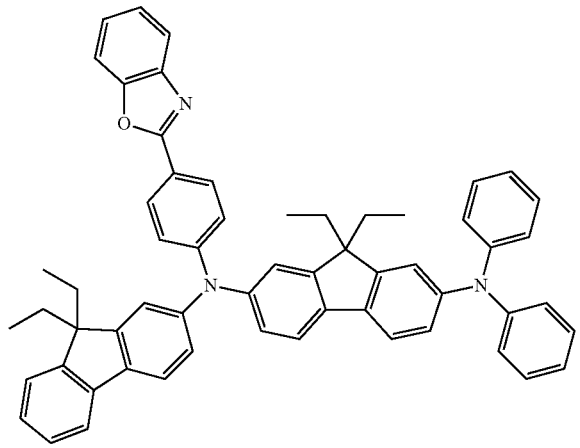

152

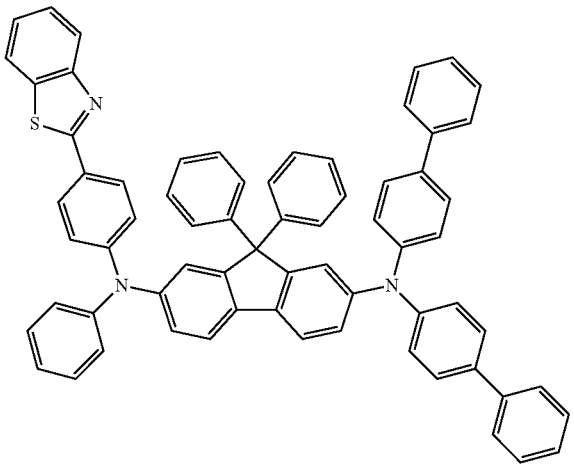

153

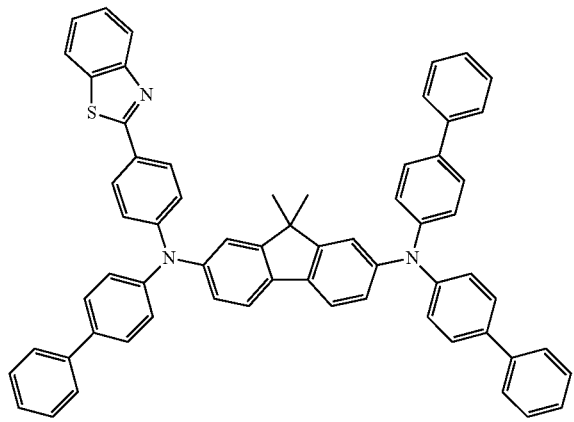

154

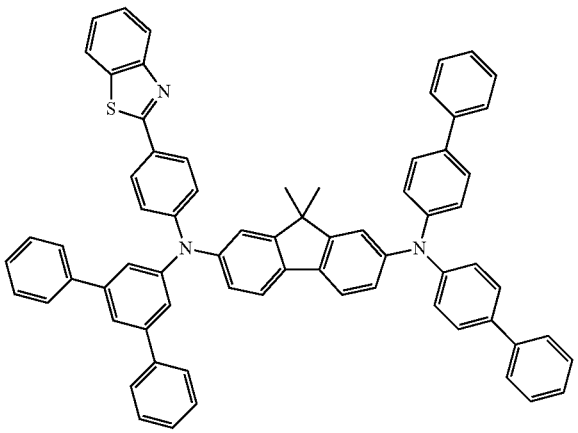

155

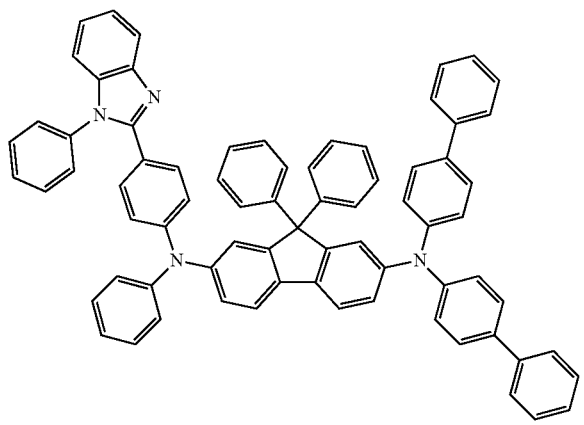

156

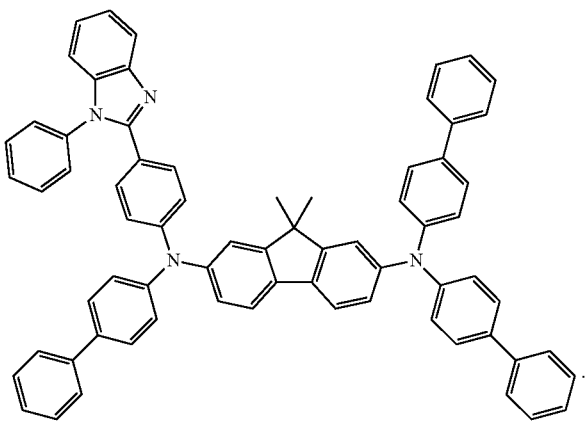

Some specific chemical structures of the amine derivatives of Formula I described in the present disclosure are enumerated above, but the present disclosure is not limited to the listed chemical structures, and the groups based on the structure represented by Formula I and limited by the substituents as defined above should be included therein.

The organic electroluminescent device of the present disclosure comprises an anode, an organic layer, a cathode and a light extraction layer, the organic layer being located between the anode and the cathode, and the light extraction layer being located on a side of the cathode away from the anode.

The light extraction layer of the organic electroluminescent device of the present disclosure may have a single layer structure or have a multilayer structure having two or more layers. The light extraction layer of the present disclosure comprises the amine derivative of the present disclosure. There is no particular limitation on the content of the amine derivative, and it can be appropriately adjusted as needed.

The organic layer of the organic electroluminescent device of the present disclosure may comprise any one or more selected from the group consisting of a hole injection layer, a hole transport layer, an electron blocking layer, a light emitting layer, a hole blocking layer, an electron transport layer, an electron injection layer or a buffer layer between an anode and a hole injection layer. The film thickness of each layer is not particularly limited. Generally, if the film is too thin, the film is liable to produce defects such as pinholes, etc., if the film is too thick, the driving voltage of the organic electroluminescent device is increased and the luminous efficiency is decreased. Therefore, the film thickness is preferably from 0.1 nm to 10 μm, more preferably from 0.5 nm to 0.5 μm.

The device structure of the organic electroluminescent device of the present disclosure is preferably:

substrate/anode/hole transport layer/light emitting layer/electron transport layer/metal cathode/light extraction layer; or substrate/anode/hole transport layer/light emitting layer/electron transport layer/electron injection layer/metal cathode/light extraction layer; or substrate/anode/hole transport layer/light emitting layer/hole blocking layer/electron transport layer/metal cathode/light extraction layer; or substrate/anode/hole injection layer/hole transport layer/light emitting layer/electron transport layer/electron injection layer/metal cathode/light extraction layer; or substrate/anode/hole injection layer/hole transport layer/light emitting layer/hole blocking layer/electron transport layer/electron injection layer/metal cathode/light extraction layer.

The organic electroluminescent device of the present disclosure can be produced by a known method using known materials. However, the structure of the organic electroluminescent device is not limited thereto.

The substrate according to the present disclosure is preferably a glass plate, a quartz plate, a polymer plate, etc., but is not limited thereto. The glass includes soda lime glass, lead glass, aluminosilicate glass, borosilicate glass, barium borosilicate glass, etc. The polymer includes polycarbonate, polyarylate, polyethersulfone, polypropylene, polyvinyl fluoride, polyvinyl chloride, etc.

The anode of the present disclosure has a function of injecting holes into the hole transport layer, and the anode material is required to have a high work function, and generally a material having a work function of 4.5 eV or more is effective. Since the organic electroluminescent device of the present disclosure is a top emitting device, it is required that the anode material have a higher reflectivity and a lower absorptivity in the visible light range. The anode material of the present disclosure may be selected from one or more of the following materials, a metal oxide, a metal, a metal alloy, and a polymer, etc. Specifically, indium tin oxide (abbreviation: ITO), indium zinc oxide (abbreviation: IZO), aluminum zinc oxide (abbreviation: AZO), indium oxide, zinc oxide, Ag, Au, Al, Cu, Ni, Mo, Ti, Zn, Pd, Pt, polypyrrole, etc., but is not limited thereto. The film thickness of the anode varies depending on the materials, and is usually selected from the range of 10 nm to 1 μm, preferably 10 nm to 200 nm. The anode of the present disclosure may be a single-layer structure or a multilayer structure with two or more layers, and the anode material contained in each layer may be a single material or a mixed material.

The buffer layer of the present disclosure refers to a very thin layer of insulating material evaporated on the anode, which can improve hole injection efficiency and lower the driving voltage. Specifically, the buffer layer may be a material selected from the group consisting of silica, carbon tetrafluoride, lithium fluoride, etc., but is not limited thereto.

The hole injection layer of the present disclosure has a function of lowering the barrier of the interface between the hole transport layer and the anode in the organic electroluminescent device, improving the hole injection efficiency, and prolonging the life of the device. The hole injection material of the present disclosure is preferably a material having good hole injection properties, and can be selected from one or more of the following materials: a metal oxide such as molybdenum oxide, silver oxide, vanadium oxide, tungsten oxide, ruthenium oxide nickel oxide, copper oxide, titanium oxide, and aluminum oxide, etc., a low molecular organic compound such as phthalocyanine compound, aromatic amine derivative, and conjugated organic material containing polycyano groups, etc., and a polymer, and the like, but is not limited thereto. Specifically, it can be selected from the group consisting of molybdenum trioxide, silver oxide, vanadium pentoxide, tungsten trioxide, antimony oxide, nickel oxide, copper oxide, titanium dioxide, aluminum oxide, copper (II) phthalocyanine (abbreviation: CuPc), titanyl phthalocyanine (abbreviation: TiOPC), N,N'-bis(N,N'-diphenyl-4-aminophenyl)-N,N'-diphenyl-4,4'-diamino-1,1'-biphenyl, N4,N4,N4',N4'-tetrakis([1,1'-biphenyl]-4-yl)-[1,1'-biphenyl]-4,4'-diamine, 4,4'4"-tris(N,N-diphenylamino)triphenylamine (abbreviation: NATA), 4,4',4"-tris(N-(naphthalen-1-yl)-N-phenyl-amino) triphenylamine (abbreviation: 1T-NATA), 4,4',4"-tris[2-naphthylphenylamino]triphenylamine (abbreviation: 2T-NATA), 4,4',4"-Tris(N-3-methylphenyl-N-phenylamino) triphenylamine (abbreviation: m-MTDATA), N4,N4,N4',N4'-tetrakis (4-methoxyl)phenyl)-[1,1'-biphenyl]-4,4'-diamine (abbreviation: MeO-TPD), 2,7-bis[N,N-bis(4-methoxyphenyl)ammonia]-9,9-spirobis[9H-fluorene] (abbreviation: MeO-Spiro-TPD), N,N'-bis[4-di(m-tolypaminophenyl]-N,N'-diphenylbenzidine (abbreviation: DNTPD), 7,7,8,8-tetracyanoquinodimethane (abbreviation: TCNQ), 2,3,5,6-tetrafluoro-7,7',8,8'-tetracyanodimethyl p-benzoquinone (abbreviation: F4-TCNQ), pyrazolo[2,3-F][1,10] phenanthroline-2,3-dinitrile (abbreviation: PPDN), 1,4,5,8,9,11-hexaazabenzonitrile (abbreviation: HAT-CN), poly (N-vinylcarbazole) (abbreviation: PVK), poly(4-vinyltriphenylamine) (abbreviation: PVTPA), poly[N,N'-bis(4-butylphenyl)-N,N'-Bis(phenyl)benzidine] (abbreviation: Poly-TPD), poly(3,4-ethylenedioxythiophene)/poly(styrenesulfonic acid) (abbreviation: PEDOT/PSS), etc., but is not limited thereto. The hole injection layer of the present disclosure may be a single-layer structure or a multilayer structure with two or more layers, and the hole injection material contained in each layer may be a single material or a mixed material.

The hole transport layer of the present disclosure has an effect of improving the transport efficiency of holes in the device and blocking electrons in the light-emitting layer. The hole transport material of the present disclosure is preferably a material having good hole transport properties, and can be selected from one or more of the following materials: a small molecular material such as an aromatic amine derivative, a pyrazoline compound, a carbazole derivative, a hydrazone compound, a styrene compound, and a butadiene compound, etc., and a polymer material, but is not limited thereto. Specifically, it can be selected from the group consisting of N4,N4,N4',N4'-tetrakis([1,1'-biphenyl]-4-yl)-[1,1'-biphenyl]-4,4'-diamine, 4,4',4"-Tris(N,N-diphenylamino)triphenylamine (abbreviation: TDATA), 4,4',4"-tris[N-(3-methylphenyl)-N-phenylamino]triphenylamine (abbreviation:

MTDATA), N,N'-diphenyl-N,N'-diphenanthrene-9-yl-4,4'-benzidine (abbreviation: PPD), N, N'-bis(naphthalen-1-yl)-N,N'-di(phenyl)-2,2'-dimethylbenzidine (abbreviation: α-NPD), N,N'-diphenyl-N,N'-(1-naphthyl)-1,1'-biphenyl-4,4'-diamine (abbreviation: NPB), N,N'-di(naphthalen-2-yl)-N,N'-di(phenyl)biphenyl-4,4'-diamine (abbreviation: β-NPB), N,N'-diphenyl-N,N'-bis(α-naphthyl)-1,1'-binaphthyl-4,4'-diamine (abbreviation: α-NPN), 4,4'-cyclohexyl bis[N,N-bis(4-methylphenyl)aniline] (abbreviation: TAPC), N,N'-diphenyl-N,N'-bis(3-methylphenyl)-1,1'-biphenyl-4,4'-diamine (abbreviation: TPD), 2,2,7,7-tetrakis(diphenylamino)-9,9-spirobifluorene (abbreviation: Spiro-TAD), 3,3'-(1,4-phenylene)bis(1,5-diphenyl-4,5-dihydro-1H-pyrazole) (abbreviation: PYR-D1), 4,4',4''-tris(carbazol-9-yl)triphenylamine (abbreviation: TCTA); poly(N-vinylcarbazole) (abbreviation: PVK), 4-(N,N-di-p-methylphenyl)aminobenzaldehyde-1,1-diphenylhydrazone, 1,4-bis[4-(N,N-di-p-methylphenylamino)styryl]benzene (abbreviation: DPD), etc., but is not limited thereto. The hole transport layer of the present disclosure may be a single-layer structure or a multilayer structure with two or more layers, and the hole transport material contained in each layer may be a single material or a mixed material.

The light-emitting layer of the present disclosure refers to an organic layer capable of emitting photons. The light-emitting layer of the present disclosure may comprise a single material or two or more mixed materials, and the light-emitting material is divided into a blue light-emitting material, a green light-emitting material, and a red light-emitting material.

The blue light-emitting material is selected from one or more of the following materials, a pyrene derivative, an anthracene derivative, a fluorene derivative, a perylene derivative, a styrylamine derivative, and a metal complex, etc., but is not limited thereto. Specifically, it can be selected from the group consisting of $N^1,N^6$-bis([1,1'-biphenyl]-2-yl)-$N^1,N^6$-bis([1,1'-biphenyl]-4-yl)pyrene-1,6-diamine, 9,10-di-(2-naphthyl)anthracene (abbreviation: ADN), 2-methyl-9,10-di-2-naphthylanthracene (abbreviation: MADN), 2,7-bis(4-diphenylaminophenyl)-9,9-bis(4-diphenylaminophenyl)fluorene (abbreviation: XB10), 2,5,8,11-tetra-tert-butylperylene (abbreviation: TBPe), 4,4'-bis[4-(diphenylamino)styryl]biphenyl (abbreviation: BDAVBi), 4,4'-bis[4-(di-p-tolylamino)styrene]biphenyl (abbreviation: DPAVBi), 1,4-bis[4-(N,N-diphenyl)amino]styrene (abbreviation: DSA-Ph), tris[1-(2,6-diisopropylphenyl)-2-phenyl-1H-imidazole]iridium (abbreviation: fac-Ir(iprpmi)$_3$), bis(2-hydroxyphenylpyridine)beryllium (abbreviation: Bepp$_2$), bis(4,6-difluorophenylpyridine)-C2,N)picolinatoiridium (abbreviation: FIrpic), bis(2,4-difluorophenylpyridine)-tetrakis(1-pyrazolyl)iridiumborate (III) (abbreviation: Fir6), etc., but is not limited thereto.

The above green light-emitting material is selected from one or more of the following materials, a coumarin dye, a quinacridone derivative, a polycyclic aromatic hydrocarbon, a diamine anthracene derivative, a carbazole derivative, and a metal complex, etc., but is not limited thereto. Specifically, it can be selected from the group consisting of coumarin 6 (abbreviation: C-6), coumarin 545T (abbreviation: C-525T), quinacridone (abbreviation: QA), N, N'-dimethyl quinacridone (Abbreviation: DMQA), 5,12-diphenyltetracene (abbreviation: DPT), N10,N10,N10',N10'-tetraphenyl-9,9'-dianthracene-10,10'-diamine (abbreviation: BA-TAD), N10,N10'-diphenyl-N10, N10'-diphthaloyl-9,9'-dianthracene-10,10'-diamine (abbreviation: BA-NPB), 9,9',9''-(5-(4,6-diphenyl-1,3,5-triazin-2-yl)benzene-1,2,3-triyl)tris(3,6-dimethyl-9H-carbazole) (abbreviation: TmCzTrz), tris(8-hydroxyquinoline)aluminum (III) (abbreviation: Alq$_3$), tris(2-phenylpyridine)iridium (abbreviation: Ir(ppy)$_3$), bis(2-phenylpyridinium)iridium acetylacetonate (abbreviation: Ir(ppy)$_2$(acac)), tris[2-(p-tolyl)pyridine-C2,N]iridium (III) (abbreviation: Ir(mppy)$_3$), tris[2-(3-methyl-2-pyridyl)phenyl]iridium (abbreviation: Ir(3mppy)$_3$), bis[2-(2-benzothiazole)phenol]zinc (abbreviation: Zn(BTZ)$_2$), etc., but is not limited thereto.

The red light-emitting material is selected from one or more of the following materials, a DCM series material, and a metal complex, etc., but is not limited thereto. Specifically, it can be selected from the group consisting of 4-(dicyanomethylidene)-2-methyl-6-(4-dimethylaminostyryl)-4H-pyran (abbreviation: DCM), 4-(dicyanomethylene)-2-tert-butyl-6-(1,1,7,7-tetramethyllulolidin-9-enyl)-4H-pyran (abbreviation: DCJTB), bis(1-phenylisoquinoline) (acetylacetone)iridium (III) (abbreviation: Ir(piq)$_2$(acac)), octaethylporphyrin platinum (abbreviation: PtOEP), bis(2-(2'-benzothienyl)pyridine-N, C3') (acetylacetone)iridium (abbreviation: Ir(btp)$_2$(acac), bis[1-(9,9-dimethyl-9H-fluorene-2-yl)-isoquinoline (acetylacetone)iridium (III) (abbreviation: Ir(fliq)$_2$(acac)), bis[2-(9,9-dimethyl-9H-fluorene-2-yl)-quinoline](acetylacetone)iridium(III) (abbreviation: Ir(flq)$_2$(acac)), tris(dibenzoylmethane)mono(phenanthroline) europium (III) (abbreviation: Eu(dbm)$_3$(Phen)), etc., but it is not limited thereto.

When the above-mentioned light-emitting material is used as a guest material, it is necessary to select a suitable host material to be matched thereto, and the host material is preferably a material having a high lowest unoccupied orbital energy level and a low highest occupied orbital energy level as compared with the guest material. The above host material includes a metal complex such as an aluminum complex or a zinc complex, a fluorene derivative, an anthracene derivative, and a carbazole derivative, etc., but is not limited thereto. Specifically, it can be selected from the group consisting of tris(8-hydroxyquinoline)aluminum (III) (abbreviation: Alq$_3$), zinc 8-hydroxyquinoline (abbreviation: Znq$_2$), 2,7-bis[9,9-di(4-methylphenyl)-fluorene-2-yl]-9,9-bis(4-methylphenyl)fluorene (abbreviation: TDAF), 9,10-di(2-naphthyl)anthracene (abbreviation: ADN), 9-(1-naphthyl)-10-[4-(2-naphthyl)phenyl]anthracene, 1,3,5-tris (9-carbazolyl)benzene (abbreviation: TCP), 9,9'-(1,3-phenyl)di-9H-carbazole (abbreviation: MCP), 4,4'-bis(9-carbazole)biphenyl (abbreviation: CBP), 4,4',4''-tris (carbazol-9-yl)triphenylamine (abbreviation: TCTA), etc., but is not limited thereto.

The hole blocking layer of the present disclosure has a function of preventing holes from leaking from the light emitting layer to the electron transport layer. The hole blocking material of the present disclosure is preferably a material having good hole blocking properties, and can be selected from one or more of the following materials: a phenanthroline derivative, an aluminum complex, a benzimidazole derivative, an aromatic compound, an organic boron compound, etc., but is not limited thereto. Specifically, it can be selected from the group consisting of 4,7-diphenyl-1,10-phenanthroline (abbreviation: Bphen), 2,9-di(naphthalen-2-yl)-4,7-diphenyl-1,10-phenanthroline (abbreviation: NBphen), 2,9-dimethyl-4,7-diphenyl-1,10-phenanthroline (abbreviation: BCP), bis(8-hydroxy-2-methylquinoline)-(4-phenylphenoxy)aluminum (abbreviation: BAlq), 1,3,5-tris(N-phenyl-2-benzimidazole)benzene (abbreviation: TPBi), (1,3,5-terphenyl)benzene (abbreviation: TBB), 1,3,5-tris(9,9-dimethyl-9H-fluorene-2-yl)benzene (abbreviation: TFB), Trimesitylborane (abbreviation: TPhB), etc., but is not limited thereto. The hole blocking layer of the present disclosure may be a single-layer structure or a multilayer structure with two or more layers, and the hole blocking material contained in each layer may be a single material or a mixed material.

The electron transport layer of the present disclosure has an effect of improving the transmission efficiency of electrons in the device and blocking holes in the light-emitting layer. The electron transport material of the present disclosure is preferably a material having good electron transport properties, and can be selected from one or more of the following materials: a metal complex such as an aluminum complex, a beryllium complex and a zinc complex, etc., and an aromatic heterocyclic compound such as an oxazole derivative, an imidazole derivative, a triazole compound, a phenanthroline derivative, and a pyridine derivative, and a polymer, etc., but is not limited thereto. Specifically, it can be selected from the group consisting of tris(8-hydroxyquinoline)aluminum (III) (abbreviation: Alq$_3$), tris(4-methyl-8-hydroxyquinoline)aluminum (abbreviation: Almq$_3$), bis(10-hydroxybenzo[h]quinoline)beryllium (abbreviation: Bepq$_2$), bis(2-methyl-8-hydroxyquinoline)(4-phenylphenol)aluminum(III) (abbreviation: BAlq), bis(8-hydroxyquinoline)zinc (II) (abbreviation: Znq), 2,5-di-(4-naphthyl)-1,3,4-oxadiazole (abbreviation: BND), 2-(4-biphenyl) 5-(4-tert-butylphenyl)-1,3,4-oxadiazole (abbreviation: PBD), 2-(4-(9,10-di (naphthalen-2-yl)anthracene-2-yl)phenyl)-1-phenyl-1H-benzo[d]imidazole, 1,3,5-tris(N-phenyl-2-benzimidazole) benzene (abbreviation: TPBi), 4,7-diphenyl-1,10-phenanthroline (abbreviation: Bphen), 2,9-dimethyl-4,7-diphenyl-1,10-phenanthroline (abbreviation: BCP), 2,9-bis (naphthalen-2-yl)-4,7-diphenyl-1,10-phenanthroline (abbreviation: NBphen), 3,3'-[5'43-(3-pyridyl)phenyl](abbreviation: TmPyPB), 1,3,5-tris(4-pyridin-3-ylphenyl)benzene (abbreviation: TpPyPB), 1,3,5-tris(6-(3-(3-pyridyl) phenyl)pyridin-2-yl)benzene (abbreviation: Tm$_3$PyP$_{26}$PyB), 2,4,6-tris(3-(3-pyridyl)-(1,1'-biphenyl)-3-yl)-1,3,5-triazine (abbreviation: TmPPPyTz), poly[9,9-bis[6'-(N,N,N-trimethylammonium)hexyl]fluorene-alt-co-1,4-phenylene] bromide (abbreviation: FPQ-Br), etc., but is not limited thereto. The electron transport layer of the present disclosure may also be a mixed material formed by doping the above electron transport material and the following electron injection material with each other, such as Alq$_3$/LiF, Alq$_3$/Liq, BAlq/LiF, and BAlq/Liq, etc., but is not limited thereto. The electron transport layer of the present disclosure may be a single-layer structure or a multilayer structure with two or more layers, and the electron transport material contained in each layer may be a single material or a mixed material.

The electron injection layer of the present disclosure functions to increase the efficiency of electron injection from the cathode into the electron transport layer and the light emitting layer. The electron injection material of the present disclosure is preferably a material having good electron injection properties, and can be selected from one or more of the following materials: an alkali metal, an alkaline earth metal or a compound containing an alkali metal or an alkaline earth metal, but is not limited thereto. Specifically, it can be selected from the group consisting of Li, Na, K, Rb, Cs, Be, Mg, Ca, Sr, Ba, lithium fluoride, sodium fluoride, potassium fluoride, rubidium fluoride, cesium fluoride, magnesium fluoride, calcium fluoride, lithium oxide, cesium carbonate, lithium metaborate, potassium silicate, lithium acetate, sodium acetate, rubidium acetate, potassium acetate, cesium acetate, lithium tetra(8-hydroxyquinolinato)boron, and 8-hydroxyquionline lithium, etc., but is not limited thereto. The electron injection layer of the present disclosure may be a single-layer structure or a multilayer structure with two or more layers, and the electron injection material contained in each layer may be a single material or a mixed material.

The cathode of the present disclosure has a function of injecting electrons into the electron transport layer, and the cathode material is required to have a lower work function, and since the light of the top emitting device is transmitted from the cathode, the cathode is required to have a high transmittance. The cathode material of the present disclosure can be selected from one or more of the following materials: a metal or an alloy such as a main group metal, an alkali metal, an alkaline earth metal, a transition metal, and a lanthanide metal, but is not limited thereto. Specifically, it can be selected from the group consisting of Al, In, Li, Mg, Ca, Ag, Ti, Sm, Mg/Ag, and Li/Al, etc., but is not limited thereto. The film thickness of the cathode varies depending on the materials, and is usually selected from the range of 10 nm to 1 µm, preferably 10 nm to 300 nm. The cathode of the present disclosure may be a single-layer structure or a multilayer structure with two or more layers, and the cathode material contained in each layer may be a single material or a mixed material.

The light extraction layer according to the present disclosure can be selected from one or more of the following materials: a metal compound, an aromatic amine derivative, a carbazole derivative or an amine derivative according to the present disclosure, etc., but is not limited thereto. Specifically, tris(8-hydroxyquinoline)aluminum (III) (abbreviation: Alq$_3$), magnesium oxide, zinc selenide, zinc sulfide, tin oxide, molybdenum oxide, tellurium oxide, N, N'-di(naphthalene-1-yl)-N,N'-bis(phenyl)-2,2'-dimethylbenzidine (abbreviation: α-NPD), N,N'-diphenyl-N,N'-(1-naphthyl)-1,1'-biphenyl-4,4'-diamine (abbreviation: NPB), N4, N4, N4', N4'-tetrakis(4-methoxyphenyl)-[1, 1'-biphenyl]-4,4'-diamine (abbreviation: MeO-TPD), 4,4'-bis(9-carbazole)biphenyl (abbreviation: CBP), etc., but is not limited thereto. Preferred is the amine derivative of the present disclosure. The light extraction material of the present disclosure may be a single-layer structure or a multilayer structure with two or more layers, and the light extraction material contained in each layer may be a single material or a mixed material.

The method for forming each layer of the organic electroluminescent device of the present disclosure is not particularly limited, and a well-known method such as a dry film forming method or a wet film forming method, etc., can be employed. The dry film forming method includes a vacuum deposition method, a sputtering method, and a plasma method, etc. The wet film forming method includes a spin coating method, a dipping method, an ink-jet method, etc., but is not limited thereto.

The organic electroluminescent device of the present disclosure can be widely used in the fields of flat panel display, solid lighting, organic photoreceptor or organic thin film transistor, etc.

The synthetic route of the amine derivative as shown in Formula I according to the present disclosure is as follows:

Step I:

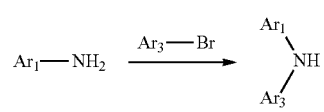

In the above synthetic route,

is obtained by $Ar_1$—$NH_2$ and $Ar_3$—Br and through Buchwald reaction.

Step II:

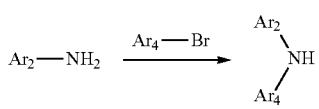

In the above synthetic route, $Ar_2$—$NH_2$ is obtained by $Ar_4$—Br and

through Buchwald reaction.

Step III:
1. When

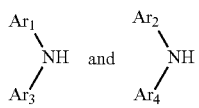

are different:

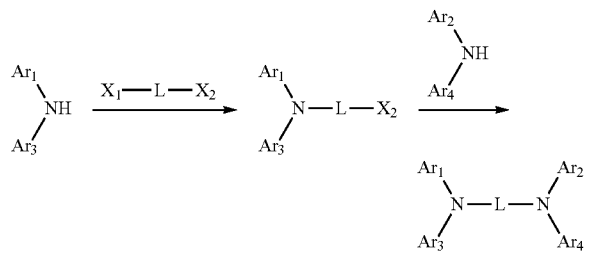

In the above synthetic route, $X_1$ and $X_2$ are independently selected from one of I, Br, and Cl, and

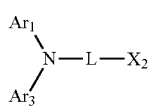

is obtained by

and $X_1$-L-$X_2$ through Buchwald reaction, and an amine derivative of Formula I is obtained by the above intermediate product and

through Buchwald reaction.

2. When

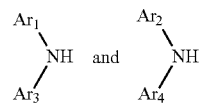

are same:

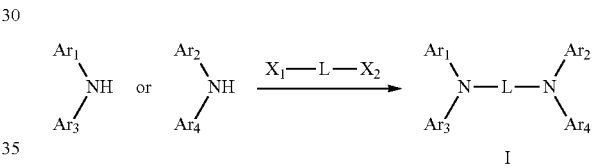

In the above synthetic route, an amine derivative of Formula I is obtained by

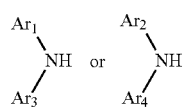

and $X_1$-L-$X_2$ through Buchwald reaction.

The raw materials used in the following examples are not particularly limited in the present disclosure, and may be a commercially available product or be prepared by a production method well known to those skilled in the art.

Preparation and Characterization of Compounds

Description of Raw Materials, Reagents, and Characterization Equipment:

The raw materials and reagents used in the present disclosure are all reagent pure;

Mass spectrometry was performed using AXIMA-CFR plus matrix-assisted laser desorption ionization flight mass spectrometer from Kratos Analytical Inc., Shimadzu, UK, with chloroform as solvent;

Elemental analysis was performed using the Vario EL cube type organic element analyzer from Elementar, Germany, with a sample mass of 5-10 mg;

Nuclear magnetic resonance ($^1$HNMR) was performed using a Bruker-510 type nuclear magnetic resonance spectrometer (Bruker, Germany) at 600 MHz, with CDCl$_3$ as the solvent and TMS as the internal standard.

Synthesis Example 1: Synthesis of Compound 1

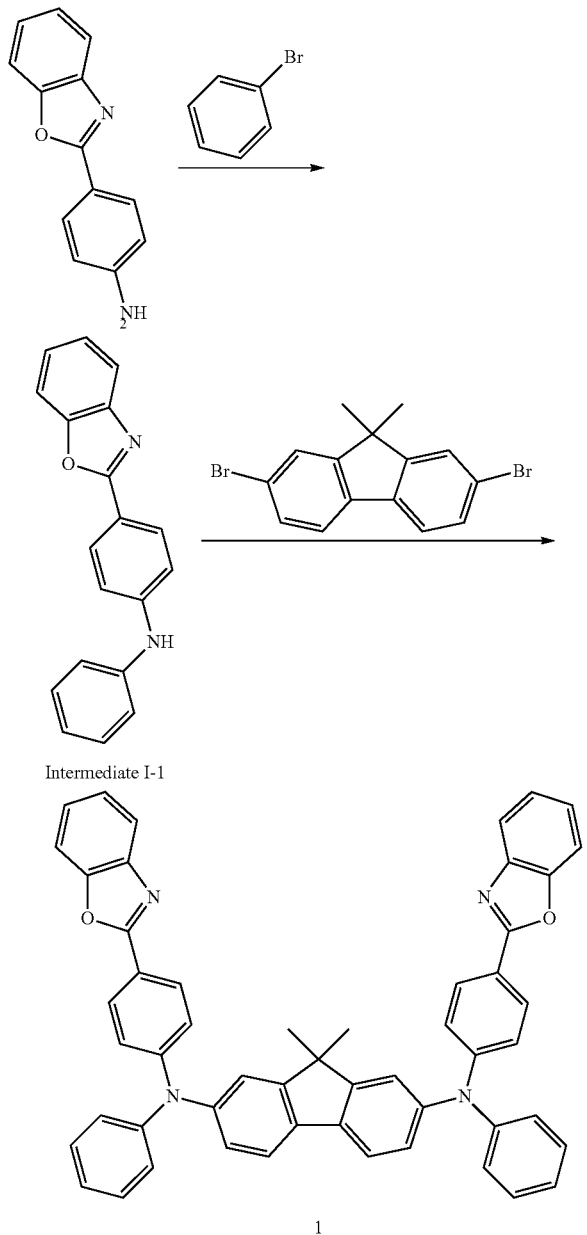

Intermediate I-1

1

Synthesis of Intermediate I-1

Degassed toluene solvent (400 mL) was added to a 1 L reaction flask, and then the starting material 4-(2-benzoxazolyl)aniline (37.8 g, 0.18 mol), bromobenzene (19.0 ml, 0.18 mol) and sodium tert-butoxide (22.8 g, 0.234 mol) were added therein, sequentially. After purged with nitrogen for three times, palladium acetate (0.4 g, 0.0018 mol) was added. After purged with nitrogen for three times, tri-tert-butylphosphine (7.2 mL of a 1.0 M solution in toluene, 0.0072 mol) was added. After purged with nitrogen for three times again, the mixture was refluxed for 2 hours under a nitrogen atmosphere. After the reaction ceased, the mixture was cooled to room temperature and filtered through Celite to give a filtrate. The filtrate was concentrated, and a small amount of methanol was added thereto, the mixture was allowed to stand still and recrystallize. After a period of time, a solid was formed, which was filtered with suction and eluted with methanol to give a recrystallized solid as Intermediate I-1 (46.3 g, yield: about 90%), the purity of the solid was 98.1% when detected by HPLC.

Synthesis of Compound 1

Degassed toluene solvent (100 mL) was added to a 250 mL reaction flask, and then the starting material intermediate I-1 (17.6 g, 0.062 mol), 2,7-dibromo-9,9-dimethylfluorene (9.8 g, 0.028 mol) and sodium tert-butoxide (8.0 g, 0.084 mol) were added therein, sequentially. After purged with nitrogen for three times, palladium acetate (0.12 g, 0.00056 mol) was added. After purged with nitrogen for three times, tri-tert-butylphosphine (2.24 mL of a 1.0 M solution in toluene, 0.00224 mol) was added. After purged with nitrogen for three times again, the mixture was refluxed for 2 hours under a nitrogen atmosphere. After the reaction ceased, the mixture was cooled to room temperature and filtered through Celite to give a filtrate. The filtrate was concentrated and heated to 60° C., and then a small amount of ethanol was added thereto, and the mixture was allowed to stand still at room temperature to recrystallize. After a period of time, a solid was formed, which was filtered with suction and eluted with ethanol to obtain a recrystallized solid to give a pale yellow solid compound 1 (18.1 g, yield of about 85%), the purity of the solid was 99.9% when detected by HPLC.

Mass spectrum m/z: 762.85 (calc.: 762.91). Theoretical element content (%) $C_{53}H_{38}N_4O_2$: C, 83.44; H, 5.02; N, 7.34; O, 4.19 Measured element content (%): C, 83.52; H, 5.02; N, 7.35; O, 4.11. $^1$H NMR (600 MHz, CDCl$_3$) (δ, ppm): 8.10 (d, J=8.6 Hz, 4H), 7.82-7.67 (m, 2H), 7.67-7.50 (m, 4H), 7.40-7.28 (m, 8H), 7.23 (d, J=8.5 Hz, 6H), 7.20-6.99 (m, 8H), 1.40 (s, 6H). The above results confirmed that the obtained product was the target product.

Synthesis Example 2: Synthesis of Compound 10

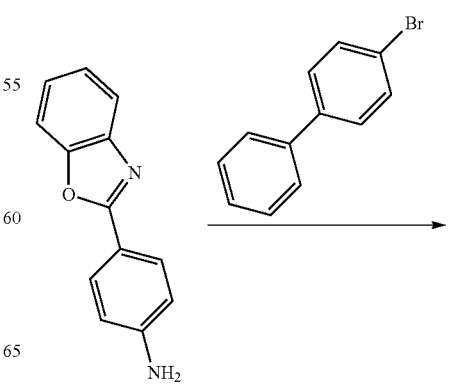

111

-continued

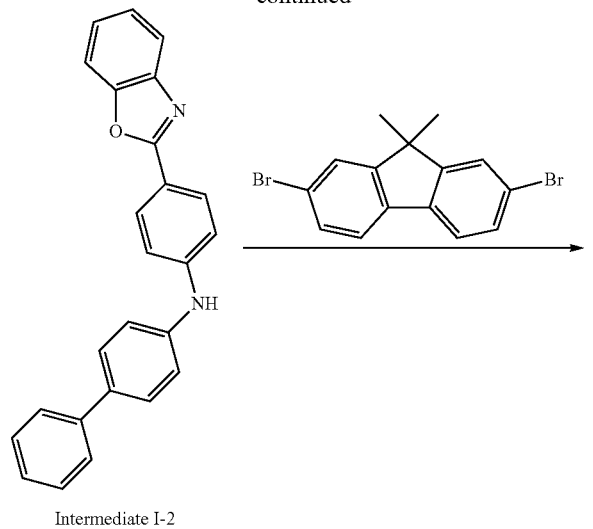

Intermediate I-2

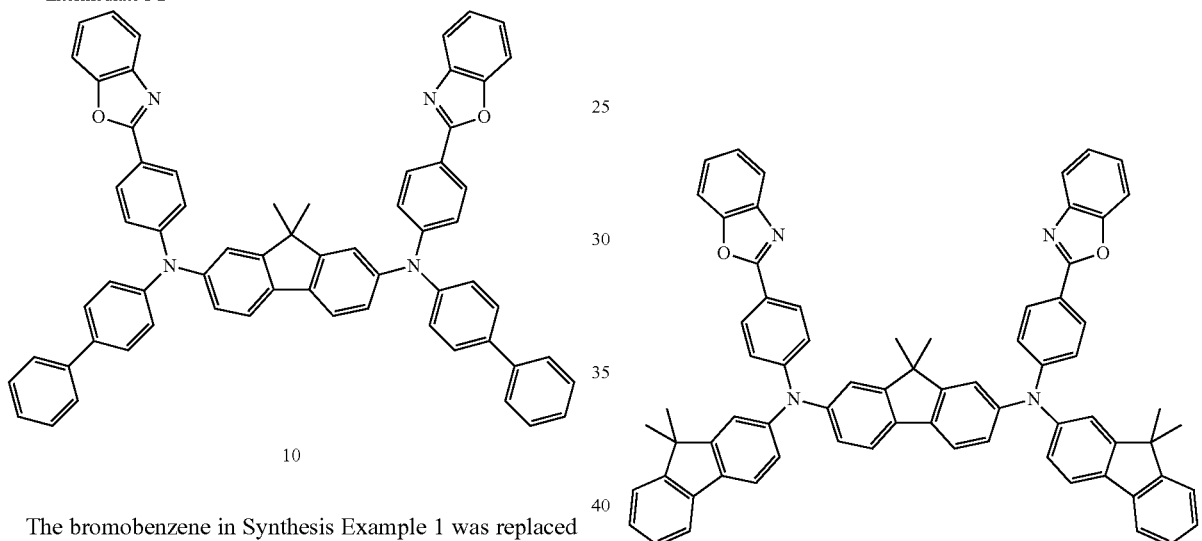

10

The bromobenzene in Synthesis Example 1 was replaced with an equimolar amount of 4-bromobiphenyl, and the other steps were the same to obtain a yellow solid compound 10 (22.5 g, yield of about 88%). Mass spectrum m/z: 914.41 (calc.: 915.11). Theoretical element content (%) $C_{65}H_{46}N_4O_2$: C, 85.31; H, 5.07; N, 6.12; O, 3.50 Measured element content (%): C, 85.28; H, 4.95 N, 6.08; O, 3.55. The above results confirmed that the obtained product was the target product.

Synthesis Example 3: Synthesis of Compound 22

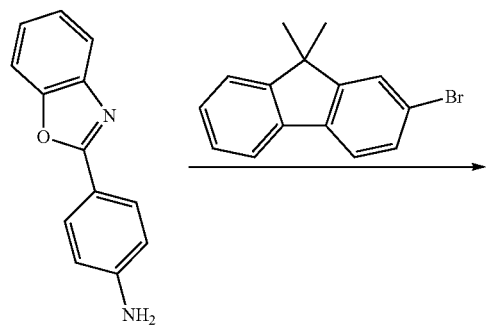

112

-continued

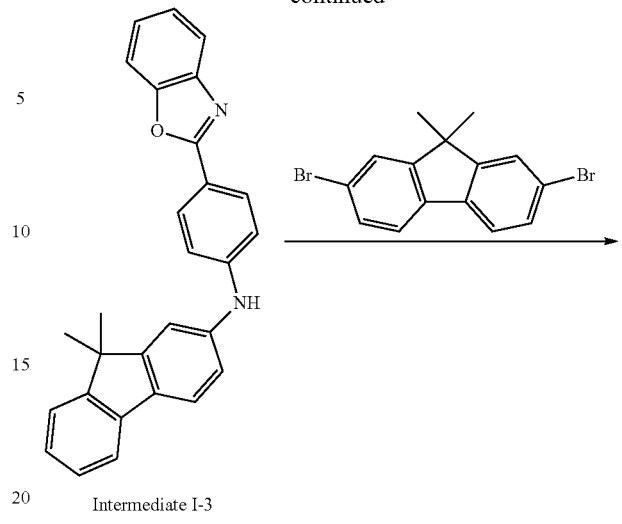

Intermediate I-3

22

The bromobenzene in Synthesis Example 1 was replaced with an equimolar amount of 2-bromo-9,9-dimethylfluorene, and the other steps were the same to obtain a yellow solid compound 22 (20.0 g, yield of about 72%). Mass spectrum m/z: 995.32 (calc.: 995.24). Theoretical element content (%) $C_{71}H_{54}N_4O_2$: C, 85.69; H, 5.47; N, 5.63; O, 3.22 Measured element content (%): C, 85.77; H, 5.48; N, 5.62; O, 3.12. $^1$H NMR (600 MHz, CDCl$_3$) (δ, ppm): 7.92 (d, J=3.3 Hz, 1H), 7.89 (d, J=3.2 Hz, 1H), 7.88 (s, 2H), 7.85 (s, 2H), 7.79-7.70 (m, 8H), 7.56 (d, J=3.2 Hz, 1H), 7.53 (dd, J=2.8, 1.3 Hz, 5H), 7.42-7.33 (m, 9H), 7.31 (dd, J=5.3, 2.3 Hz, 3H), 7.28 (dd, J=6.6, 3.3 Hz, 3H), 7.24 (d, J=3.2 Hz, 1H), 1.47 (d, J=30.9 Hz, 12H), 1.39 (s, 6H). The above results confirmed that the obtained product was the target product.

Synthesis Example 4: Synthesis of Compound 26
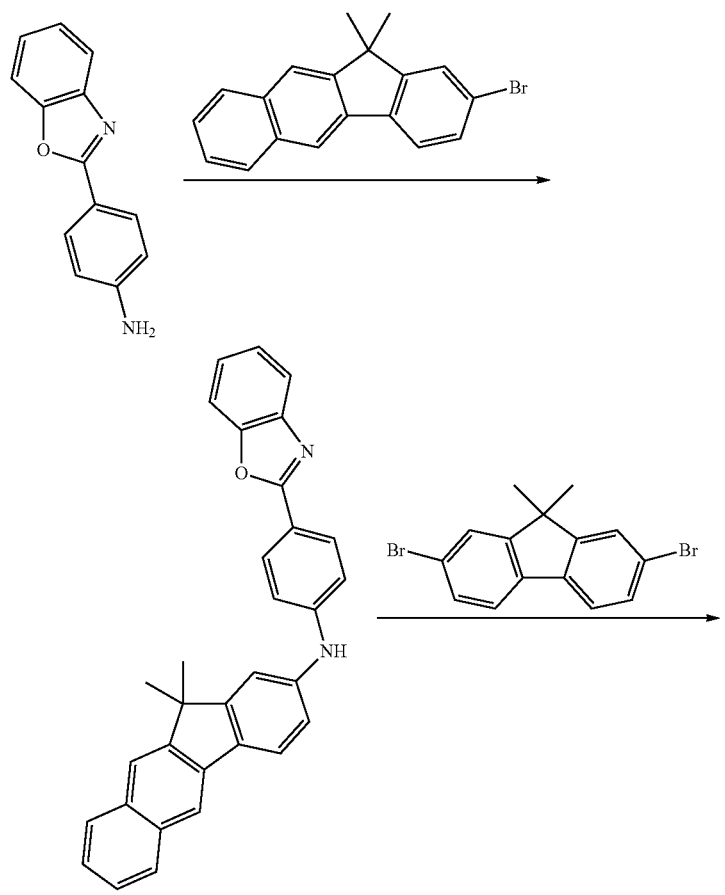
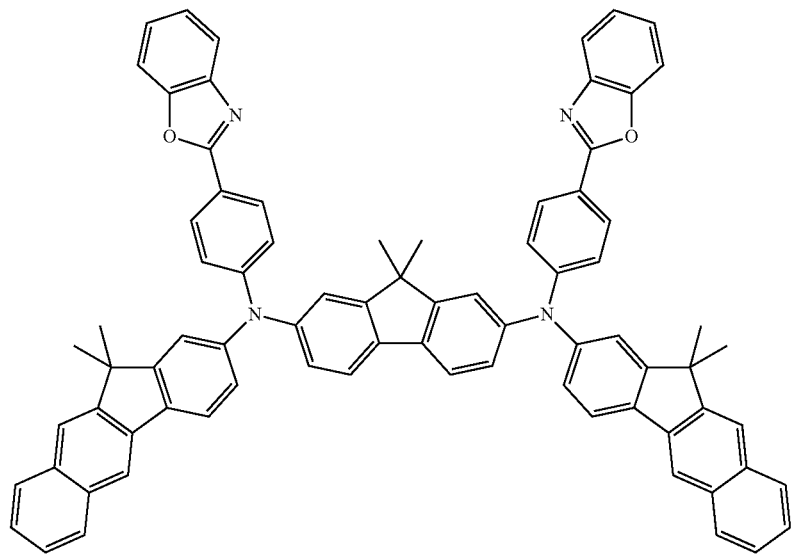
26
The bromobenzene in Synthesis Example 1 was replaced with an equimolar amount of 2-bromo-11,11-dimethyl-benzo[b]fluorene, and the other steps were the same to obtain a yellow solid compound 26 (20.8 g, yield of about 68%). Mass spectrum m/z: 1095.44 (calc.: 1095.36). Theoretical element content (%) $C_{79}H_{58}N_4O_2$: C, 86.63; H, 5.34; N, 5.12; O, 2.92 Measured element content (%): C, 86.71; H, 5.32; N, 5.12; O, 2.87. $^1$H NMR (600 MHz, CDCl$_3$) (δ, ppm): 8.15 (d, J=8.6 Hz, 4H), 8.02 (s, 2H), 7.86 (dt, J=6.8, 2.1 Hz, 6H), 7.79-7.74 (m, 2H), 7.73 (s, 2H), 7.65 (d, J=8.1 Hz, 2H), 7.60-7.53 (m, 2H), 7.49-7.39 (m, 6H), 7.34 (dd, J=9.5, 4.0 Hz, 6H), 7.25 (s, 2H), 7.23-7.16 (m, 4H), 1.63 (s, 12H), 1.45 (s, 6H). The above results confirmed that the obtained product was the target product.

Synthesis Example 5: Synthesis of Compound 27

The bromobenzene in Synthesis Example 1 was replaced with an equimolar amount of 9-bromo-11,11-dimethyl-11H-benzo[A]fluorene, and the other steps were the same to obtain a yellow solid compound 27 (20.24 g, yield of about 66%). Mass spectrum m/z: 1094.48 (calc.: 1095.36). Theoretical element content (%) $C_{79}H_{58}N_4O_2$: C, 86.63; H, 5.34; N, 5.12; O, 2.92 Measured element content (%): C, 86.56; H,

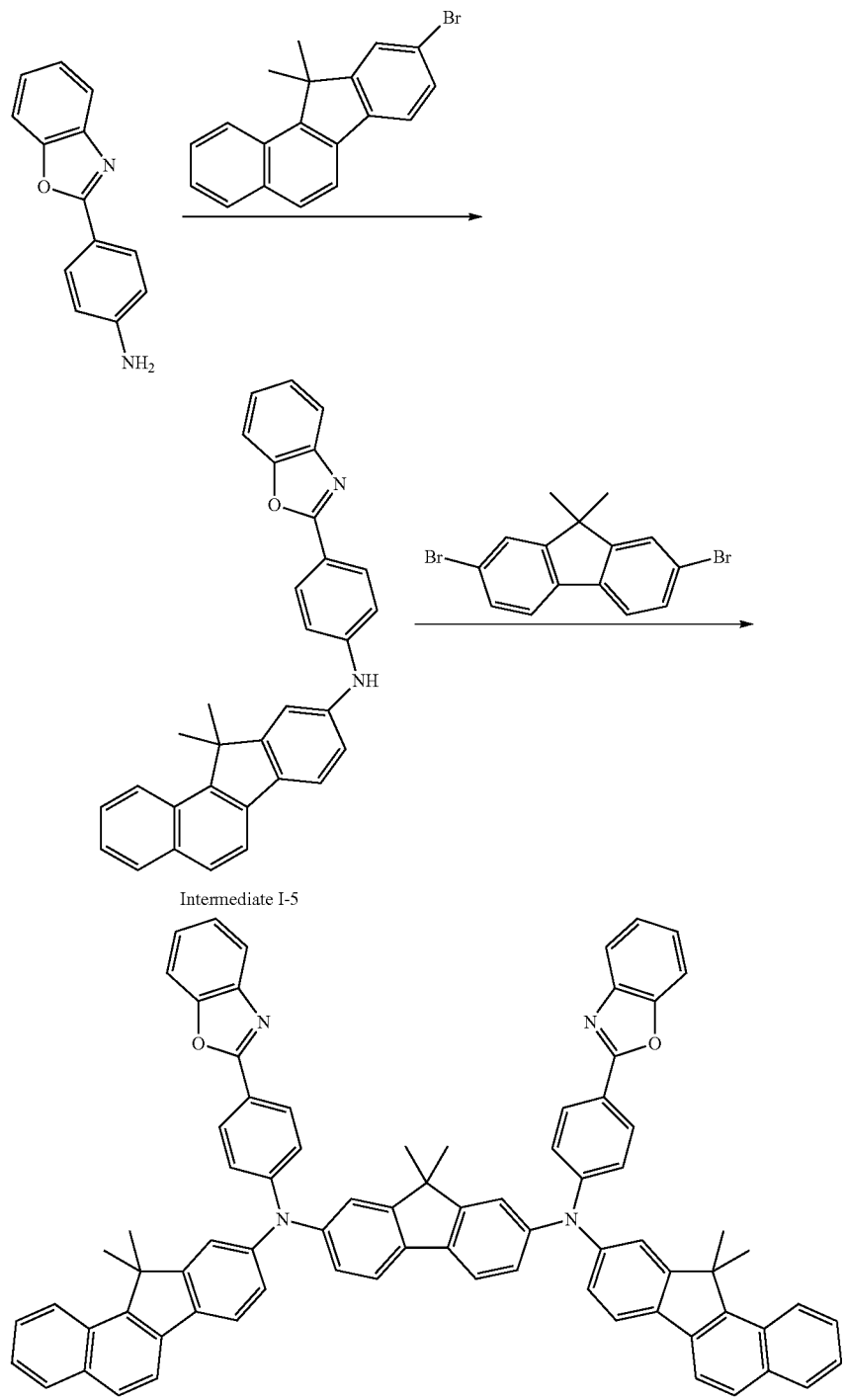

5.30; N, 5.16; O, 2.88. The above results confirmed that the obtained product was the target product.

Synthesis Example 6: Synthesis of Compound 35

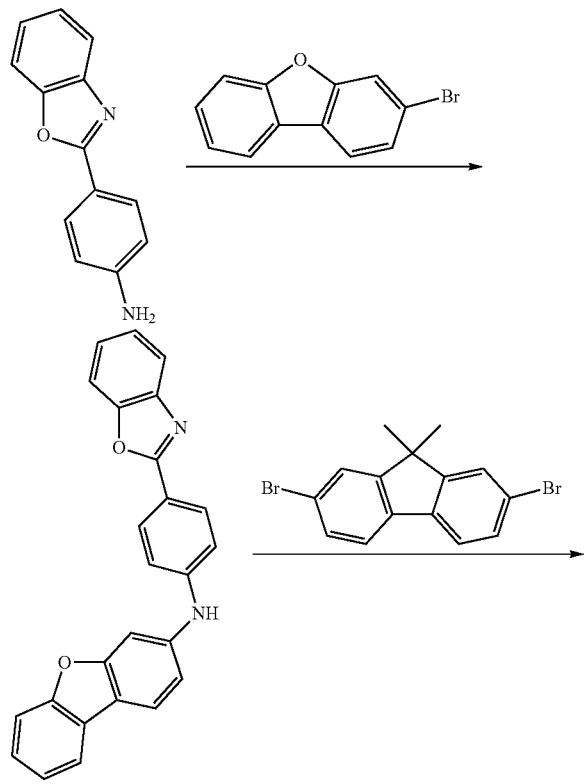

Intermediate I-6

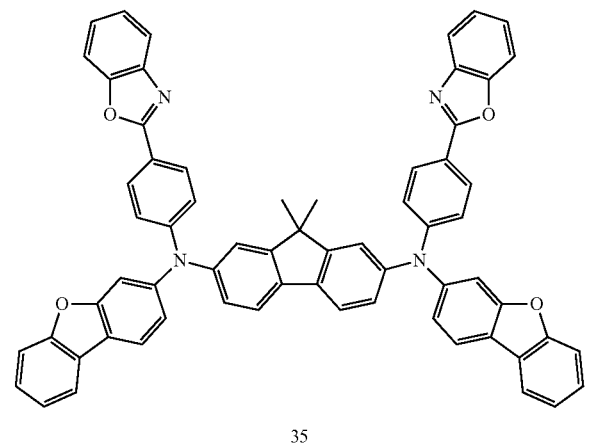

35

The bromobenzene in Synthesis Example 1 was replaced with an equimolar amount of 3-bromodibenzo[b,d]furan, and the other steps were the same to obtain a yellow solid compound 35 (19.5 g, yield of about 74%). Mass spectrum m/z: 943.31 (calc.: 943.08). Theoretical element content (%) $C_{65}H_{42}N_4O_4$: C, 82.78; H, 4.49; N, 5.94; O, 6.79 Measured element content (%): C, 82.83; H, 4.50; N, 5.92; O, 6.75. $^1$H NMR (600 MHz, CDCl$_3$) (δ, ppm): 8.12-8.08 (m, 4H), 7.88-7.81 (m, 4H), 7.76-7.71 (m, 2H), 7.62-7.53 (m, 8H), 7.47 (d, J=1.0 Hz, 2H), 7.38-7.30 (m, 8H), 7.28 (s, 2H), 7.18-7.15 (m, 6H), 1.39 (s, 6H). The above results confirmed that the obtained product was the target product.

Synthesis Example 7: Synthesis of Compound 41

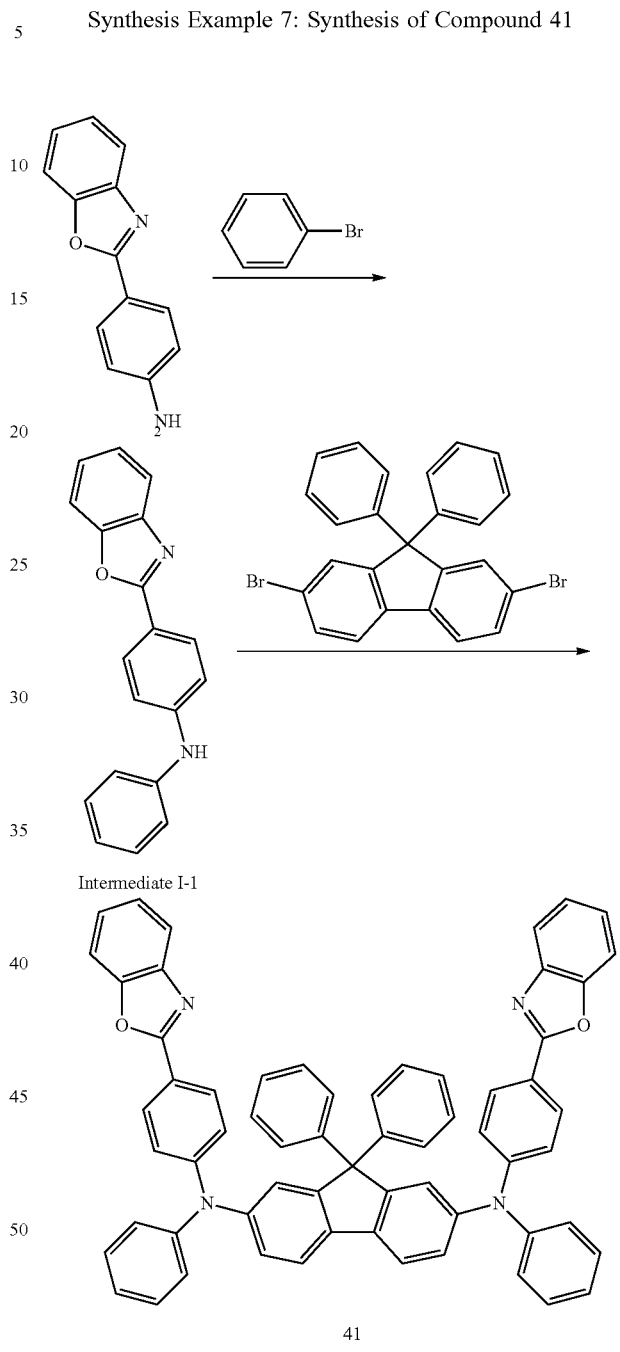

The 2,7-dibromo-9,9-dimethylfluorene in Synthesis Example 1 was replaced with an equimolar amount of 2,7-dibromo-9,9-diphenylfluorene, and the other steps were the same to obtain a pale yellow solid compound 41 (20.6 g, yield of about 83%). Mass spectrum m/z: 887.31 (calc.: 887.06). Theoretical element content (%) $C_{63}H_{42}N_4O_2$: C, 85.30; H, 4.77; N, 6.32; O, 3.61 Measured element content (%): C, 85.38; H, 4.85; N, 6.38; O, 3.70. $^1$H NMR (600 MHz, CDCl$_3$) (δ, ppm): 8.06 (d, J=7.9 Hz, 4H), 7.80-7.69 (m, 2H), 7.62 (d, J=6.6 Hz, 2H), 7.58-7.53 (m, 6H), 7.51 (t, J=9.5 Hz, 4H), 7.43 (t, J=7.7 Hz, 4H), 7.37-7.30 (m, 6H), 7.22-7.18 (m, 8H), 7.14-7.10 (m, 6H). The above results confirmed that the obtained product was the target product.

Synthesis Example 8: Synthesis of Compound 44

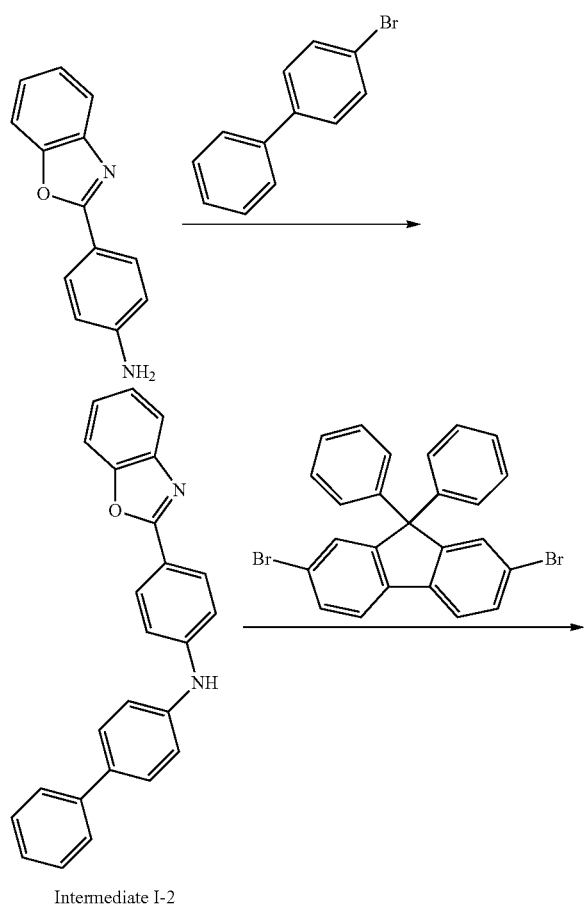

Intermediate I-2

44

The bromobenzene in Synthesis Example 1 was replaced with an equimolar amount of 4-bromobiphenyl, the 2,7-dibromo-9,9-dimethylfluorene was replaced with an equimolar amount of 2,7-dibromo-9,9-diphenylfluorene, and the other steps were the same to obtain a pale yellow solid compound 44 (23.6 g, yield of about 81%). Mass spectrum m/z: 1038.43 (calc.: 1039.25). Theoretical element content (%) $C_{75}H_{50}N_4O_2$: C, 86.68; H, 4.85; N, 5.39; O, 3.08 Measured element content (%): C, 86.56; H, 4.82; N, 5.49; O, 3.08. The above results confirmed that the obtained product was the target product.

Synthesis Example 9: Synthesis of Compound 73

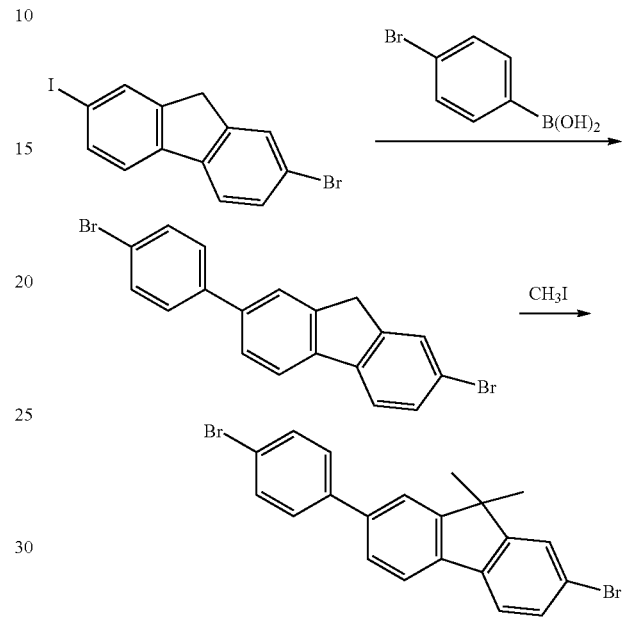

Intermediate a

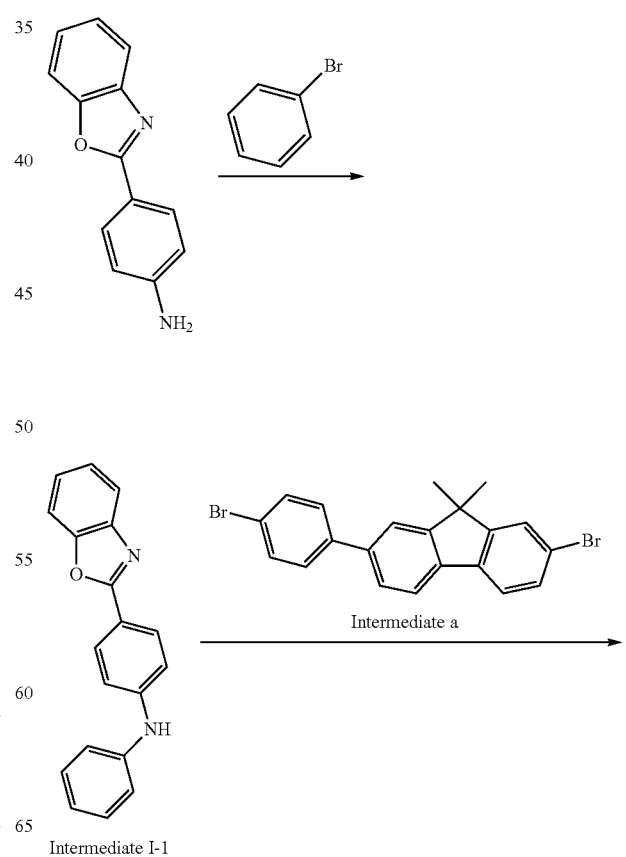

Intermediate I-1

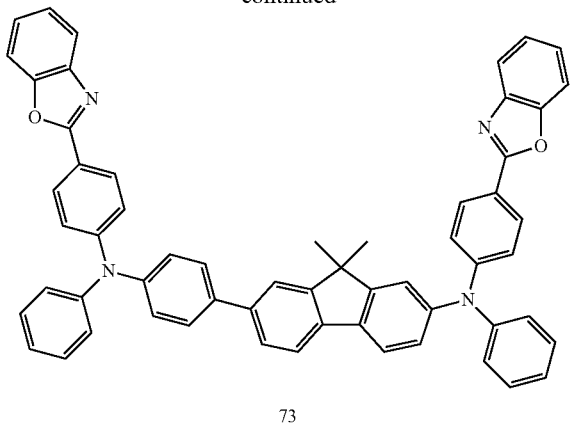

73

Synthesis of Intermediate a

The solid raw materials of 2-bromo-7-iodofluorene (37.1 g, 0.1 mol) and p-bromobenzeneboronic acid (22.1 g, 0.11 mol) were added to a 1 L reaction flask, sequentially, followed by ultrasonic degassed toluene (250 mL), ethanol (100 mL) and 150 mL of aqueous potassium carbonate (41.4 g, 0.3 mol). The mixture was vacuum purged with nitrogen three times, and the catalyst tetrakis(triphenylphosphine) palladium (1.15 g, 0.001 mol) was added under a nitrogen atmosphere. The mixture was vacuum purged with nitrogen three times, continuously, and reacted under reflux at 80° C. for 4 hours with stirring, and then the heating was stopped, then 150 mL of water was added to the mixture, which was stirred for 30 minutes, cooled down to about 40° C. and filtered under reduced pressure, the filter cake was rinsed with hot water (100 mL) and acetone (150 mL) sequentially to ensure the pH of the filtrate was about 7. The filter cake was dissolved in 1 L of chloroform, the solution was passed through a silica gel funnel, and the filtrate was concentrated to 500 mL, then a small amount of methanol (about 25 mL) was added to recrystallize, filtered under reduced pressure to give a solid (36.0 g, yield of about 90%), the purity of the solid was 98.6% when detected by HPLC.

The above solid (20 g, 0.05 mol) was dissolved in 700 mL of toluene, and iodomethane (6.2 mL, 0.1 mol) and potassium t-butoxide (16.8 g, 0.15 mol) were added under a nitrogen atmosphere, followed by the addition of a ligand 3-cyclohexylphenol (1.41 g, 0.008 mol) and the catalyst palladium acetate (1.12 g, 0.005 mol), after purged with nitrogen for three times, the mixture was refluxed overnight. At the end of the reaction, the temperature was lowered to room temperature. After passing through a silica gel funnel, the filtrate was poured into 400 mL of water, stirred for half an hour, and then extracted with toluene. The organic phase was combined, dried and concentrated to 500 mL, and recrystallized by adding 200 mL of methanol. After a period of time, a solid was formed, i.e, intermediate a (19.3 g, yield of about 90%), the purity of the solid was 99.2% when detected by HPLC.

Synthesis of Compound 73

The 2,7-dibromo-9,9-dimethylfluorene in Synthesis Example 1 was replaced with an equimolar amount of intermediate a, and the other steps were the same to obtain a pale yellow solid compound 73 (18.3 g, yield of about 78%). Mass spectrum m/z: 839.29 (calc.: 839.01). Theoretical element content (%) $C_{59}H_{42}N_4O_2$: C, 84.46; H, 5.05; N, 6.68; O, 3.81 Measured element content (%): C, 84.54; H, 5.05; N, 6.66; O, 3.75. NMR (600 MHz, CDCl$_3$) (δ, ppm): 8.19-8.05 (m, 4H), 7.74 (ddd, J=14.1, 8.0, 4.9 Hz, 3H), 7.67 (d, J=8.1 Hz, 1H), 7.63 (dd, J=5.0, 3.5 Hz, 3H), 7.60-7.52 (m, 3H), 7.39-7.29 (m, 8H), 7.29-7.26 (m, 2H), 7.26-7.21 (m, 5H), 7.21-7.10 (m, 7H), 1.49 (s, 6H). The above results confirmed that the obtained product was the target product.

Synthesis Example 10: Synthesis of Compound 75

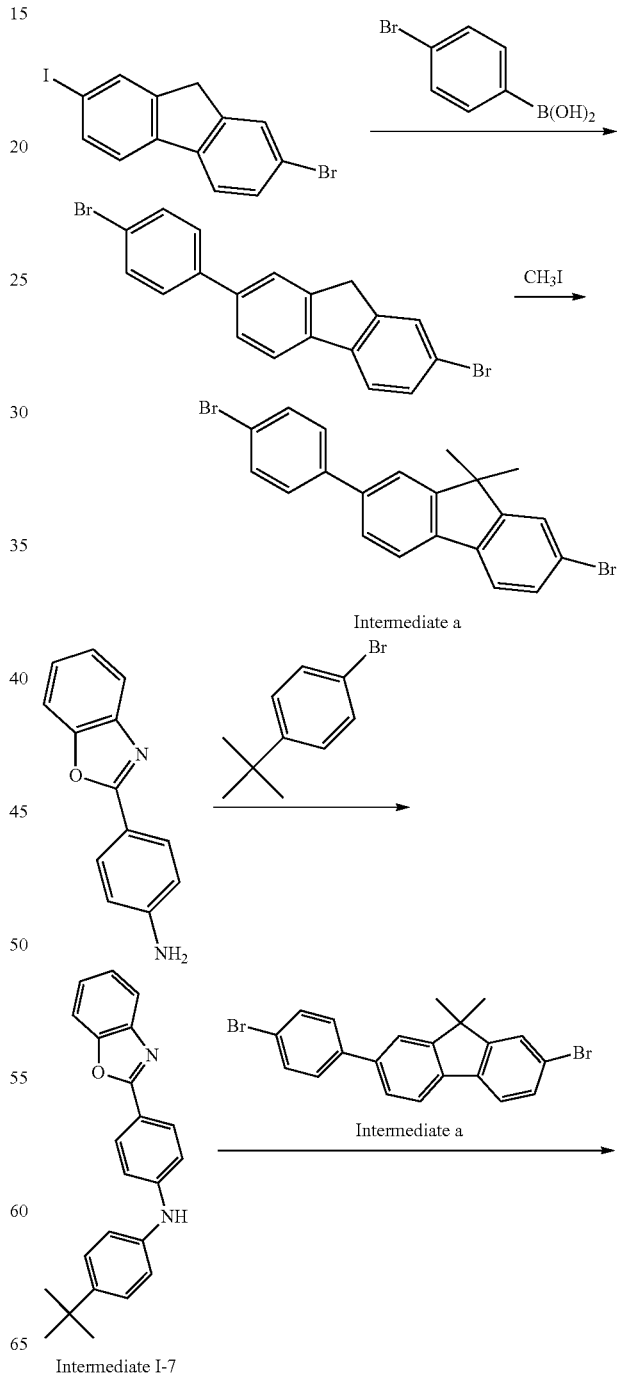

Intermediate I-7

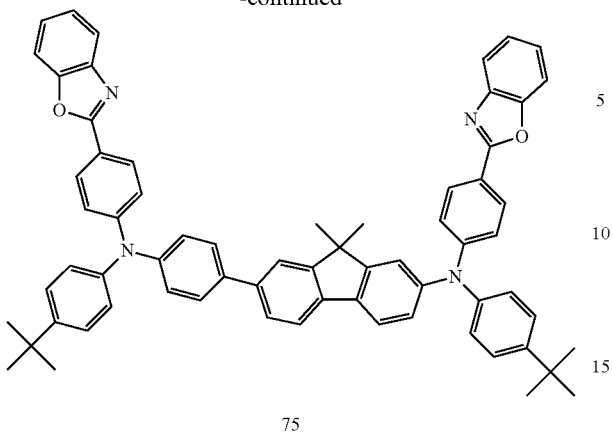

75

The bromobenzene in Synthesis Example 9 was replaced with an equimolar amount of 4-tert-butyl bromobenzene, and the other steps were the same to obtain a yellow solid compound 75 (21.0 g, yield of about 79%). Mass spectrum m/z: 950.51 (calc.: 951.23). Theoretical element content (%) $C_{67}H_{58}N_4O_2$: C, 84.60; H, 6.15; N, 5.89; O, 3.36 Measured element content (%): C, 84.56; H, 6.18; N, 5.83; O, 3.43. The above results confirmed that the obtained product was the target product.

Synthesis Example 11: Synthesis of Compound 78

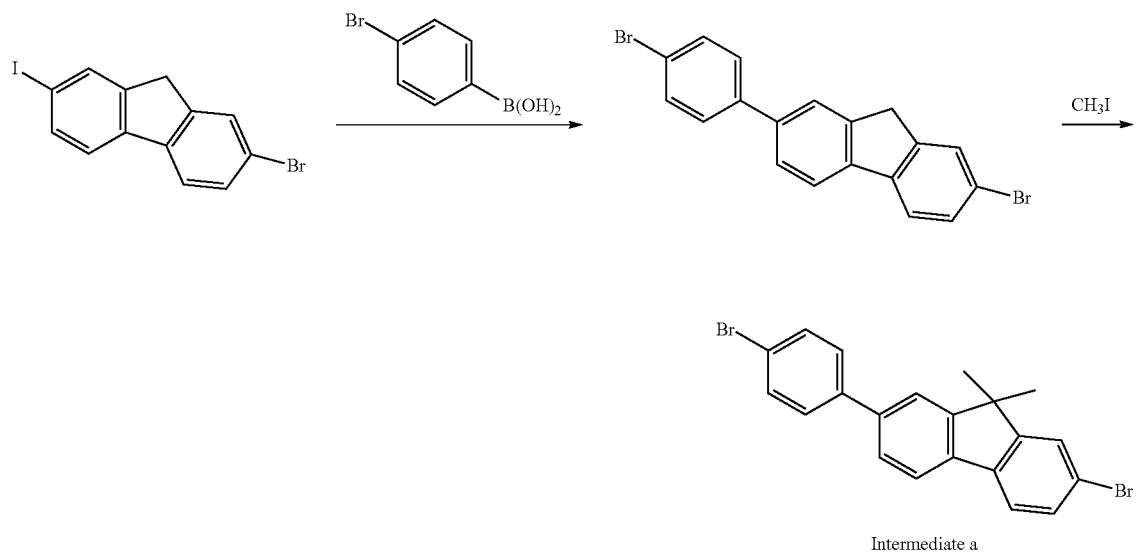 [SMILES: Brc1ccc2c(c1)Cc1cc(I)ccc1-2 ; OB(O)c1ccc(Br)cc1 ; Brc1ccc(-c2ccc3c(c2)Cc2cc(Br)ccc2-3)cc1 ; "CH3I" ; CC1(C)c2cc(Br)ccc2-c2ccc(-c3ccc(Br)cc3)cc21]

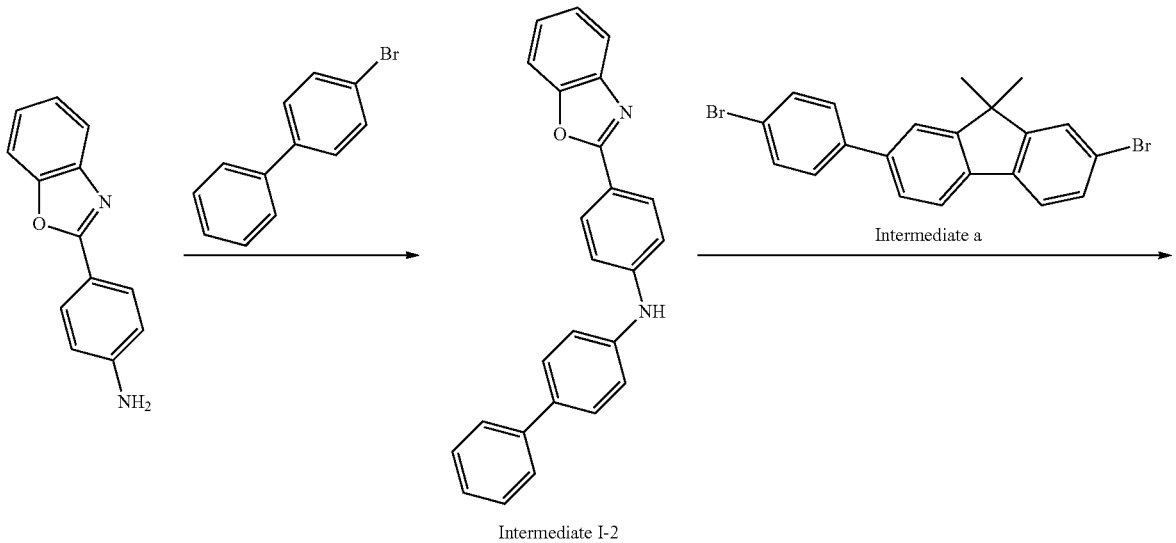

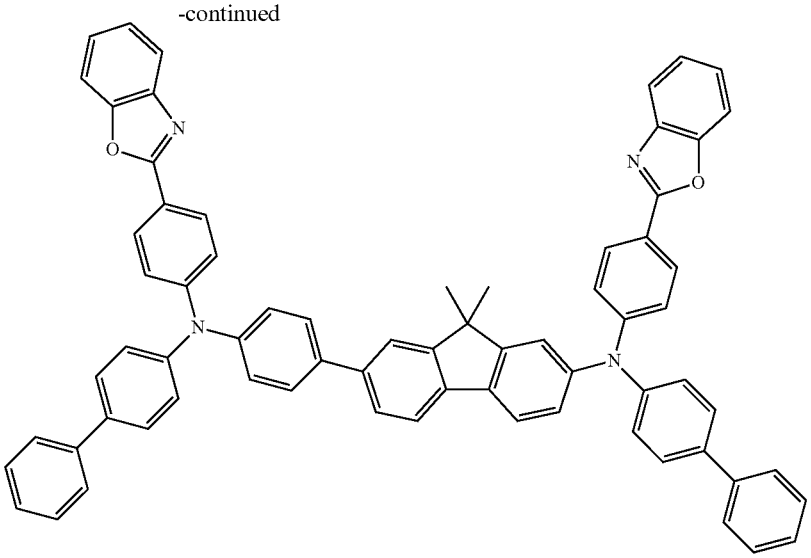

78

The bromobenzene in Synthesis Example 9 was replaced with an equimolar amount of 4-bromobiphenyl, and the other steps were the same to obtain a pale yellow solid compound 78 (20.8 g, yield of about 75%). Mass spectrum m/z: 990.40 (calc.: 991.21). Theoretical element content (%) $C_{71}H_{50}N_4O_2$: C, 86.03; H, 5.08; N, 5.65; O, 3.23 Measured element content (%): C, 86.11; H, 5.04; N, 5.69; O, 3.20. The above results confirmed that the obtained product was the target product.

Synthesis Example 12: Synthesis of Compound 89

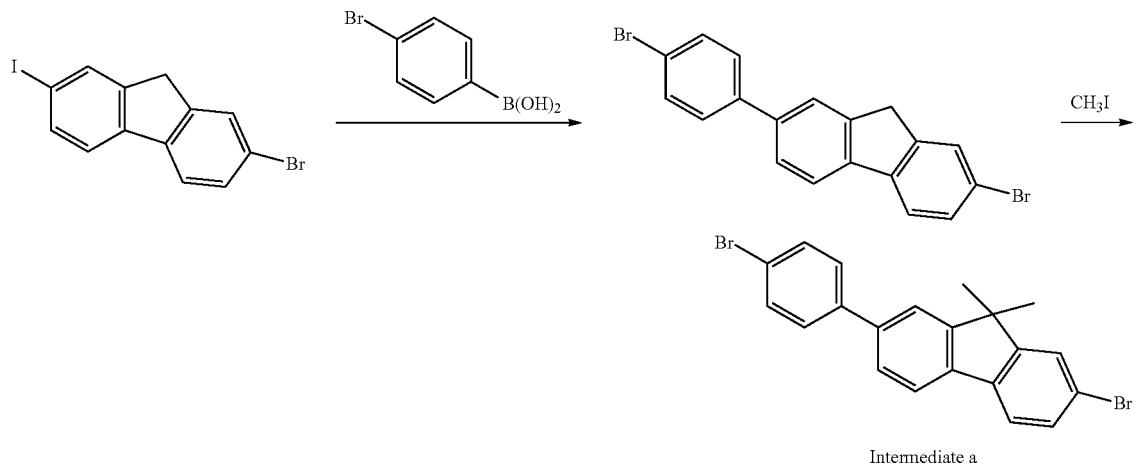

Intermediate a

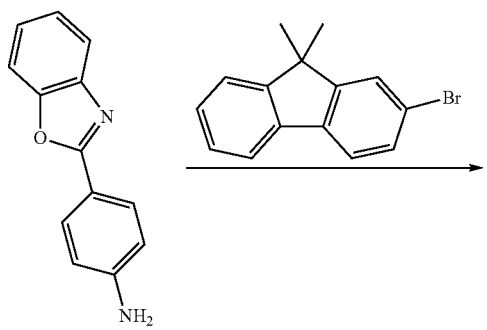

-continued

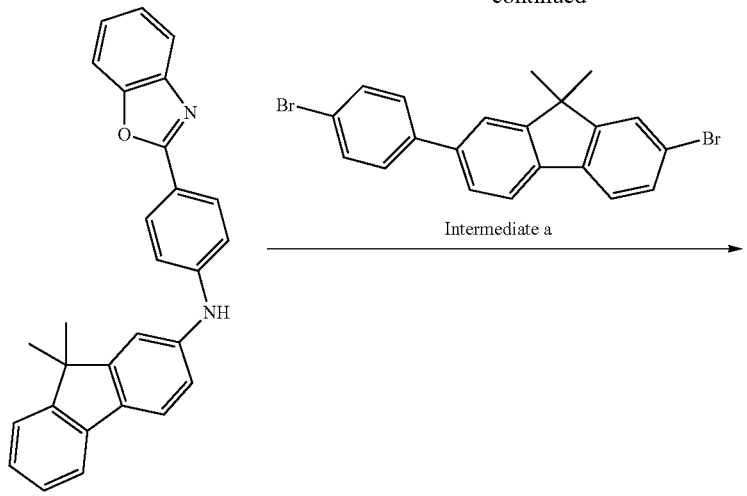

Intermediate a

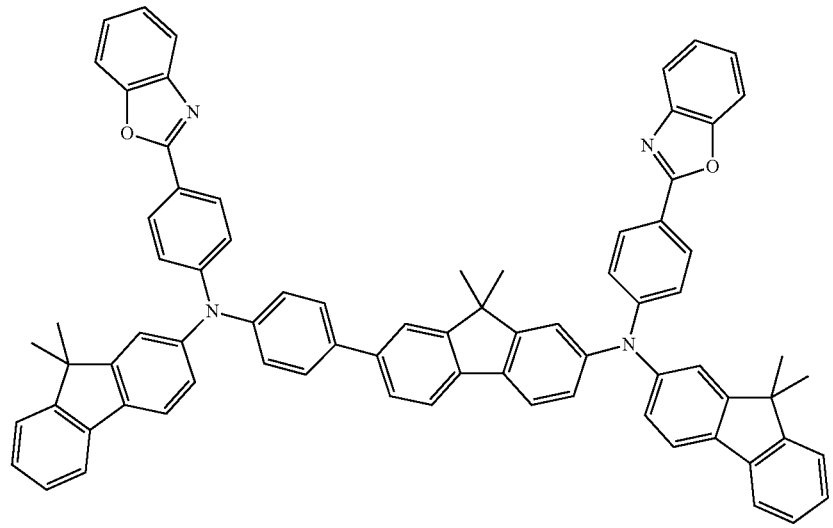

89

The bromobenzene in Synthesis Example 9 was replaced with an equimolar amount of 4-bromobiphenyl, and the other steps were the same to obtain a pale yellow solid compound 89 (21.9 g, yield of about 73%). Mass spectrum m/z: 1070.49 (calc.: 1071.34). Theoretical element content (%) $C_{77}H_{58}N_4O_2$: C, 86.33; H, 5.46; N, 5.23; O, 2.99 Measured element content (%): C, 86.27; H, 5.41; N, 5.29; O, 2.88. The above results confirmed that the obtained product was the target product.

Synthesis Example 13: Synthesis of Compound 101

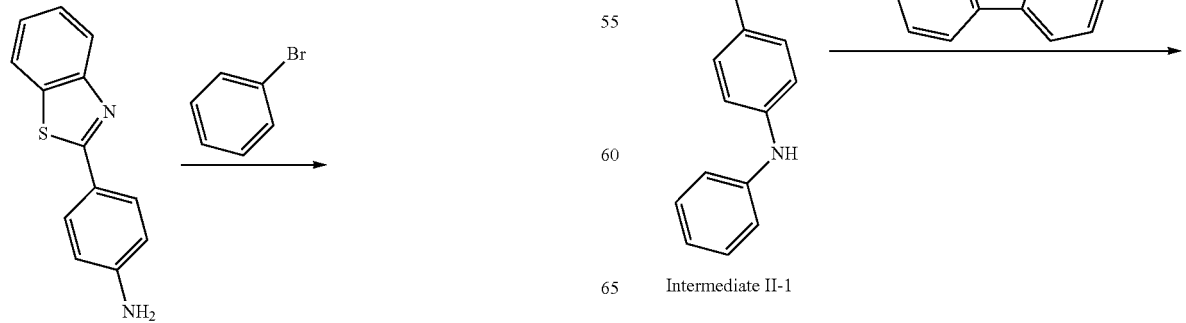

Intermediate II-1

-continued

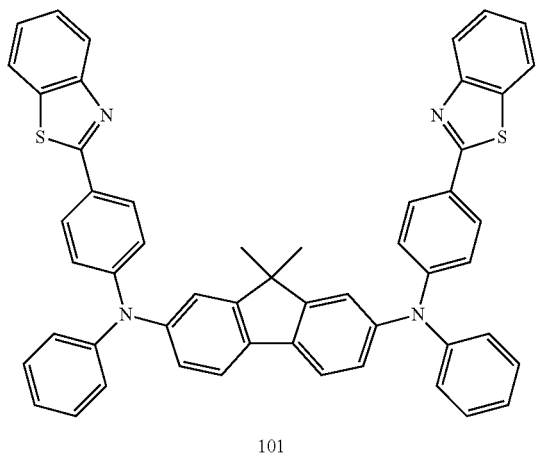

101

The 4-(2-benzoxazolyl)aniline in Synthesis Example 1 was replaced with an equimolar amount of 4-(2-benzothiazolyl) aniline, and the other steps were the same to obtain a bright yellow solid compound 101 (18.5 g, yield of about 83%). Mass spectrum m/z: 795.19 (calc.: 795.04). Theoretical element content (%) $C_{53}H_{38}N_4S_2$: C, 80.07; H, 4.82; N, 7.05; S, 8.07 Measured element content (%): C, 80.13; H, 4.80; N, 7.04; S, 8.03. $^1$H NMR (600 MHz, CDCl$_3$) (δ, ppm): 8.18 (dd, J=6.9, 2.0 Hz, 2H), 8.02 (dd, J=6.8, 2.1 Hz, 2H), 7.86 (dd, J=7.5, 5.0 Hz, 6H), 7.58-7.47 (m, 6H), 7.37 (d, J=7.5 Hz, 4H), 7.31-7.21 (m, 6H), 7.08 (dd, J=7.5, 1.4 Hz, 4H), 7.04-6.96 (m, 2H), 1.69 (s, 6H). The above results confirmed that the obtained product was the target product.

Synthesis Example 14: Synthesis of Compound 121

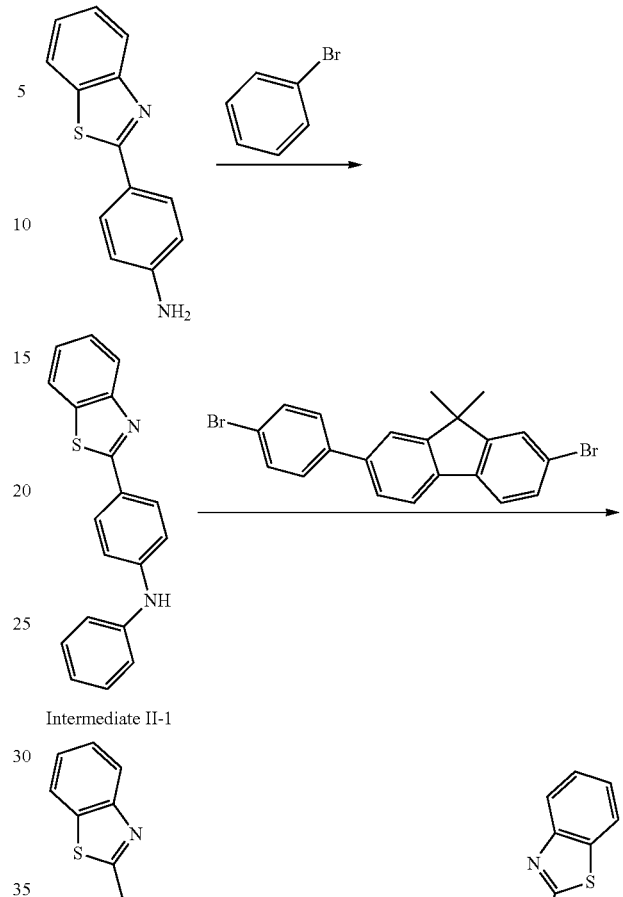

Intermediate II-1

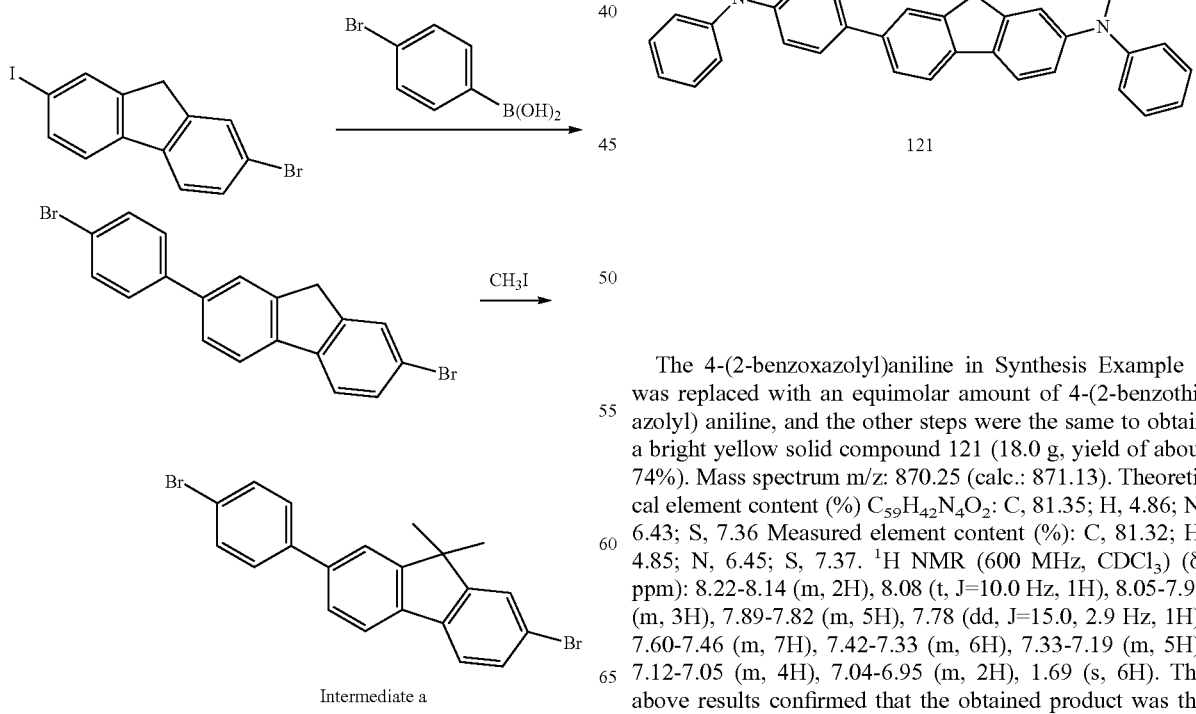

121

The 4-(2-benzoxazolyl)aniline in Synthesis Example 9 was replaced with an equimolar amount of 4-(2-benzothiazolyl) aniline, and the other steps were the same to obtain a bright yellow solid compound 121 (18.0 g, yield of about 74%). Mass spectrum m/z: 870.25 (calc.: 871.13). Theoretical element content (%) $C_{59}H_{42}N_4O_2$: C, 81.35; H, 4.86; N, 6.43; S, 7.36 Measured element content (%): C, 81.32; H, 4.85; N, 6.45; S, 7.37. $^1$H NMR (600 MHz, CDCl$_3$) (δ, ppm): 8.22-8.14 (m, 2H), 8.08 (t, J=10.0 Hz, 1H), 8.05-7.98 (m, 3H), 7.89-7.82 (m, 5H), 7.78 (dd, J=15.0, 2.9 Hz, 1H), 7.60-7.46 (m, 7H), 7.42-7.33 (m, 6H), 7.33-7.19 (m, 5H), 7.12-7.05 (m, 4H), 7.04-6.95 (m, 2H), 1.69 (s, 6H). The above results confirmed that the obtained product was the target product.

Synthesis Example 15: Synthesis of Compound 125
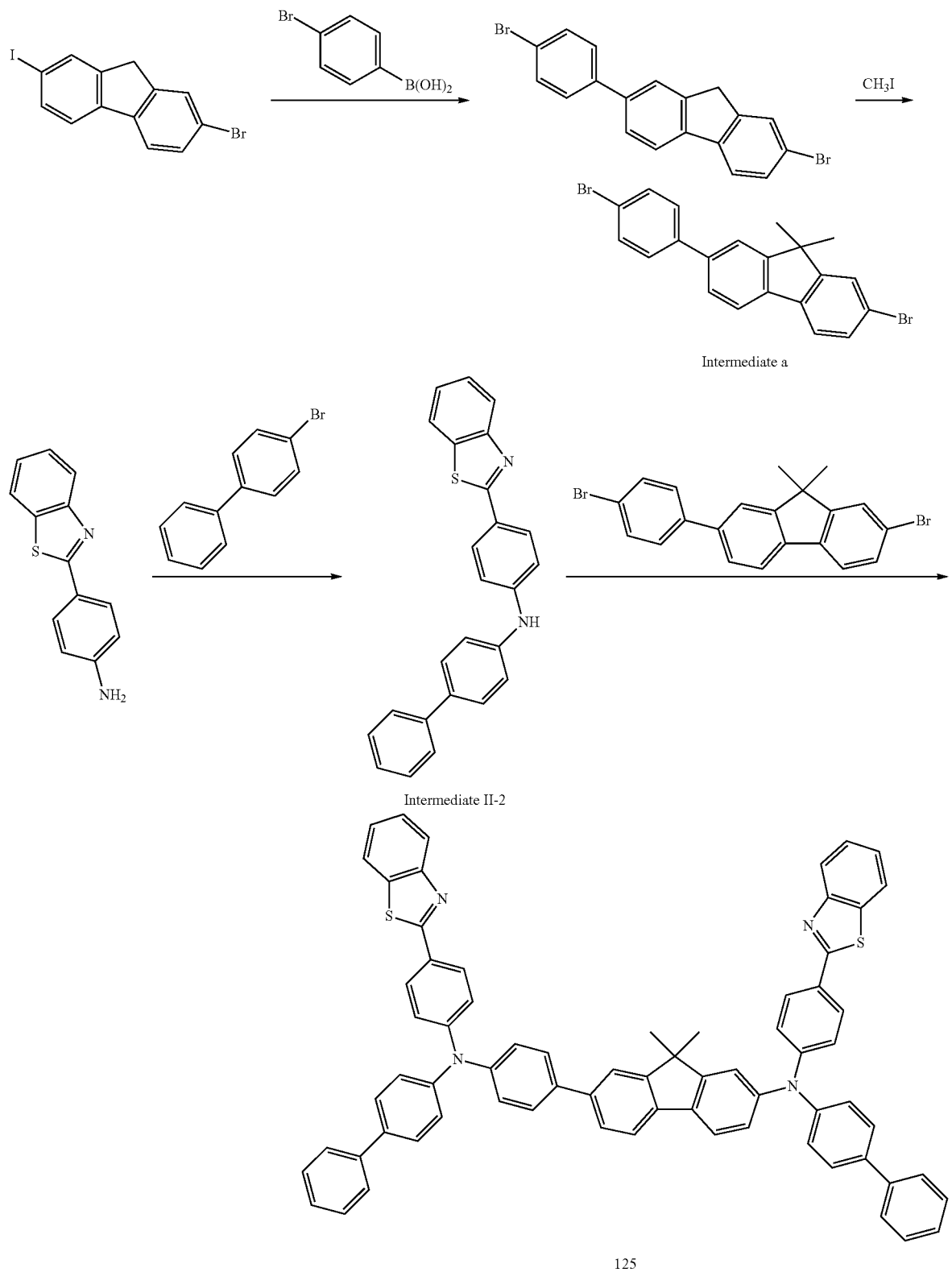
The bromobenzene in Synthesis Example 9 was replaced with an equimolar amount of 4-bromobiphenyl, the 4-(2-benzoxazolyl)aniline was replaced with an equimolar amount of 4-(2-benzothiazolyl) aniline, and the other steps were the same to obtain a bright yellow solid compound 125 (20.9 g, yield of about 73%). Mass spectrum m/z: 1022.38 (calc.: 1023.33). Theoretical element content (%) $C_{71}H_{50}N_4S_2$: C, 83.33; H, 4.93; N, 5.48; S, 6.27 Measured element content (%): C, 83.24; H, 4.97; N, 5.51; S, 6.24. The above results confirmed that the obtained product was the target product.

Synthesis Example 16: Synthesis of Compound 143

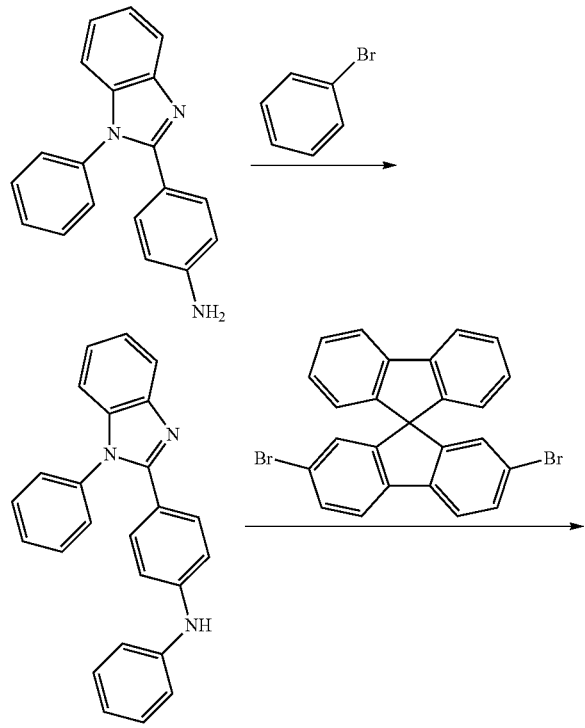

Intermediate III-1

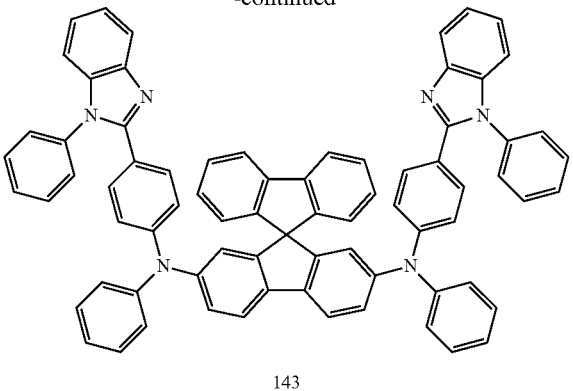

143

The 4-(2-benzoxazolyl)aniline in Synthesis Example 1 was replaced with an equimolar amount of 4-(1-phenylbenzimidazol-2-yl)aniline, 2,7-dibromo-9,9-dimethylfluorene was replaced with an equimolar amount of 2,7-dibromo-9,9'-spirobifluorene, and the other steps were the same to obtain a yellow solid compound 143 (20.58 g, yield of about 71%). Mass spectrum m/z: 1034.35 (calc.: 1035.27). Theoretical element content (%) $C_{59}H_{42}N_4O_2$: C, 87.01; H, 4.87; N, 8.12; Measured element content (%): C, 86.98; H, 4.91; N, 8.11. $^1$H NMR (600 MHz, CDCl$_3$) (δ, ppm): $^1$H NMR (600 MHz, CDCl$_3$) (δ, ppm) 7.85 (d, J=7.2 Hz, 2H), 7.70 (d, J=7.6 Hz, 2H), 7.61 (d, J=8.2 Hz, 2H), 7.48 (d, J=6.9 Hz, 6H), 7.40-7.27 (m, 12H), 7.25-7.20 (m, 2H), 7.20-7.10 (m, 8H), 7.06-6.86 (m, 8H), 6.83 (d, J=7.6 Hz, 2H), 6.77 (d, J=8.7 Hz, 4H), 6.50 (d, J=1.7 Hz, 2H). The above results confirmed that the obtained product was the target product.

Synthesis Example 17: Synthesis of Compound 144

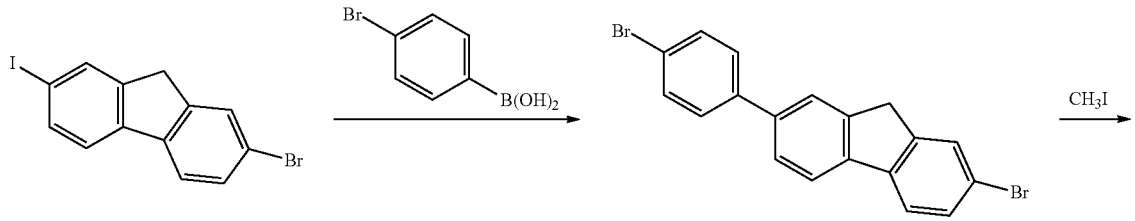

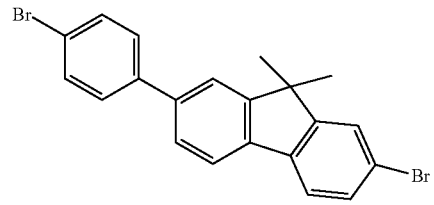

Intermediate a

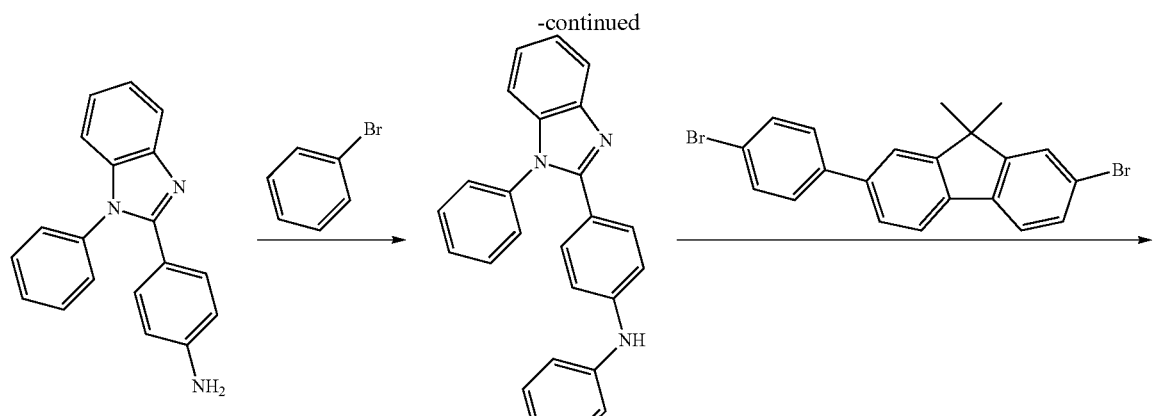

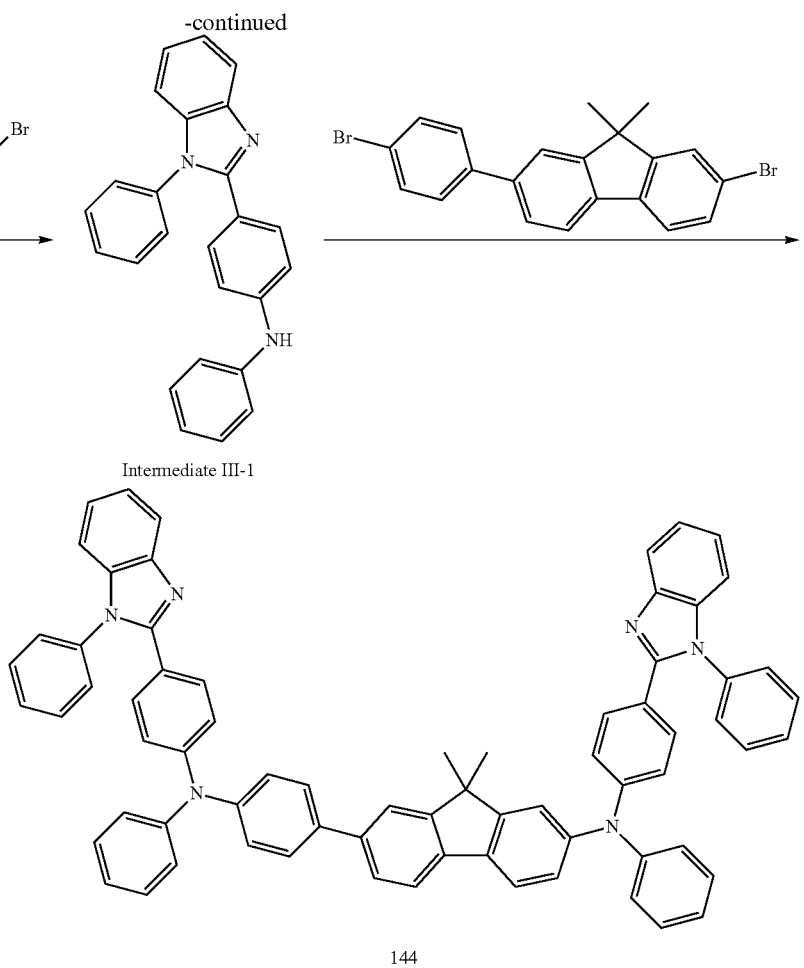

The 4-(2-benzoxazolyl)aniline in Synthesis Example 9 was replaced with an equimolar amount of 4-(1-phenylbenzimidazol-2-yl)aniline, and the other steps were the same to obtain a yellow solid compound 144 (19.4 g, yield of about 70%). Mass spectrum m/z: 988.49 (calc.: 989.24). Theoretical element content (%) $C_{71}H_{52}N_6$: C, 86.21; H, 5.30; N, 8.50 Measured element content (%): C, 86.32; H, 5.24; N, 8.56. The above results confirmed that the obtained product was the target product.

Synthesis Example 18: Synthesis of Compound 146

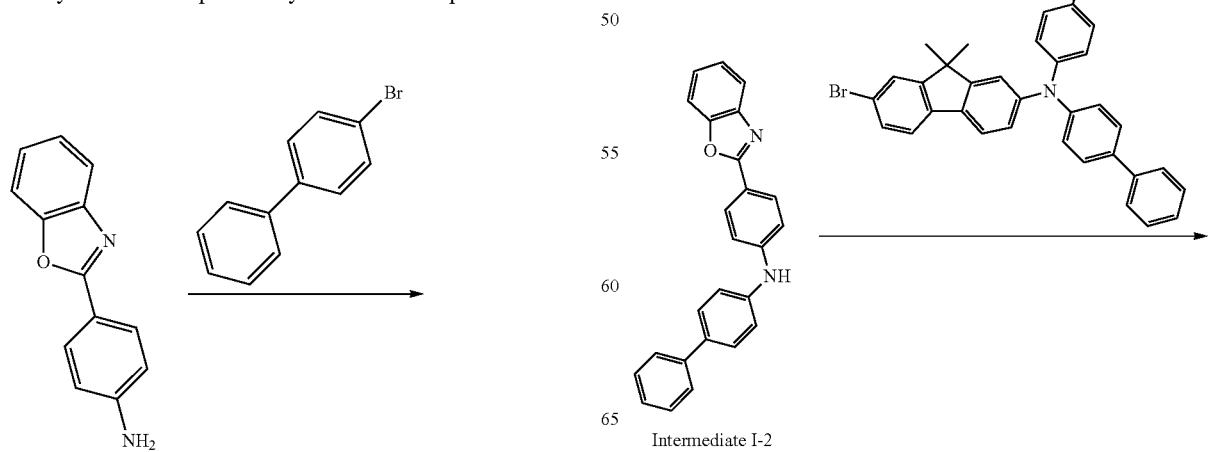

-continued

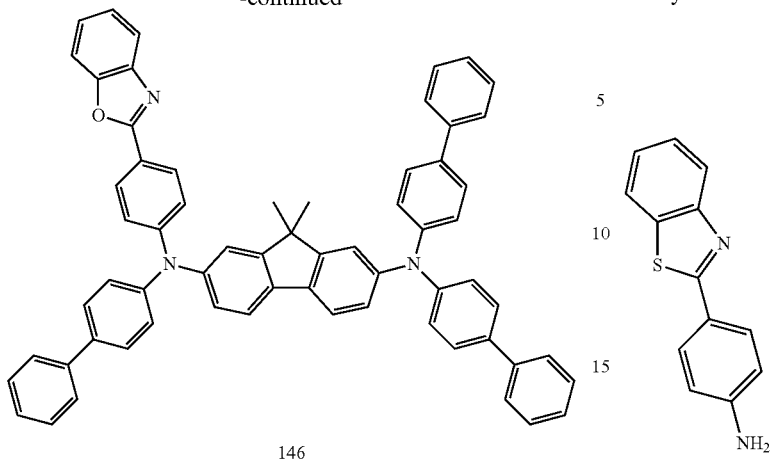

146

Degassed toluene solvent (100 mL) was added to a 250 mL reaction flask, and then the starting material intermediate I-2 (17.6 g, 0.028 mol), N,N-bis([1,1'-biphenyl]-4-yl)-7-bromo-9,9-dimethyl-9H-fluorene-2-amine (9.8 g, 0.028 mol) and sodium tert-butoxide (4.0 g, 0.042 mol) were added therein, sequentially. After purged with nitrogen for three times, palladium acetate (0.06 g, 0.00028 mol) was added. After purged with nitrogen for three times, tri-tert-butylphosphine (1.12 mL of a 1.0 M solution in toluene, 0.00112 mol) was added. After purged with nitrogen for three times again, the mixture was refluxed for 2 hours under a nitrogen atmosphere. After the reaction ceased, the mixture was cooled to room temperature and filtered through Celite to give a filtrate. The filtrate was concentrated and heated to 60° C., and then a small amount of ethanol was added thereto, and the mixture was allowed to stand still at room temperature to recrystallize. After a period of time, a solid was formed, which was filtered with suction and eluted with ethanol to obtain a recrystallized solid to give a pale yellow solid compound 146 (21.8 g, yield of about 89%), the purity of the solid was 99.9% when detected by HPLC.

Mass spectrum m/z: 873.35 (calc.: 874.10). Theoretical element content (%) $C_{64}H_{47}N_3O$: C, 87.94; H, 5.42; N, 4.81; O, 1.83 Measured element content (%): C, 87.85; H, 5.54; N, 4.84; O, 1.99. $^1$H NMR (600 MHz, CDCl$_3$) (δ, ppm): 7.88 (s, 1H), 7.85 (s, 1H), 7.77-7.75 (m, 3H), 7.75-7.73 (m, 5H), 7.72 (t, J=3.5 Hz, 2H), 7.56 (d, J=2.3 Hz, 2H), 7.55-7.51 (m, 7H), 7.49 (dd, J=3.9, 3.0 Hz, 3H), 7.48-7.45 (m, 2H), 7.43 (dd, J=7.7, 4.4 Hz, 2H), 7.41-7.39 (m, 2H), 7.39-7.37 (m, 5H), 7.37-7.34 (m, 4H), 7.32 (d, J=2.9 Hz, 1H), 7.29 (d, J=2.9 Hz, 1H), 1.69 (s, 6H). The above results confirmed that the obtained product was the target product.

Synthesis Example 19: Synthesis of Compound 153

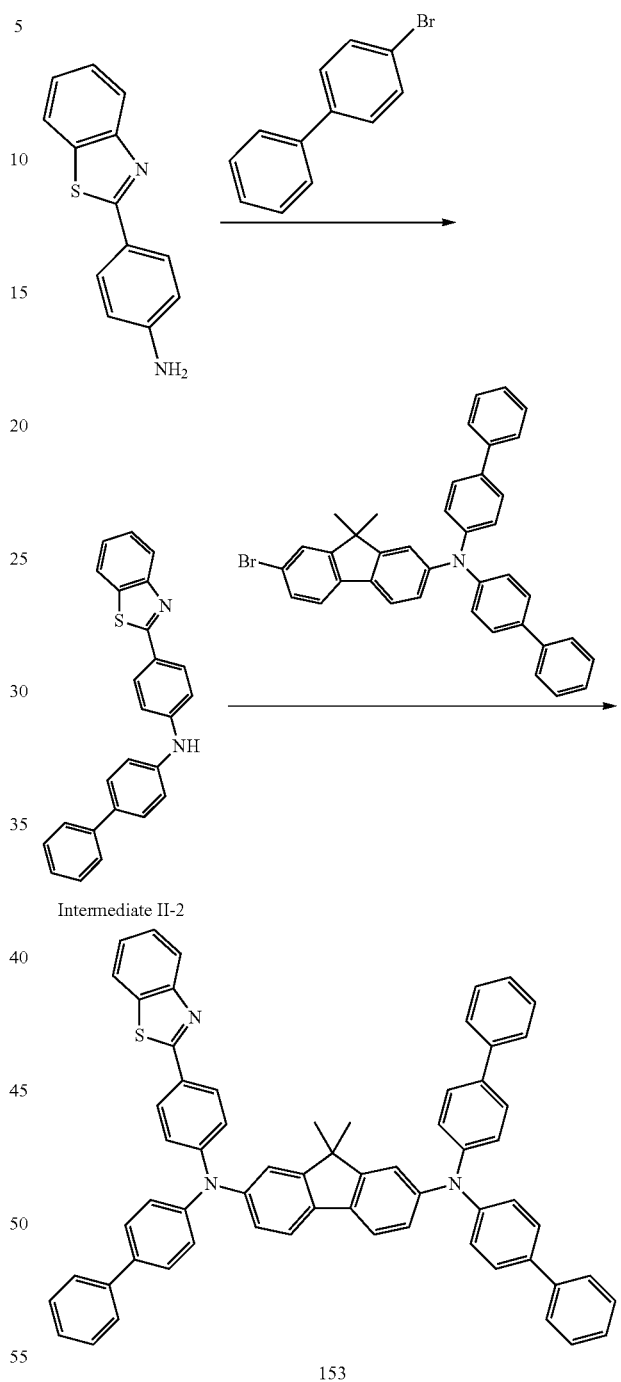

The Intermediate I-2 in Synthesis Example 18 was replaced with an equimolar amount of Intermediate 11-2, and the other steps were the same to obtain a bright yellow solid compound 153 (22.7 g, yield of about 91%). Mass spectrum m/z: 889.37 (calc.: 890.16). Theoretical element content (%) $C_{64}H_{47}N_3S$: C, 86.36; H, 5.32; N, 4.72; S, 3.60 Measured element content (%): C, 86.26; H, 5.25; N, 4.87; S, 3.55. The above results confirmed that the obtained product was the target product.

Photophysical Properties of the Compounds

Determination of the glass transition temperature ($T_g$) of the compounds: The measuring instrument was a DSC 25 type differential scanning calorimeter from TA Co., USA; the test atmosphere was nitrogen, the flow rate of nitrogen was 50 ml/min; and the heating rate was 10° C./min. The temperature range was 50-350° C.; the mass of the compound sample was 1 to 6 mg; and the type of crucible was aluminium crucible. The measured glass transition temperature ($T_g$) is shown in Table 1.

TABLE 1

Glass transition temperature ($T_g$) of the compounds

| Compounds | Glass transition temperature(° C.) |
|---|---|
| Compound 1 | 130 |
| Compound 10 | 133 |
| Compound 22 | 139 |
| Compound 26 | 140 |
| Compound 27 | 140 |
| Compound 35 | 137 |
| Compound 41 | 132 |
| Compound 44 | 135 |
| Compound 73 | 132 |
| Compound 75 | 131 |
| Compound 78 | 134 |
| Compound 89 | 140 |
| Compound 101 | 129 |
| Compound 121 | 132 |
| Compound 125 | 135 |
| Compound 143 | 131 |
| Compound 144 | 129 |
| Compound 146 | 131 |
| Compound 153 | 132 |
| CPM-1 | 125 |
| CPM-2 | 128 |

It can be seen from Table 1 that the glass transition temperature of the amine derivative of the present disclosure is higher than that of CPM-1 and CPM-2, therefore the amine derivative of the present disclosure is more excellent in thermal stability, and is a material with more stable properties.

Determination of refractive index (n) of the compounds: The measuring instrument was M-2000 Spectroscopic Ellipsometer from J. A. Woollam Co., USA; the scanning range of the instrument was 245 to 1000 nm; the size of the glass substrate was 200×200 mm, and the thickness of the material film was 20 to 60 nm. The measured refractive index (n) at 450 nm is shown in Table 2.

TABLE 2

Refractive index(n) of compounds

| Compounds | Refractive index |
|---|---|
| Compound 1 | 2.07 |
| Compound 10 | 2.11 |
| Compound 22 | 2.09 |
| Compound 26 | 2.10 |
| Compound 27 | 2.10 |
| Compound 35 | 2.12 |
| Compound 41 | 2.08 |
| Compound 44 | 2.12 |
| Compound 73 | 2.06 |
| Compound 75 | 2.05 |
| Compound 78 | 2.10 |
| Compound 89 | 2.12 |
| Compound 101 | 2.07 |
| Compound 121 | 2.05 |
| Compound 125 | 2.09 |

TABLE 2-continued

Refractive index(n) of compounds

| Compounds | Refractive index |
|---|---|
| Compound 143 | 2.04 |
| Compound 144 | 2.07 |
| Compound 146 | 2.14 |
| Compound 153 | 2.13 |
| CPM-1 | 2.10 |
| CPM-2 | 2.15 |

As can be seen from Table 2, the refractive index of the amine derivative of the present disclosure is comparable to that of the compounds CPM-1 and CPM-2, indicating that the amine derivative of the present disclosure can effectively couple the light in the device out when used as a light extraction material, improving the luminous efficiency of the organic electroluminescent device.

Preparation and Performance of the Device

In the present disclosure, the organic materials were sublimed and the purities thereof were above 99.99%. The ITO glass substrate used in the experiment was purchased from Shenzhen South Glass Display Devices Technology Co., Ltd. The ITO glass substrate was ultrasonically cleaned twice with 5% of glass cleaning solution for 20 minutes each time, and then ultrasonically washed twice with deionized water for 10 minutes each time. It was ultrasonically cleaned with acetone and isopropanone in sequence for 20 minutes, and then dried at 120° C.

The device was prepared by vacuum evaporation system and continuously evaporated under vacuum without interruption. The materials used were in quartz crucibles containing different evaporation sources, and the temperature of the evaporation sources can be controlled separately. The thermal evaporation rate of the organic material or the doped parent organic material was generally set at 0.1 nm/s, and the evaporation rate of the doping material was adjusted according to the doping ratio; the evaporation rate of the electrode metal was 0.4 to 0.6 nm/s. The treated glass substrate was placed in an OLED vacuum coating machine. During the film making process, the vacuum degree of the system should be maintained below $5 \times 10^{-5}$ Pa, and the organic layer and the metal electrode were evaporated by replacing the mask plate, respectively, the evaporation rate was measured by SQM160 Quartz Crystal Film Thickness detector from Inficon, and the film thickness was measured by a quartz crystal oscillator. The test software, computer, K2400 digital source meter manufactured by Keithley Company, USA and PR788 Spectral scanning luminometer from Photo Research Company, USA were combined to form a joint IVL test system to test the driving voltage, luminous efficiency and CIE color coordinate of the organic electroluminescent device. The life test was performed using McScience's M6000 OLED Life Test System. The test was performed in atmospheric environment and the temperature was at room temperature.

Example 1: Preparation of Organic Electroluminescent Device 1

ITO/Ag/ITO was used as an anode on the glass substrate; HIM-1 was vacuum evaporated on the anode as a first hole injection layer, and the evaporation thickness was 60 nm; HAT-CN was vacuum evaporated on the first hole injection layer as a second hole injection layer, and the evaporation thickness was 5 nm; NPB was vacuum evaporated on the second hole injection layer as a hole transport layer, and the evaporation thickness was 60 nm; BH-1 and 3% BD-1 were vacuum evaporated on the hole transport layer as a light emitting layer, and the evaporation thickness was 25 nm; Alq₃:Liq (1:1) was vacuum evaporated on the light emitting layer as an electron transport layer, and the evaporation thickness was 30 nm; LiF was vacuum evaporated on the electron transport layer as an electron injection layer, and the evaporation thickness was 1 nm; Mg/Ag (9:1) was vacuum evaporated on the electron injection layer as a cathode, and the evaporation thickness was 15 nm; the compound 1 of the present disclosure was vacuum evaporated on the cathode as a light extraction layer, and the evaporation thickness was 60 nm.

BD-1

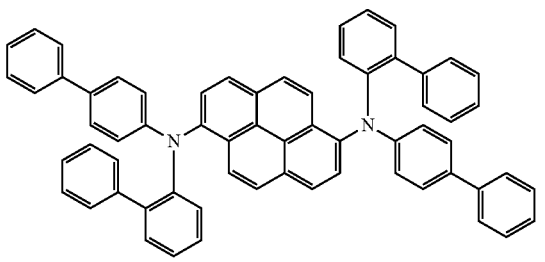

HIM-1

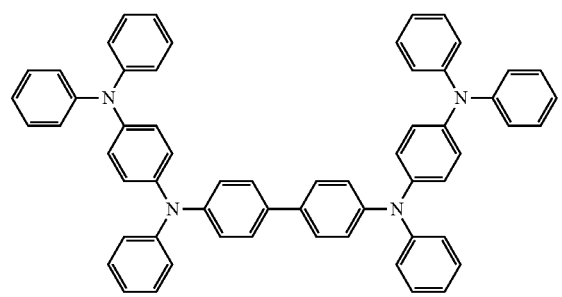

ETM-1

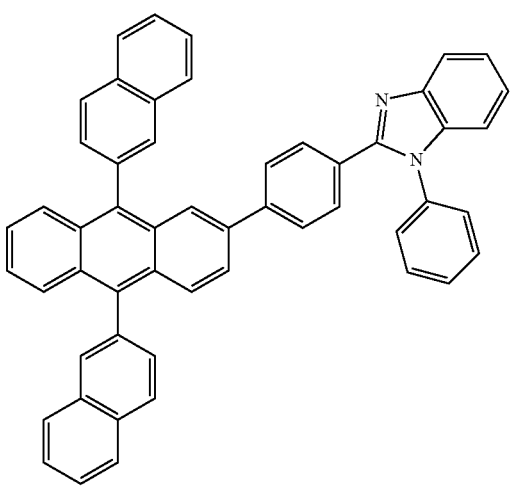

HAT-CN

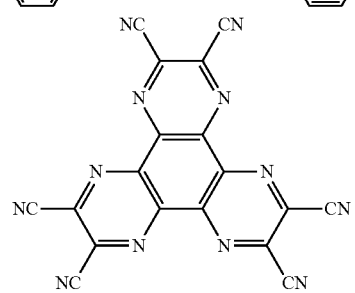

Liq

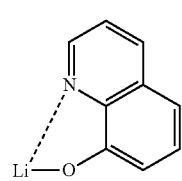

NPB

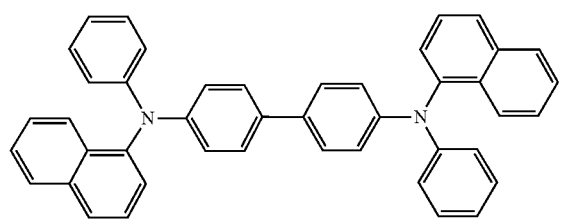

CPM-1

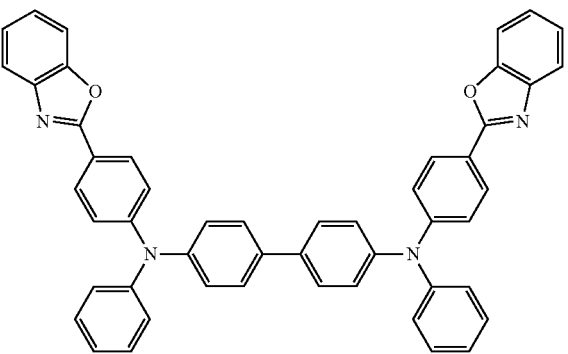

BH-1

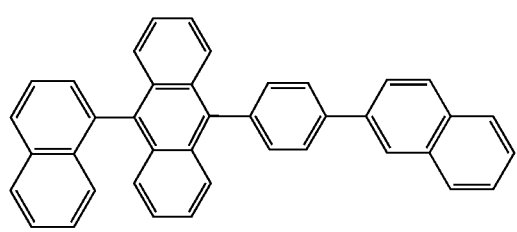

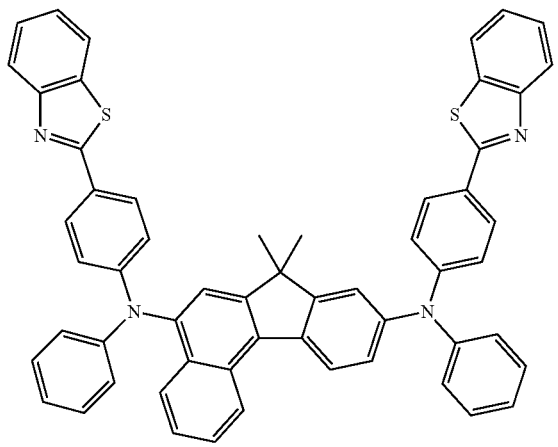

CPM-2

Example 2-19

Compound 1 in the light extraction layer of Example 1 was replaced with Compound 10, Compound 22, Compound 26, Compound 27, Compound 35, Compound 41, Compound 44, Compound 73, Compound 75, Compound 78, Compound 89, Compound 101, Compound 121, Compound 125, Compound 143, Compound 144, Compound 146, Compound 153, respectively, and the other steps were the same to obtain the organic electroluminescent devices 2-19.

Comparative Example 1

The compound 1 in the light extraction layer of Example 1 was replaced with the compound CPM-1, and the other steps were the same to obtain a comparative organic electroluminescent device 1.

Comparative Example 2

The compound 1 in the light extraction layer of Example 1 was replaced with the compound CPM-2, and the other steps were the same to obtain a comparative organic electroluminescent device 2.

Comparative Example 3

An organic electroluminescent device was prepared by referring to the procedure of Example 1, without forming a light extraction layer, and a comparative organic electroluminescent device 3 was obtained.

The luminescent property test results of the organic electroluminescent devices prepared in Examples 1 to 19 and Comparative Examples 1-3 of the present disclosure are shown in Table 3.

TABLE 3

Data of the luminescent property test of the organic electroluminescent devices

| No. | Material of light extraction layer | Driving voltage [V] (@ 10 mA/cm$^2$) | Luminous efficiency [cd/A] (@ 10 mA/cm$^2$) | Lifetime [T97, h] (@ 10 mA/cm$^2$) | Color |
|---|---|---|---|---|---|
| Example 1 | Compound 1 | 3.98 | 6.82 | 123 | Blue |
| Example 2 | Compound 10 | 3.99 | 6.86 | 132 | Blue |
| Example 3 | Compound 22 | 4.00 | 6.84 | 150 | Blue |
| Example 4 | Compound 26 | 4.00 | 6.85 | 153 | Blue |
| Example 5 | Compound 27 | 4.00 | 6.85 | 152 | Blue |
| Example 6 | Compound 35 | 3.99 | 6.87 | 144 | Blue |
| Example 7 | Compound 41 | 3.99 | 6.83 | 130 | Blue |
| Example 8 | Compound 44 | 4.00 | 6.87 | 138 | Blue |
| Example 9 | Compound 73 | 4.02 | 6.81 | 129 | Blue |
| Example 10 | Compound 75 | 4.01 | 6.80 | 127 | Blue |
| Example 11 | Compound 78 | 4.02 | 6.85 | 135 | Blue |
| Example 12 | Compound 89 | 4.02 | 6.87 | 154 | Blue |
| Example 13 | Compound 101 | 4.00 | 6.82 | 120 | Blue |
| Example 14 | Compound 121 | 4.01 | 6.80 | 131 | Blue |
| Example 15 | Compound 125 | 4.01 | 6.84 | 138 | Blue |
| Example 16 | Compound 143 | 4.00 | 6.80 | 128 | Blue |
| Example 17 | Compound 144 | 4.03 | 6.82 | 120 | Blue |
| Example 18 | Compound 146 | 3.98 | 6.89 | 126 | Blue |
| Example 19 | Compound 153 | 3.99 | 6.88 | 131 | Blue |
| Comparative Example 1 | CPM-1 | 4.01 | 6.85 | 95 | Blue |
| Comparative Example 2 | CPM-2 | 4.00 | 6.88 | 105 | Blue |
| Comparative Example 3 | — | 4.00 | 4.56 | 90 | Blue |

As can be seen from Table 3, the organic electroluminescent device using the amine derivative of the present disclosure as a light extraction material has a longer service life than Comparative Example 1 and Comparative Example 2. Compared with Comparative Example 3, the organic electroluminescent device using the amine derivative of the present disclosure as a light extraction material has higher luminous efficiency and longer service life. Therefore, the amine derivative of the present disclosure is a light extraction material having a better performance.

What is claimed is:

1. An amine derivative, wherein the amine derivative is represented by Formula I,

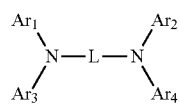

I wherein both $Ar_1$ and $Ar_2$ are selected from a group as shown in Formula II,

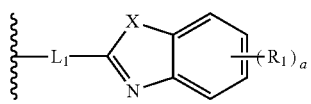

II wherein the amine derivative is as shown in Formula I-2,

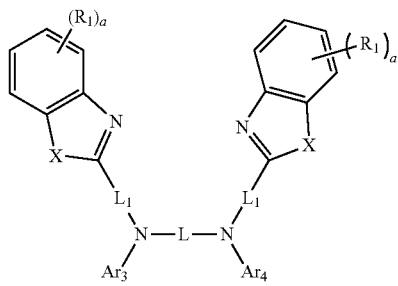

I-2

$L_1$ is selected from the group consisting of a single bond, a substituted or unsubstituted C6-C18 arylene group, and a substituted or unsubstituted C3-C18 heteroarylene group; a is selected from an integer of 0 to 4, and $R_1$ is selected from the group consisting of a substituted or unsubstituted C1-C15 alkyl group, and a substituted or unsubstituted C6-C18 aryl group, and when a is greater than 1, each $R_1$ is the same or different, X is selected from O, S or N ($R_x$), and $R_x$ is selected from the group consisting of a substituted or unsubstituted C1-C15 alkyl group, and a substituted or unsubstituted C6-C18 aryl group;

$Ar_3$ and $Ar_4$ are independently selected from the group consisting of a substituted or unsubstituted C6-C30 aryl group, and a substituted or unsubstituted C3-C30 heteroaryl group;

L is selected from the group consisting of one of the groups as shown below,

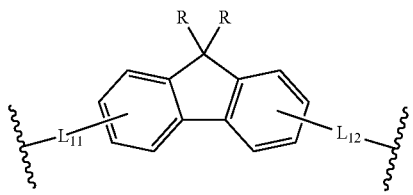

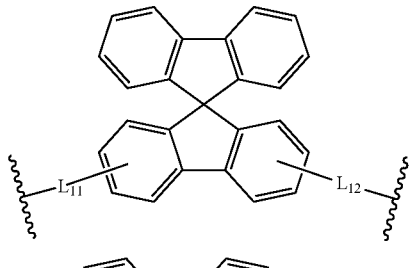

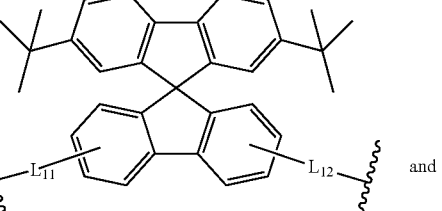

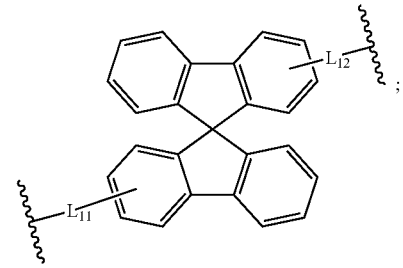

and

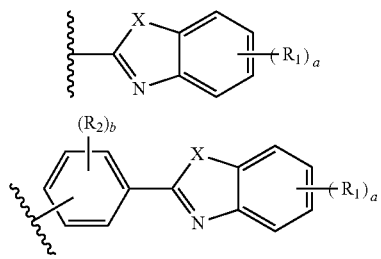

;

R is selected from the group consisting of hydrogen, a substituted or unsubstituted C1-C15 alkyl group, a substituted or unsubstituted C6-C18 aryl group, and a substituted or unsubstituted C3-C18 heteroaryl group; and $L_{11}$ and $L_{12}$ are independently selected from the group consisting of a single bond, a substituted or unsubstituted C6-C18 arylene group, and a substituted or unsubstituted C3-C18 heteroarylene group.

2. The amine derivative according to claim 1, wherein Formula II is selected from the group consisting of groups as shown below, -continued

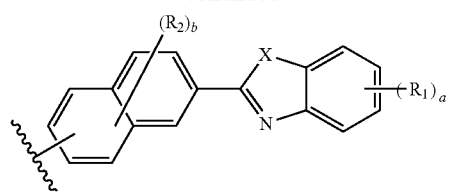

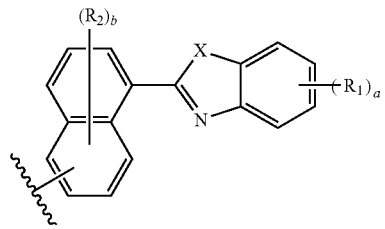

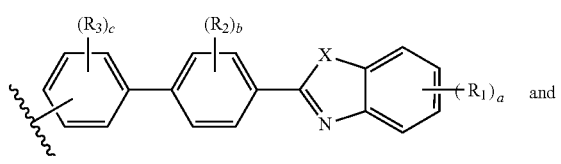 and

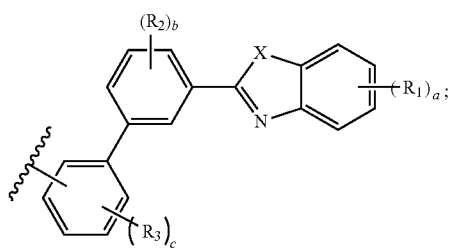

wherein, b is selected from an integer of 0 to 4, and $R_2$ is selected from the group consisting of a substituted or unsubstituted C1-C10 alkyl group, and a substituted or unsubstituted C6-C18 aryl group, when b is greater than 1, each $R_2$ is the same or different;

c is selected from an integer of 0 to 4, and $R_3$ is selected from the group consisting of a substituted or unsubstituted C1-C10 alkyl group, and a substituted or unsubstituted C6-C18 aryl group, when c is greater than 1, each $R_3$ is the same or different.

3. The amine derivative according to claim 1, wherein $Ar_3$ and $Ar_4$ are independently selected from one of the groups as shown below,

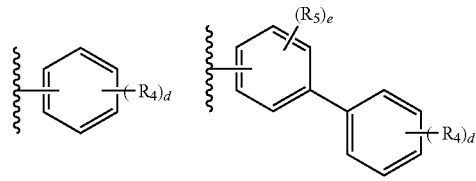

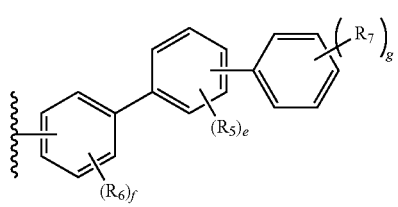

-continued

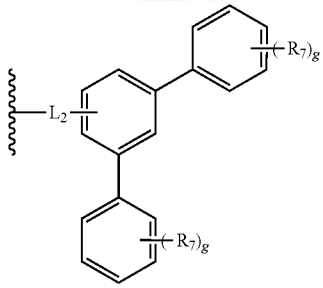

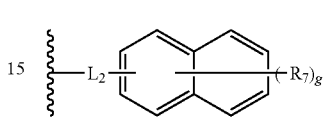 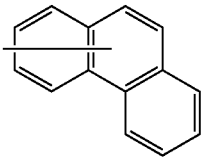

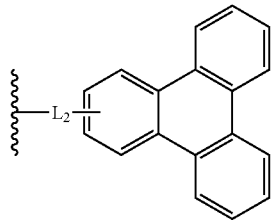

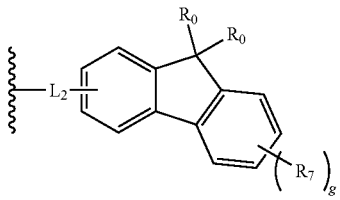

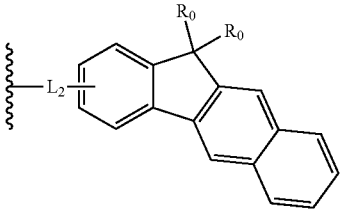

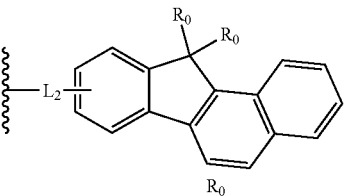

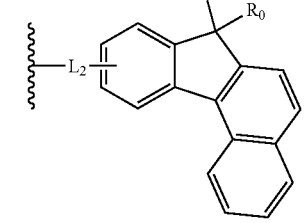

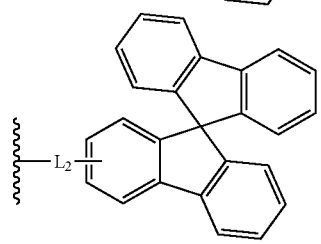

149
-continued
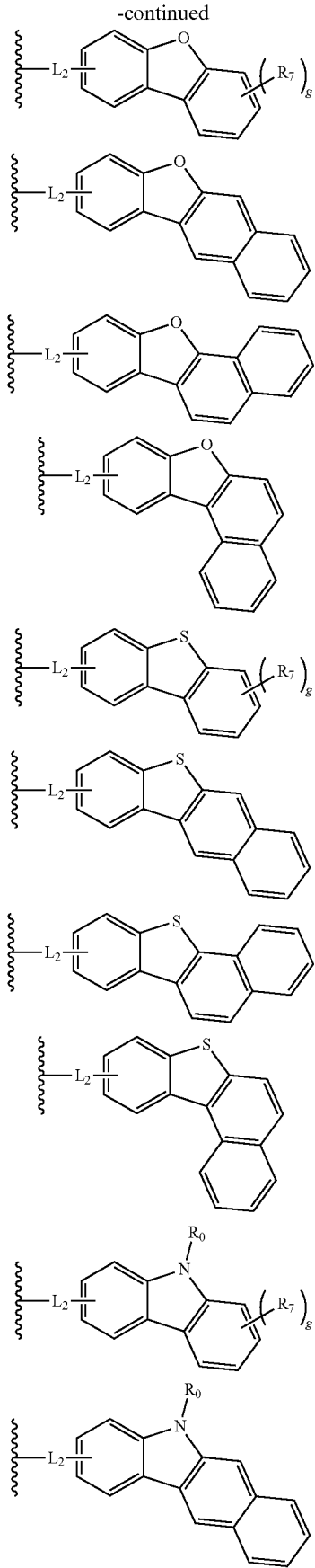
150
-continued
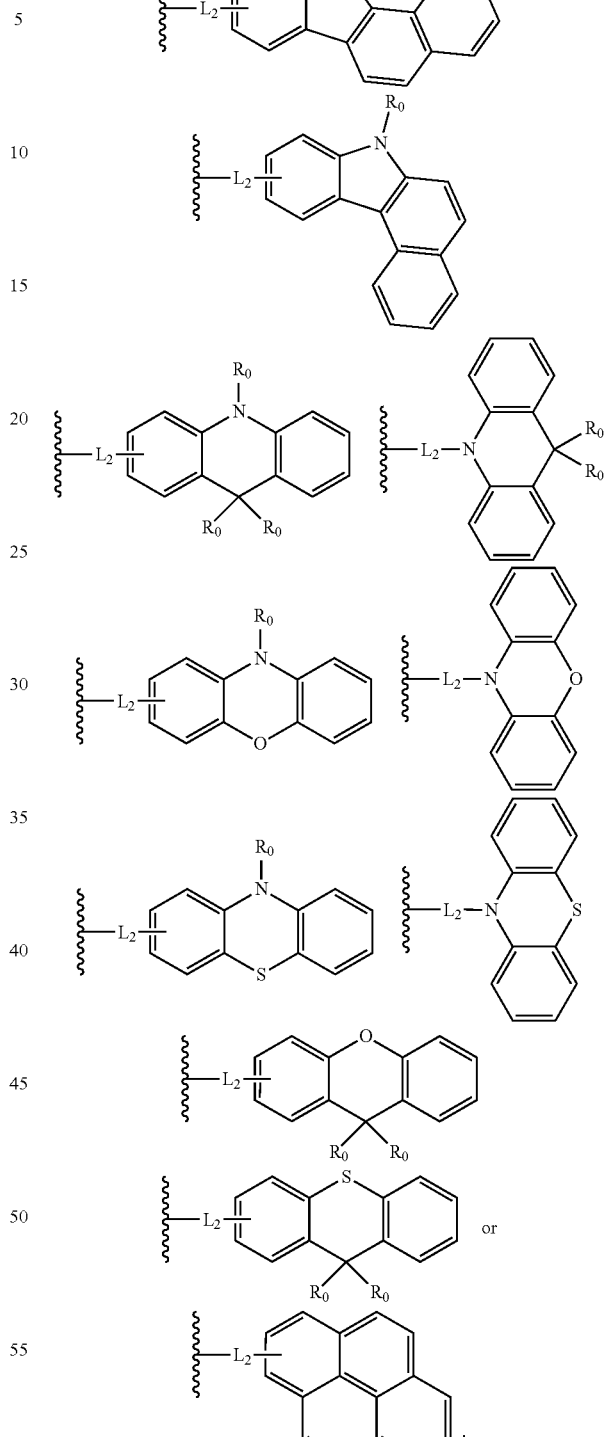
wherein, d is selected from an integer of 0 to 5, and $R_4$ is selected from a substituted or unsubstituted C1-C10 alkyl group, when d is greater than 1, each $R_4$ is the same or different;
e is selected from an integer of 0 to 4, and $R_5$ is selected from the group consisting of a substituted or unsubstituted C1-C10 alkyl group, and a substituted or unsubstituted C6-C18 aryl group, when e is greater than 1, each $R_5$ is the same or different;

f is selected from an integer of 0 to 4, and $R_6$ is selected from the group consisting of a substituted or unsubstituted C1-C10 alkyl group, and a substituted or unsubstituted C6-C18 aryl group, when f is greater than 1, each $R_6$ is the same or different;

g is selected from an integer of 0 to 5, and $R_7$ is selected from the group consisting of a substituted or unsubstituted C1-C10 alkyl group, and a substituted or unsubstituted C6-C18 aryl group, when g is greater than 1, each $R_7$ is the same or different;

$R_0$ is selected from the group consisting of a substituted or unsubstituted C1-C10 alkyl group, and a substituted or unsubstituted C6-C18 aryl group; and $L_2$ is selected from the group consisting of a single bond, a substituted or unsubstituted C6-C18 arylene group, and a substituted or unsubstituted C3-C18 heteroarylene group.

4. The amine derivative according to claim 3, wherein $Ar_3$ and $Ar_4$ are independently selected from one of the groups as shown below,

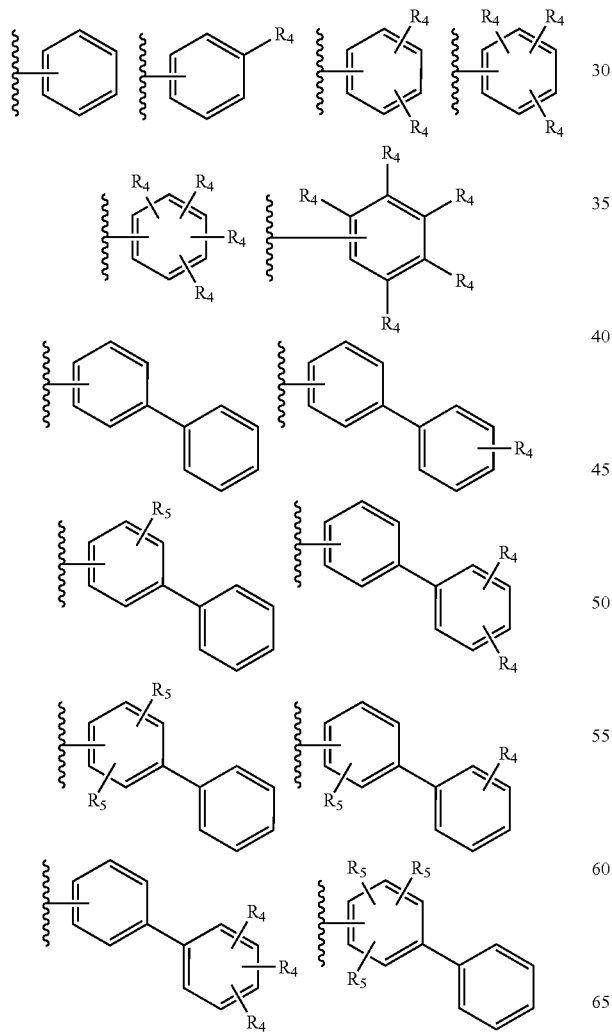

-continued

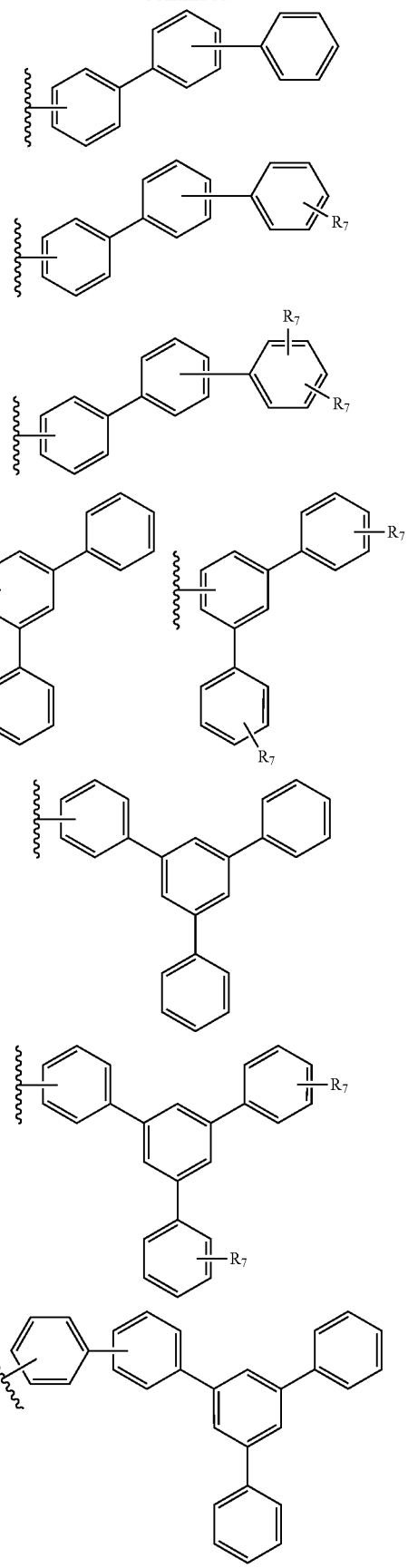

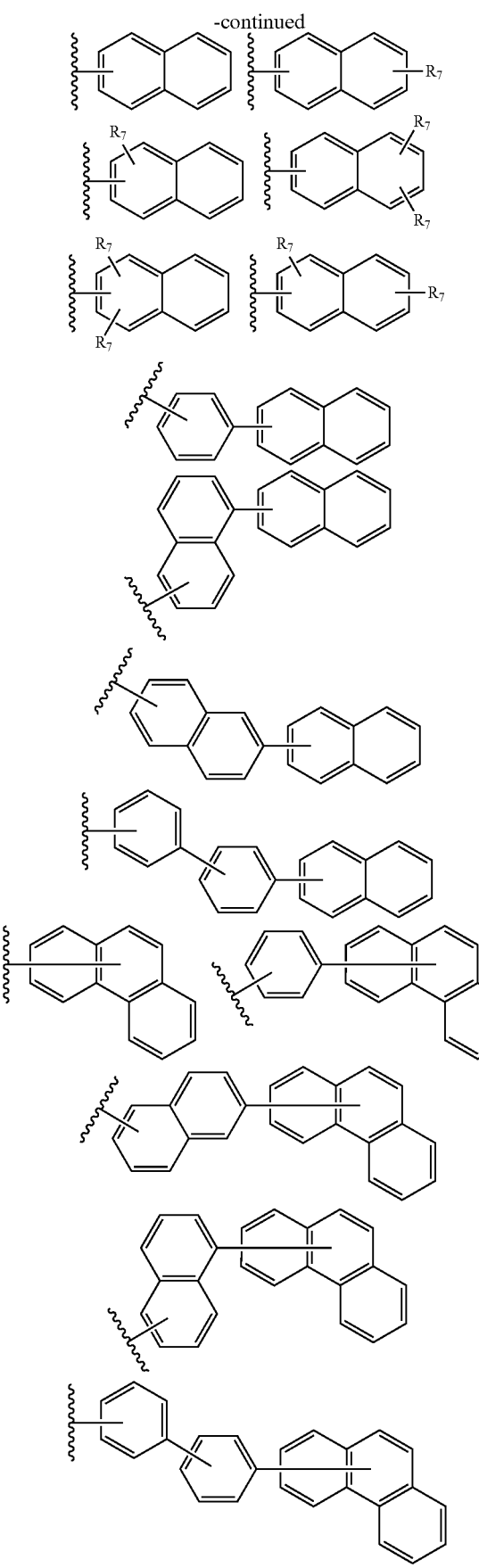
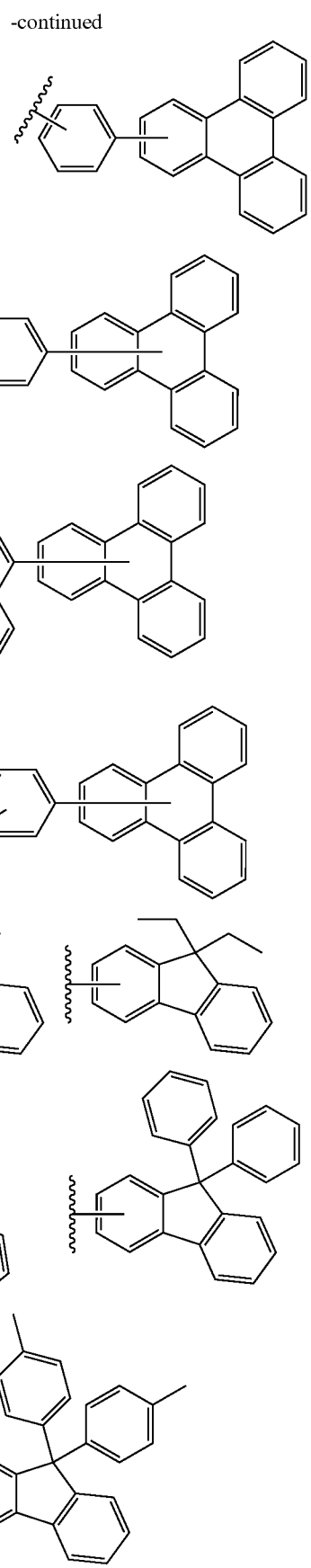

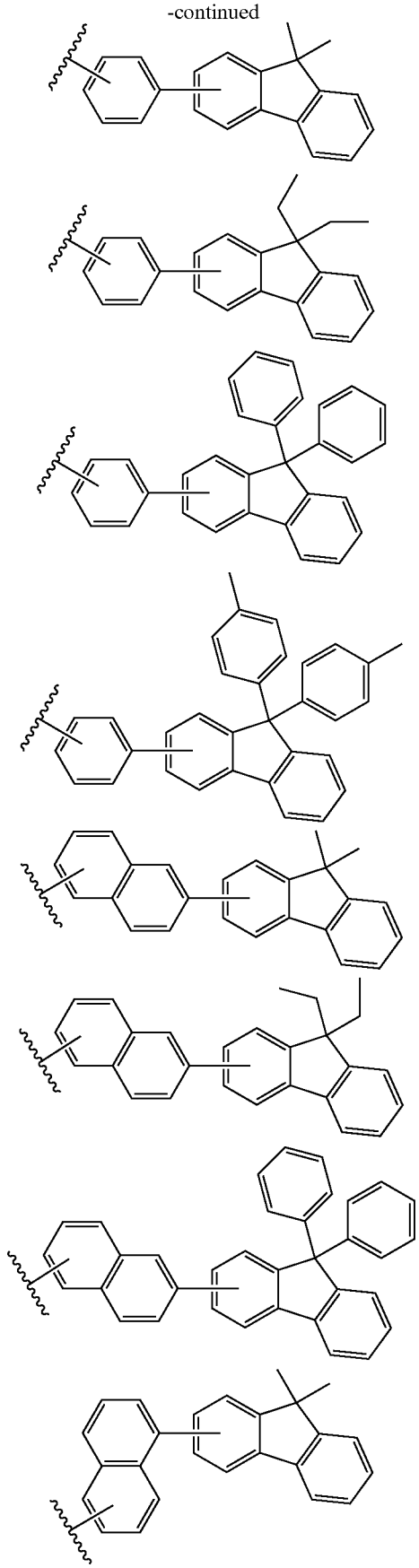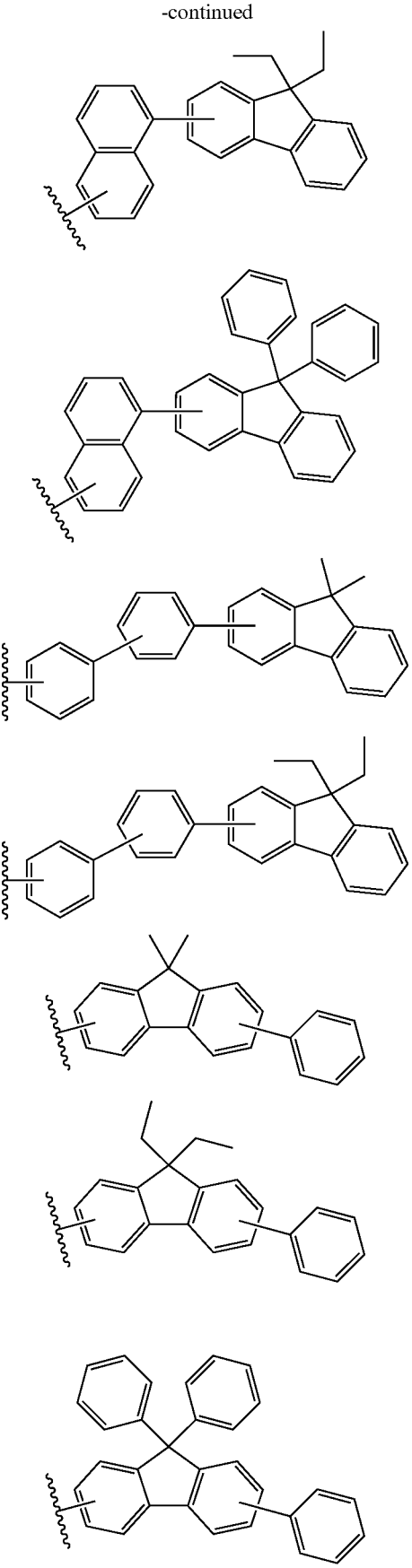

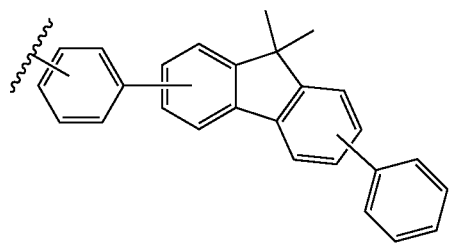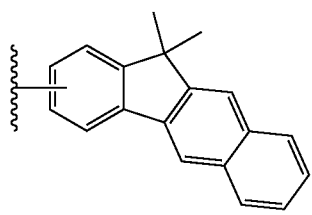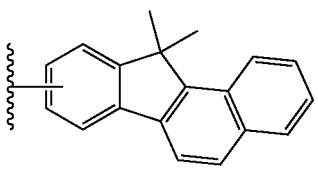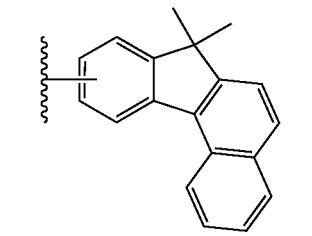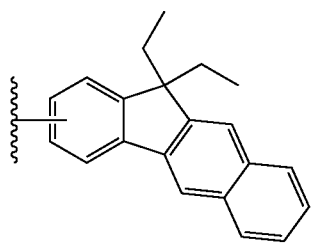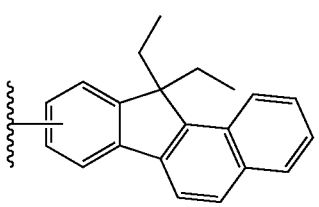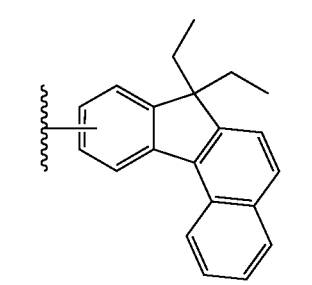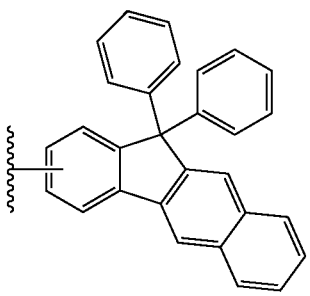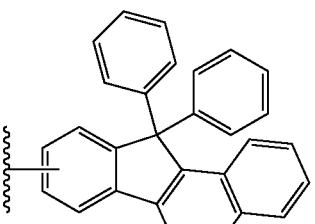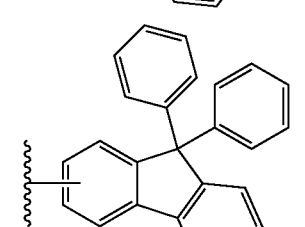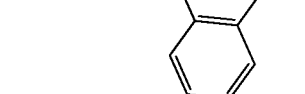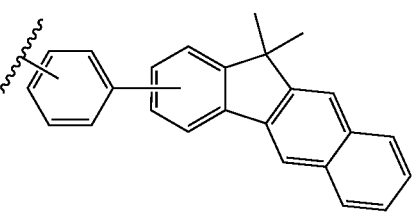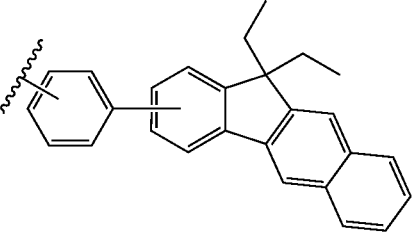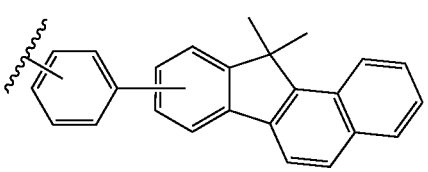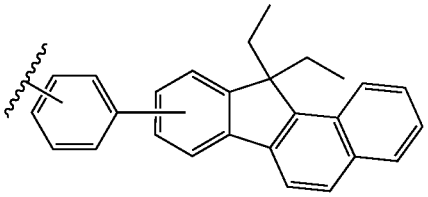

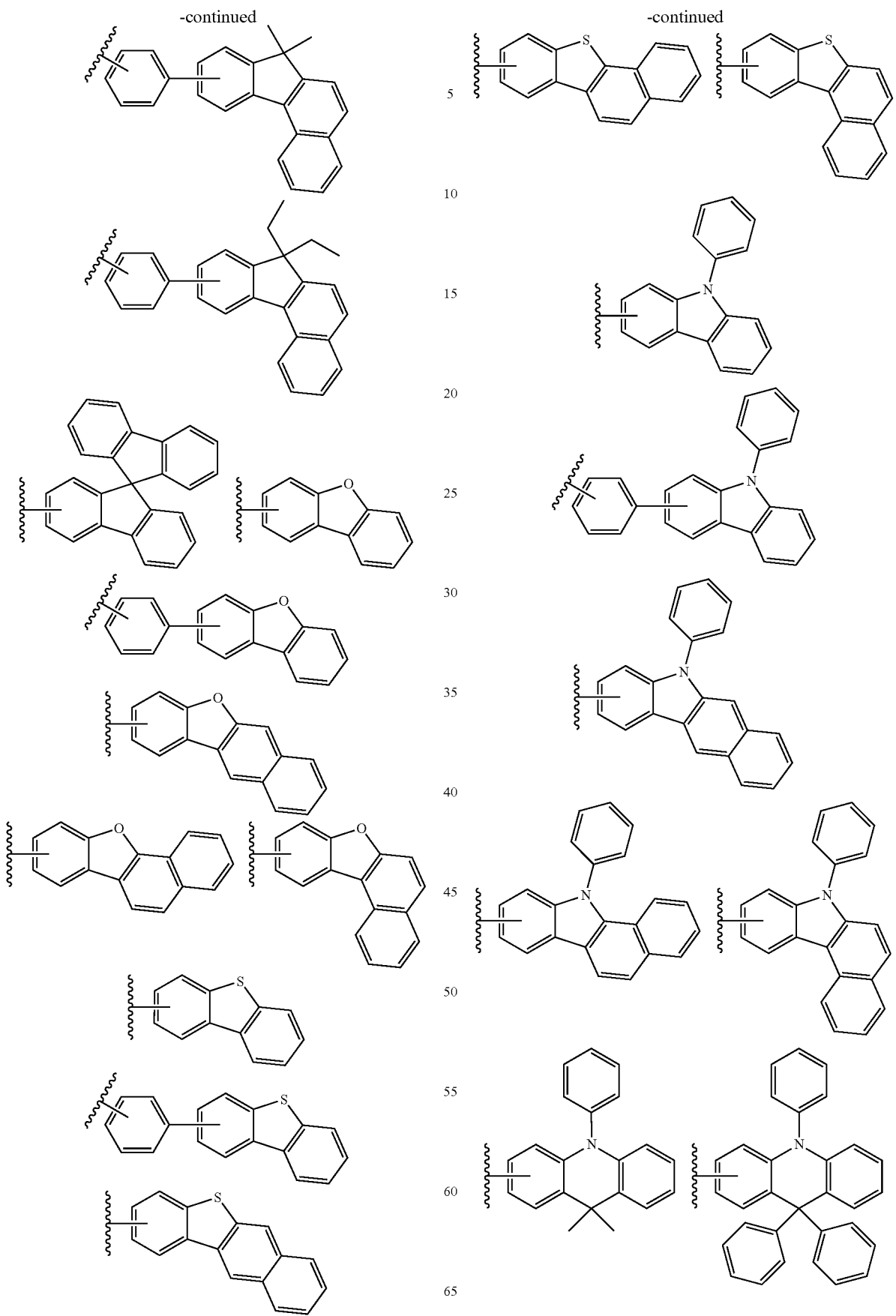

-continued

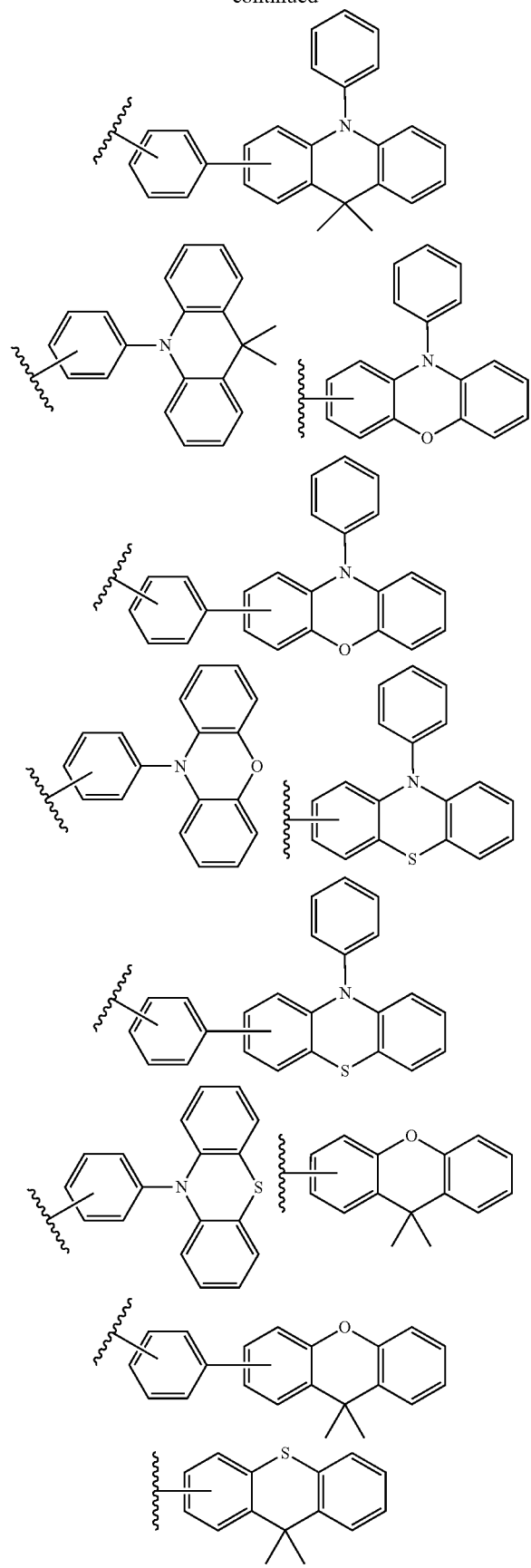

-continued

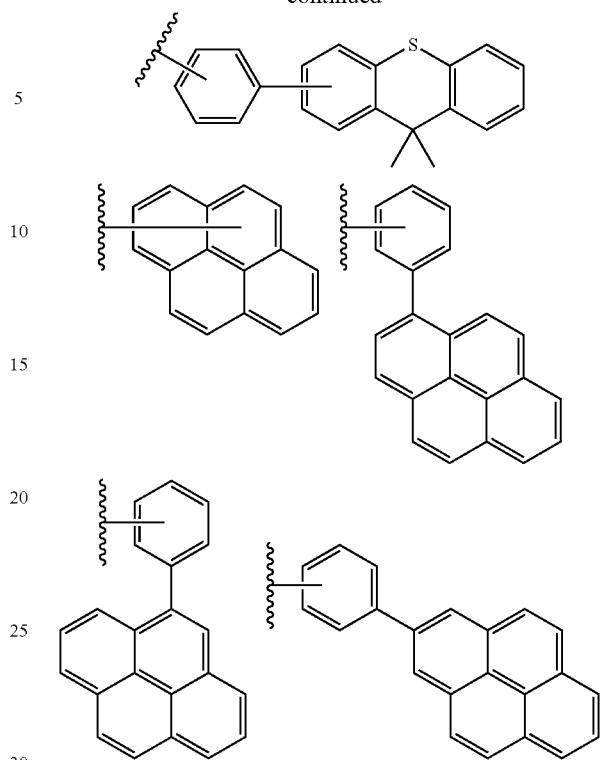

wherein, $R_4$ is selected from the group consisting of methyl, ethyl, propyl, butyl, pentyl, hexyl, heptyl, and octyl, and each $R_4$ is the same or different;

$R_5$ is selected from the group consisting of methyl, ethyl, propyl, and butyl, and each $R_5$ is the same or different; and $R_7$ is selected from the group consisting of methyl, ethyl, propyl, butyl, phenyl, tolyl, and ethylphenyl, and each $R_7$ is the same or different.

5. The amine derivative according to claim 1, wherein Formula II is selected from one of the groups as shown below,

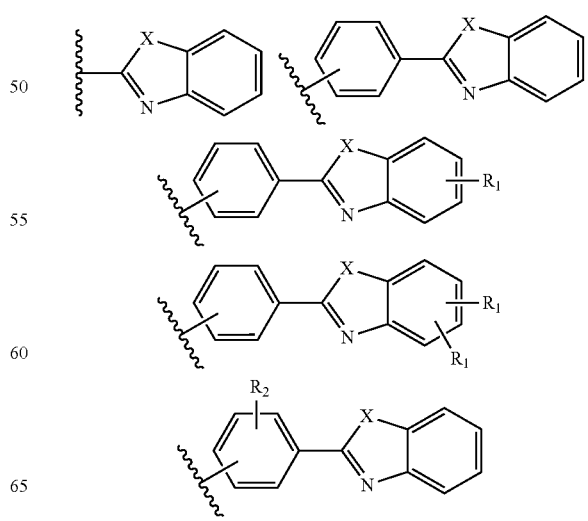

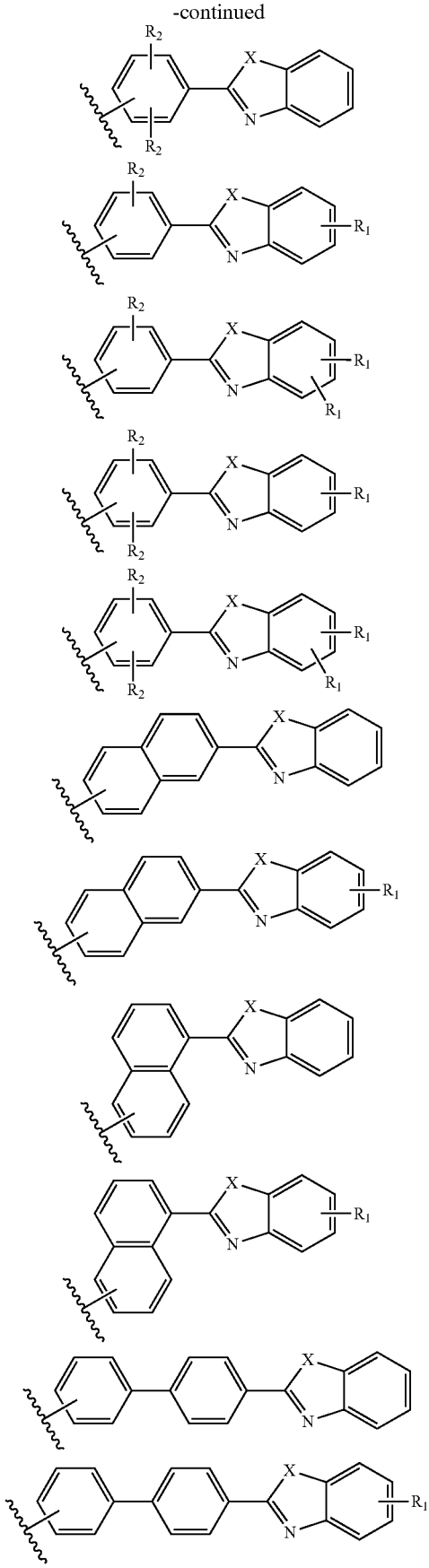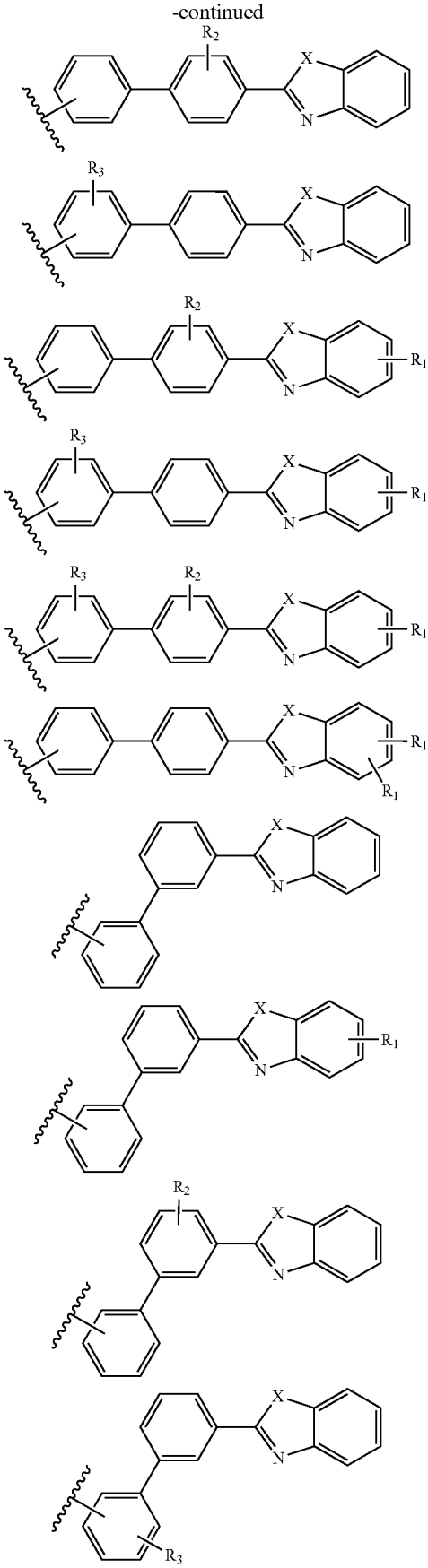

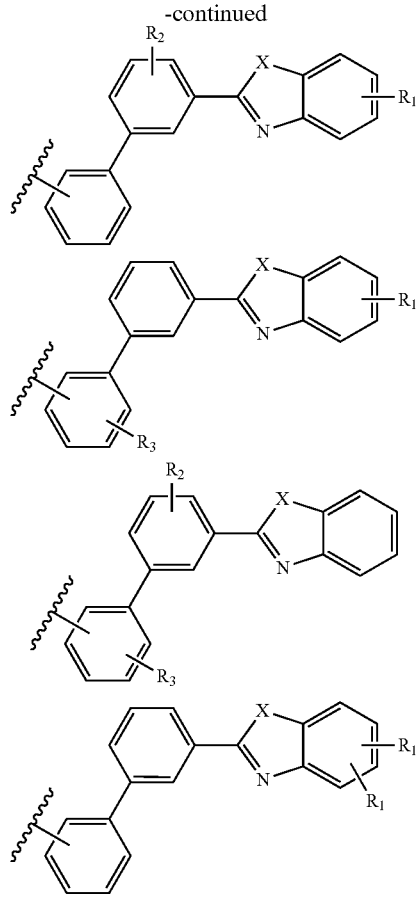

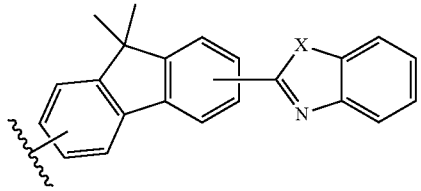

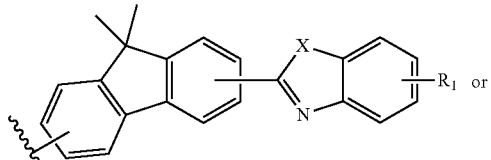

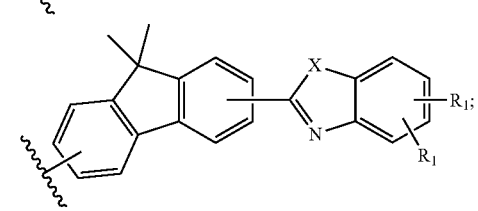

wherein, $R_1$ is selected from the group consisting of methyl, ethyl, propyl, butyl, pentyl, hexyl, heptyl, and octyl, and each $R_1$ is the same or different;

$R_2$ is selected from the group consisting of methyl, ethyl, propyl, and butyl, and each $R_2$ is the same or different; and $R_3$ is selected from the group consisting of methyl, ethyl, propyl, and butyl.

6. The amine derivative according to claim 1, wherein the amine derivative is selected from one of the structures as shown below,

1

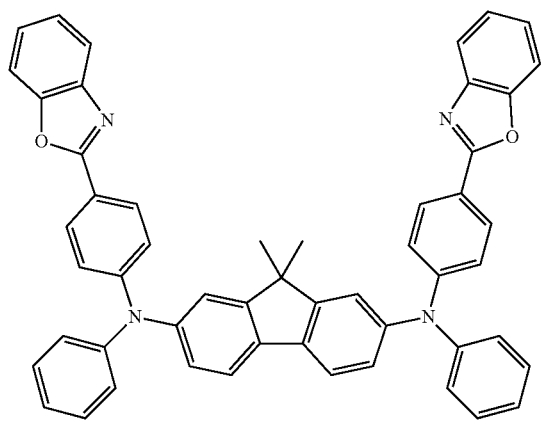

2

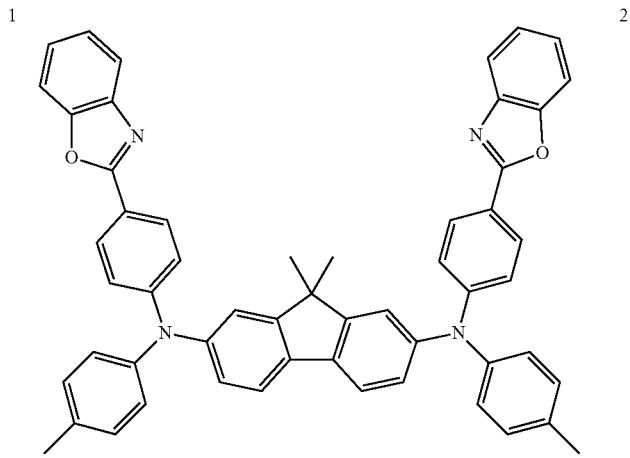

3
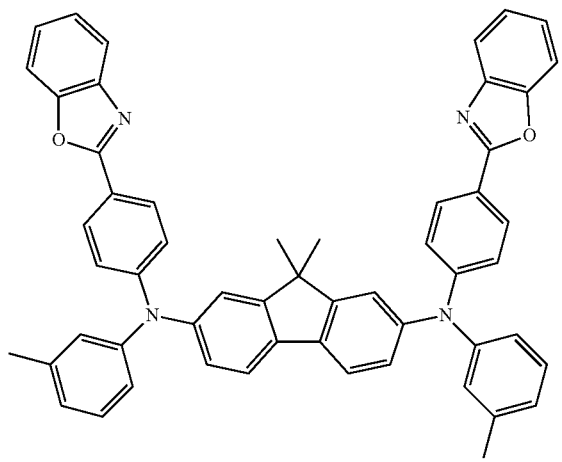
4
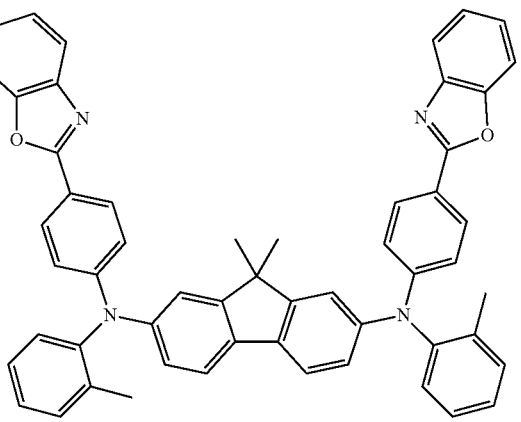
5
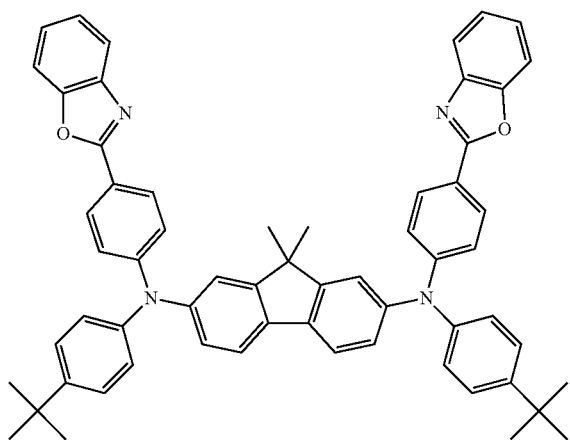
6
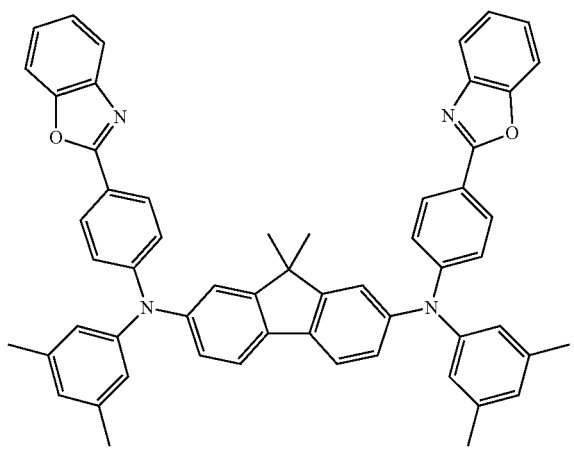
7
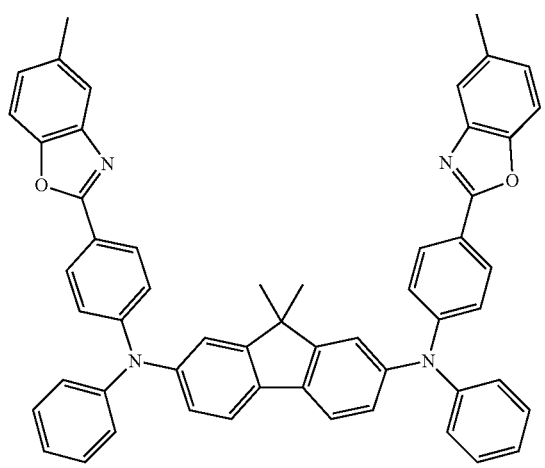
8
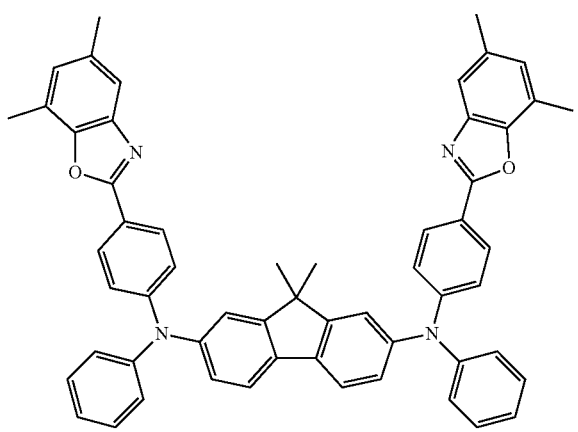

-continued
9
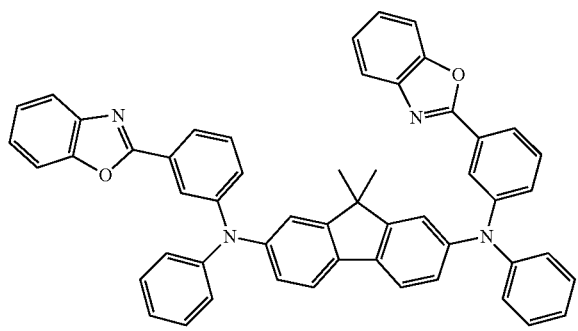
10
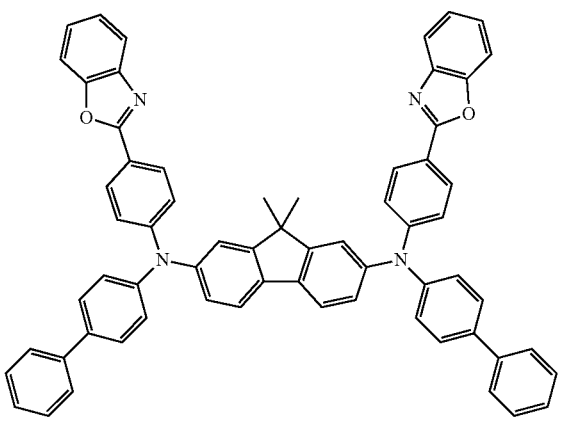
11
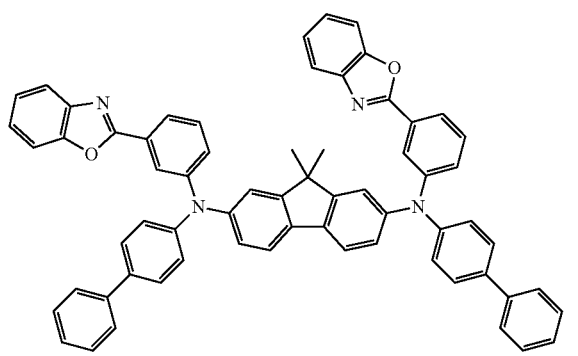
12
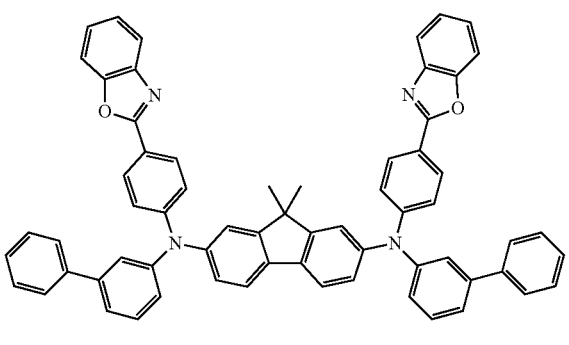
13
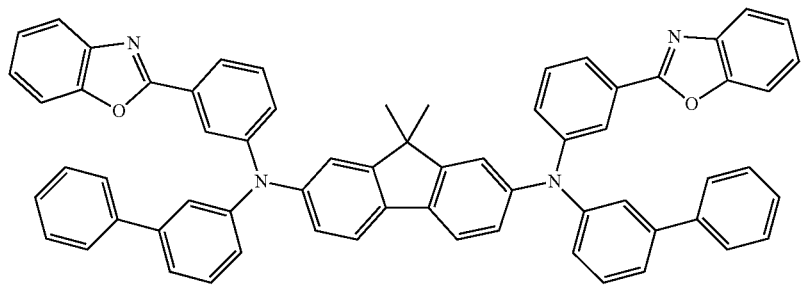
14
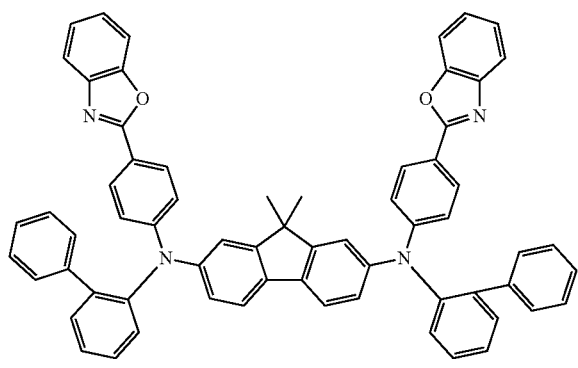
15
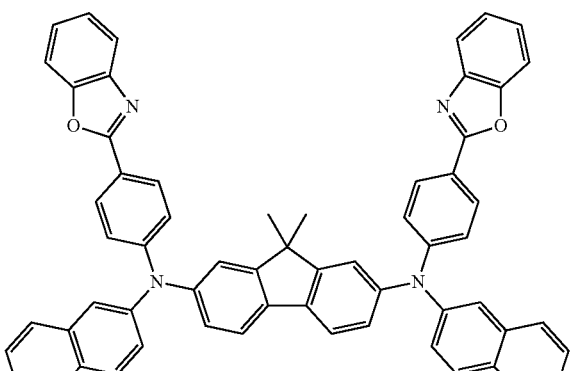

-continued
16
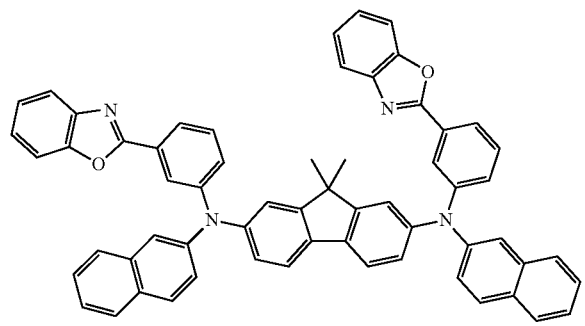
17
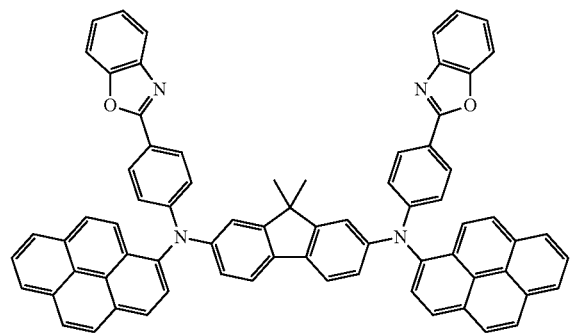
18
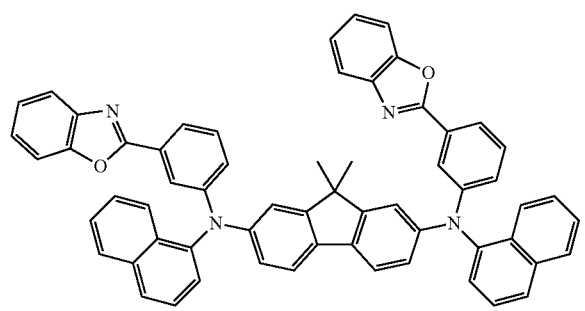
19
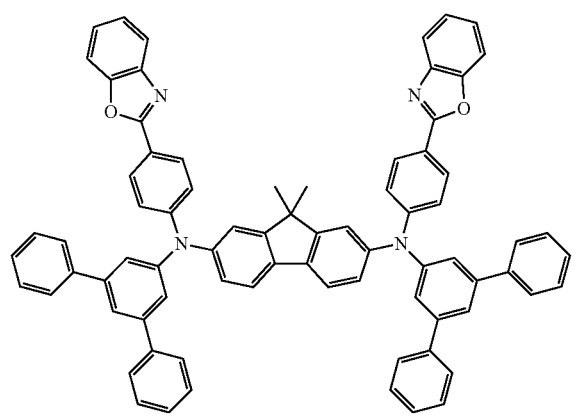
20
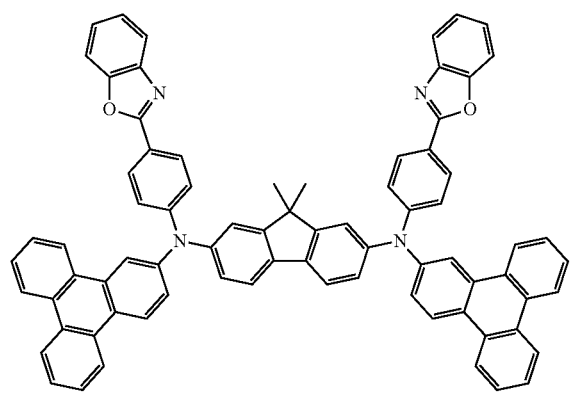
21
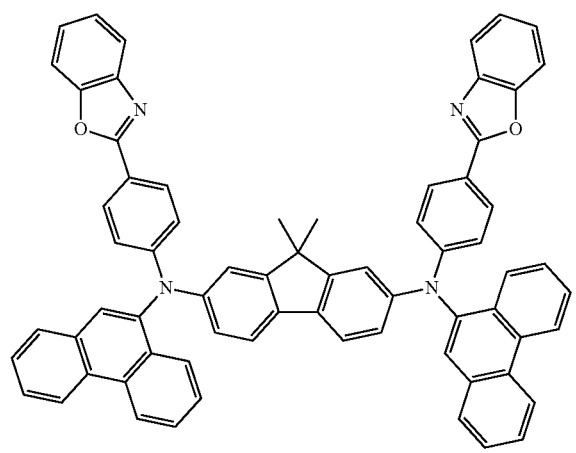

22
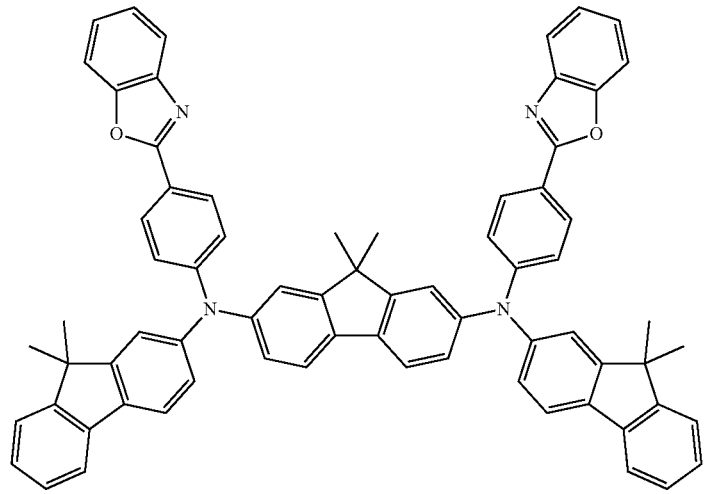
23
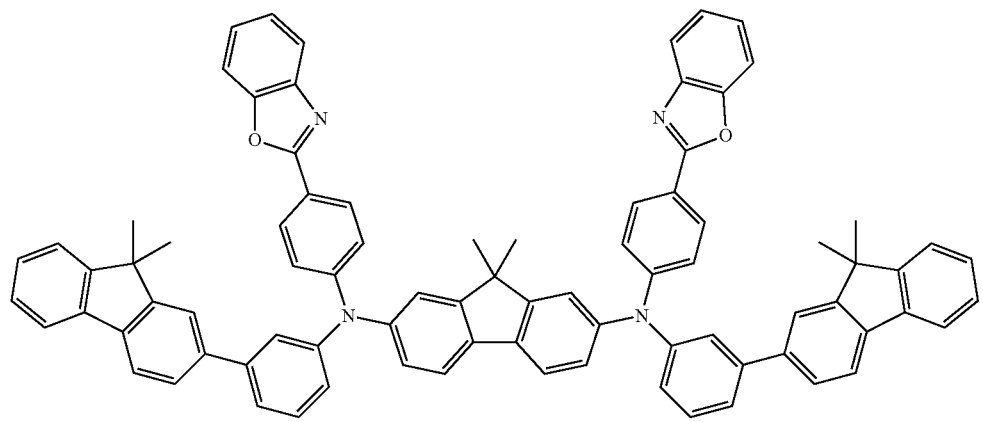
24
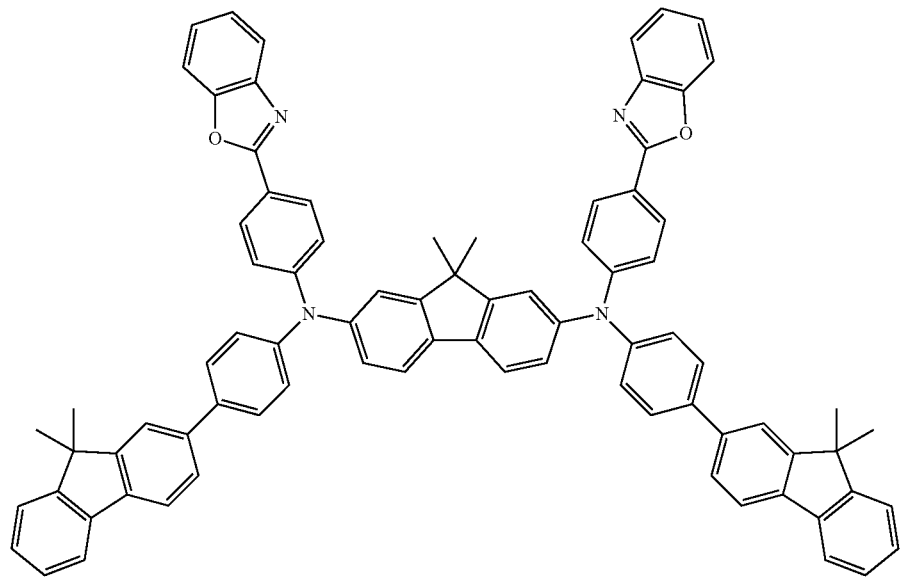

-continued
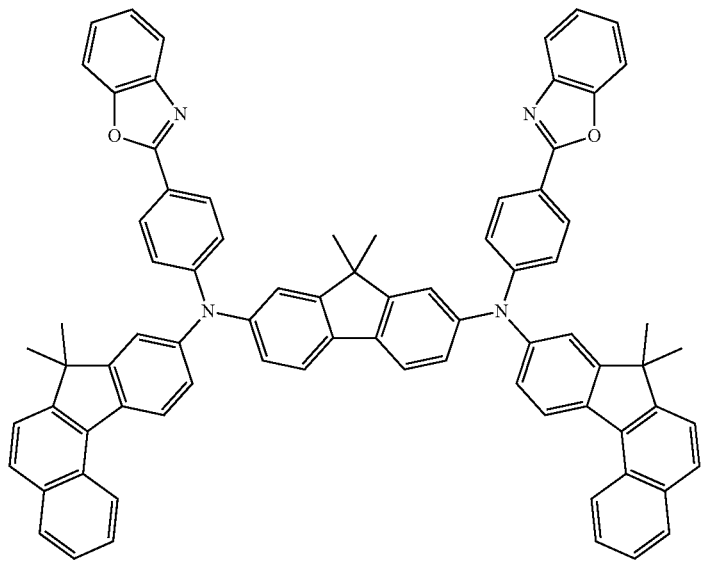
25
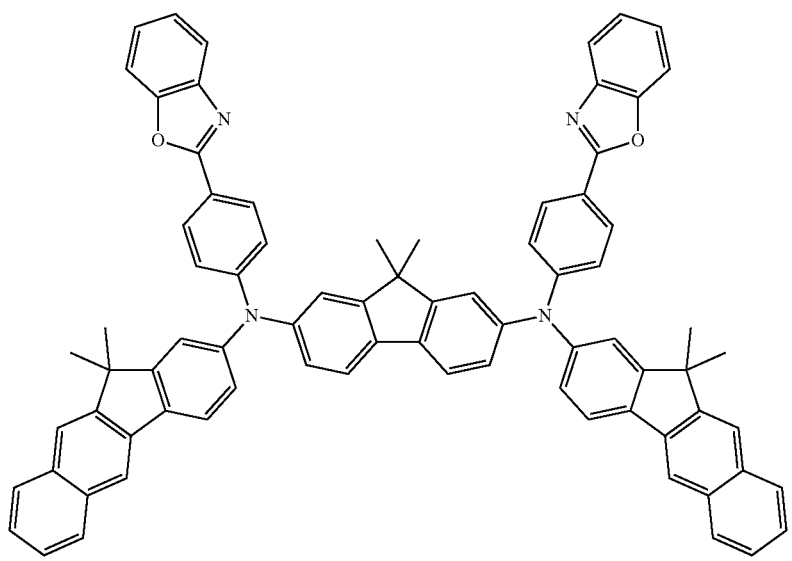
26
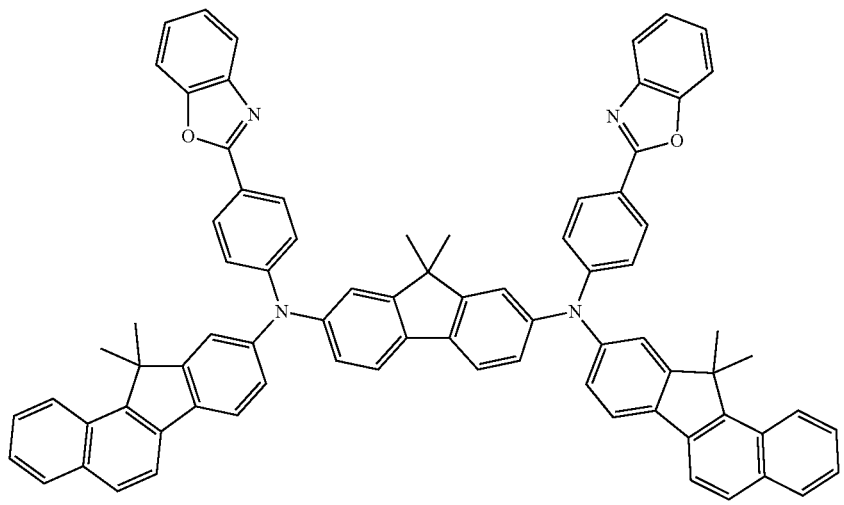
27

-continued
28
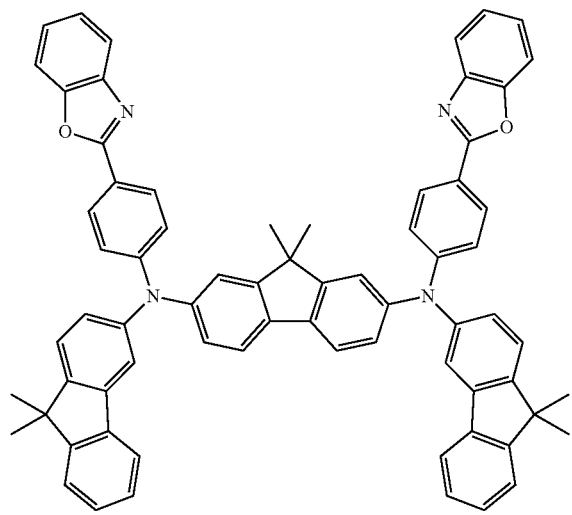
29
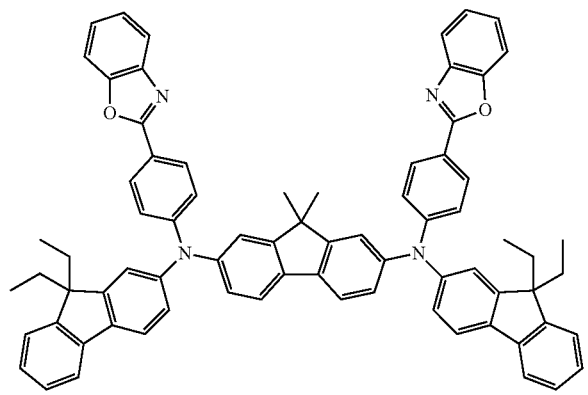
30
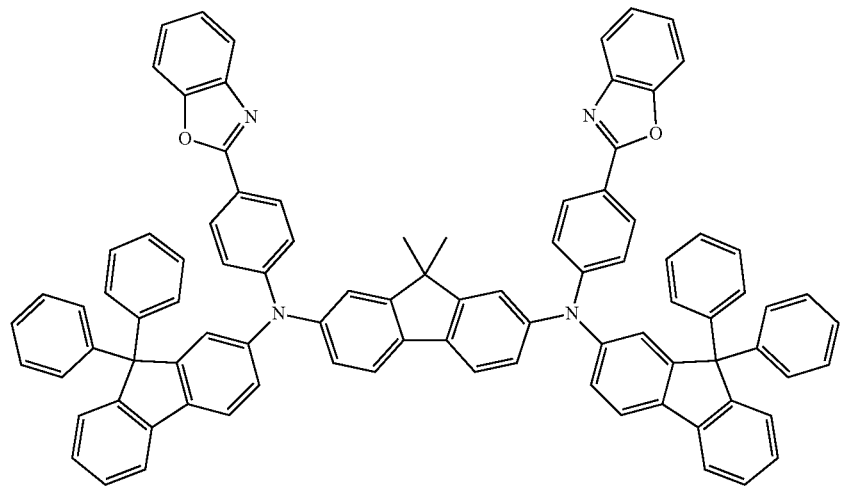
31
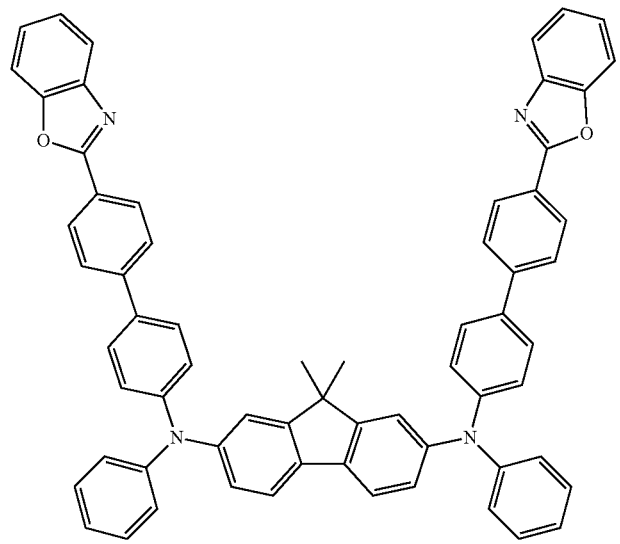

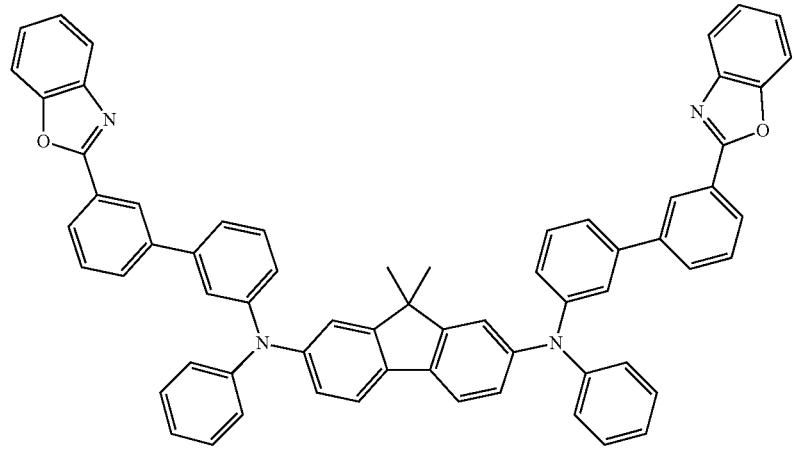
32
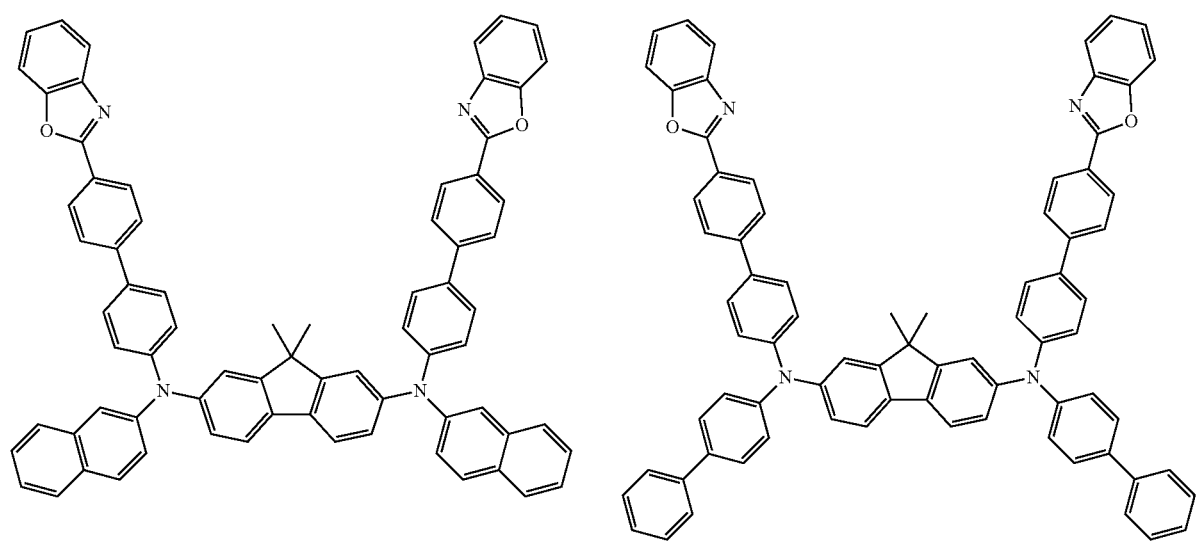
33
34
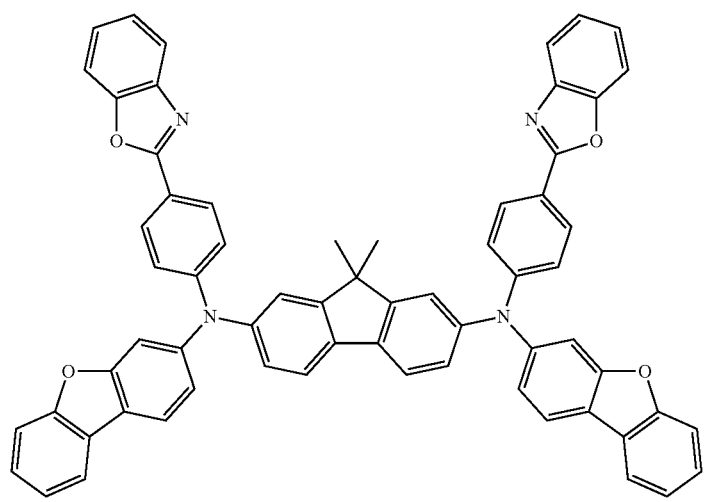
35

-continued
36
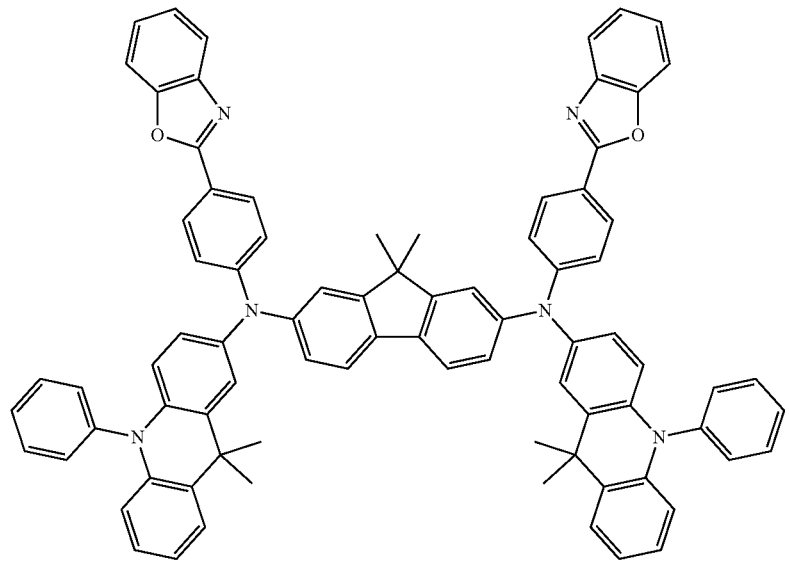
37
38
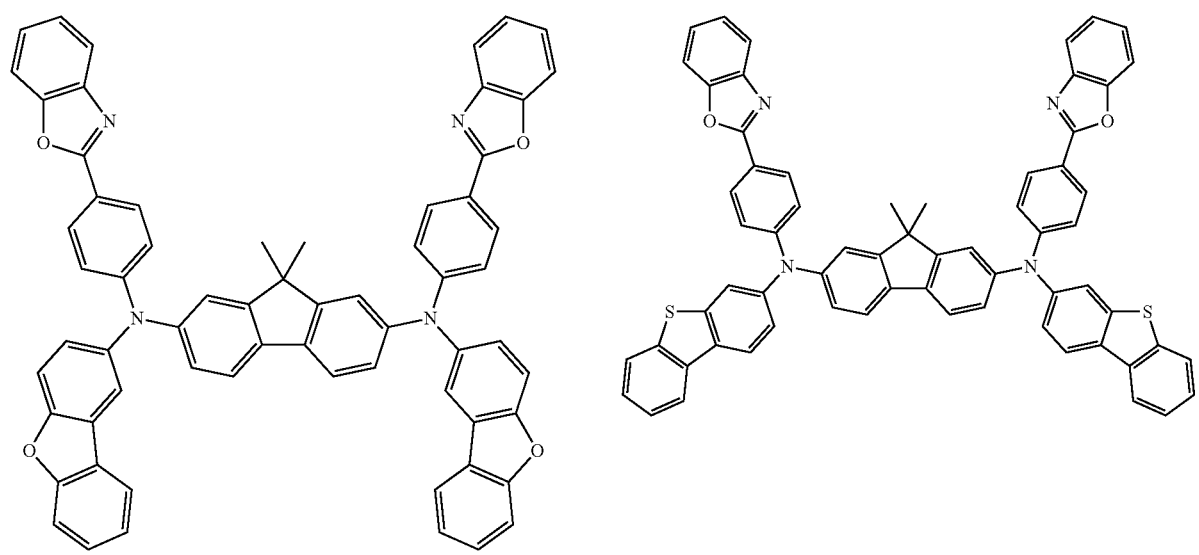
39
40
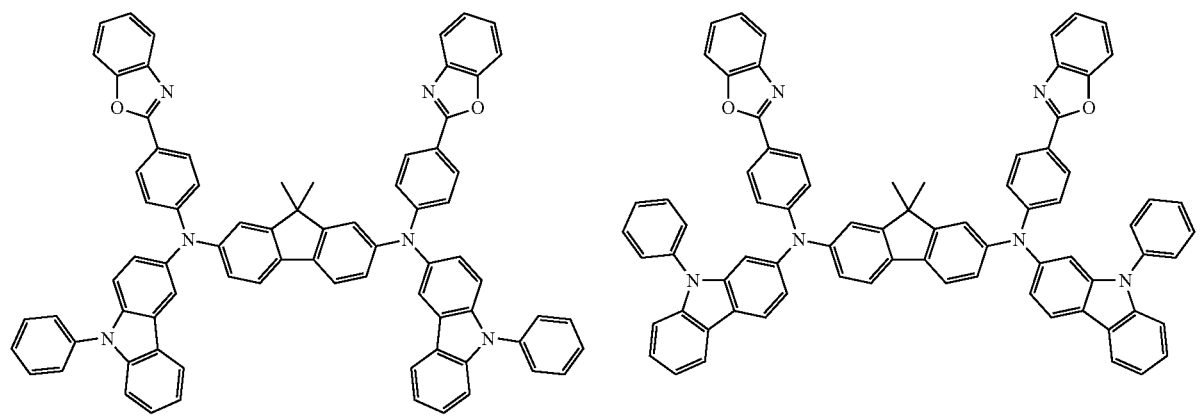

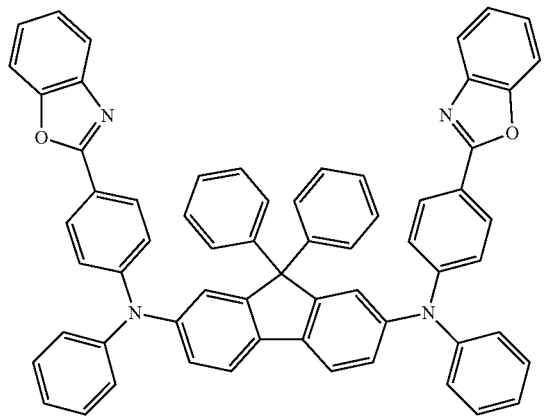
41
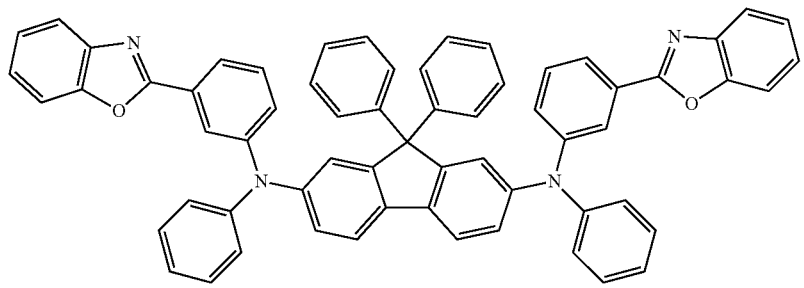
42
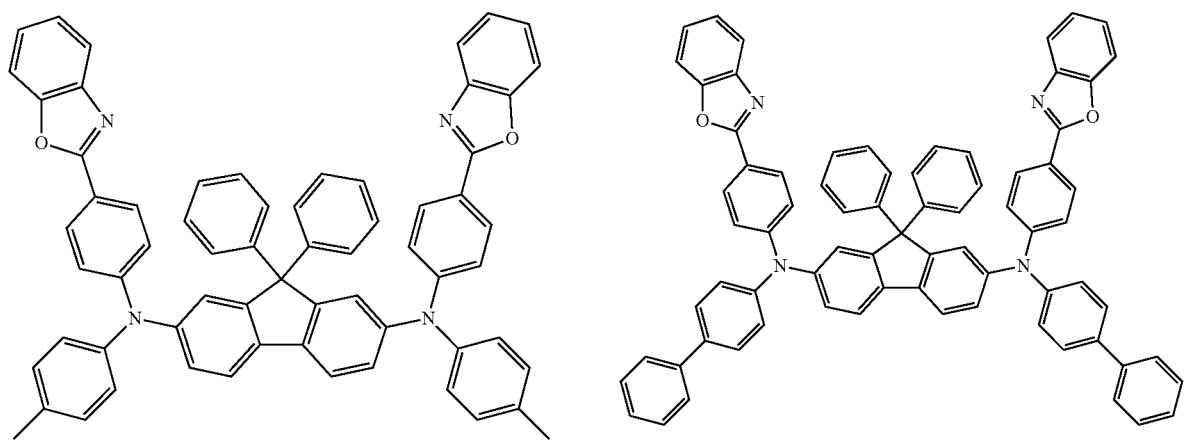
43
44
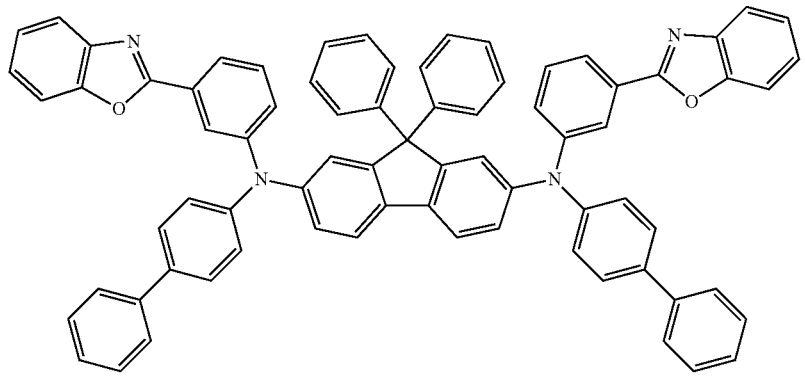
45

46
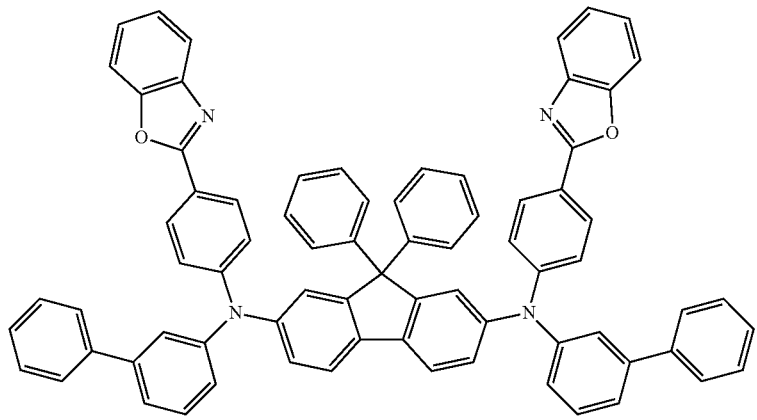
47
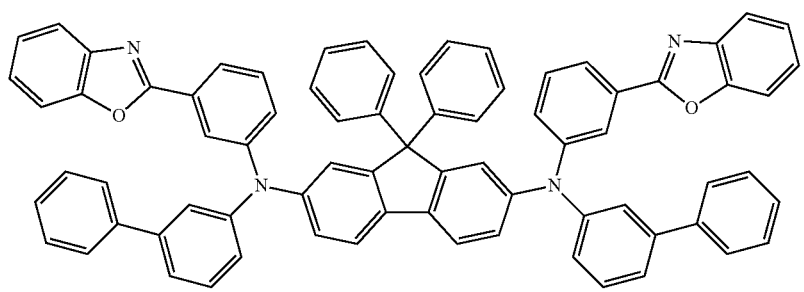
48
49
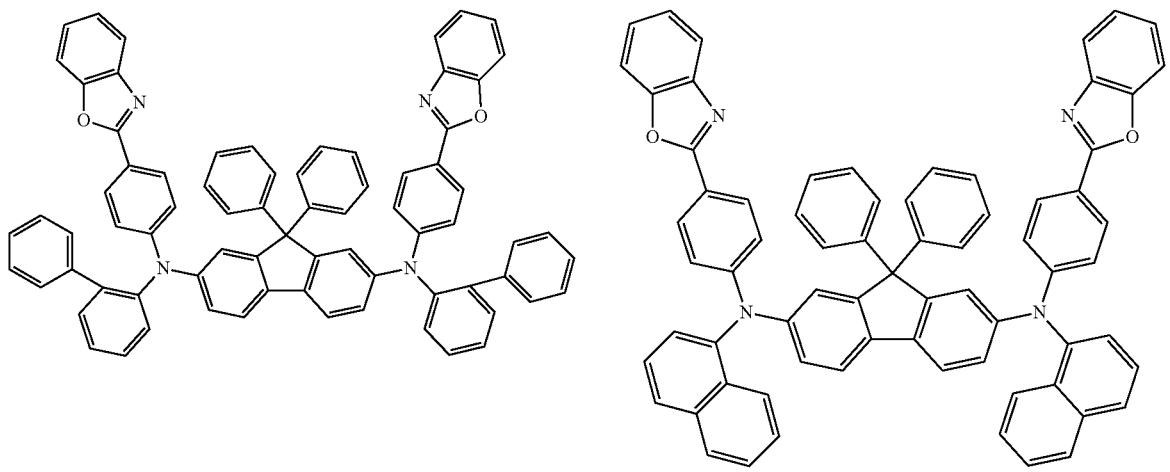
50
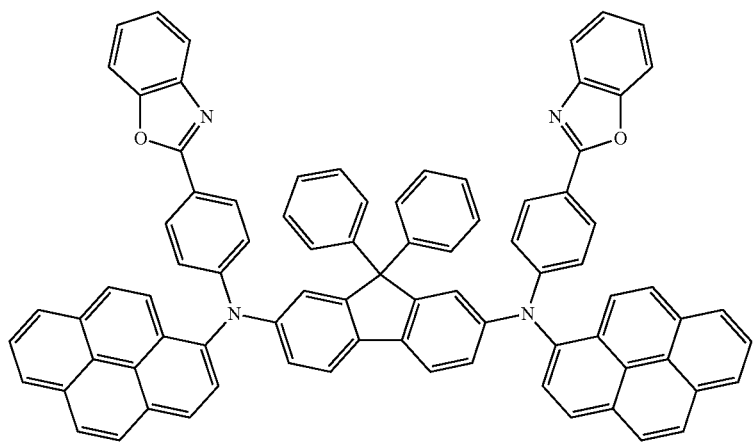

51
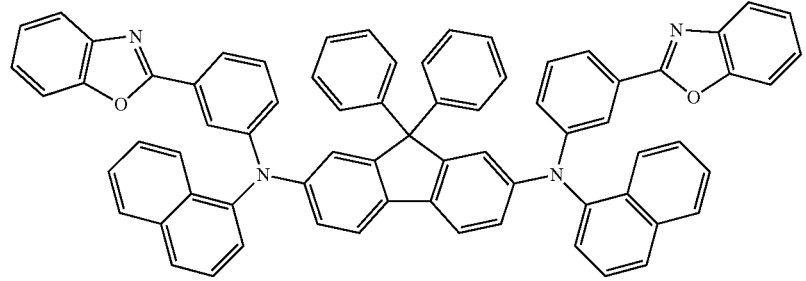
52
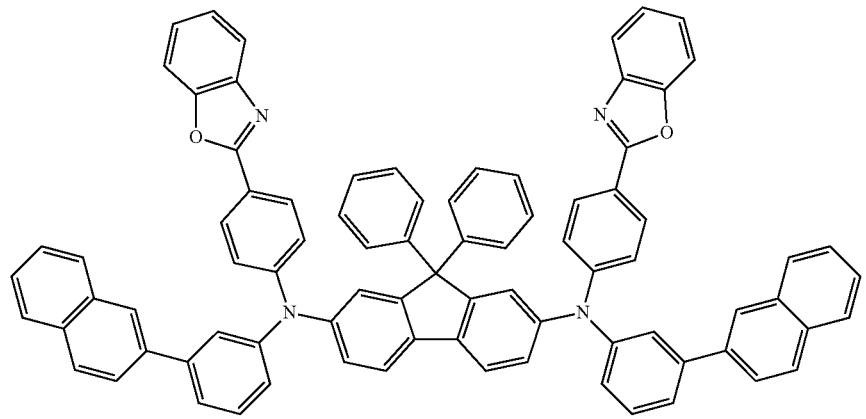
53
54
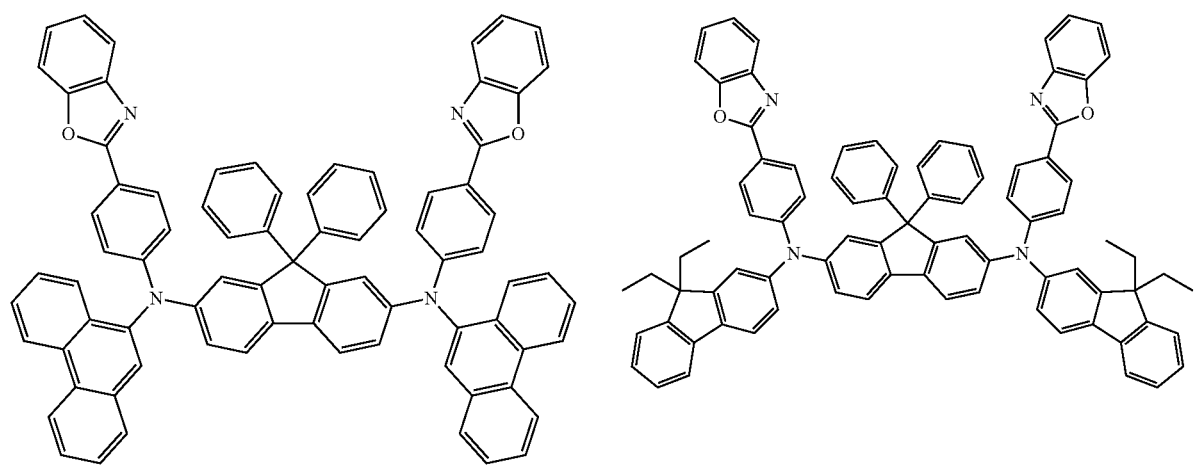
55
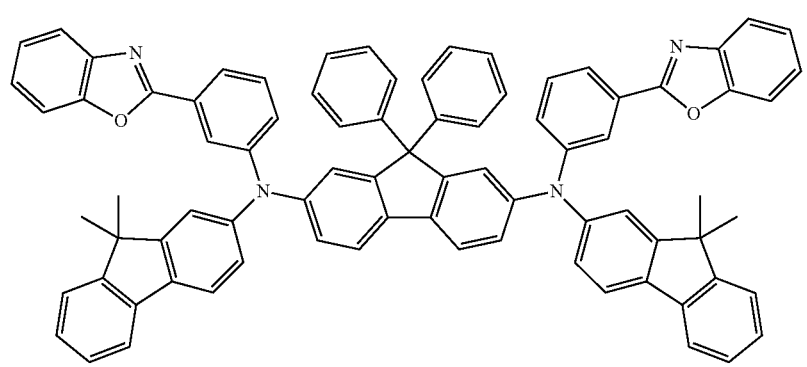

56
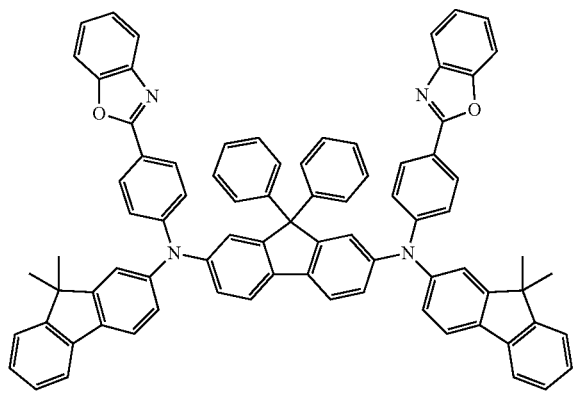
57
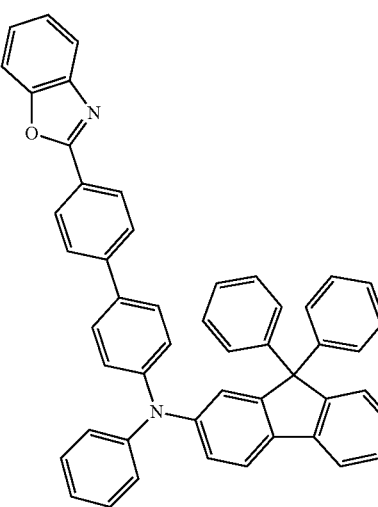
58
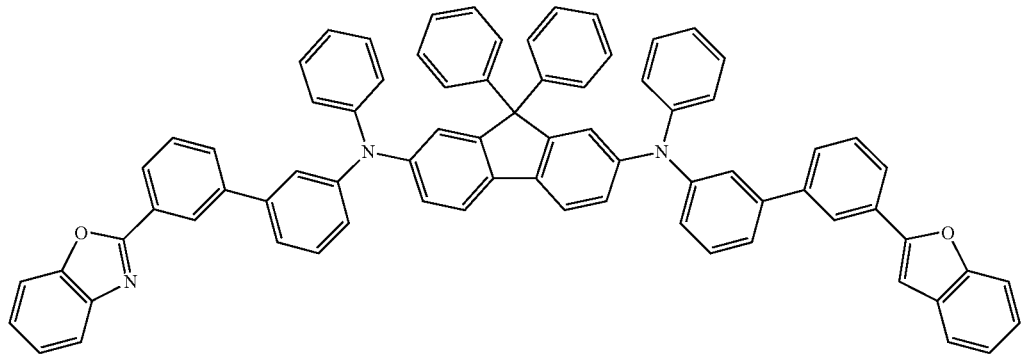
59
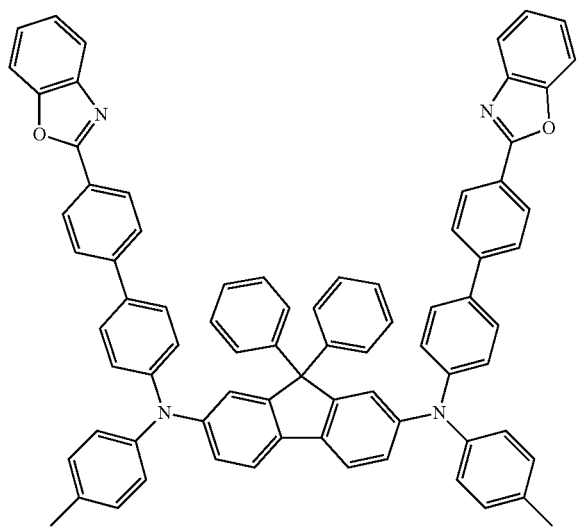
60
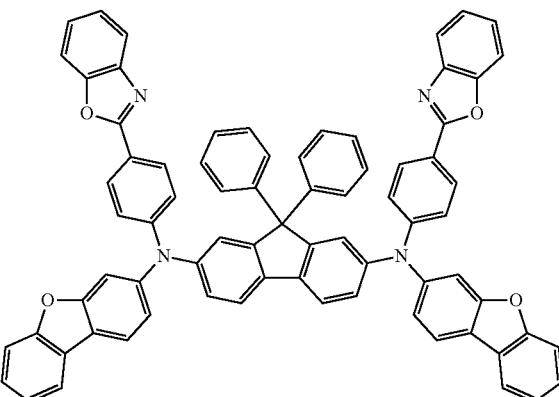

-continued
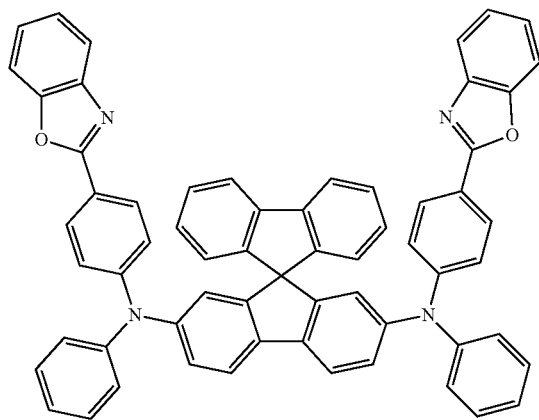
61
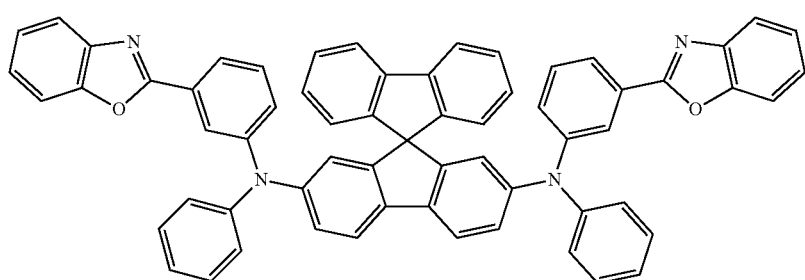
62
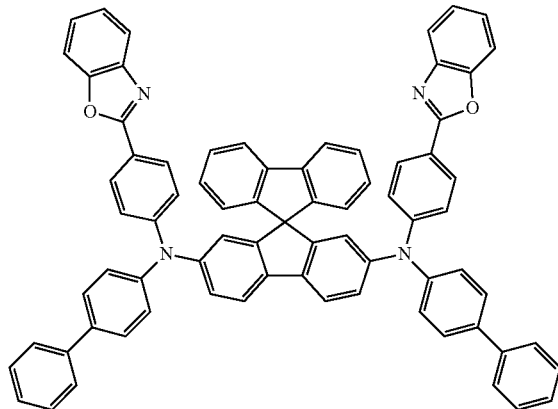
63
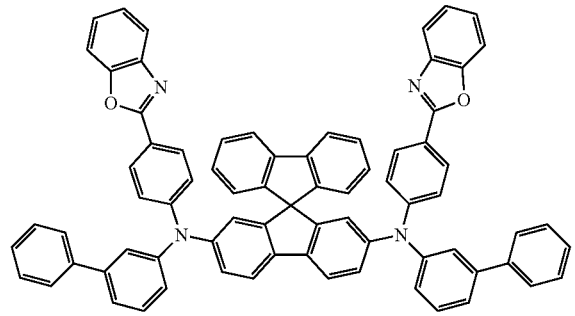
64
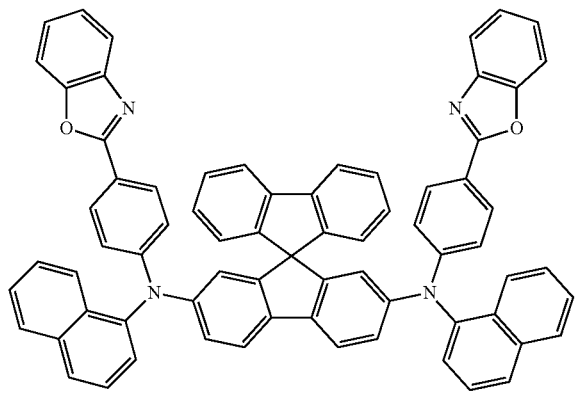
65
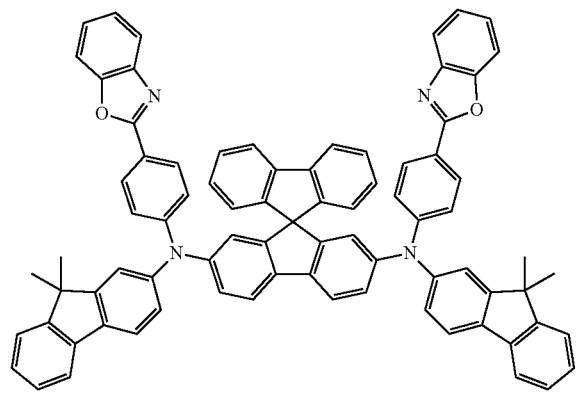
66

67
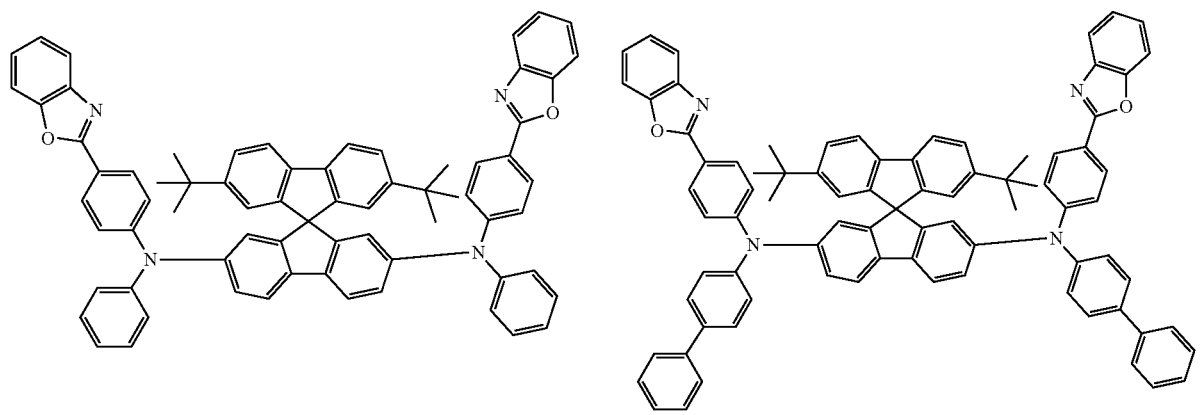
68
69
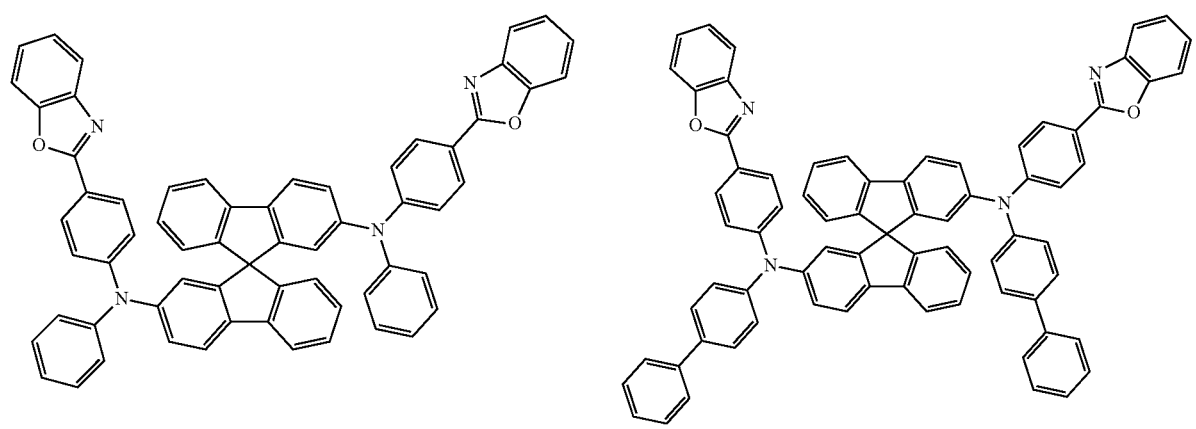
70
71
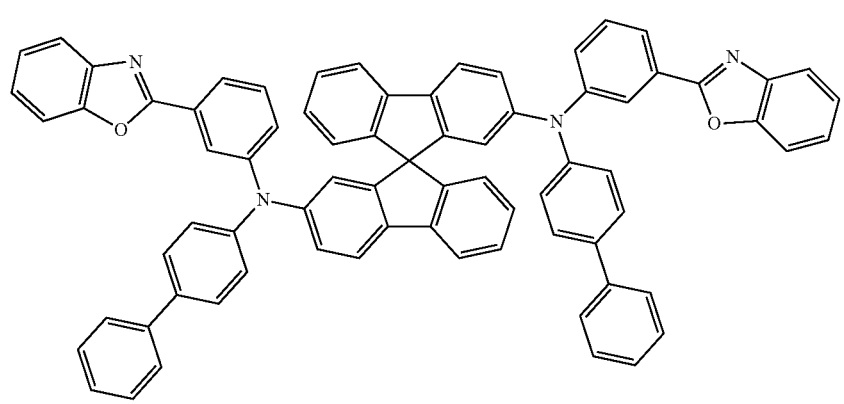

-continued
72
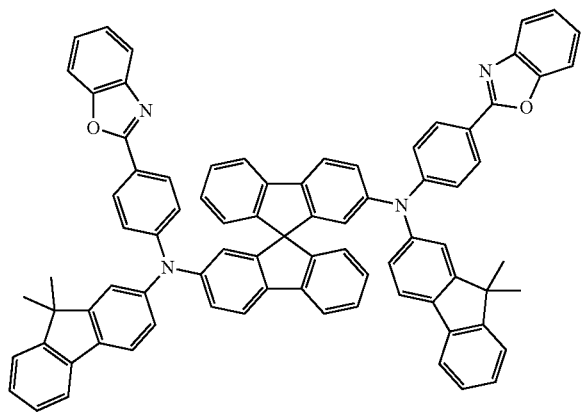
73
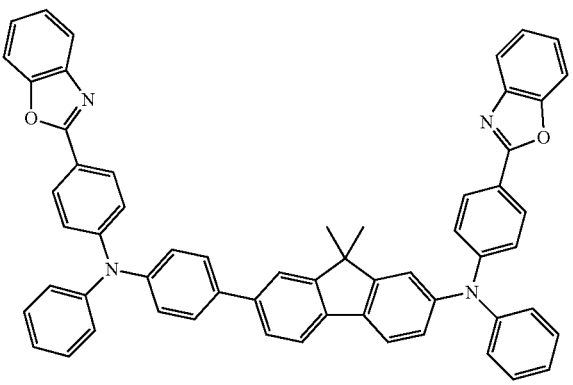
74 75
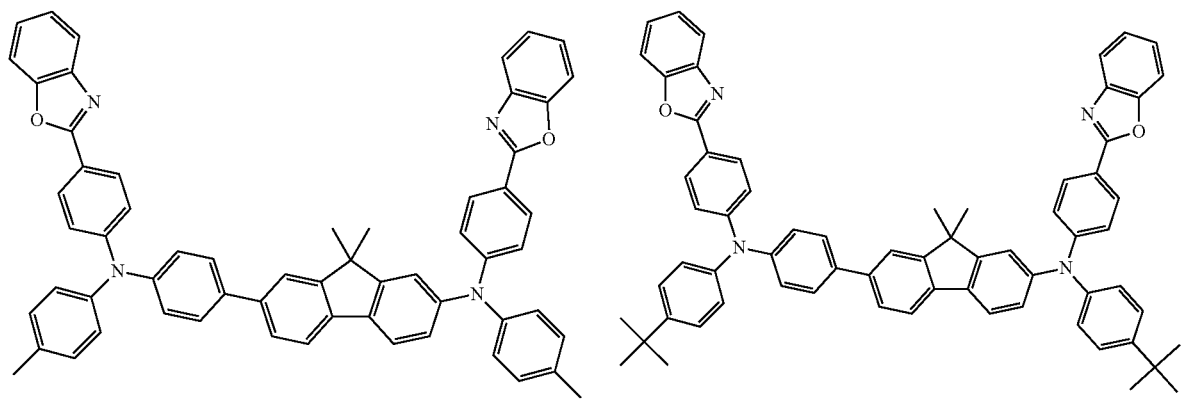
76
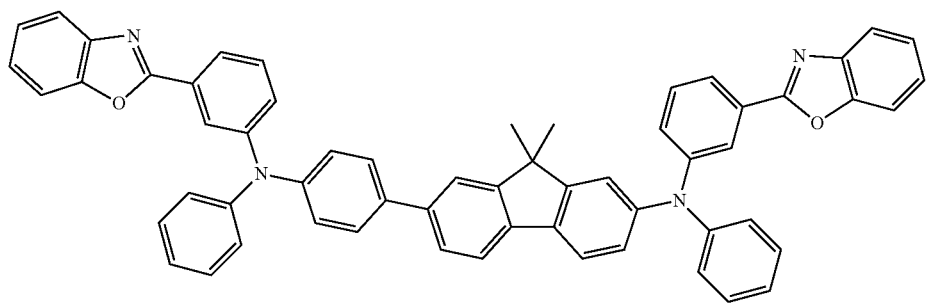
77
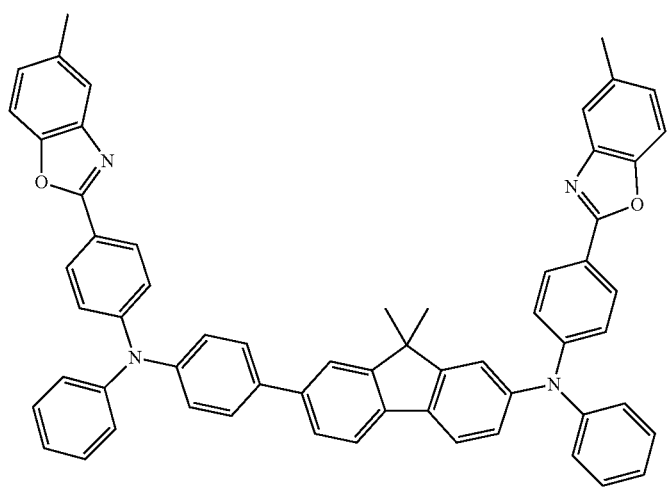

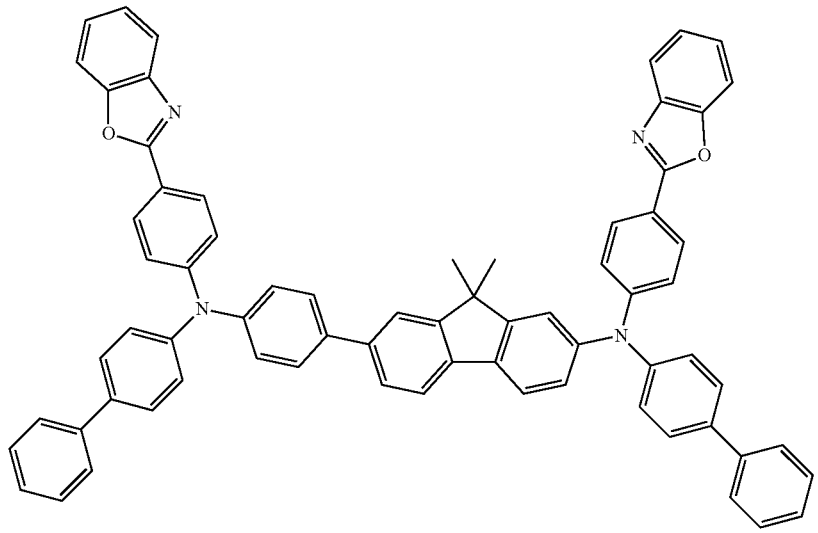
78
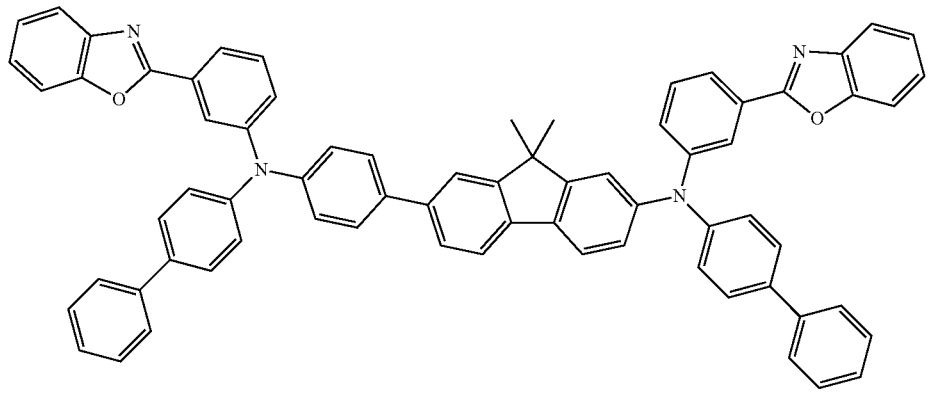
79
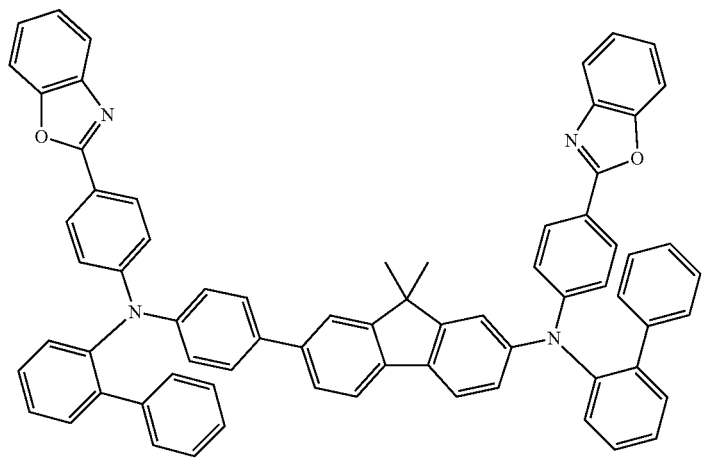
80

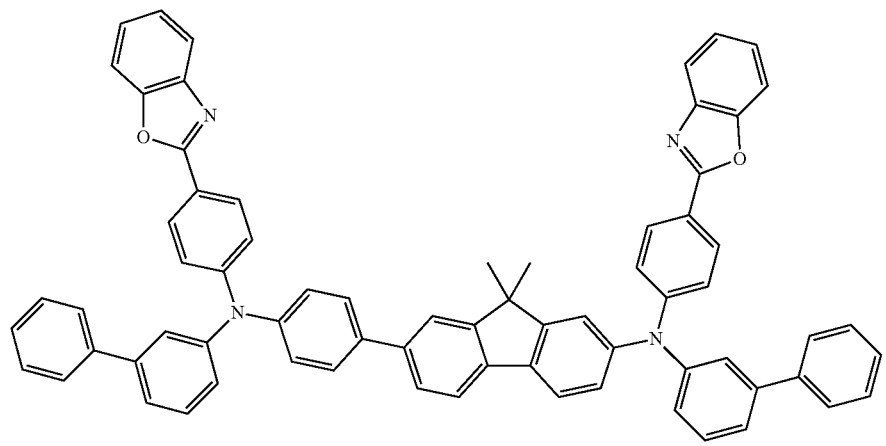
81
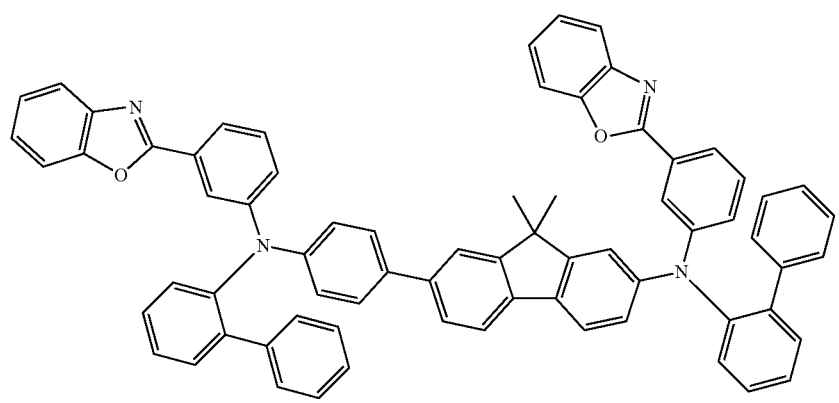
82
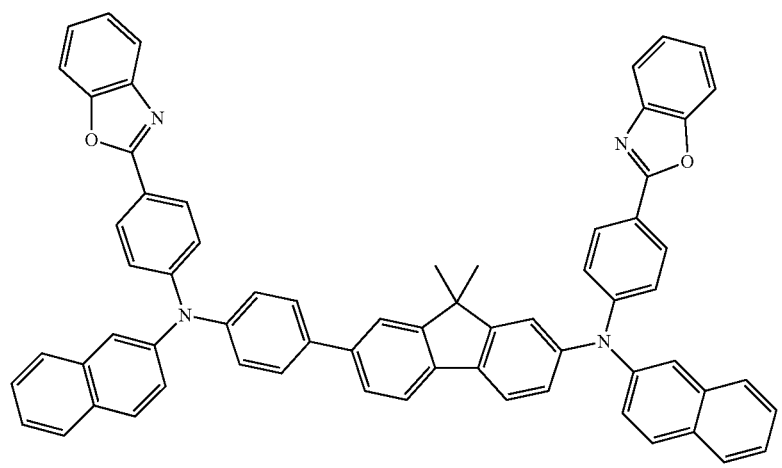
83

84
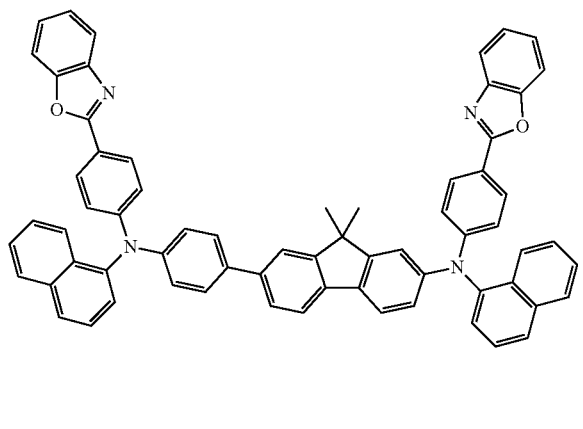
85
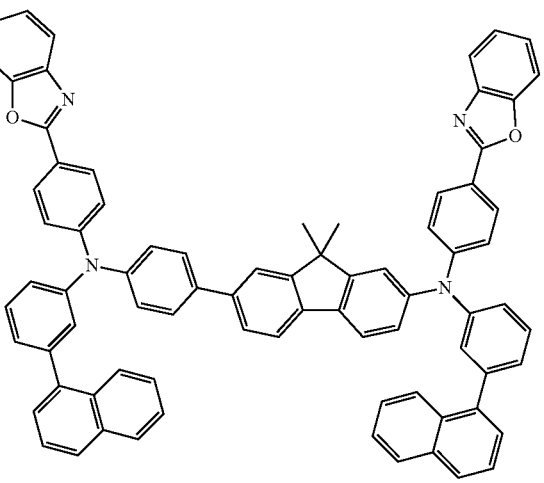
86
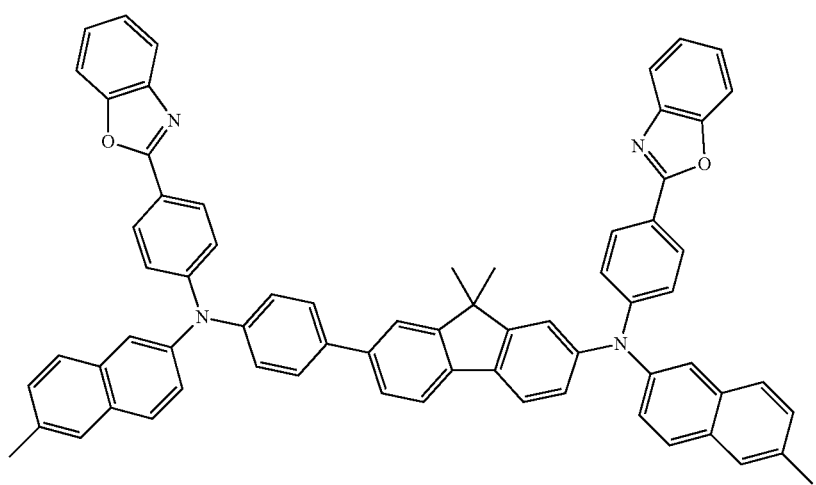
87
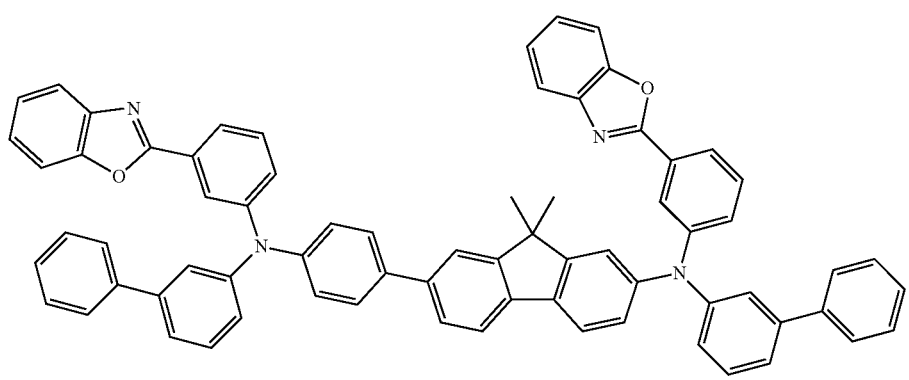

-continued
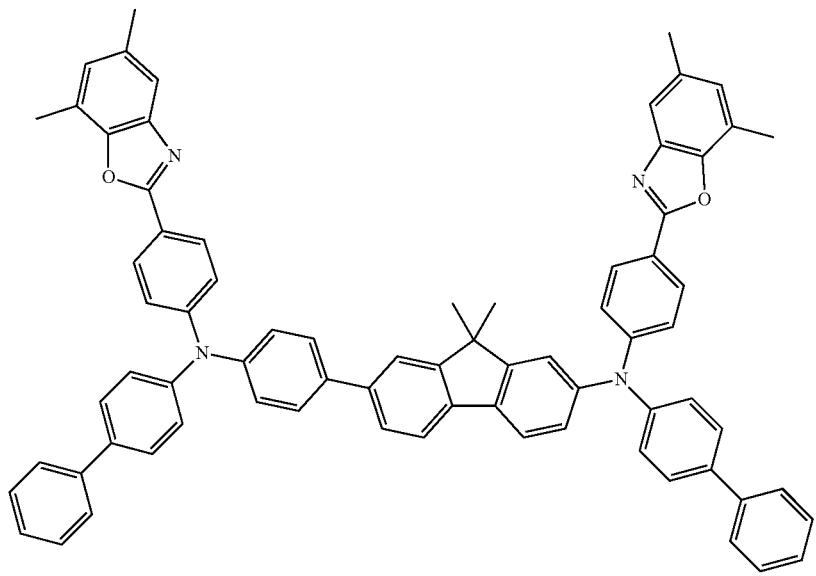
88
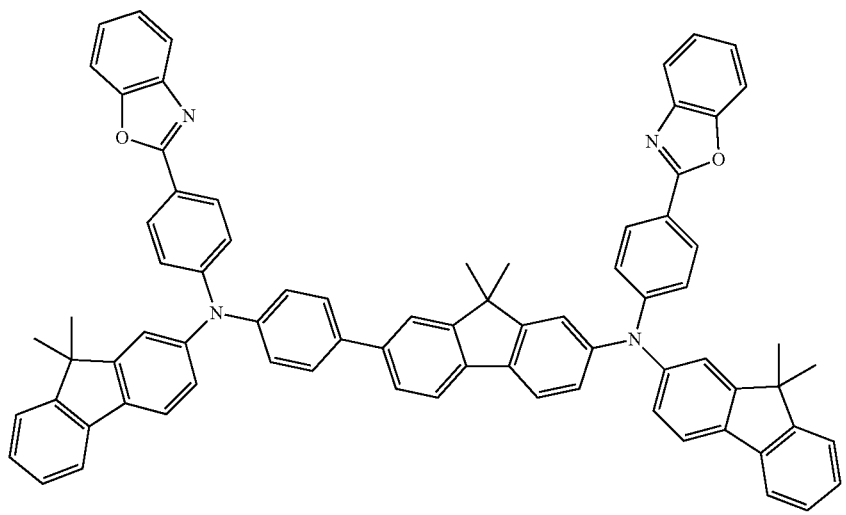
89
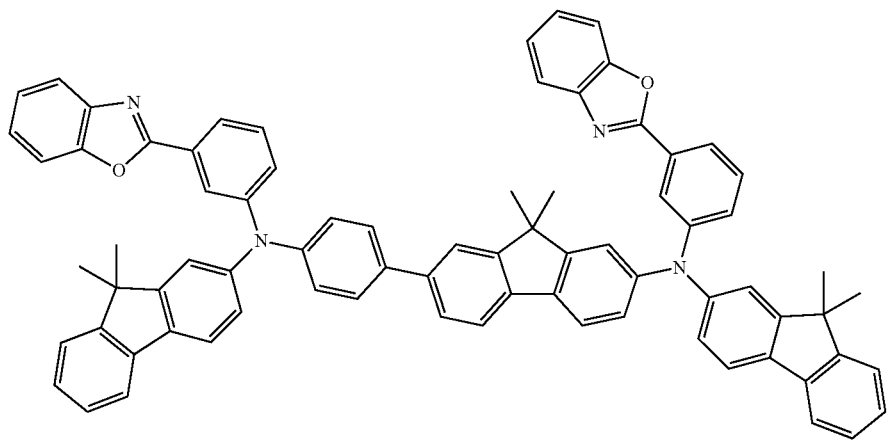
90

91
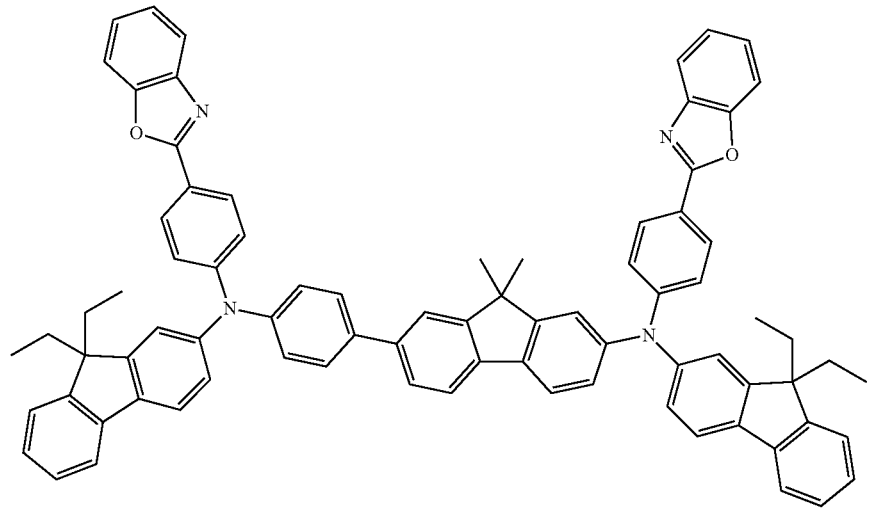
92
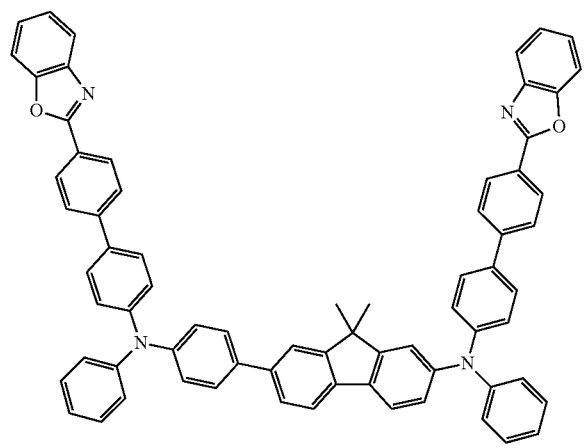
93
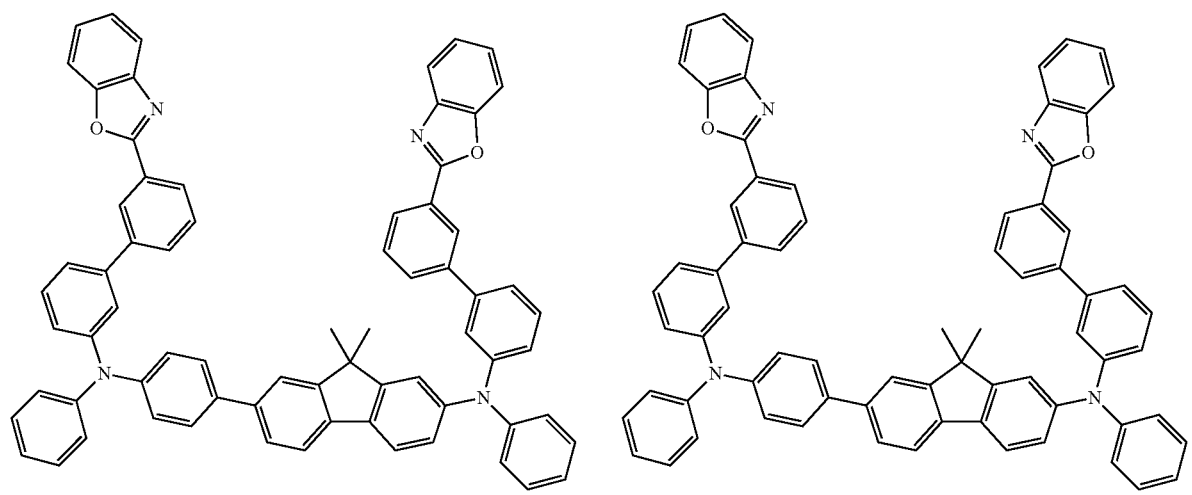
94
95
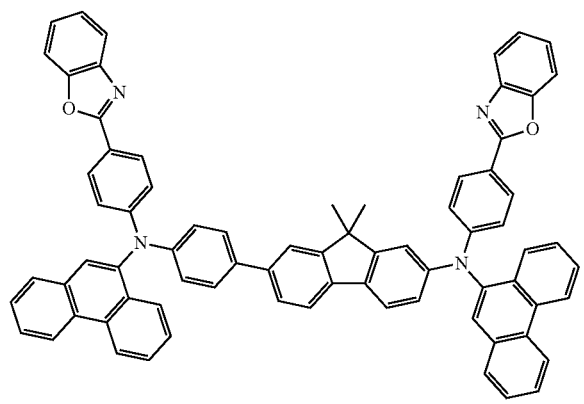

96
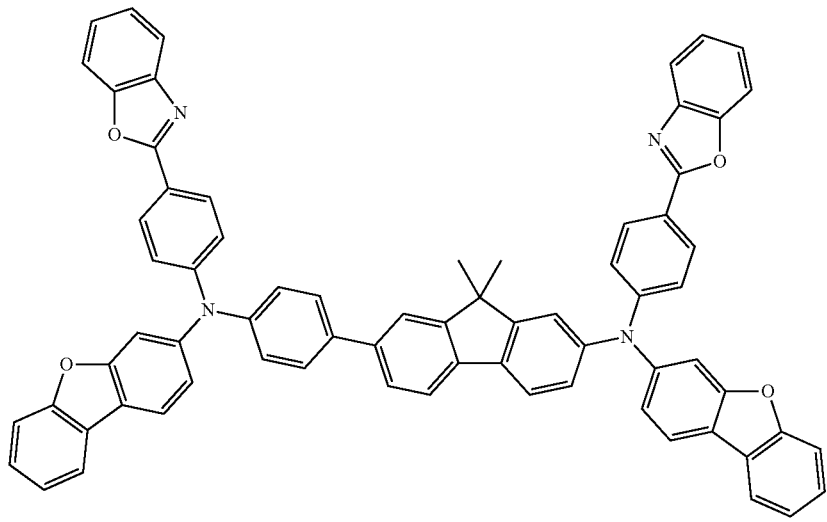
97 98
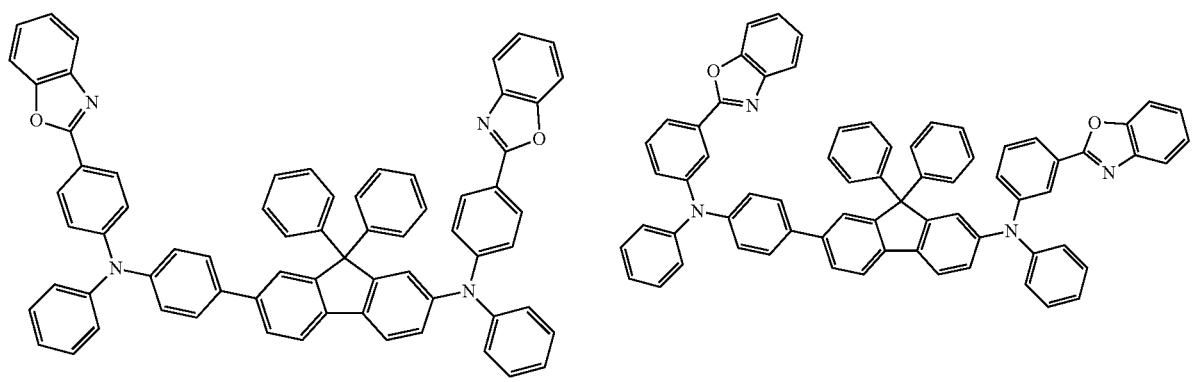
99
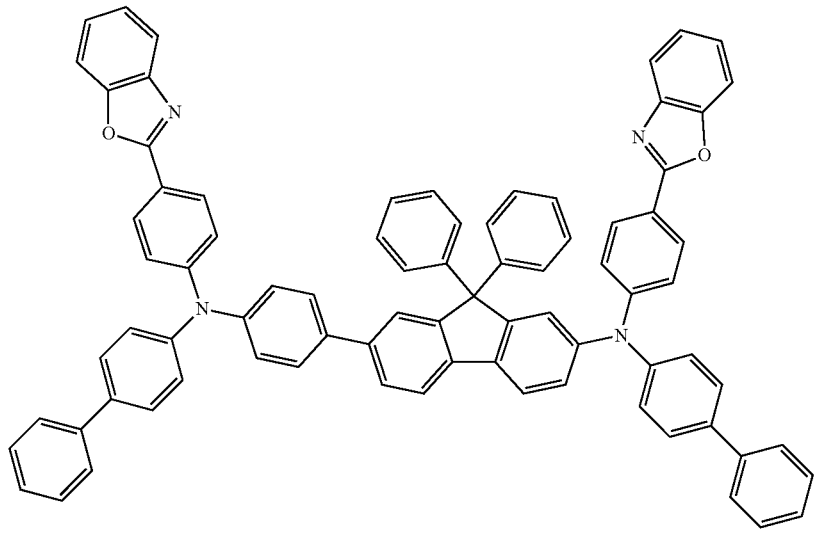

-continued
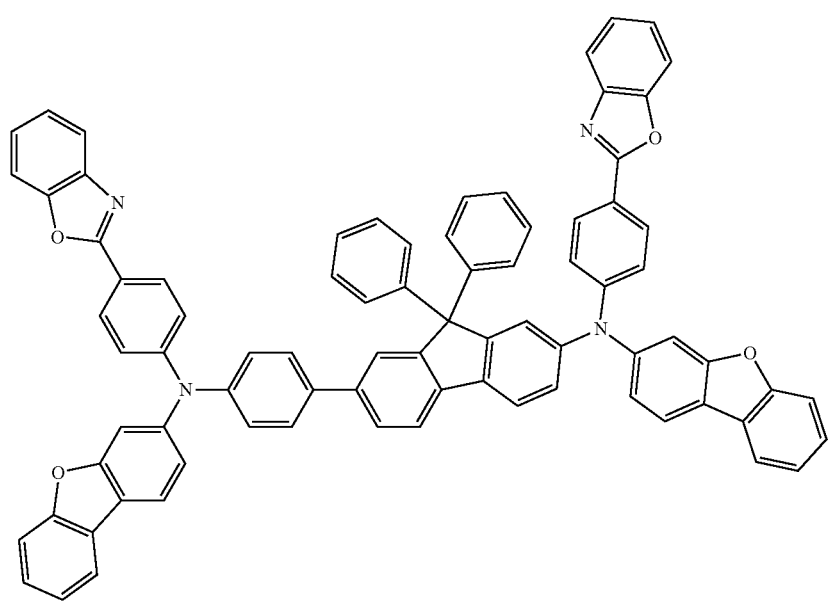
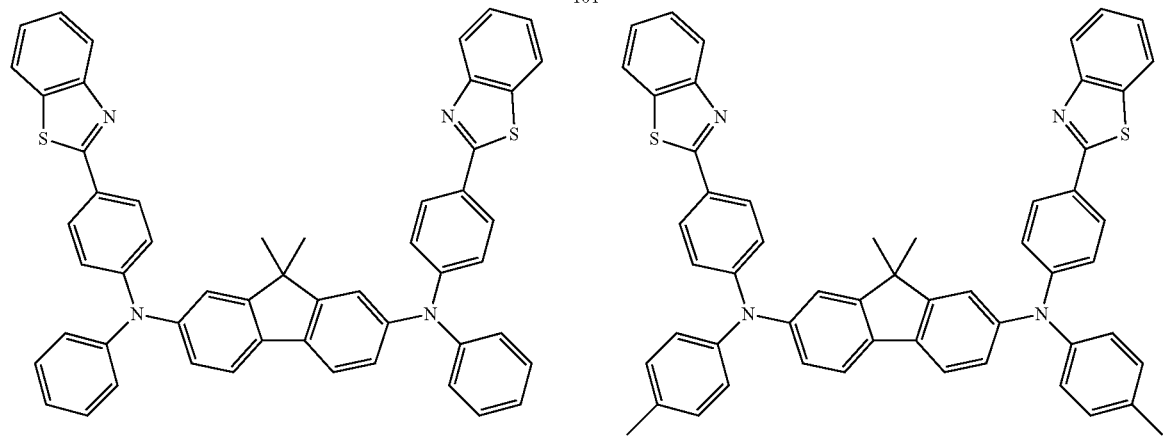
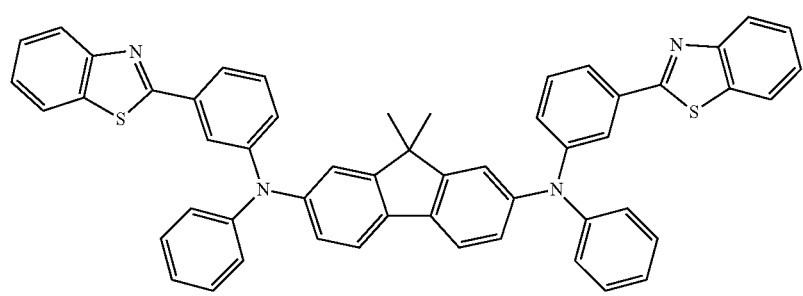

104
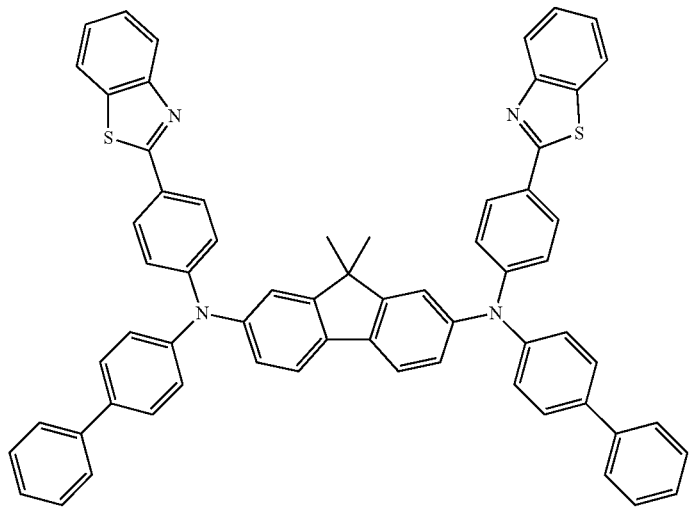
105
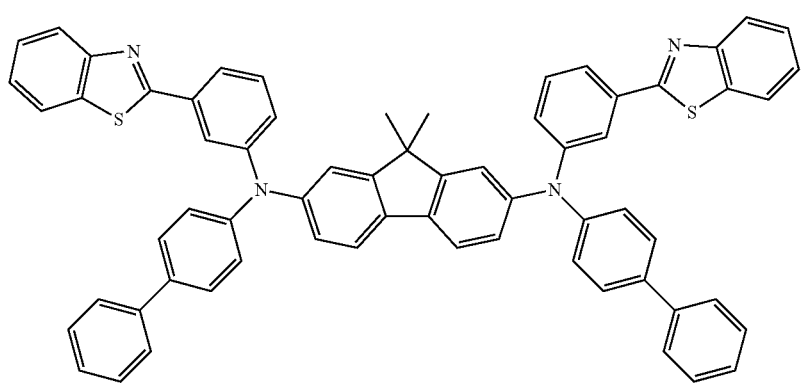
106
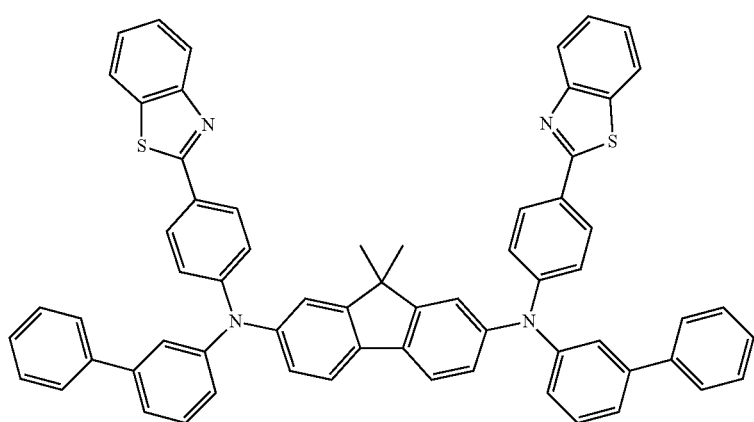

107
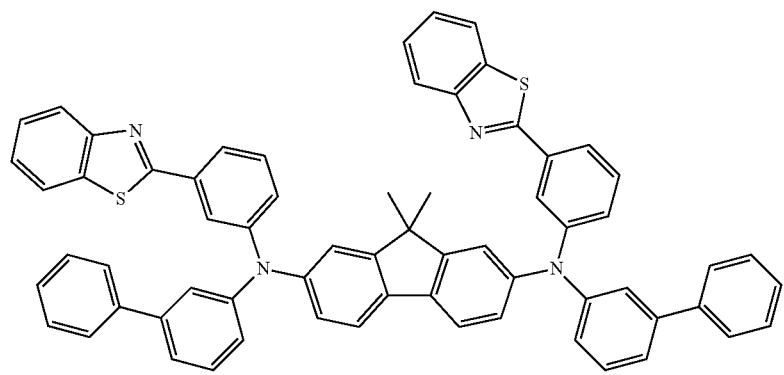
108 109
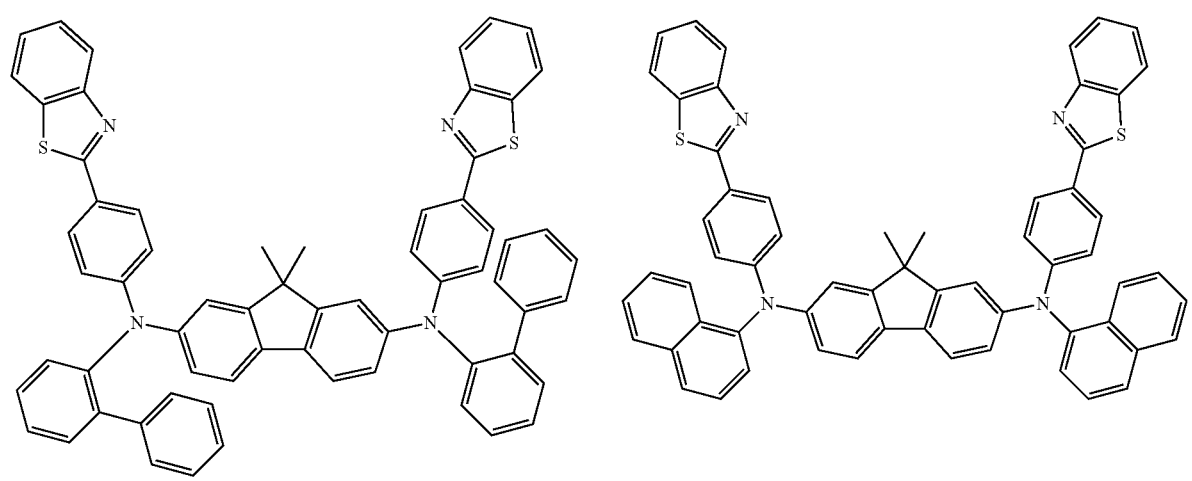
110
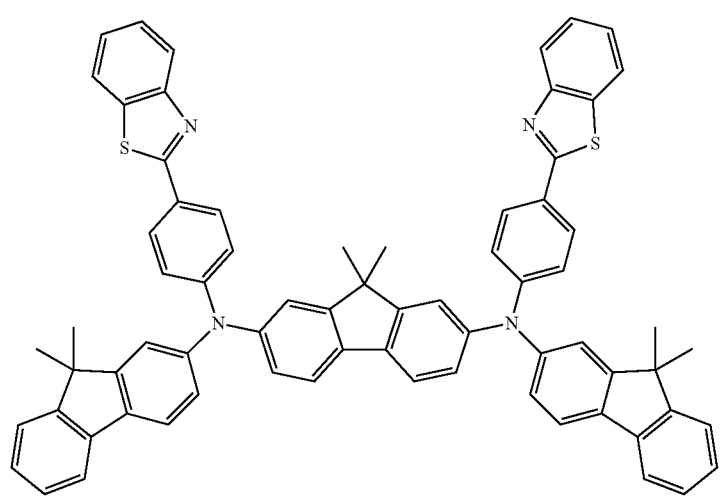

-continued
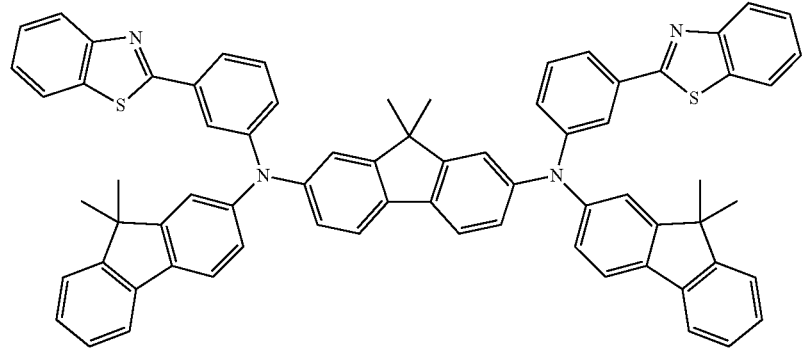
111
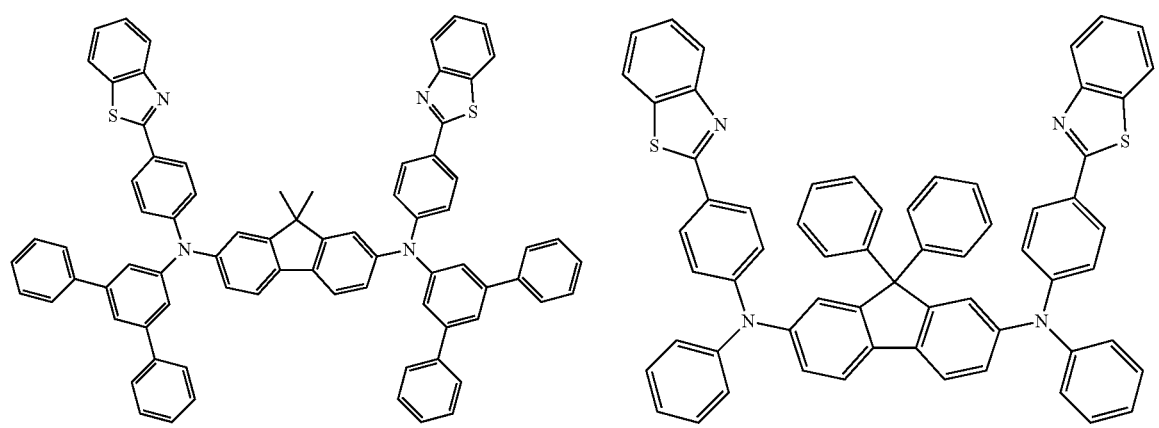
112
113
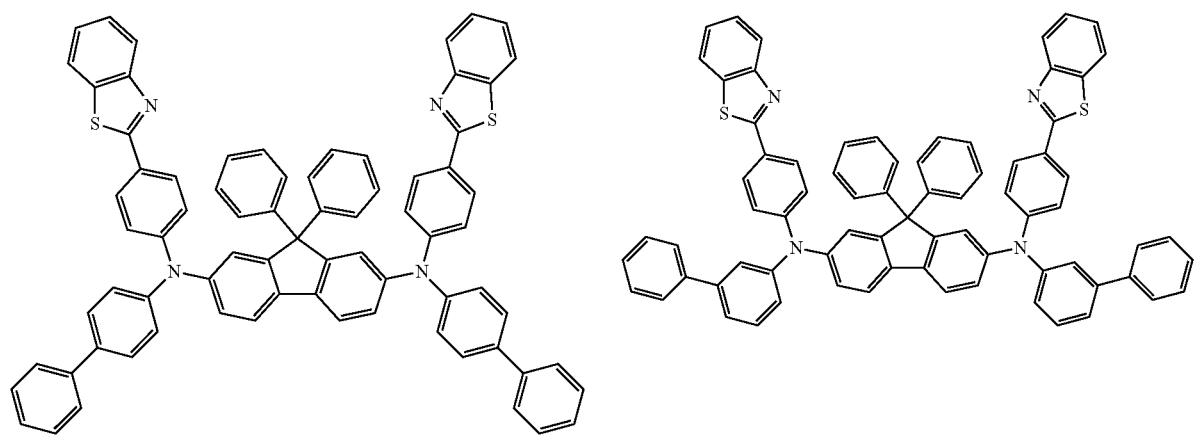
114
115

116
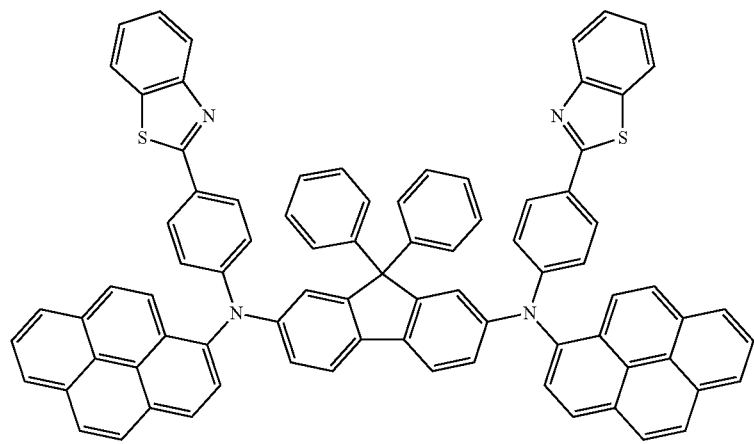
117
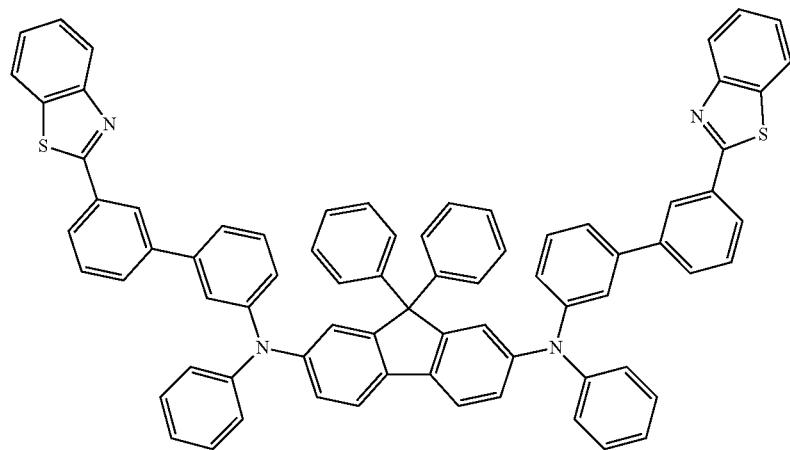
118
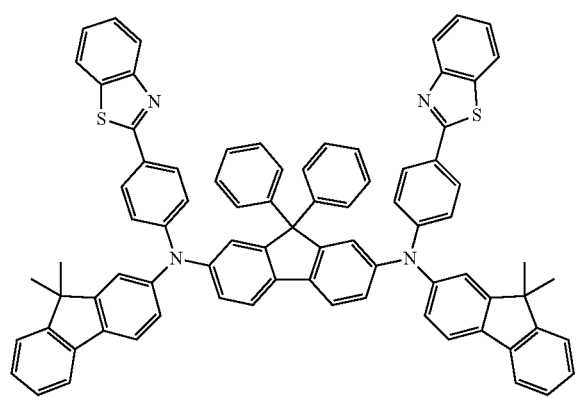
119
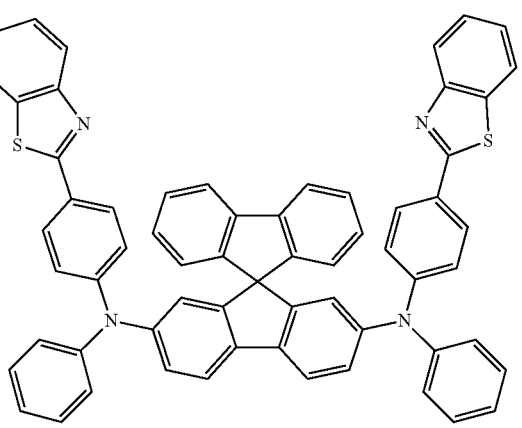

-continued
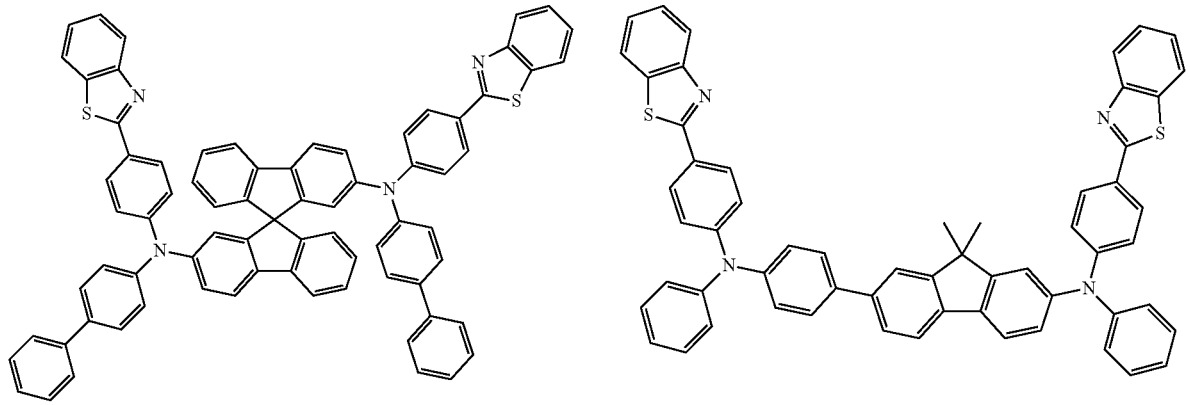
120
121
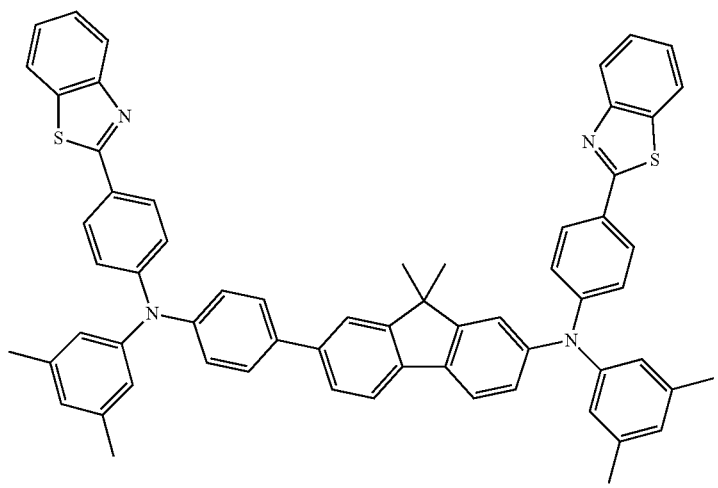
122
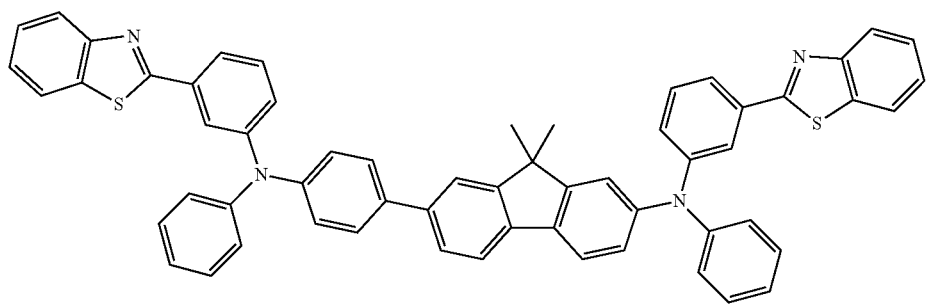
123

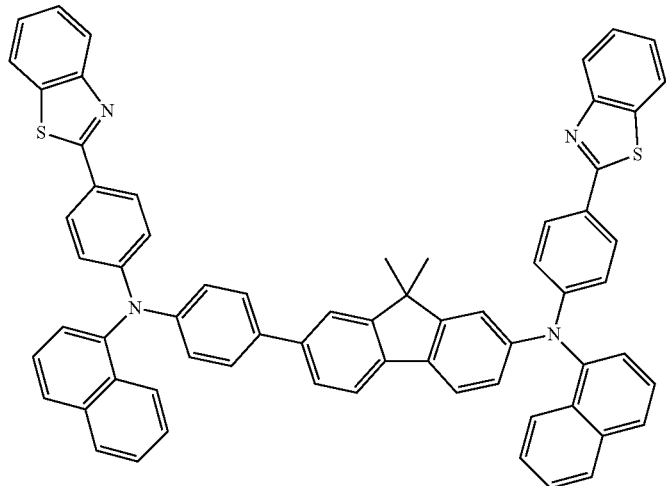
124
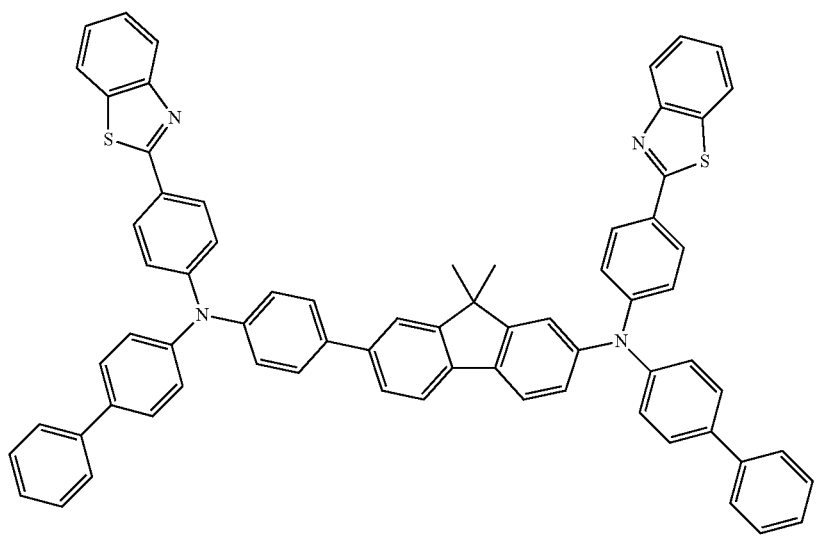
125
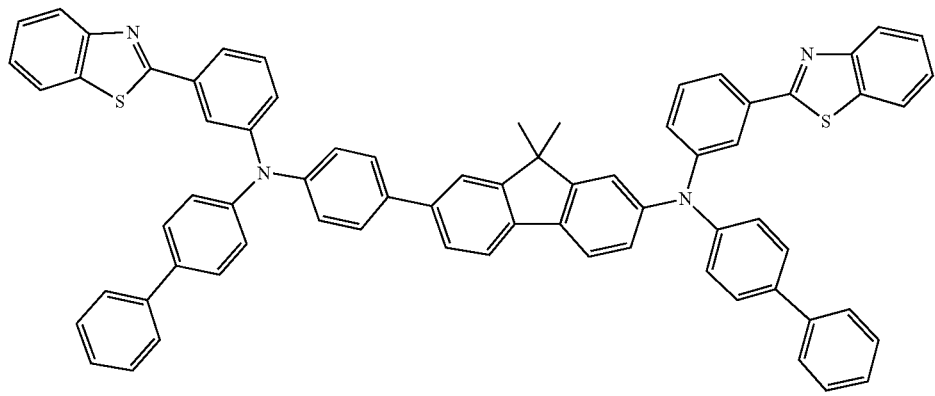
126

127
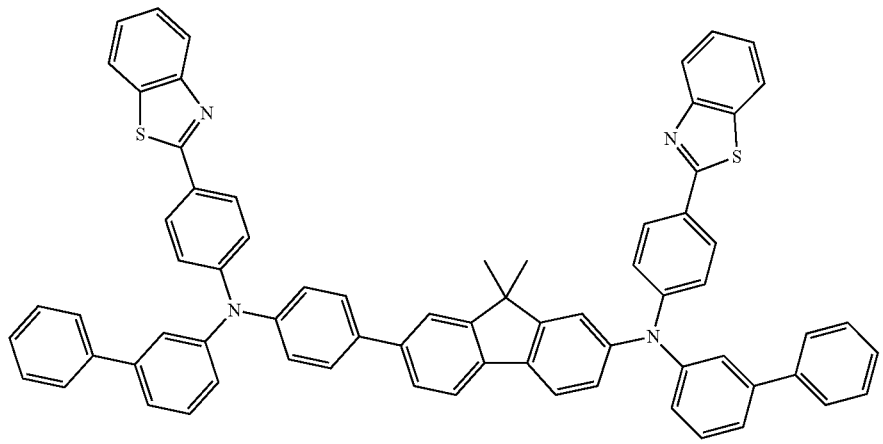
128
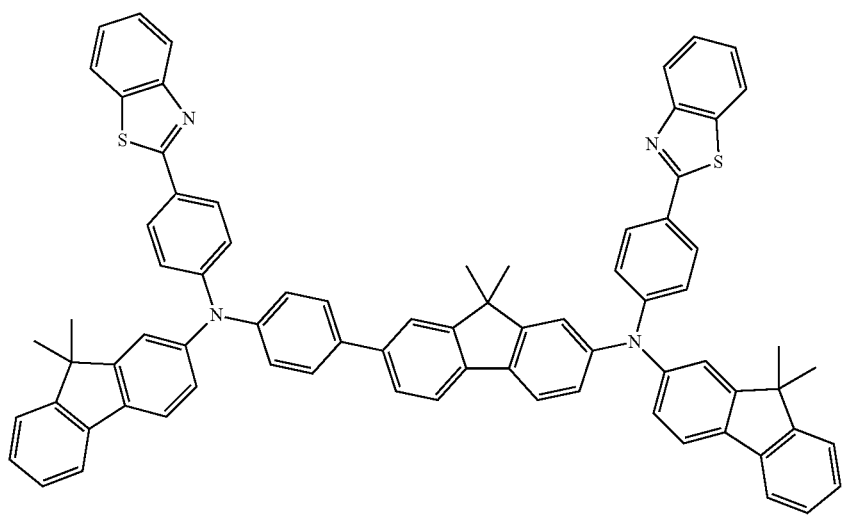
129
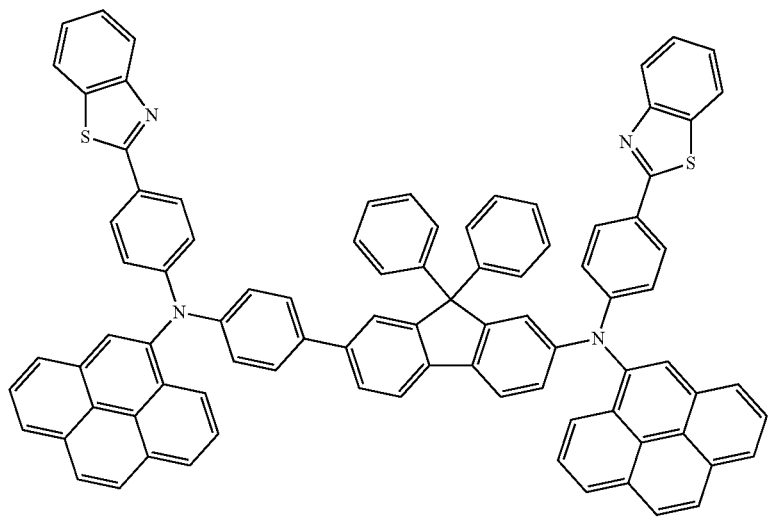

130
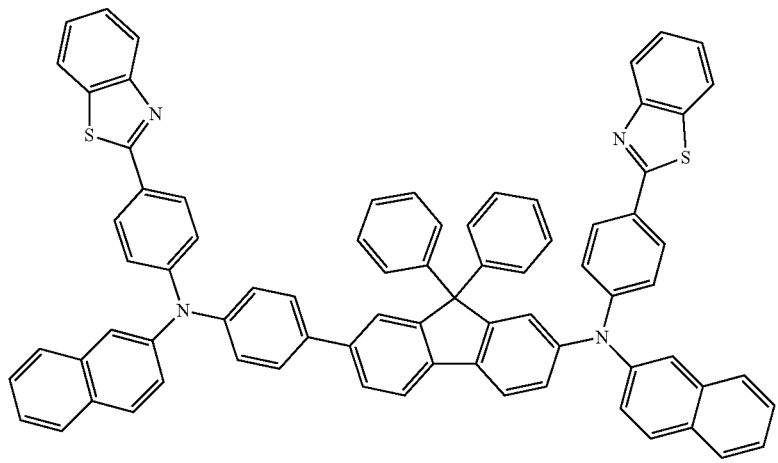
131
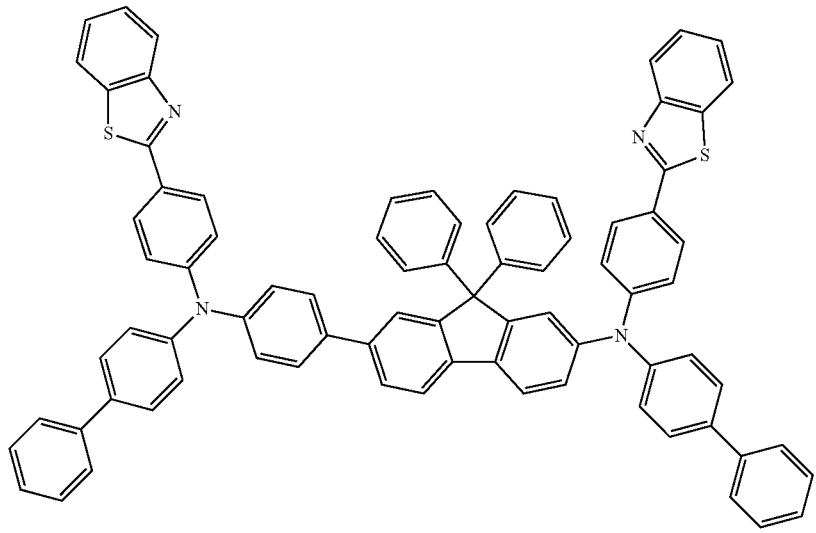
132
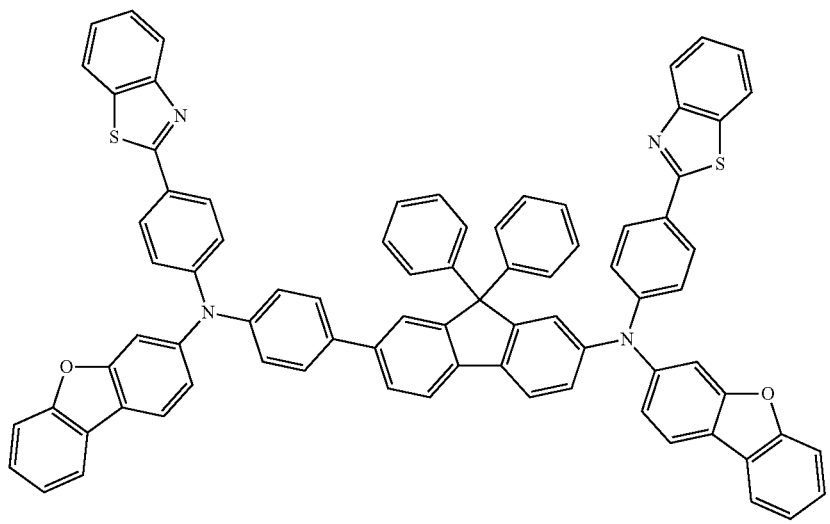

-continued
133 134
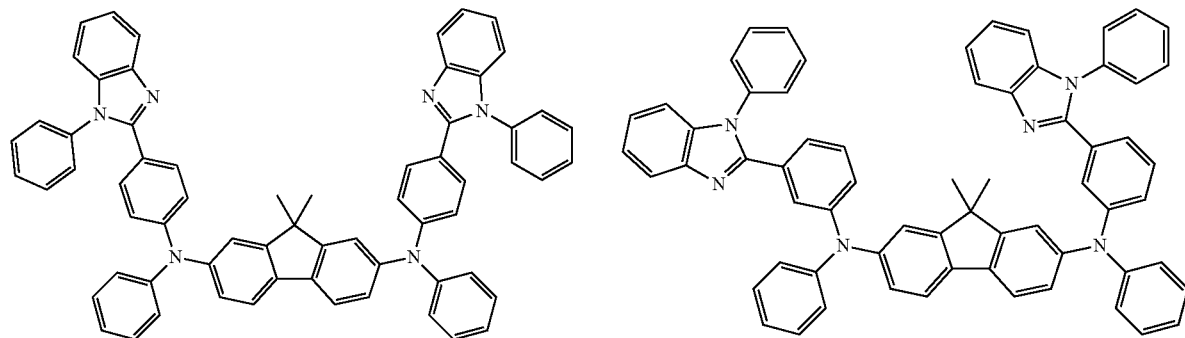
135 136
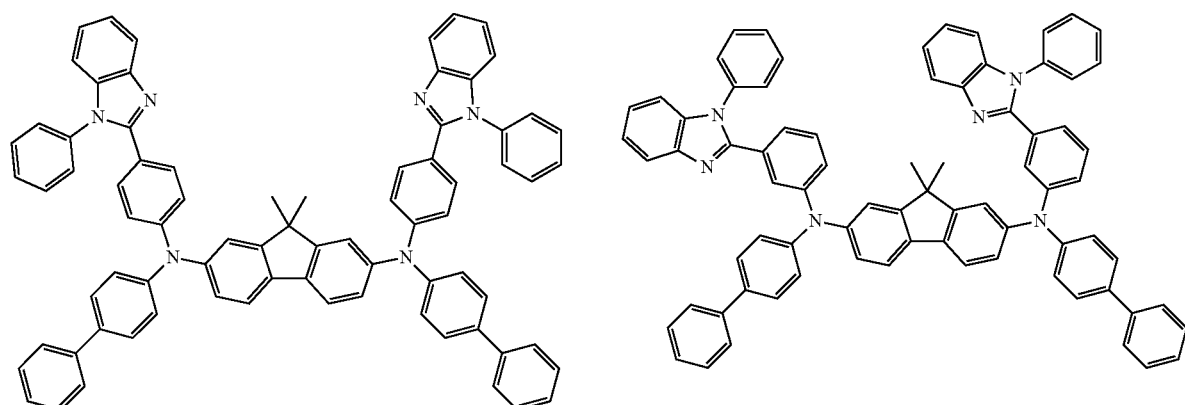
137
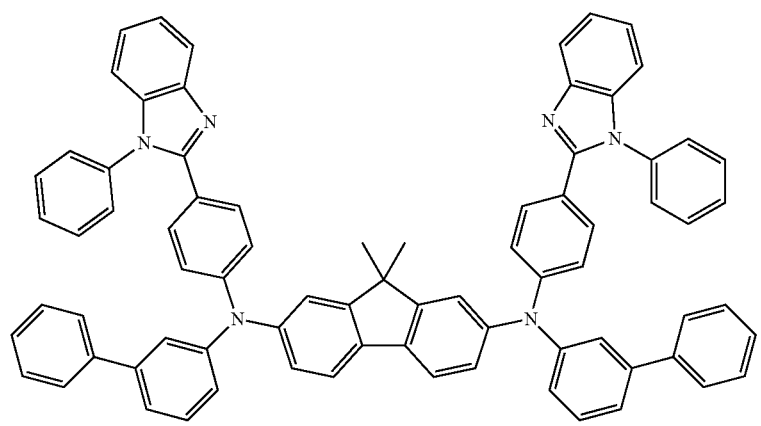

138
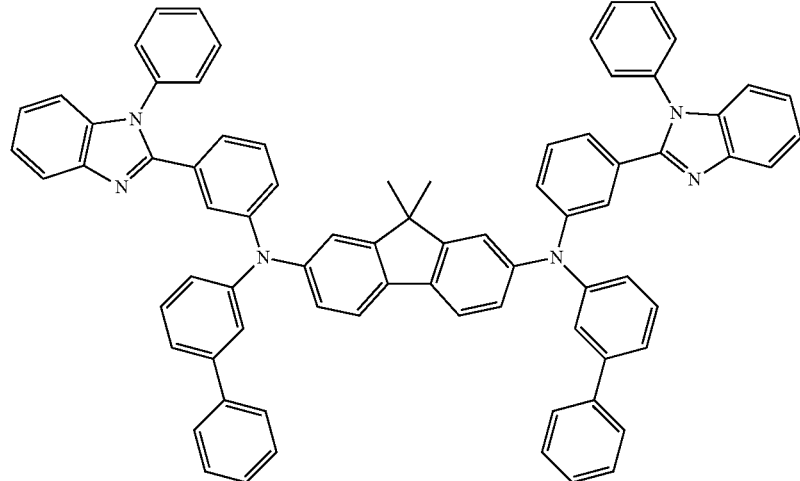
139 140
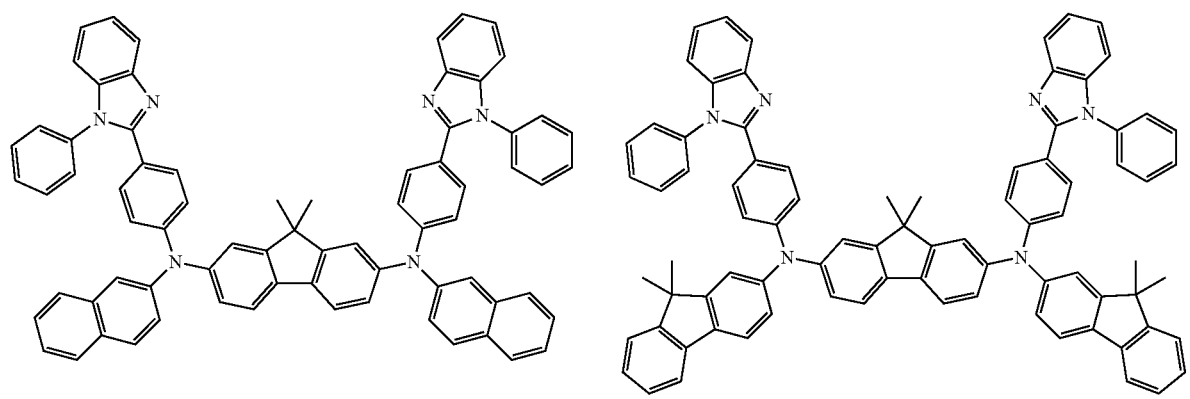
141
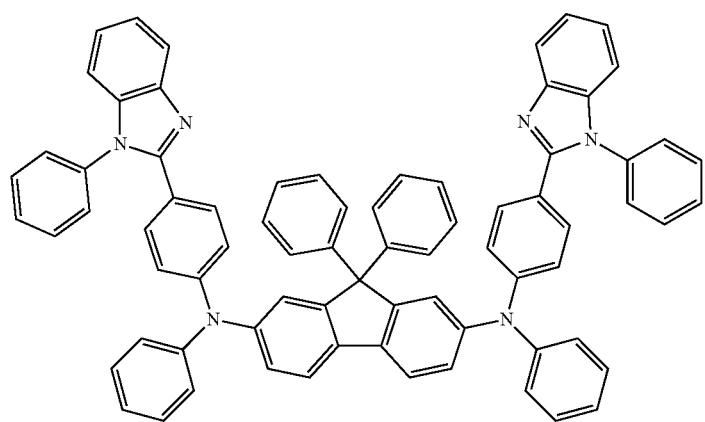

142

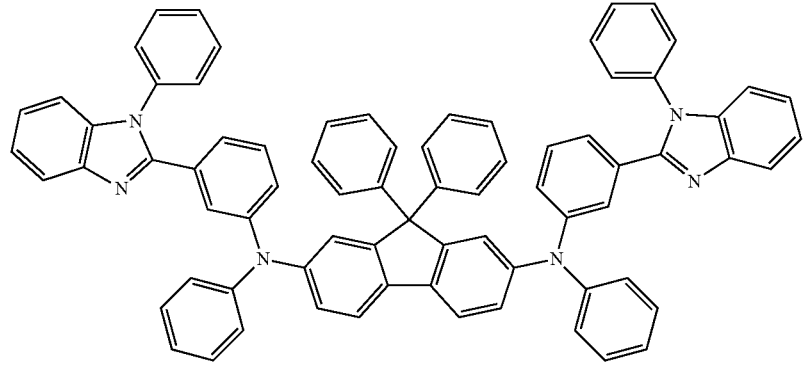

143

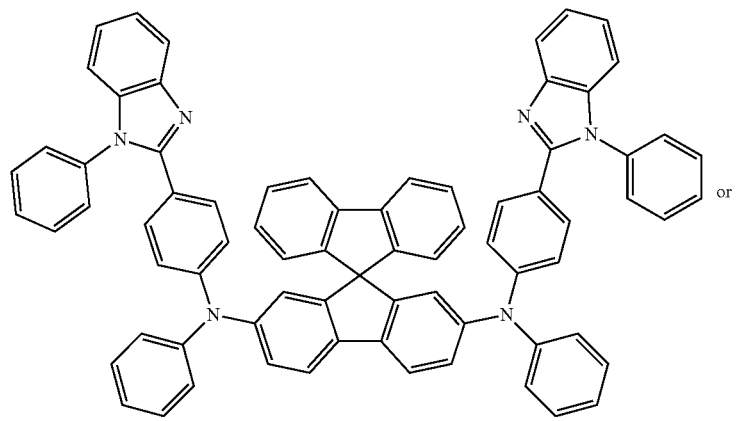

or

144

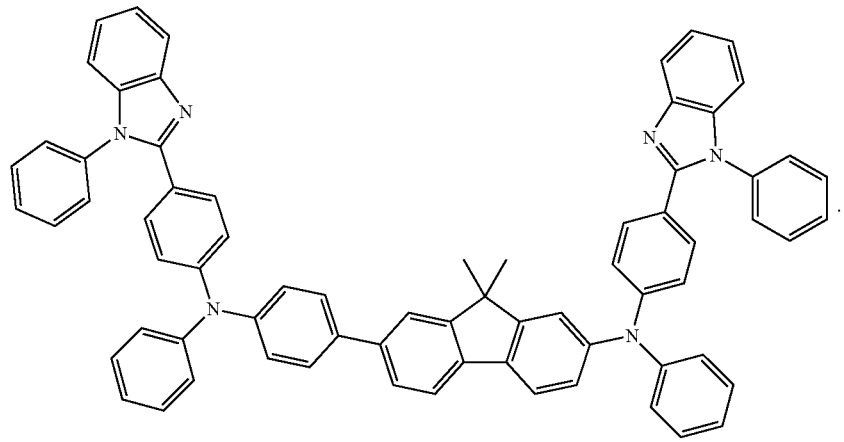

.

7. An organic electroluminescent device, comprising an anode, an organic layer, a cathode and a light extraction layer, the organic layer is located between the anode and the cathode, the organic layer comprises a hole transport layer, a light emitting layer, and an electron transport layer, with the hole transport layer being located between the anode and the light emitting layer, and the electron transport layer being located between the light emitting layer and the cathode, the light extraction layer being located on a side of the cathode away from the anode, and the light extraction layer contains the amine derivative according to claim 1.

* * * * *